United States Patent
Tuval et al.

(10) Patent No.: US 11,191,944 B2
(45) Date of Patent: Dec. 7, 2021

(54) DISTAL TIP ELEMENT FOR A VENTRICULAR ASSIST DEVICE

(71) Applicant: Magenta Medical Ltd., Kadima (IL)

(72) Inventors: Yosi Tuval, Even Yehuda (IL); Zev Sohn, Karnei Shomron (IL); Ehud Schwammenthal, Ra'anana (IL); Gad Lubinsky, Ein Vered (IL); Victor Troshin, Hod-Hasharon (IL); Shaul Jacob Leisner Mustacchi, Rosh Haayin (IL); Yinnon Elisha, Kffar Hess (IL); Yuri Sudin, Modi'in-Makkabbim-Re'ut (IL); Hagit Zemer Harel, Kfar Saba (IL); Avi Rozenfeld, Haifa (IL)

(73) Assignee: MAGENTA MEDICAL LTD., Kadima (IL)

( * ) Notice: Subject to any disclaimer, the term of this patent is extended or adjusted under 35 U.S.C. 154(b) by 209 days.

(21) Appl. No.: 16/750,354

(22) Filed: Jan. 23, 2020

(65) Prior Publication Data
US 2020/0237981 A1 Jul. 30, 2020

Related U.S. Application Data

(60) Provisional application No. 62/796,138, filed on Jan. 24, 2019, provisional application No. 62/851,716, (Continued)

(51) Int. Cl.
*A61M 1/12* (2006.01)
*A61M 1/10* (2006.01)
(Continued)

(52) U.S. Cl.
CPC ........ *A61M 60/148* (2021.01); *A61M 60/135* (2021.01); *A61M 60/414* (2021.01);
(Continued)

(58) Field of Classification Search
CPC .............. A61M 60/148; A61M 60/829; A61M 60/419; A61M 60/414; A61M 60/135;
(Continued)

(56) References Cited

U.S. PATENT DOCUMENTS

| 4,625,712 A | 12/1986 | Wampler |
| 4,753,221 A | 6/1988 | Kensey et al. |

(Continued)

FOREIGN PATENT DOCUMENTS

| AU | 2013205145 A1 | 5/2013 |
| EP | 0916359 A1 | 5/1999 |

(Continued)

OTHER PUBLICATIONS

Extended European Search Report for European Application No. 19172327.9 dated Aug. 23, 2019.
(Continued)

*Primary Examiner* — Erin M Piateski
(74) *Attorney, Agent, or Firm* — Dorsey & Whitney LLP

(57) ABSTRACT

Apparatus and methods are described including a left-ventricular assist device that includes a tube configured to traverse a subject's aortic valve, with a distal portion of the tube disposed within the subject's left ventricle. A frame is disposed within the distal portion of the tube. A pump disposed within the frame pumps blood through the tube. A distal-tip element defines a straight proximal portion that defines a longitudinal axis, and a curved distal portion that is shaped such as to curve in a first direction with respect to the longitudinal axis before passing through an inflection point and curving in a second direction with respect to the longitudinal axis, such that the curved distal portion defines a bulge on one side of the longitudinal axis. Other applications are also described.

16 Claims, 81 Drawing Sheets

Related U.S. Application Data filed on May 23, 2019, provisional application No. 62/870,821, filed on Jul. 5, 2019, provisional application No. 62/896,026, filed on Sep. 5, 2019.

(51) Int. Cl.
| | |
|---|---|
| *A61M 60/148* | (2021.01) |
| *A61M 60/419* | (2021.01) |
| *A61M 60/422* | (2021.01) |
| *A61M 60/818* | (2021.01) |
| *A61M 60/829* | (2021.01) |
| *A61M 60/857* | (2021.01) |
| *A61M 60/896* | (2021.01) |
| *A61M 60/414* | (2021.01) |
| *A61M 60/135* | (2021.01) |
| *F04D 29/52* | (2006.01) |
| *F04D 29/54* | (2006.01) |
| *A61M 60/205* | (2021.01) |
| *A61M 60/122* | (2021.01) |

(52) U.S. Cl.
CPC ........ *A61M 60/419* (2021.01); *A61M 60/422* (2021.01); *A61M 60/818* (2021.01); *A61M 60/829* (2021.01); *A61M 60/857* (2021.01); *A61M 60/896* (2021.01); *F04D 29/526* (2013.01); *F04D 29/545* (2013.01); *A61M 60/122* (2021.01); *A61M 60/205* (2021.01); *A61M 2205/0216* (2013.01); *A61M 2205/3344* (2013.01); *A61M 2230/30* (2013.01)

(58) Field of Classification Search
CPC .............. A61M 60/422; A61M 60/896; A61M 60/857; A61M 60/818; A61M 60/122; A61M 60/205; A61M 2205/0216; A61M 2205/3344; A61M 2230/30; F04D 29/526; F04D 29/545
USPC .......................................................... 600/16
See application file for complete search history.

(56) References Cited

U.S. PATENT DOCUMENTS

| | | |
|---|---|---|
| 4,919,647 A | 4/1990 | Nash |
| 4,954,055 A | 9/1990 | Raible et al. |
| 4,969,865 A | 11/1990 | Hwang et al. |
| 4,985,014 A | 1/1991 | Orejola |
| 5,011,469 A | 4/1991 | Buckberg et al. |
| 5,061,256 A | 10/1991 | Wampler |
| 5,169,378 A | 12/1992 | Figuera |
| 5,275,580 A | 1/1994 | Yamazaki |
| 5,531,789 A | 7/1996 | Yamazaki et al. |
| 5,569,275 A | 10/1996 | Kotula et al. |
| 5,613,935 A | 3/1997 | Jarvik |
| 5,692,882 A | 12/1997 | Bozeman, Jr. et al. |
| 5,713,730 A | 2/1998 | Nose et al. |
| 5,749,855 A | 5/1998 | Reitan |
| 5,772,693 A | 6/1998 | Brownlee |
| 5,843,158 A | 12/1998 | Lenker et al. |
| 5,863,179 A | 1/1999 | Westphal et al. |
| 5,876,385 A | 3/1999 | Ikari et al. |
| 5,911,685 A | 6/1999 | Siess et al. |
| 5,928,132 A | 7/1999 | Leschinsky |
| 5,947,892 A | 9/1999 | Benkowski et al. |
| 5,964,694 A | 10/1999 | Siess et al. |
| 6,007,478 A | 12/1999 | Siess et al. |
| 6,086,527 A | 7/2000 | Talpade |
| 6,116,862 A | 9/2000 | Rau et al. |
| 6,135,729 A | 10/2000 | Aber |
| 6,162,017 A | 12/2000 | Raible |
| 6,217,541 B1 | 4/2001 | Yu |
| 6,247,892 B1 | 6/2001 | Kazatchkov et al. |
| 6,355,001 B1 | 3/2002 | Quinn et al. |
| 6,413,222 B1 | 7/2002 | Pantages et al. |
| 6,482,228 B1 | 11/2002 | Norred |
| 6,506,146 B1 | 1/2003 | Mohl |
| 6,533,716 B1 | 3/2003 | Schmutz-Rode et al. |
| 6,537,315 B2 | 3/2003 | Yamazaki et al. |
| 6,544,216 B1 | 4/2003 | Sammler et al. |
| 6,592,567 B1 | 7/2003 | Levin et al. |
| 6,616,624 B1 | 9/2003 | Kieval |
| 6,884,210 B2 | 4/2005 | Nose et al. |
| 6,949,066 B2 | 9/2005 | Bearnson et al. |
| 7,004,925 B2 | 2/2006 | Navia et al. |
| 7,010,954 B2 | 3/2006 | Siess et al. |
| 7,022,100 B1 | 4/2006 | Aboul-hosn et al. |
| 7,027,875 B2 | 4/2006 | Siess et al. |
| 7,144,364 B2 | 12/2006 | Barbut et al. |
| 7,159,593 B2 | 1/2007 | Mccarthy et al. |
| 7,201,772 B2 | 4/2007 | Schwammenthal et al. |
| 7,258,679 B2 | 8/2007 | Moore et al. |
| 7,335,192 B2 | 2/2008 | Keren et al. |
| 7,338,521 B2 | 3/2008 | Antaki et al. |
| 7,341,570 B2 | 3/2008 | Keren et al. |
| 7,393,181 B2 | 7/2008 | Mcbride et al. |
| 7,485,104 B2 | 2/2009 | Kieval |
| 7,717,952 B2 | 5/2010 | Case et al. |
| 7,744,642 B2 | 6/2010 | Rittgers et al. |
| 7,762,941 B2 | 7/2010 | Jarvik |
| 7,766,853 B2 | 8/2010 | Lane |
| 7,766,892 B2 | 8/2010 | Keren et al. |
| 7,766,961 B2 | 8/2010 | Patel et al. |
| 7,780,628 B1 | 8/2010 | Keren et al. |
| 7,811,221 B2 | 10/2010 | Gross |
| 7,841,976 B2 | 11/2010 | McBride et al. |
| 7,914,436 B1 | 3/2011 | Kung |
| 7,914,503 B2 | 3/2011 | Goodson et al. |
| 8,012,121 B2 | 9/2011 | Goodson et al. |
| 8,079,948 B2 | 12/2011 | Shifflette |
| 8,118,723 B2 | 2/2012 | Richardson et al. |
| 8,123,669 B2 | 2/2012 | Siess et al. |
| 8,157,758 B2 | 4/2012 | Pecor et al. |
| 8,192,451 B2 | 6/2012 | Cambronne et al. |
| 8,216,122 B2 | 7/2012 | Kung |
| 8,221,492 B2 | 7/2012 | Case et al. |
| 8,235,933 B2 | 8/2012 | Keren et al. |
| 8,277,470 B2 | 10/2012 | Demarais et al. |
| 8,376,707 B2 | 2/2013 | Mcbride et al. |
| 8,439,859 B2 | 5/2013 | Pfeffer et al. |
| 8,449,443 B2 | 5/2013 | Rodefeld et al. |
| 8,485,961 B2 | 7/2013 | Campbell et al. |
| 8,489,190 B2 | 7/2013 | Pfeffer et al. |
| 8,512,262 B2 | 8/2013 | Gertner |
| 8,535,211 B2 | 9/2013 | Walters et al. |
| 8,538,535 B2 | 9/2013 | Ariav et al. |
| 8,579,858 B2 | 11/2013 | Reitan et al. |
| 8,591,393 B2 | 11/2013 | Walters et al. |
| 8,591,539 B2 | 11/2013 | Gellman |
| 8,597,170 B2 | 12/2013 | Walters et al. |
| 8,617,239 B2 | 12/2013 | Reitan |
| 8,672,868 B2 | 3/2014 | Simons |
| 8,690,749 B1 | 4/2014 | Nunez |
| 8,721,517 B2 | 5/2014 | Zeng et al. |
| 8,734,331 B2 | 5/2014 | Evans et al. |
| 8,734,508 B2 | 5/2014 | Hastings et al. |
| 8,777,832 B1 | 7/2014 | Wang et al. |
| 8,814,543 B2 | 8/2014 | Liebing |
| 8,814,776 B2 | 8/2014 | Hastie et al. |
| 8,814,933 B2 | 8/2014 | Siess |
| 8,827,887 B2 | 9/2014 | Curtis et al. |
| 8,849,398 B2 | 9/2014 | Evans |
| 8,864,642 B2 | 10/2014 | Scheckel |
| 8,888,728 B2 | 11/2014 | Aboul-hosn et al. |
| 8,900,060 B2 | 12/2014 | Liebing |
| 8,926,492 B2 | 1/2015 | Scheckel |
| 8,932,141 B2 | 1/2015 | Liebing |
| 8,944,748 B2 | 2/2015 | Liebing |
| 8,979,493 B2 | 3/2015 | Roehn |
| 8,998,792 B2 | 4/2015 | Scheckel |
| 9,028,216 B2 | 5/2015 | Schumacher et al. |
| 9,072,825 B2 | 7/2015 | Pfeffer et al. |

(56) References Cited

U.S. PATENT DOCUMENTS

| | | |
|---|---|---|
| 9,138,518 B2 | 9/2015 | Campbell et al. |
| 9,162,017 B2 | 10/2015 | Evans et al. |
| 9,259,521 B2 | 2/2016 | Simons |
| 9,278,189 B2 | 3/2016 | Corbett |
| 9,314,558 B2 | 4/2016 | Er |
| 9,328,741 B2 | 5/2016 | Liebing |
| 9,358,329 B2 | 6/2016 | Fitzgerald et al. |
| 9,358,330 B2 | 6/2016 | Schumacher |
| 9,364,592 B2 | 6/2016 | Mcbride et al. |
| 9,364,593 B2 | 6/2016 | Mcbride et al. |
| 9,370,613 B2 | 6/2016 | Hsu et al. |
| 9,381,288 B2 | 7/2016 | Schenck et al. |
| 9,404,505 B2 | 8/2016 | Scheckel |
| 9,416,791 B2 | 8/2016 | Toellner |
| 9,421,311 B2 | 8/2016 | Tanner et al. |
| 9,446,179 B2 | 9/2016 | Keenan et al. |
| 9,474,840 B2 | 10/2016 | Siess |
| 9,512,839 B2 | 12/2016 | Liebing |
| 9,533,082 B2 | 1/2017 | Reichenbach et al. |
| 9,533,084 B2 | 1/2017 | Siess et al. |
| 9,545,468 B2 | 1/2017 | Aboul-hosn et al. |
| 9,550,017 B2 | 1/2017 | Spanier et al. |
| 9,561,314 B2 | 2/2017 | Aboul-hosn et al. |
| 9,597,205 B2 | 3/2017 | Tuval |
| 9,597,437 B2 | 3/2017 | Aboul-hosn et al. |
| 9,603,983 B2 | 3/2017 | Roehn et al. |
| 9,611,743 B2 | 4/2017 | Toellner et al. |
| 9,616,159 B2 | 4/2017 | Anderson et al. |
| 9,623,161 B2 | 4/2017 | Medvedev et al. |
| 9,669,142 B2 | 6/2017 | Spanier et al. |
| 9,669,144 B2 | 6/2017 | Spanier et al. |
| 9,675,738 B2 | 6/2017 | Tanner et al. |
| 9,713,663 B2 | 7/2017 | Medvedev et al. |
| 9,717,833 B2 | 8/2017 | Mcbride et al. |
| 9,759,237 B2 | 9/2017 | Liebing |
| 9,764,113 B2 | 9/2017 | Tuval et al. |
| 9,789,238 B2 | 10/2017 | Aboul-hosn et al. |
| 9,795,727 B2 | 10/2017 | Schumacher |
| 9,814,814 B2 | 11/2017 | Corbett et al. |
| 9,821,146 B2 | 11/2017 | Tao et al. |
| 9,827,356 B2 | 11/2017 | Muller et al. |
| 9,833,550 B2 | 12/2017 | Siess |
| 9,835,550 B2 | 12/2017 | Kakuno et al. |
| 9,850,906 B2 | 12/2017 | Ozaki et al. |
| 9,872,947 B2 | 1/2018 | Keenan et al. |
| 9,872,948 B2 | 1/2018 | Siess |
| 9,878,079 B2 | 1/2018 | Pfeffer et al. |
| 9,889,242 B2 | 2/2018 | Pfeffer et al. |
| 9,907,890 B2 | 3/2018 | Muller |
| 9,919,087 B2 | 3/2018 | Pfeffer et al. |
| 9,962,475 B2 | 5/2018 | Campbell et al. |
| 9,974,893 B2 | 5/2018 | Toellner |
| 9,999,714 B2 | 6/2018 | Spanier et al. |
| 10,029,037 B2 | 7/2018 | Muller et al. |
| 10,029,040 B2 | 7/2018 | Taskin |
| 10,039,872 B2 | 8/2018 | Zeng et al. |
| 10,039,874 B2 | 8/2018 | Schwammenthal et al. |
| 10,052,420 B2 | 8/2018 | Medvedev et al. |
| 10,071,192 B2 | 9/2018 | Zeng |
| 10,086,121 B2 | 10/2018 | Fitzgerald et al. |
| 10,105,475 B2 | 10/2018 | Muller |
| 10,117,980 B2 | 11/2018 | Keenan et al. |
| 10,119,550 B2 | 11/2018 | Bredenbreuker et al. |
| 10,149,932 B2 | 12/2018 | Mcbride et al. |
| 10,183,104 B2 | 1/2019 | Anderson et al. |
| 10,221,866 B2 | 3/2019 | Liebing |
| 10,231,838 B2 | 3/2019 | Chin et al. |
| 10,238,783 B2 | 3/2019 | Aboul-hosn et al. |
| 10,245,363 B1 | 4/2019 | Rowe |
| 10,265,447 B2 | 4/2019 | Campbell et al. |
| 10,265,448 B2 | 4/2019 | Liebing |
| 10,279,095 B2 | 5/2019 | Aboul-hosn et al. |
| 10,300,185 B2 | 5/2019 | Aboul-hosn et al. |
| 10,300,186 B2 | 5/2019 | Aboul-hosn et al. |
| 10,316,853 B2 | 6/2019 | Toellner |
| 10,330,101 B2 | 6/2019 | Toellner |
| 10,363,349 B2 | 7/2019 | Muller et al. |
| 10,369,260 B2 | 8/2019 | Smith et al. |
| 10,376,162 B2 | 8/2019 | Edelman et al. |
| 10,449,276 B2 | 10/2019 | Pfeffer et al. |
| 10,449,279 B2 | 10/2019 | Muller |
| 10,583,231 B2 | 3/2020 | Schwammenthal et al. |
| 10,799,626 B2 | 10/2020 | Siess et al. |
| 2001/0041934 A1 | 11/2001 | Yamazaki et al. |
| 2002/0107536 A1 | 8/2002 | Hussein |
| 2002/0151799 A1 | 10/2002 | Pantages et al. |
| 2003/0055486 A1 | 3/2003 | Adams et al. |
| 2004/0064090 A1 | 4/2004 | Keren et al. |
| 2004/0064091 A1 | 4/2004 | Keren et al. |
| 2004/0111006 A1 | 6/2004 | Alferness et al. |
| 2004/0116769 A1 | 6/2004 | Jassawalla et al. |
| 2004/0167415 A1 | 8/2004 | Gelfand et al. |
| 2004/0210236 A1 | 10/2004 | Allers et al. |
| 2004/0260389 A1 | 12/2004 | Case et al. |
| 2005/0033406 A1 | 2/2005 | Barnhart et al. |
| 2005/0049692 A1 | 3/2005 | Numamoto et al. |
| 2005/0079274 A1 | 4/2005 | Palasis et al. |
| 2005/0085848 A1 | 4/2005 | Johnson et al. |
| 2005/0119682 A1 | 6/2005 | Nguyen et al. |
| 2005/0180854 A1 | 8/2005 | Grabau et al. |
| 2006/0106449 A1 | 5/2006 | Ben |
| 2006/0265051 A1 | 11/2006 | Caro et al. |
| 2007/0100415 A1 | 5/2007 | Licata et al. |
| 2007/0100435 A1 | 5/2007 | Case et al. |
| 2007/0142729 A1 | 6/2007 | Pfeiffer et al. |
| 2007/0162103 A1 | 7/2007 | Case et al. |
| 2007/0208291 A1 | 9/2007 | Patel |
| 2007/0260327 A1 | 11/2007 | Case et al. |
| 2007/0293808 A1 | 12/2007 | Williams et al. |
| 2008/0009668 A1 | 1/2008 | Cohn |
| 2008/0103591 A1 | 5/2008 | Siess |
| 2008/0132747 A1 | 6/2008 | Shifflette |
| 2008/0132748 A1 | 6/2008 | Shifflette |
| 2008/0140189 A1 | 6/2008 | Nguyen et al. |
| 2008/0154236 A1 | 6/2008 | Elkins et al. |
| 2008/0183280 A1 | 7/2008 | Agnew et al. |
| 2008/0306327 A1 | 12/2008 | Shifflette |
| 2009/0024195 A1 | 1/2009 | Rezai et al. |
| 2009/0062597 A1 | 3/2009 | Shifflette |
| 2009/0093764 A1 | 4/2009 | Pfeffer et al. |
| 2009/0093796 A1 | 4/2009 | Pfeffer et al. |
| 2009/0264991 A1 | 10/2009 | Paul et al. |
| 2009/0287299 A1 | 11/2009 | Tabor et al. |
| 2009/0318857 A1 | 12/2009 | Goodson et al. |
| 2010/0130810 A1 | 5/2010 | Mohl |
| 2010/0268017 A1 | 10/2010 | Siess |
| 2011/0004046 A1 | 1/2011 | Campbell et al. |
| 2011/0034874 A1 | 2/2011 | Reitan et al. |
| 2011/0106244 A1 | 5/2011 | Ferrari et al. |
| 2011/0152999 A1 | 6/2011 | Hastings et al. |
| 2011/0190874 A1 | 8/2011 | Celermajer et al. |
| 2011/0213408 A1 | 9/2011 | Gross et al. |
| 2011/0230949 A1 | 9/2011 | Haverkost et al. |
| 2011/0257462 A1 | 10/2011 | Rodefeld et al. |
| 2011/0264075 A1 | 10/2011 | Leung et al. |
| 2011/0282128 A1 | 11/2011 | Reitan et al. |
| 2011/0301662 A1 | 12/2011 | Bar-yoseph et al. |
| 2012/0022579 A1 | 1/2012 | Fulton |
| 2012/0059460 A1 | 3/2012 | Reitan |
| 2012/0089047 A1 | 4/2012 | Ryba et al. |
| 2012/0116382 A1 | 5/2012 | Ku et al. |
| 2012/0130469 A1 | 5/2012 | Cragg et al. |
| 2012/0143141 A1 | 6/2012 | Verkaik et al. |
| 2012/0172654 A1 | 7/2012 | Bates |
| 2012/0172655 A1* | 7/2012 | Campbell ............. A61M 25/04 600/16 |
| 2012/0178986 A1 | 7/2012 | Campbell et al. |
| 2012/0224970 A1 | 9/2012 | Schumacher et al. |
| 2012/0234411 A1 | 9/2012 | Scheckel |
| 2012/0237357 A1 | 9/2012 | Schumacher et al. |
| 2012/0245680 A1 | 9/2012 | Masuzawa et al. |
| 2012/0303112 A1 | 11/2012 | Armstrong et al. |
| 2012/0316586 A1 | 12/2012 | Demarais et al. |
| 2012/0328460 A1 | 12/2012 | Horvath et al. |

(56) References Cited

U.S. PATENT DOCUMENTS

| | | |
|---|---|---|
| 2013/0053623 A1 | 2/2013 | Evans et al. |
| 2013/0053732 A1 | 2/2013 | Heuser |
| 2013/0060077 A1 | 3/2013 | Liebing |
| 2013/0079874 A1 | 3/2013 | Doss et al. |
| 2013/0085319 A1 | 4/2013 | Evans et al. |
| 2013/0177409 A1 | 7/2013 | Schumacher et al. |
| 2013/0177432 A1 | 7/2013 | Toellner et al. |
| 2014/0018840 A1* | 1/2014 | Morgan ............... A61F 2/0108 606/200 |
| 2014/0025041 A1 | 1/2014 | Fukuoka et al. |
| 2014/0128659 A1* | 5/2014 | Heuring ............ A61M 60/205 600/16 |
| 2014/0255176 A1 | 9/2014 | Bredenbreuker et al. |
| 2014/0275720 A1* | 9/2014 | Ferrari .................... A61B 5/06 600/16 |
| 2014/0275722 A1 | 9/2014 | Zimmermann et al. |
| 2015/0018597 A1 | 1/2015 | Fierens et al. |
| 2015/0119633 A1 | 4/2015 | Haselby et al. |
| 2015/0157777 A1 | 6/2015 | Tuval et al. |
| 2015/0164662 A1 | 6/2015 | Tuval |
| 2015/0176582 A1 | 6/2015 | Liebing |
| 2015/0258262 A1 | 9/2015 | Pfeffer et al. |
| 2015/0343136 A1 | 12/2015 | Nitzan et al. |
| 2015/0343179 A1 | 12/2015 | Schumacher et al. |
| 2015/0343186 A1 | 12/2015 | Nitzan et al. |
| 2016/0022890 A1 | 1/2016 | Schwammenthal et al. |
| 2016/0051741 A1 | 2/2016 | Schwammenthal et al. |
| 2016/0053768 A1 | 2/2016 | Schumacher et al. |
| 2016/0106896 A1 | 4/2016 | Pfeffer et al. |
| 2016/0129170 A1 | 5/2016 | Siess |
| 2016/0136341 A1 | 5/2016 | Pfeffer et al. |
| 2016/0136342 A1 | 5/2016 | Pfeffer et al. |
| 2016/0136343 A1 | 5/2016 | Anagnostopoulos |
| 2016/0144089 A1 | 5/2016 | Woo et al. |
| 2016/0256620 A1 | 9/2016 | Scheckel et al. |
| 2016/0279310 A1* | 9/2016 | Scheckel ............ A61M 60/808 |
| 2017/0014562 A1 | 1/2017 | Liebing |
| 2017/0028115 A1 | 2/2017 | Muller |
| 2017/0035954 A1 | 2/2017 | Muller et al. |
| 2017/0071769 A1 | 3/2017 | Mangiardi |
| 2017/0087286 A1 | 3/2017 | Spanier et al. |
| 2017/0087288 A1 | 3/2017 | Groß-hardt et al. |
| 2017/0100527 A1 | 4/2017 | Schwammenthal et al. |
| 2017/0173237 A1 | 6/2017 | Pfeifer et al. |
| 2017/0215918 A1 | 8/2017 | Tao et al. |
| 2017/0232168 A1 | 8/2017 | Reichenbach et al. |
| 2017/0333067 A1 | 11/2017 | Wilson |
| 2017/0333607 A1 | 11/2017 | Zarins |
| 2017/0340791 A1 | 11/2017 | Aboul-hosn et al. |
| 2017/0348470 A1 | 12/2017 | D'ambrosio et al. |
| 2018/0050142 A1 | 2/2018 | Siess et al. |
| 2018/0055979 A1 | 3/2018 | Corbett et al. |
| 2018/0064861 A1 | 3/2018 | Dur et al. |
| 2018/0080326 A1 | 3/2018 | Schumacher et al. |
| 2018/0100507 A1 | 4/2018 | Wu et al. |
| 2018/0104453 A1 | 4/2018 | Tao et al. |
| 2018/0149164 A1 | 5/2018 | Siess |
| 2018/0149165 A1 | 5/2018 | Siess et al. |
| 2018/0169312 A1 | 6/2018 | Barry |
| 2018/0169313 A1 | 6/2018 | Schwammenthal et al. |
| 2018/0207334 A1 | 7/2018 | Siess |
| 2018/0228952 A1 | 8/2018 | Pfeffer et al. |
| 2018/0228953 A1 | 8/2018 | Siess et al. |
| 2018/0264182 A1 | 9/2018 | Spanier et al. |
| 2018/0264183 A1 | 9/2018 | Jahangir |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0303992 A1 | 10/2018 | Taskin |
| 2018/0303993 A1 | 10/2018 | Schwammenthal et al. |
| 2018/0353667 A1 | 12/2018 | Moyer et al. |
| 2019/0015570 A1 | 1/2019 | Muller |
| 2019/0030228 A1 | 1/2019 | Keenan et al. |
| 2019/0046702 A1 | 2/2019 | Siess et al. |
| 2019/0060539 A1 | 2/2019 | Siess et al. |
| 2019/0070345 A1 | 3/2019 | Mcbride et al. |
| 2019/0076167 A1 | 3/2019 | Fantuzzi et al. |
| 2019/0083690 A1 | 3/2019 | Siess et al. |
| 2019/0101130 A1 | 4/2019 | Bredenbreuker et al. |
| 2019/0117865 A1 | 4/2019 | Walters et al. |
| 2019/0134287 A1 | 5/2019 | Demou |
| 2019/0143018 A1 | 5/2019 | Salahieh et al. |
| 2019/0143019 A1 | 5/2019 | Mehaffey et al. |
| 2019/0170153 A1 | 6/2019 | Scheckel |
| 2019/0175803 A1 | 6/2019 | Pfeffer et al. |
| 2019/0175806 A1 | 6/2019 | Tuval et al. |
| 2019/0209755 A1 | 7/2019 | Nix et al. |
| 2019/0209758 A1 | 7/2019 | Tuval et al. |
| 2019/0216994 A1 | 7/2019 | Pfeffer et al. |
| 2019/0224391 A1 | 7/2019 | Liebing |
| 2019/0224392 A1 | 7/2019 | Pfeffer et al. |
| 2019/0224393 A1 | 7/2019 | Pfeffer et al. |
| 2019/0239998 A1 | 8/2019 | Tuval et al. |
| 2019/0262518 A1 | 8/2019 | Molteni et al. |
| 2019/0269840 A1 | 9/2019 | Tuval et al. |
| 2019/0282741 A1 | 9/2019 | Franano et al. |
| 2019/0290817 A1 | 9/2019 | Guo et al. |
| 2019/0321527 A1 | 10/2019 | King et al. |
| 2019/0321530 A1 | 10/2019 | Cambronne et al. |
| 2019/0321531 A1 | 10/2019 | Cambronne et al. |
| 2019/0328948 A1 | 10/2019 | Salahieh et al. |
| 2019/0336664 A1 | 11/2019 | Liebing |
| 2019/0344001 A1 | 11/2019 | Salahieh et al. |
| 2019/0351118 A1 | 11/2019 | Graichen et al. |
| 2020/0038567 A1 | 2/2020 | Siess et al. |

FOREIGN PATENT DOCUMENTS

| | | |
|---|---|---|
| EP | 2040639 B1 | 2/2014 |
| EP | 2662099 B1 | 9/2014 |
| EP | 2427230 B1 | 12/2014 |
| EP | 2396050 B1 | 1/2015 |
| EP | 3115070 A1 | 1/2017 |
| EP | 3205360 B1 | 8/2018 |
| EP | 3359215 A1 | 8/2018 |
| EP | 3398624 A1 | 11/2018 |
| EP | 3398625 A1 | 11/2018 |
| EP | 3407930 A1 | 12/2018 |
| EP | 3446729 A1 | 2/2019 |
| EP | 3446730 A1 | 2/2019 |
| GB | 2451161 A | 1/2009 |
| JP | 2012505038 A | 3/2012 |
| WO | 9001972 A1 | 3/1990 |
| WO | 90/13321 | 11/1990 |
| WO | 1994/01148 A1 | 1/1994 |
| WO | 99/34847 | 7/1999 |
| WO | 2001/083016 A2 | 5/2000 |
| WO | 2000043053 A1 | 7/2000 |
| WO | 0062838 A2 | 10/2000 |
| WO | 2002/070039 A2 | 3/2001 |
| WO | 2002/038085 | 5/2002 |
| WO | 03/006096 | 1/2003 |
| WO | 03/103745 A2 | 12/2003 |
| WO | 2004073796 A2 | 9/2004 |
| WO | 2005020848 A2 | 3/2005 |
| WO | 2007081818 A2 | 7/2007 |
| WO | 2007127477 A2 | 11/2007 |
| WO | 2008005747 A2 | 1/2008 |
| WO | 2008005990 A2 | 1/2008 |
| WO | 2008055301 A1 | 5/2008 |
| WO | 2008104858 A2 | 9/2008 |
| WO | 2009010963 A2 | 1/2009 |
| WO | 2009046096 A1 | 4/2009 |
| WO | 2009129481 A1 | 10/2009 |
| WO | 2010042546 | 4/2010 |
| WO | 2010063494 A1 | 6/2010 |
| WO | 2010127871 A1 | 11/2010 |
| WO | 2010150208 A2 | 12/2010 |
| WO | 2011035926 A1 | 3/2011 |
| WO | 2011076441 A1 | 6/2011 |
| WO | 2012007141 A1 | 1/2012 |
| WO | 2013032849 A1 | 3/2013 |
| WO | 2013070186 A1 | 5/2013 |
| WO | 2013093001 A2 | 6/2013 |

(56) References Cited

FOREIGN PATENT DOCUMENTS

| | | |
|---|---|---|
| WO | 2013148697 A1 | 10/2013 |
| WO | 2013183060 A2 | 12/2013 |
| WO | 2014141284 A2 | 9/2014 |
| WO | 2015063277 A2 | 5/2015 |
| WO | 2015160943 A1 | 10/2015 |
| WO | 2015177793 A2 | 11/2015 |
| WO | 2016001218 A1 | 1/2016 |
| WO | 2016005803 A2 | 1/2016 |
| WO | 2016185473 A1 | 11/2016 |
| WO | 2016207293 A1 | 12/2016 |
| WO | 2017060254 A1 | 4/2017 |
| WO | 2017137604 A1 | 8/2017 |
| WO | 2017147291 A1 | 8/2017 |
| WO | 2018061001 A2 | 4/2018 |
| WO | 2018061002 A1 | 4/2018 |
| WO | 2018067410 A1 | 4/2018 |
| WO | 2018078615 A1 | 5/2018 |
| WO | 2018096531 A1 | 5/2018 |
| WO | 2018220589 A1 | 12/2018 |
| WO | 2018226991 A1 | 12/2018 |
| WO | 2018234454 A1 | 12/2018 |
| WO | 2019094963 A1 | 5/2019 |
| WO | 2019138350 A2 | 7/2019 |
| WO | 2019152875 A1 | 8/2019 |
| WO | 2020152611 A2 | 7/2020 |

OTHER PUBLICATIONS

International Search Report and Written Opinion from International Application No. PCT/IL2017/051158 dated Jan. 17, 2018.
International Search Report and Written Opinion from International Application No. PT/IB2019/050186 dated Jul. 18, 2019.
U.S. Appl. No. 14/567,439, filed Dec. 11, 2014.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,482, filed Feb. 18, 2019.
U.S. Appl. No. 16/279,352, filed Feb. 19, 2019.
U.S. Appl. No. 16/280,566, filed Feb. 20, 2019.
U.S. Appl. No. 16/281,237, filed Feb. 21, 2019.
U.S. Appl. No. 16/281,264, filed Feb. 21, 2019.
U.S. Appl. No. 61/656,244, filed Jun. 6, 2012.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/401,403, filed Sep. 29, 2016.
U.S. Appl. No. 62/412,631, filed Oct. 25, 2016.
U.S. Appl. No. 62/425,814, filed Nov. 23, 2016.
U.S. Appl. No. 62/543,540, filed Aug. 10, 2017.
U.S. Appl. No. 62/615,538, filed Jan. 10, 2018.
U.S. Appl. No. 62/665,718, filed May 2, 2018.
U.S. Appl. No. 62/681,868, filed Jun. 7, 2018.
U.S. Appl. No. 62/727,605, filed Sep. 6, 2018.
U.S. Appl. No. 62/796,138, filed Jan. 24, 2019.
U.S. Appl. No. 62/851,716, filed May 23, 2019.
U.S. Appl. No. 62/870,821, filed Jul. 5, 2019.
U.S. Appl. No. 62/896,026, filed Sep. 5, 2019.
"Tanslation of decision of Board 4 (Nullity Board) of the German Federal Patent Court re German patent 10336902", pronounced Nov. 15, 2016, and appendices to decision, 62 pages.
Agarwal, et al., "Newer-generation ventricular assist devices.", Best Practice & Research Clinical Anaesthesiology, 26.2, 2012, pp. 117-130.
Alba, et al., "The future is here: ventricular assist devices for the failing heart", Expert review of cardiovascular therapy, 7.9, 2009, pp. 1067-1077.
Burnett, et al., "Renal Interstitial Pressure And Sodium Excretion During Renal Vein Constriction", American Physiological Society, 1980, pp. F279-F282.
Cassidy, et al., "The Conductance Volume Catheter Technique for Measurement of Left Ventricular Volume in Young Piglets", Pediatric Research, Val. 31, No. 1, 1992, pp. 85-90.
Coxworth, , "Artificial Vein Valve Could Replace Drugs For Treating Common Circulatory Problem", Published on Gizmag website (http://www.gizmag.com/artificial-venous-valve-cvi/21785/), Mar. 9, 2012.
Damman, et al., "Decreased Cardiac Output, Venous Congestion And The Association With Renal Impairment In Patients With Cardiac Dysfunction", European Journal of Heart Failure, vol. 9, 2007, pp. 872-878.
Damman, et al., "Increased Central Venous Pressure Is Associated With Impaired Renal Function And Mortality In A Broad Spectrum Of Patients With Cardiovascular Disease", Journal of American College of Cardiology, vol. 53, 2009, pp. 582-588.
Doty, et al., "The Effect Of Increased Renal Venous Pressure On Renal Function", The Journal of Trauma,, vol. 47(6), Dec. 1999, pp. 1000-1003.
Felker, et al., "Anemia As A Risk Factor And Therapeutic Target In Heart Failure", Journal of the American College of Cardiology, vol. 44, 2004, pp. 959-966.
Firth, et al., "Raised Venous Pressure: A Direct Cause Of Sodium Retention In Oedema?", The Lancet, May 7, 1988, pp. 1033-1036.
Forman, et al., "Incidence, Predictors At Admission, And Impact Of Worsening Renal Function Among Patients Hospitalized With Heart Failure", Journal of American College of Cardiology, vol. 43, 2004, pp. 61-67.
Fraser, et al., "The use of computational fluid dynamics in the development of ventricular assist devices", Medical engineering & physics, 33.3, 2011, pp. 263-280.
Frazier, et al., "First Human Use of the Hemopump, a CatheterMounted Ventricular Assist Device", Ann Thorac Surg, 49, 1990, pp. 299-304.
Gomes, et al., "Heterologous Valve Implantation In The Infra-Renal Vena Cava For Treatment Of The Iliac Venous Valve Regurgitation Disease: Experimental Study", Rev Bras Cir Cardiovasc, vol. 17(4), 2002, pp. 367-369.
Haddy, et al., "Effect Of Elevation Of Intraluminal Pressure On Renal Vascular Resistance", Circulation Research Journal Of The American Heart Association, vol. 4, 1956, pp. 659-663.
Heywood, et al., "High Prevalence Of Renal Dysfunction And Its Impact On Outcome In 118,465 Patients Hospitalized With Acute Decompensated Heart Failure: A Report From The ADHERE Database", Journal of Cardiac Failure, vol. 13, 2007, pp. 422-430.
Hillege, et al., "Renal Function As A Predictor Of Outcome In A Broad Spectrum Of Patients With Heart Failure", Circulation Journal of the American Heart Association, vol. 113, 2006, pp. 671-678.
Hillege, et al., "Renal Function, Neurohormonal Activation, And Survival In Patients With Chronic Heart Failure", Circulation Journal of the American Heart Association, vol. 102, 2000, pp. 203-210.
Hsu, et al., "Review of recent patents on foldable ventricular assist devices", Recent Patents on Biomedical Engineering, 5.3, 2012, pp. 208-222.
Ikari, , "The Physics Of Guiding Catheter; The IKARI Guiding Catheter In TRI", available at httu:i /www.docstoc.com/docs/148136553/The-[KARI-catheter---anovel-guide-for-TRI--, uploaded on Mar. 8, 2013.
Kafagy, et al., "Design of axial blood pumps for patients with dysfunctional fontan physiology: computational studies and performance testing", Artificial organs, 39.1, 2015, pp. 34-42.
Kang, et al., "Fluid dynamics aspects of miniaturized axial-flow blood pump", Bio-medical materials and engineering, 24.1, 2014, pp. 723-729.
Koochaki, et al., "A new design and computational fluid dynamics study of an implantable axial blood pump", Australasian Physical & Engineering Sciences in Medicine, 36.4, 2013, pp. 417-422.
Lauten, et al., "Heterotopic Transcatheter Tricuspid Valve Implantation First-In-Man Application Of A Novel Approach To Tricuspid Regurgitation", European Heart Journal, (1-7 as printed), Feb. 15, 2011, pp. 1207-1213.

(56) References Cited

OTHER PUBLICATIONS

McAlister, et al., "Renal Insufficiency And Heart Failure: Prognostic And Therapeutic Implications From A Prospective Cohort Study", Circulation Journal of the American Heart Association, 109, 2004, pp. 1004-1009.
Meyns, et al., "The Heart-Hemopump Interaction: A Study of Hemopump Flow as a Function of Cardiac Activity", Artificial Organs, Vot. 20, No. 6, 1996, pp. 641-649.
Mullens, et al., "Elevated Intra-Abdominal Pressure In Acute Decompensated Heart Failure. A Potential Contributor To Worsening Renal Function", Journal of the American College of Cardiology, vol. 51, 2008, pp. 300-306.
Mullens, et al., "Importance Of Venous Congestion For Worsening Of Renal Function In Advanced Decompensated Heart Failure", Journal of American College of Cardiology, vol. 53, 2009, pp. 589-596.
Mullens, et al., "Prompt Reduction In Intra-Abdominal Pressure Following Large-Volume Mechanical Fluid Removal Improves Renal Insufficiency In Refractory Decompensated Heart Failure", Journal of Cardiac Failure, vol. 14, 2008, pp. 508-514.
Notarius, et al., "Central Venous Pressure During Exercise: Role Of Muscle Pump", Canadian Journal of Physiology and Pharmacology, vol. 74(6), 1996, pp. 647-651.
Park, et al., "Nutcracker Syndrome: Intravascular Stenting Approach", Nephrol Dial Transplant, vol. 15, 2000, pp. 99-101.
Reul, et al., "Blood pumps for circulatory support", Perfusion-Sevenoaks, 15.4, 2000, pp. 295-312.
Reul, et al., "Rotary blood pumps in circulatory assist", Perfusion, 10(3), May 1995, pp. 153-158.
Rodefeld, , "Cavopulmonary assist for the univentricular Fontan circulation: von Karman viscous impeller pump", The Journal of Thoracic and Cardiovascular Surgery, vol. 140, No. 3, 2010, pp. 529-536.
Schmitz-Rode, et al., "An Expandable Percutaneous Catheter Pump For Left Ventricular Support", Journal of the American College of Cardiology, vol. 45, 2005, pp. 1856-1861.
Schmitz-Rode, et al., "Axial flow catheter pump for circulatory support", Biomed Tech (Berl), 47 Suppl 1 Pt 1, 2002, pp. 142-143.
Semple, et al., "Effect Of Increased Renal Venous Pressure On Circulatory "Autoregulation" Of Isolated Dog Kidneys", Circulation Research Journal of The American Heart Association, vol. 7, 1959, pp. 643-648.
Sianos, et al., "The Recover® LP 2.5 catheter-mounted left ventricular assist device", EuroIntervention, EuroPCROnline.com, 2006, pp. 116-119.
Siess, et al., "Concept, realization, and first in vitro testing of an intraarterial microaxial blood pump", Artificial Organs, vol. 15, No. 7, 1995, pp. 644-652.
Siess, et al., "Hemodynamic system analysis of intraarterial microaxial pumps in vitro and in vivo", Artificial Organs, vol. 20, No. 6, Jun. 1996, pp. 650-661.
Siess, , "PhD Chapter 3—English translation", (citation info here https://www.shaker.eu/en/content/catalogue/index.asp?lang=en&ID=8&ISBN=978-3-8265-6150-4&search=yes ).
Song, et al., "Axial flow blood pumps", ASAIO journal, 49, 2003, pp. 355-364.
Tang, et al., "Anemia In Chronic Heart Failure: Prevalence, Etiology, Clinical Correlates, And Treatment Options", Circulation Journal of the American Heart Association, vol. 113, 2006, pp. 2454-2461.
Throckmorton, et al., "Design of a protective cage for an intra vascular axial flow blood pump to mechanically assist the failing Fontan", Artificial organs, 33.8, 2009, pp. 611-621.
Throckmorton, et al., "Mechanical Cavopulmonary Assist for the Univentricular Fontan Circulation Using a Novel Folding Propeller Blood Pump", ASAIO Journal, 2007, pp. 734-741.
Thunberg, et al., "Ventricular assist devices today and tomorrow", Journal of cardiothoracic and vascular anesthesia, 24.4, 2010, pp. 656-680.

Timms, , "A review of clinical ventricular assist devices", Medical engineering & physics, 33.9, 2011, pp. 1041-1047.
Triep, et al., "Computational Fluid Dynamics and Digital Particle Image Velocimetry Study of the Flow Through an Optimized Micro-axial Blood Pump", Artificial Organs, vol. 30, No. 5, May 2006, pp. 384-391.
Uthoff, et al., "Central venous pressure at emergency room presentation predicts cardiac rehospitalization in patients with decompensated heart failure", European Journal of Heart Failure, 12, 2010, pp. 469-476.
Van Mieghem, et al., "Design and Principle of Operation of the HeartMate PHPTM (Percutaneous Heart Pump)", EuroIntervention, Jaa-035 2016, doi: 10.4244/ EIJ-D-15-00467, 2016.
Vercaemst, et al., "Impella: A Miniaturized Cardiac Support System in an Era of Minimal Invasive Cardiac Surgery", Presented at the 39th International Conference of the American Society of Extra-Corporeal Technology, Miami, Florida, Mar. 22-25, 2001.
Wampler, , "The first co-axial flow pump for human use: the Hemopump", Flameng W. (eds) Temporary Cardiac Assist with an Axial Pump System, 1991.
Wencker, , "Acute Cardio-Renal Syndrome: Progression From Congestive Heart Failure To Congestive Kidney Failure", Current Heart Failure Reports, vol. 4, 2007, pp. 134-138.
Winton, , "The Control Of Glomerular Pressure By Vascular Changes Within The Mammalian Kidney, Demonstrated By The Actions Of Adrenaline", Journal of Physiology, vol. 73, Nov. 1931, pp. 151-162.
Winton, , "The Influence Of Venous Pressure On The Isolated Mammalian Kidney", Journal of Physiology, vol. 72(1), Jun. 6, 1931, pp. 49-61.
Wood, , "The Mechanism Of The Increased Venous Pressure With Exercise In Congestive Heart Failure", Journal of Clinical Investigation, vol. 41(11), 1962, pp. 2020-2024.
Wu, et al., "Design and simulation of axial flow maglev blood pump", International Journal of Information Engineering and Electronic Business, 3.2, 2011, p. 42.
Yancy, et al., "Clinical Presentation, Management, And In-Hospital Outcomes Of Patients Admitted With Acute Decompensated Heart Failure With Preserved Systolic Function. A Report From The Acute Decompensated Heart Failure National Registry (ADHERE) Database", Journal of the American College of Cardiology, vol. 47(1), 2006, pp. 76-84.
Decompensated Heart Failure National Registry (ADHERE) Database, Journal of the American College of Cardiology, vol. 47(1), pp. 76-84.
Corrected Notice of Allowability for U.S. Appl. No. 16/281,237 dated Mar. 31, 2021.
Extended Search Report for European Application No. 20195082.1 dated Nov. 5, 2020.
Extended Search Report for European Application No. 20195084.7 dated Nov. 5, 2020.
Extended Search Report for European Application No. 20195085.4 dated Nov. 4, 2020.
Extended Search Report for European Application No. 20195987.1 dated Nov. 5, 2020.
Extended Search Report for European Application No. 21158903.1 dated Apr. 9, 2021.
Final Office Action for U.S. Appl. No. 16/276,965 dated Apr. 13, 2021.
Issue Notification received for U.S. Appl. No. 16/281,237 dated Apr. 14, 2021.
U.S. Appl. No. 17/176,344, filed Feb. 16, 2021.
U.S. Appl. No. 17/177,296, filed Feb. 17, 2021.
U.S. Appl. No. 17/180,041, filed Feb. 19, 2021.
U.S. Appl. No. 17/182,482, filed Feb. 23, 2021.
Extended European Search Report for European Application No. 20159714.3 dated Jul. 3, 2020.
Extended European Search Report for European Application No. 20159716.8 dated Jul. 3, 2020.
Extended European Search Report for European Application No. 20159718.4 dated Jul. 9, 2020.
Final Office Action for U.S. Appl. No. 16/275,559 dated Jan. 4, 2021.

(56) References Cited

OTHER PUBLICATIONS

International Search Report and Written Opinion from International Application No. PCT/IB2020/050515 dated Sep. 9, 2020.
Invitation to Pay Additional Fees for International Application No. PCT/IB2020/050515 dated Mar. 31, 2020.
Invitation to Pay Additional Fees in International Application No. PCT/IB2020/050515 dated Mar. 31, 2020.
Issue Notification for U.S. Appl. No. 16/278,482 dated Jan. 13, 2021.
Issue Notification for U.S. Appl. No. 16/281,264 dated Dec. 16, 2020.
Non-Final Office Action for U.S. Appl. No. 16/275,559 dated Sep. 4, 2020.
Non-Final Office Action for U.S. Appl. No. 16/276,965 dated Jun. 19, 2020.
Non-Final Office Action for U.S. Appl. No. 16/276,965 dated Nov. 30, 2020.
Non-Final Office Action for U.S. Appl. No. 16/277,411 dated Feb. 9, 2021.
Non-Final Office Action for U.S. Appl. No. 16/278,482 dated Jun. 23, 2020.
Non-Final Office Action for U.S. Appl. No. 16/279,352 dated Nov. 10, 2020.
Non-Final Office Action for U.S. Appl. No. 16/280,566 dated Dec. 21, 2020.
Non-Final Office Action for U.S. Appl. No. 16/281,237 dated Aug. 21, 2020.
Non-Final Office Action for U.S. Appl. No. 16/281,264 dated Jun. 29, 2020.
Notice of Allowance for U.S. Appl. No. 16/278,482 dated Dec. 2, 2020.
Notice of Allowance for U.S. Appl. No. 16/281,237 dated Feb. 1, 2021.
Notice of Allowance for U.S. Appl. No. 16/281,264 dated Nov. 12, 2020.
Restriction Requirement for U.S. Appl. No. 16/275,559 dated Jun. 2, 2020.
Restriction Requirement for U.S. Appl. No. 16/279,352 dated Aug. 11, 2020.
Restriction Requirement for U.S. Appl. No. 16/280,566 dated Aug. 11, 2020.
Supplemental Notice of Allowability for U.S. Appl. No. 16/278,482 dated Dec. 24, 2020.
U.S. Appl. No. 16/750,354, filed Jan. 23, 2020.
U.S. Appl. No. 16/952,327, filed Nov. 19, 2020.
U.S. Appl. No. 16/952,389, filed Nov. 19, 2020.
U.S. Appl. No. 16/952,444, filed Nov. 19, 2020.
U.S. Appl. No. 17/069,064, filed Oct. 13, 2020.
U.S. Appl. No. 17/069,321, filed Oct. 13, 2020.
U.S. Appl. No. 17/069,570, filed Oct. 13, 2020.
U.S. Appl. No. 17/070,323, filed Oct. 14, 2020.
U.S. Appl. No. 17/070,670, filed Oct. 14, 2020.
U.S. Appl. No. 17/077,769, filed Oct. 22, 2020.
U.S. Appl. No. 17/078,439, filed Oct. 23, 2020.
U.S. Appl. No. 17/078,472, filed Oct. 23, 2020.
Bai, et al., "A Split-Array, C-2C Switched-Capacitor Power Amplifier in 65 nm CMOS", IEEE Radio Frequency Integrated Circuits Symposium, 2017, pp. 336-339.

* cited by examiner

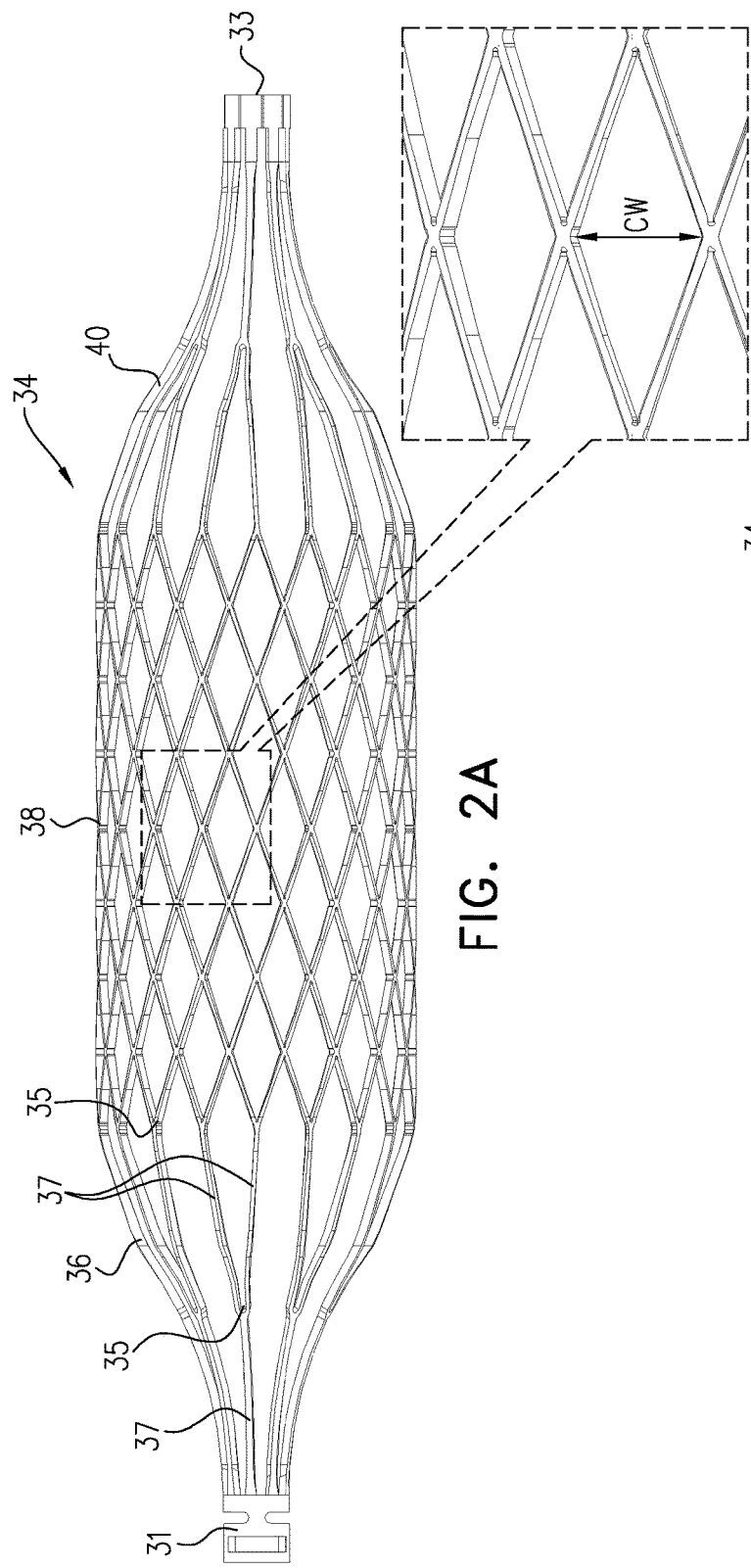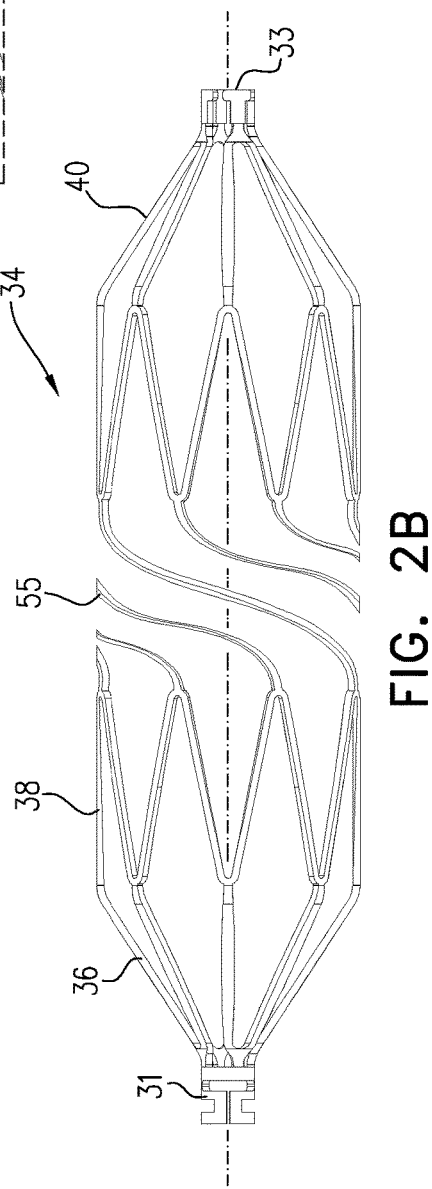
FIG. 2A
FIG. 2B

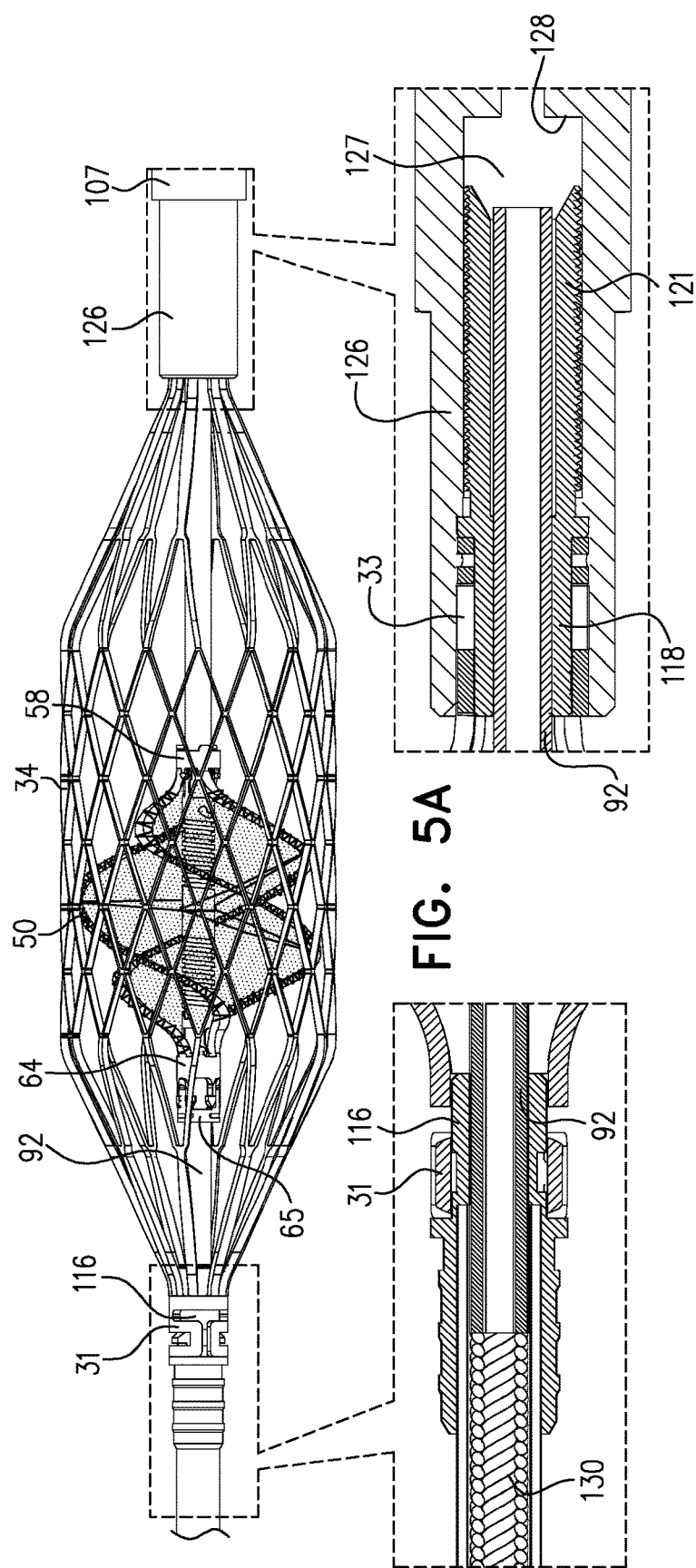
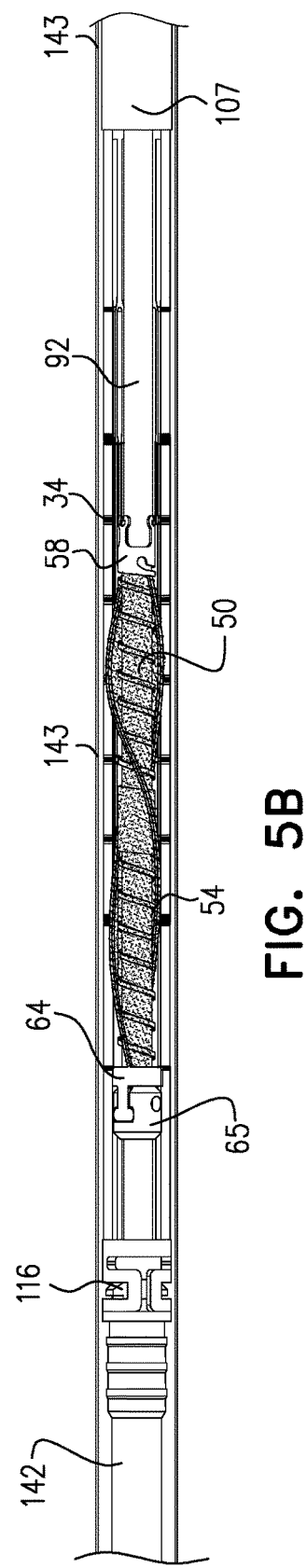
FIG. 5A
FIG. 5B

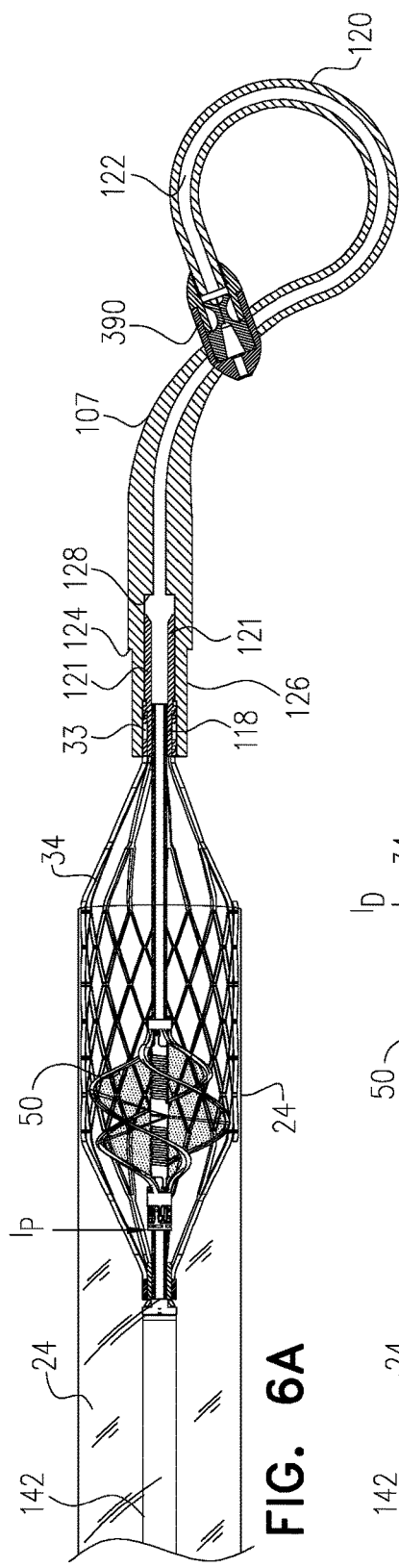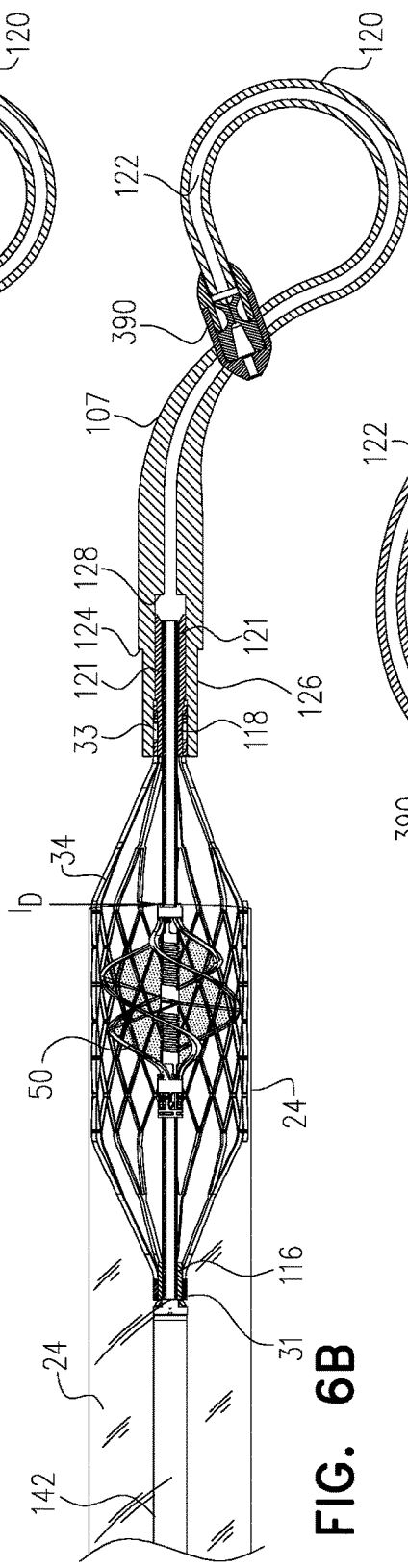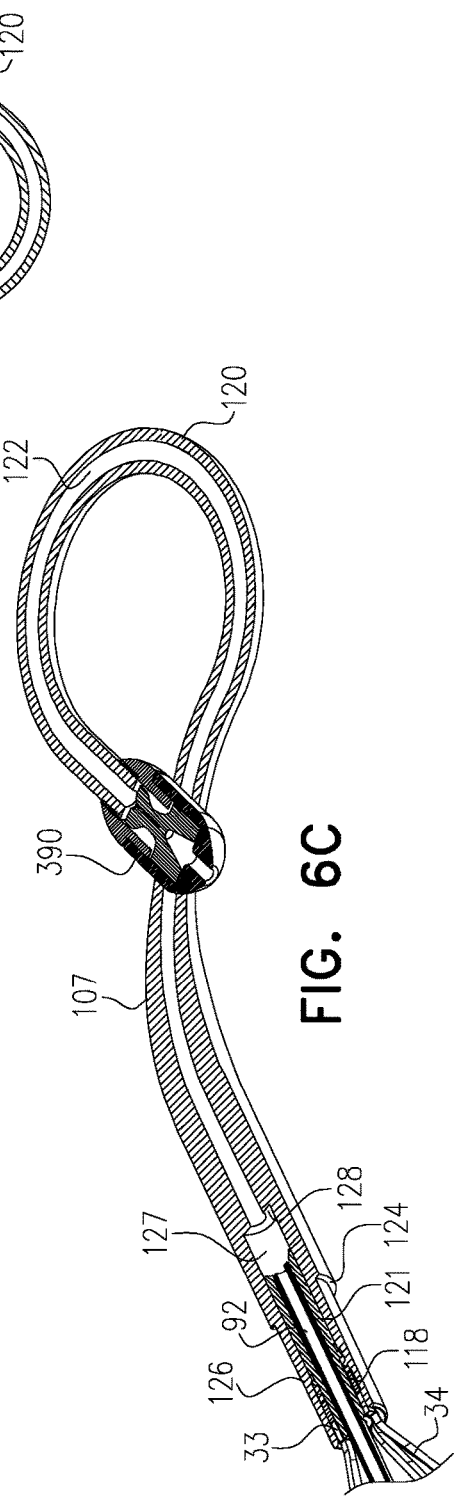

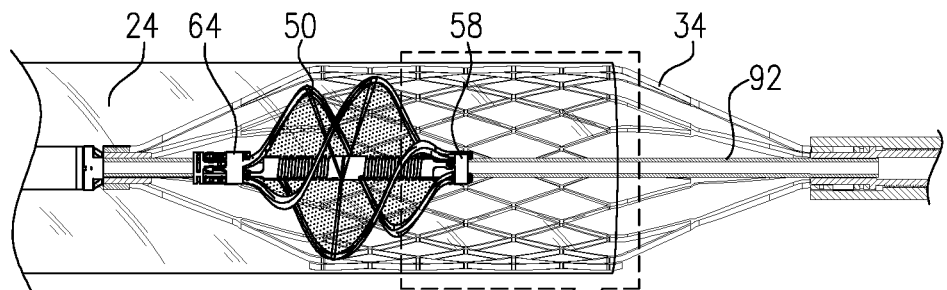
FIG. 6D
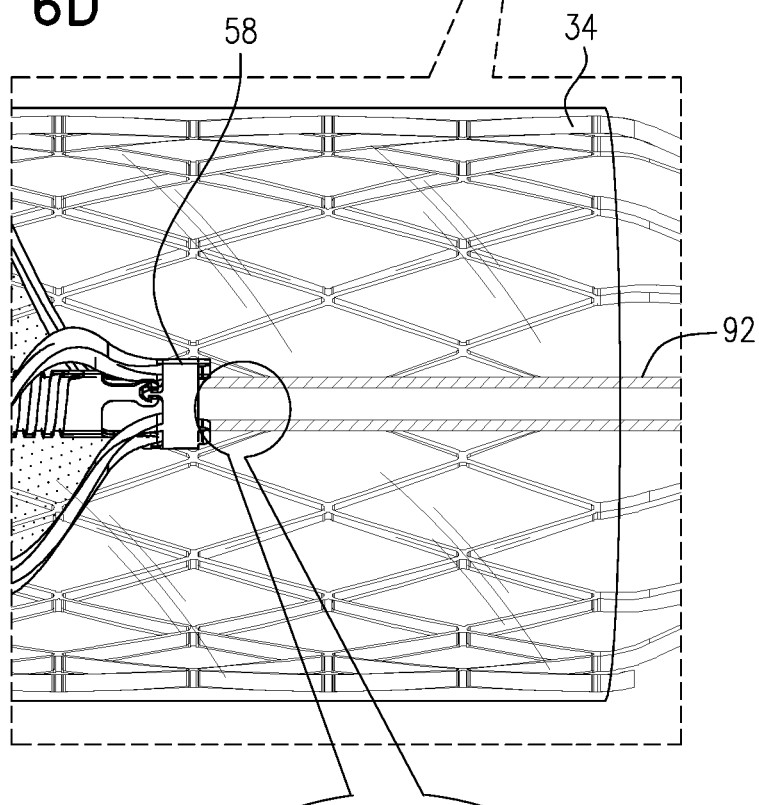
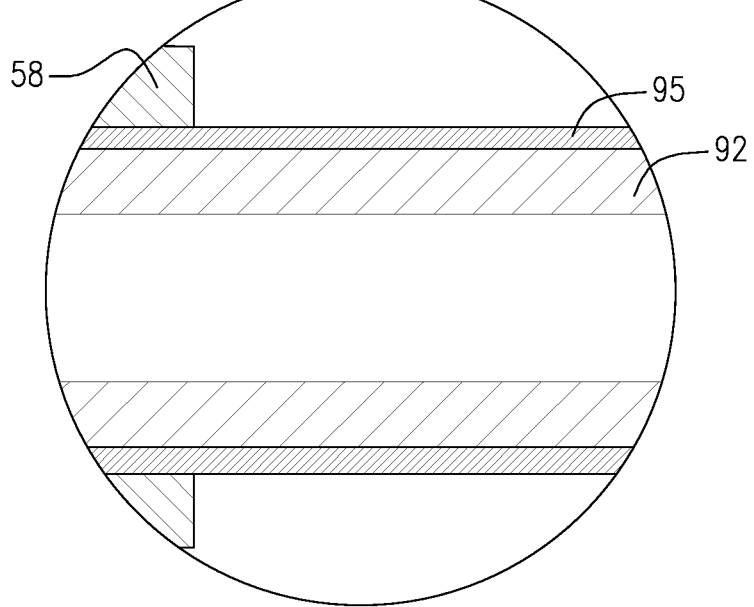

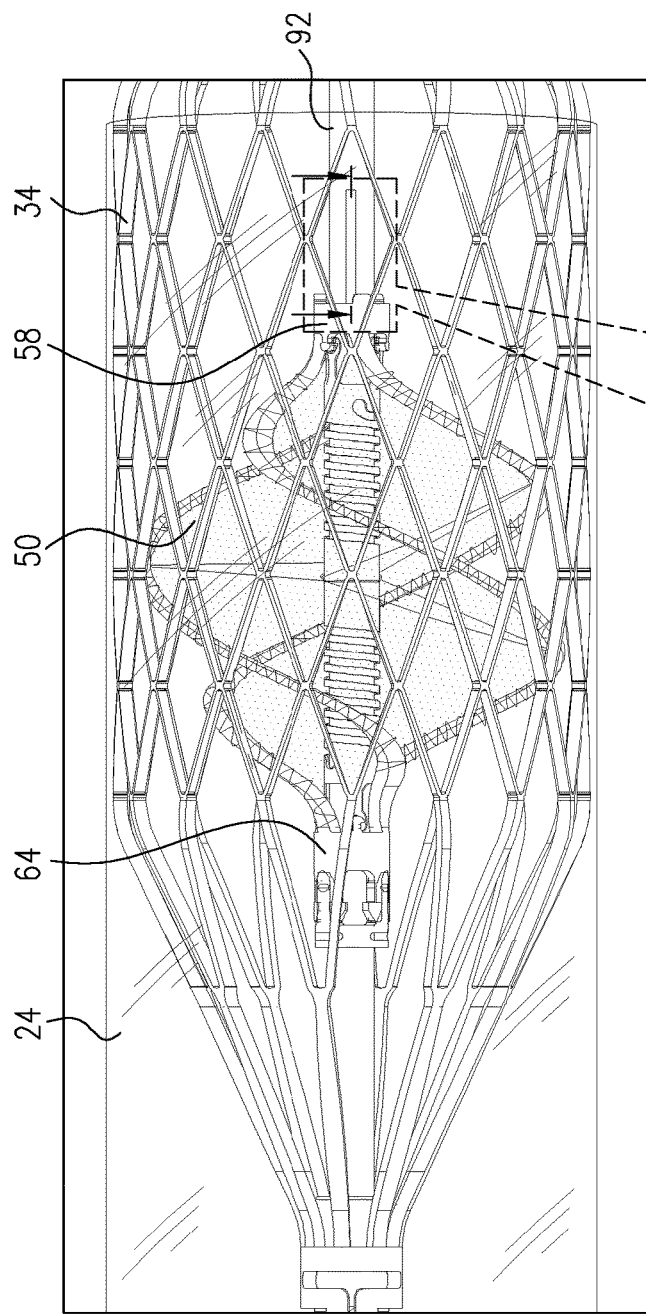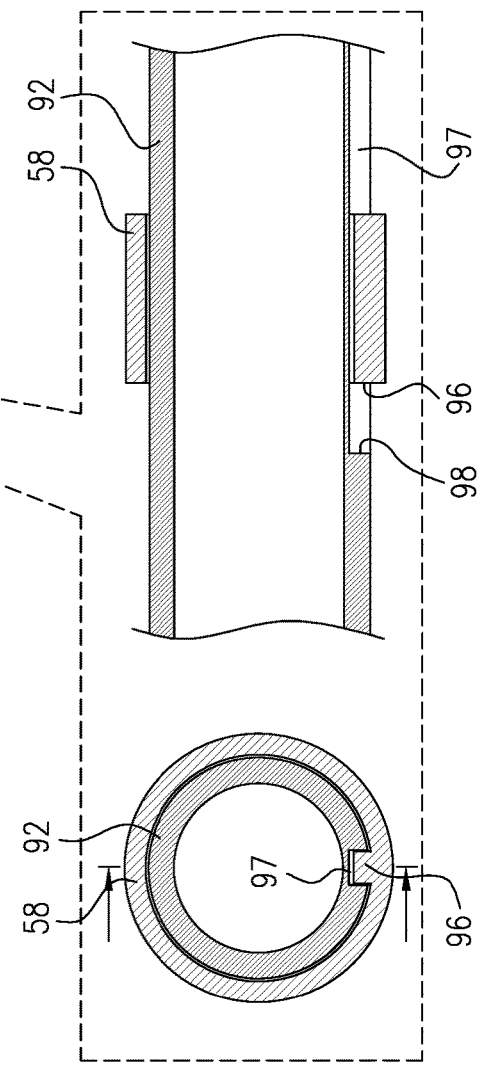
FIG. 6E

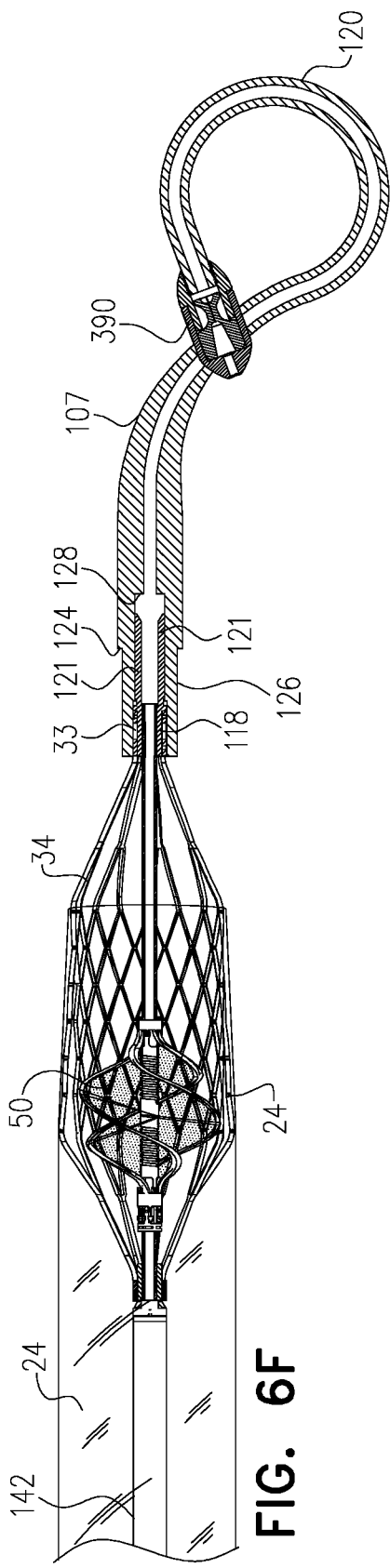
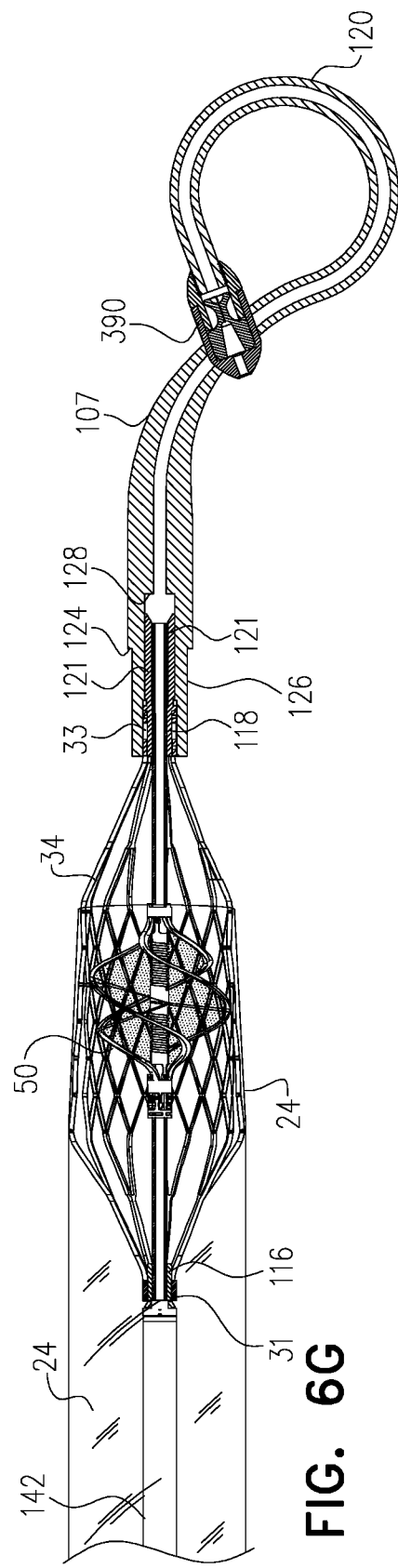
FIG. 6F
FIG. 6G

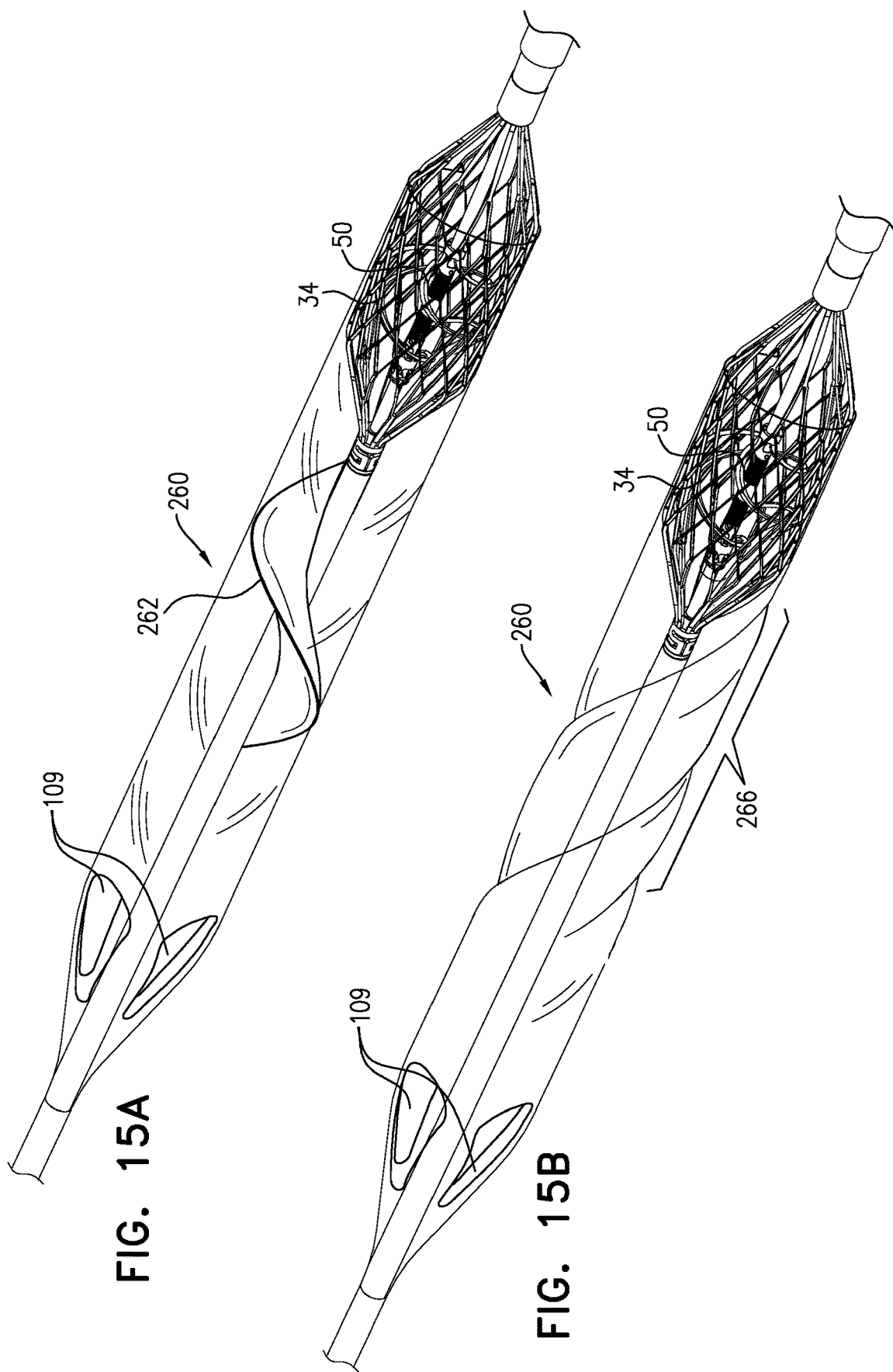

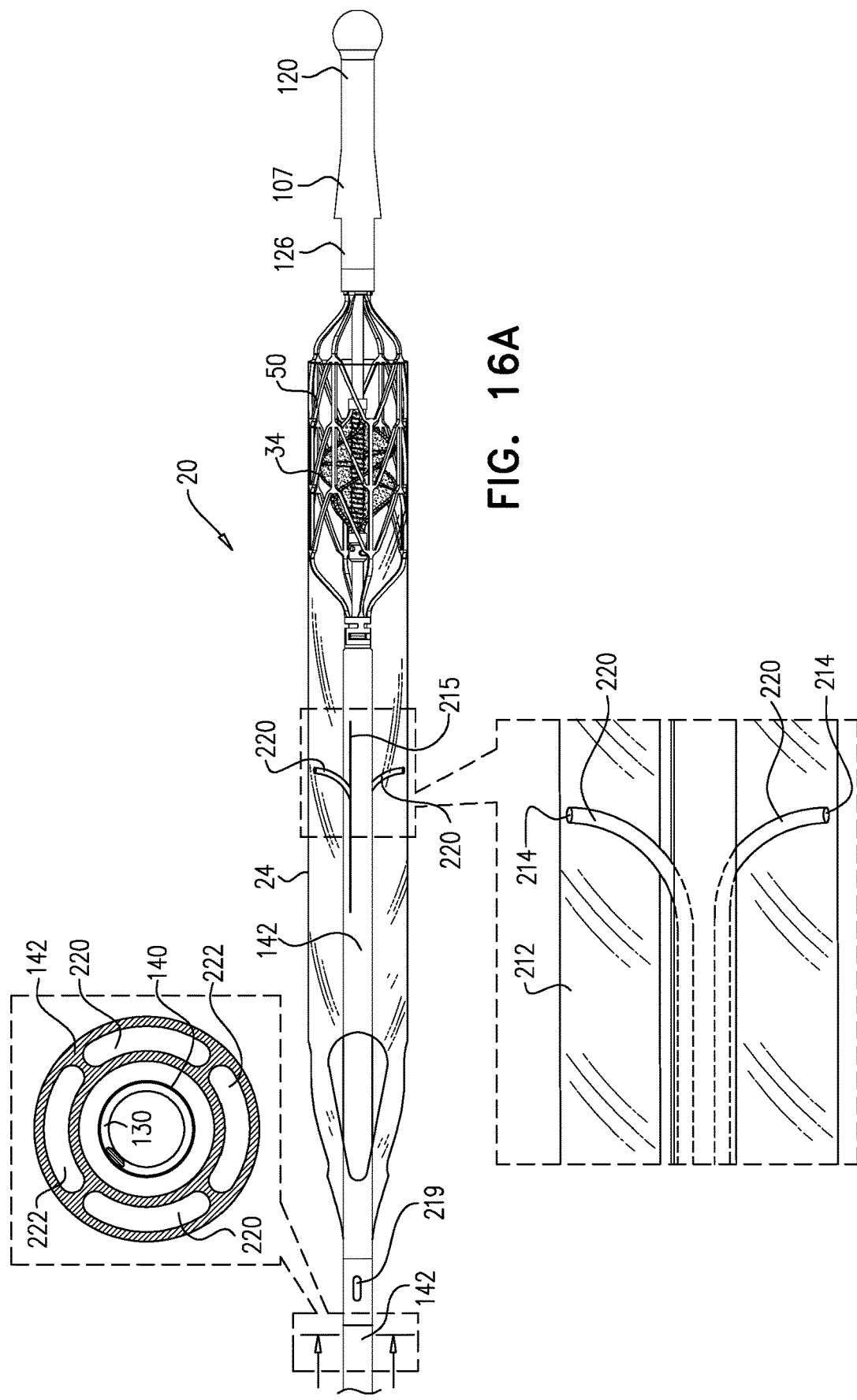

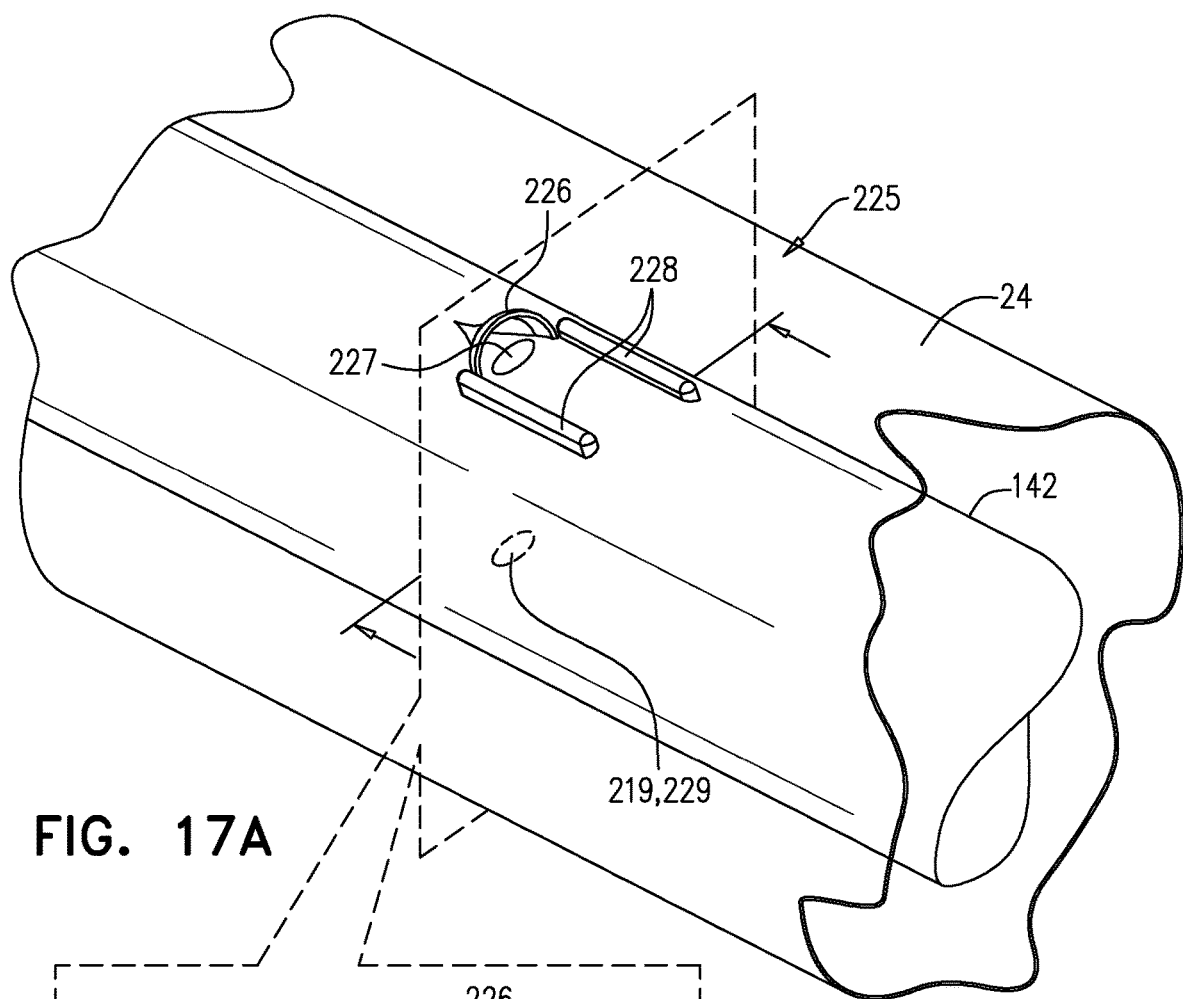
FIG. 17A
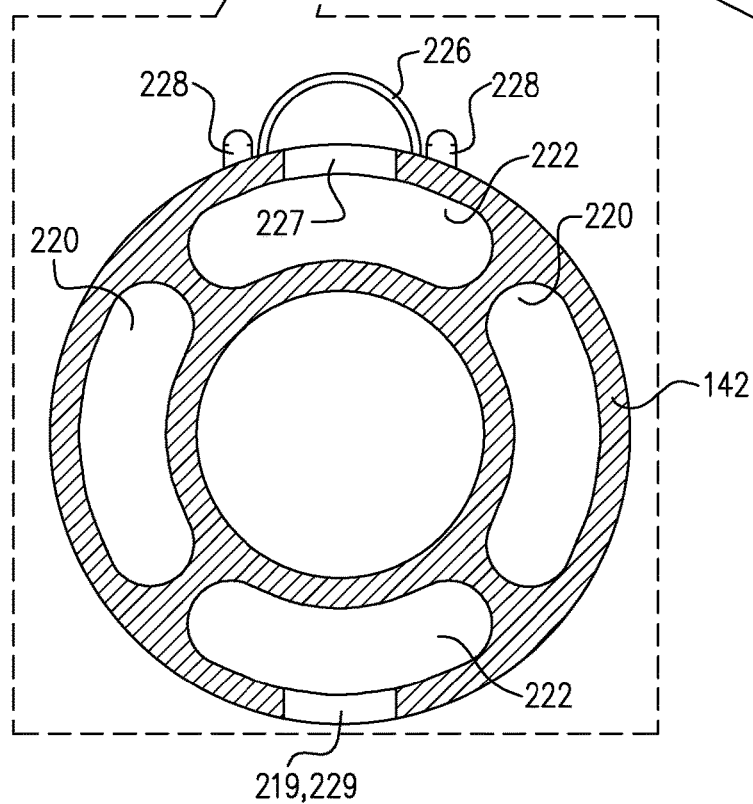

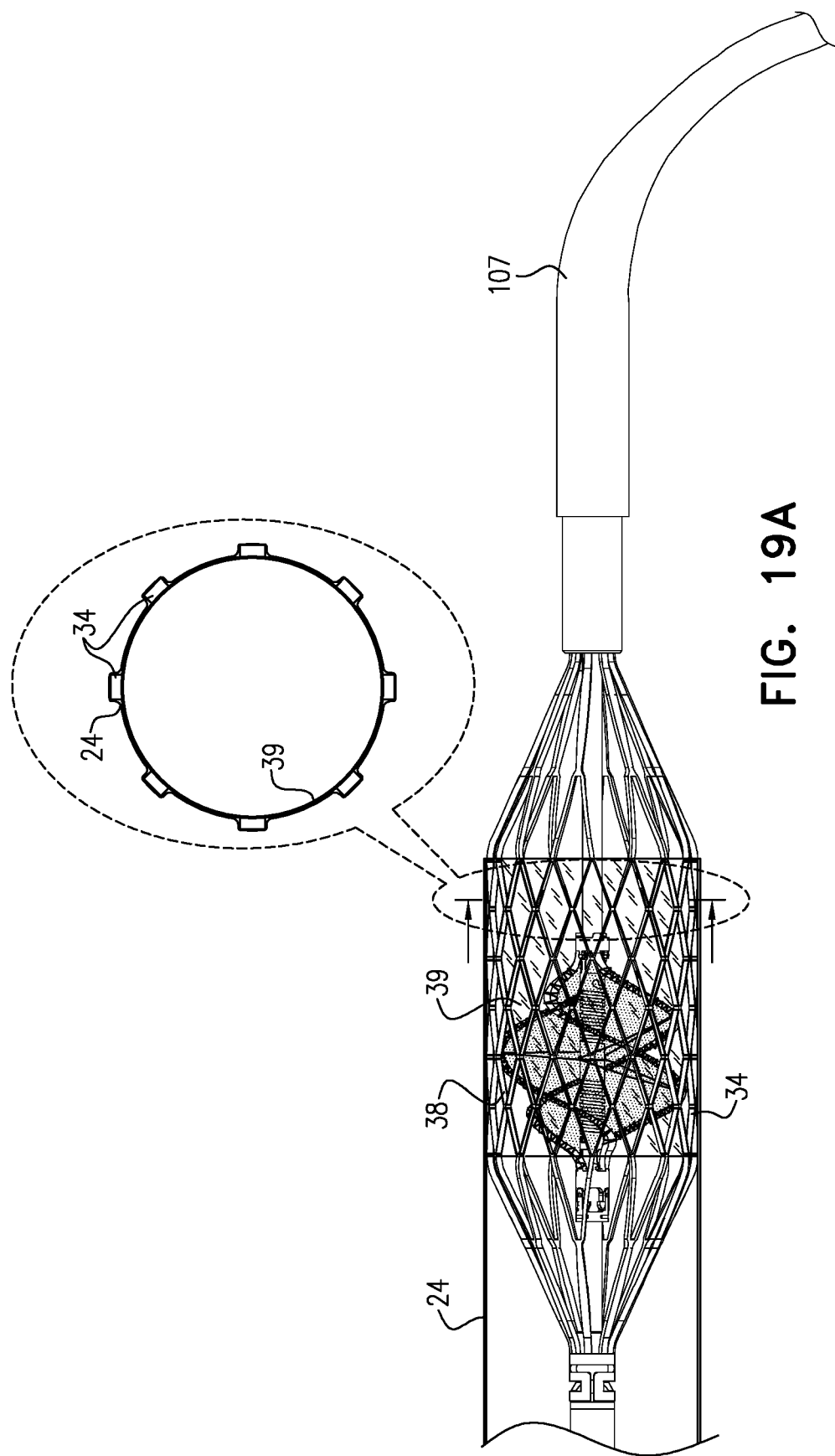

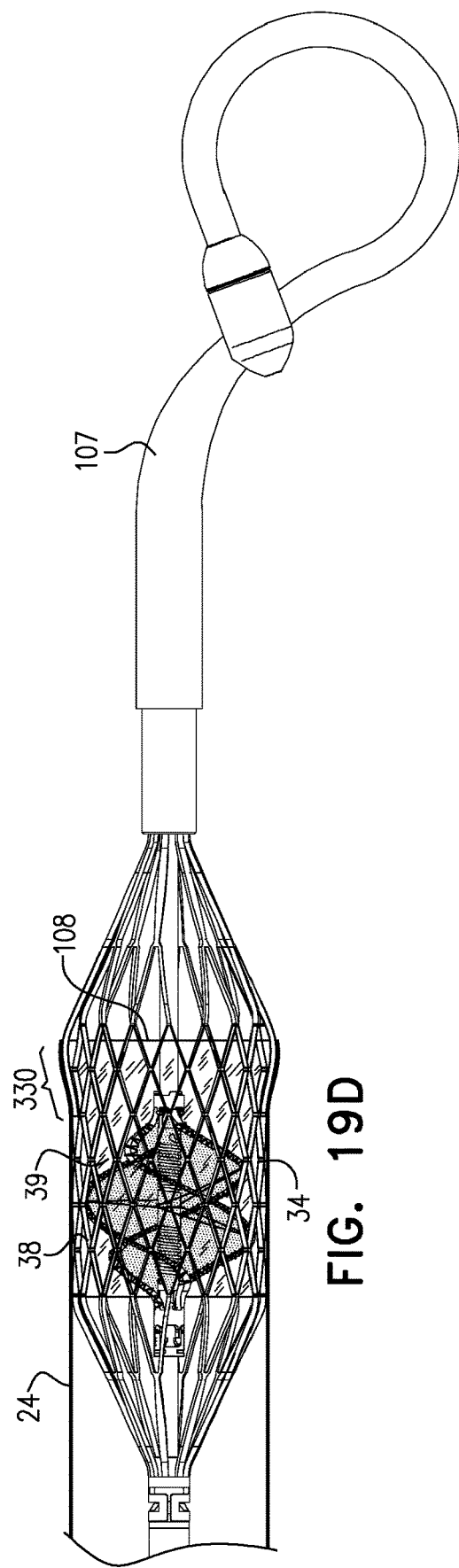
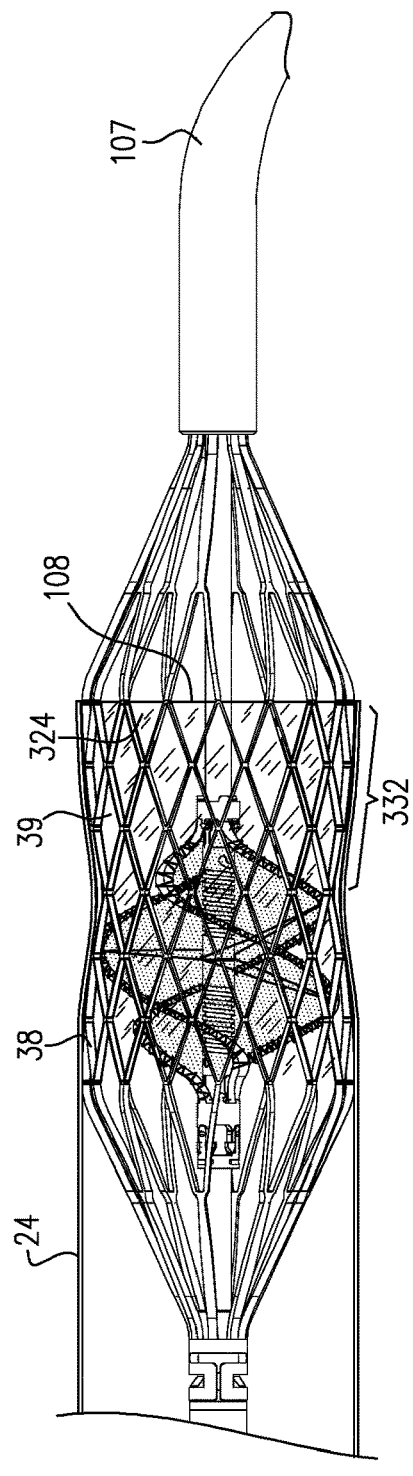
FIG. 19D
FIG. 19E

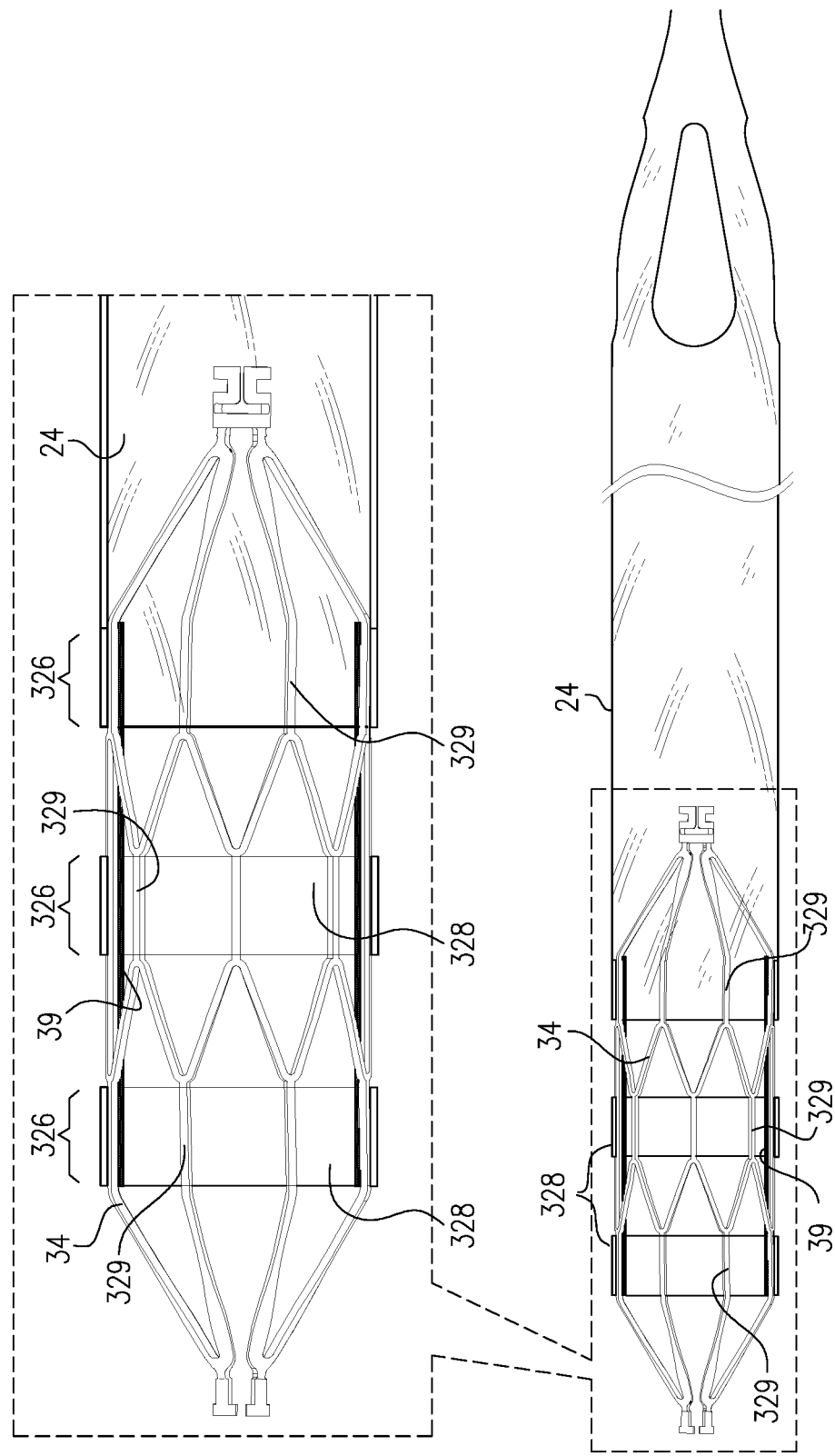

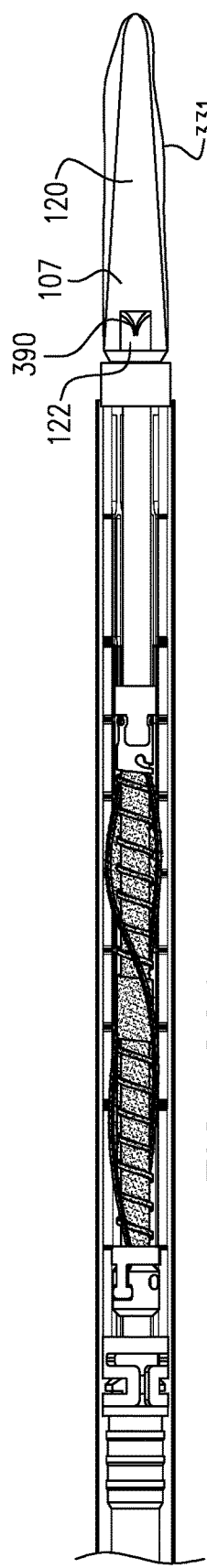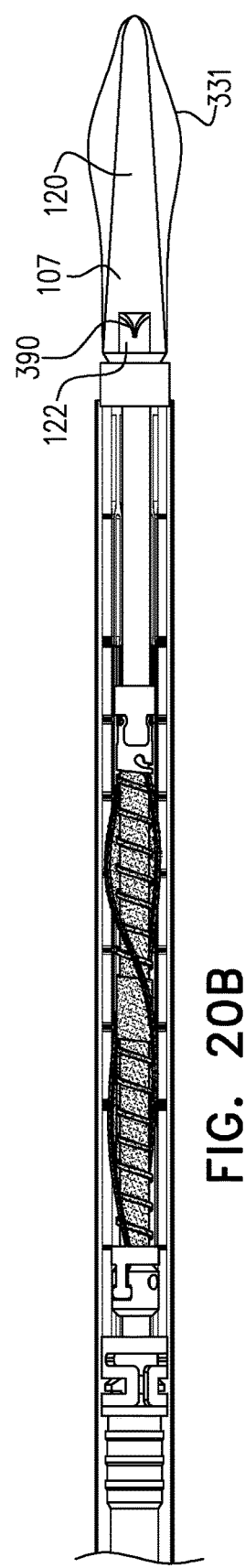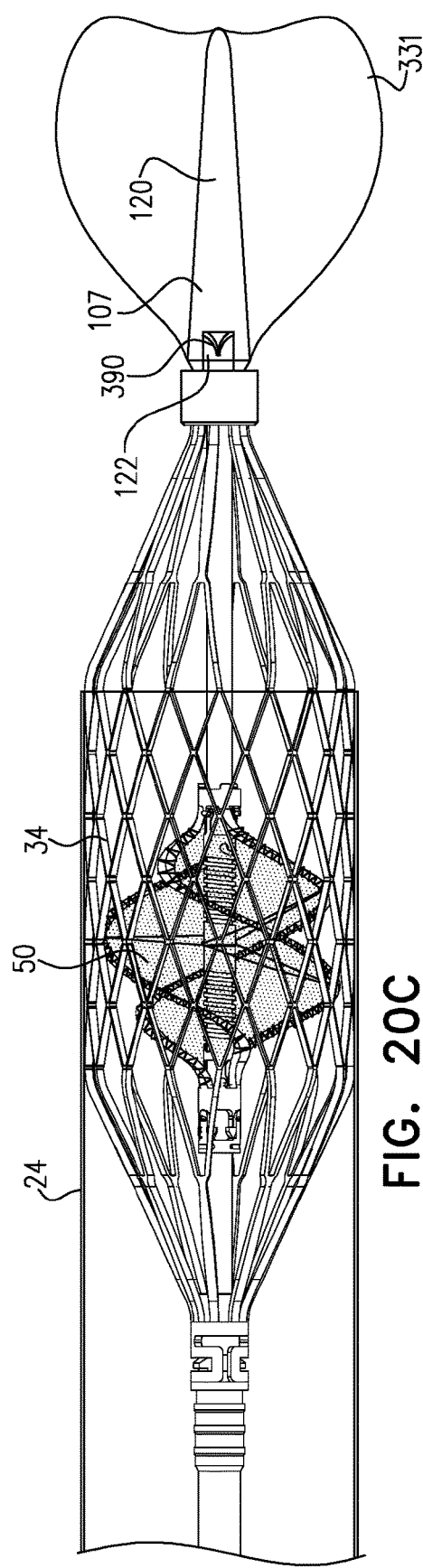

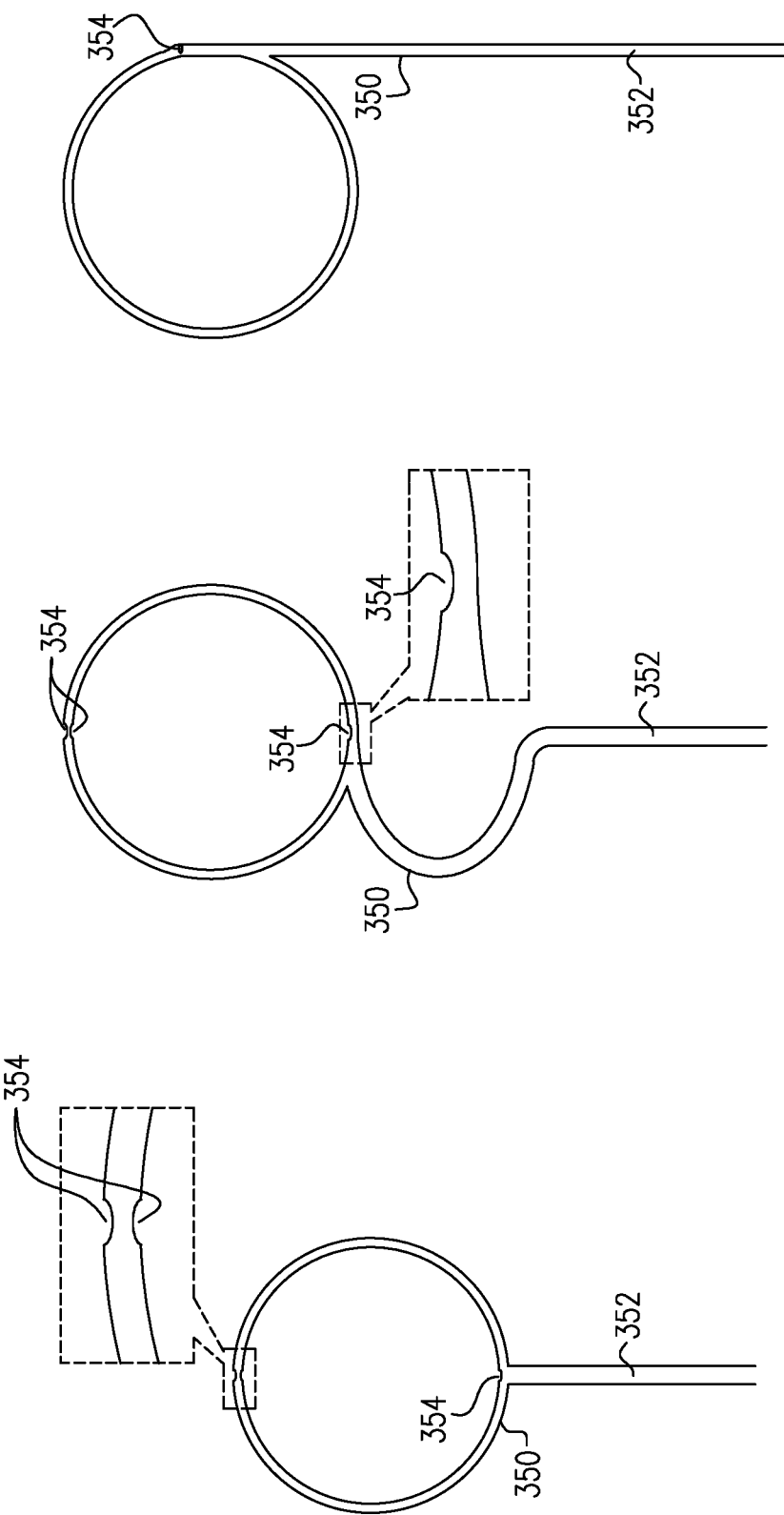

DISTAL TIP ELEMENT FOR A VENTRICULAR ASSIST DEVICE

CROSS-REFERENCES TO RELATED APPLICATIONS

The present application claims priority from:

U.S. Provisional Patent Application No. 62/796,138 to Tuval, entitled "Ventricular assist device," filed Jan. 24, 2019;

U.S. Provisional Patent Application No. 62/851,716 to Tuval, entitled "Ventricular assist device," filed May 23, 2019;

U.S. Provisional Patent Application No. 62/870,821 to Tuval, entitled "Ventricular assist device," filed Jul. 5, 2019; and U.S. Provisional Patent Application No. 62/896,026 to Tuval, entitled "Ventricular assist device," filed Sep. 5, 2019.

The present application is related to PCT International Application No. PCT/IB2020/050515 filed Jan. 23, 2020, entitled "Ventricular assist device," which claims priority from the above-referenced US Provisional applications.

All of the above-referenced applications are incorporated herein by reference.

FIELD OF EMBODIMENTS OF THE INVENTION

Some applications of the present invention generally relate to medical apparatus. Specifically, some applications of the present invention relate to a ventricular assist device and methods of use thereof.

BACKGROUND

Ventricular assist devices are mechanical circulatory support devices designed to assist and unload cardiac chambers in order to maintain or augment cardiac output. They are used in patients suffering from a failing heart and in patients at risk for deterioration of cardiac function during percutaneous coronary interventions. Most commonly, a left-ventricular assist device is applied to a defective heart in order to assist left-ventricular functioning. In some cases, a right-ventricular assist device is used in order to assist right-ventricular functioning. Such assist devices are either designed to be permanently implanted or mounted on a catheter for temporary placement.

SUMMARY OF EMBODIMENTS

In accordance with some applications of the present invention, a ventricular assist device includes an impeller disposed upon an axial shaft, with a frame disposed around the impeller. The ventricular assist device typically includes a tube, which traverses the subject's aortic valve, such that a proximal end of the tube is disposed in the subject's aorta and a distal end of the tube is disposed within the subject's left ventricle. The impeller, the axial shaft and the frame are disposed within a distal portion of the tube inside the subject's left ventricle. Typically, the impeller is configured to pump blood from the left ventricle into the aorta by rotating. The tube typically defines one or more blood inlet openings at the distal end of the tube, via which blood flows into the tube from the left ventricle, during operation of the impeller. For some applications, the proximal portion of the tube defines one or more blood outlet openings, via which blood flows from the tube into the ascending aorta, during operation of the impeller.

For some applications, the ventricular assist device includes a distal-tip element configured to define a straight proximal portion that defines a longitudinal axis, and a curved distal portion shaped such as to curve in a first direction with respect to the longitudinal axis of the straight proximal portion before passing through an inflection point and curving in a second direction with respect to the longitudinal axis of the straight proximal portion, such that the curved distal portion defines a bulge on one side of the longitudinal axis of the straight proximal portion. Typically, the distal-tip element has a question-mark shape and/or a tennis-racket shape.

For some applications, the distal-tip element is configured to separate the blood inlet opening from a posterior wall of the subject's left ventricle when the distal-tip element is placed against the apex of the subject's left ventricle. Typically, the distal-tip element is configured to separate the blood inlet opening from a septal wall of the subject's left ventricle as the distal-tip element contacts the apex of the subject's left ventricle. Further typically, the distal-tip element is configured such that, when distal-tip element is inserted into the left ventricle such that the bulge bulges toward the septal wall, in response to the distal-tip element being pushed against the apex of the subject's left ventricle, the blood inlet opening gets pushed away from the septal wall and toward a free wall of the subject's left ventricle. For some applications, the blood inlet opening gets pushed away from the septal wall and toward the free wall of the subject's left ventricle by the straight proximal portion of the distal-tip element pivoting about the curved distal portion of the distal-tip element.

For some applications, a duckbill valve is disposed within a distal-most 10 mm of the distal-tip element. Typically, the duckbill valve defines a wide inlet and a narrow tip that defines a slit therethrough, the duckbill valve being proximally facing, such that the wide inlet faces a distal end of the distal-tip element and such that the narrow tip faces away from the distal end of the distal-tip element. For some applications, the ventricular assist device is configured for use with a guidewire, and the distal-tip element defines a guidewire lumen. For some such applications, the ventricular assist device further comprises a guidewire guide disposed within the guidewire lumen at a location that is proximal to the duckbill valve. The guidewire guide is typically shaped to define a hole therethrough, which narrows in diameter from a proximal end of the guidewire guide to a distal end of the guidewire guide, the shape of the guidewire guide being configured to guide a tip of the guidewire toward the slit at the narrow, proximal end of the duckbill valve, when the guidewire is inserted from a proximal end of the left-ventricular assist device. For some applications, the duckbill valve is shaped to define a converging guide portion at its proximal end, the converging guide portion converging toward the slit, such that the guide portion is configured to further guide the tip of the guidewire toward the slit.

Typically, the frame that is disposed around the impeller defines a plurality of cells, and the frame is configured such that, in a non-radially-constrained configuration of the frame, the frame comprises a generally cylindrical portion. Further typically, a width of each of the cells within the cylindrical portion, as measured around a circumference of the cylindrical portion, is less than 2 mm (e.g., 1.4-1.6 mm, or 1.6-1.8 mm). For some applications, an inner lining lines at least the cylindrical portion of the frame, and the impeller is disposed inside the frame such that, in a non-radially-constrained configuration of the impeller, at a location at which a span of the impeller is at its maximum, the impeller is disposed within the cylindrical portion of the frame, such that a gap between an outer edge of the impeller and the inner lining is less than 1 mm (e.g., less than 0.4 mm). Typically, the impeller is configured to rotate such as to pump blood from the left ventricle to the aorta, and to be stabilized with respect to the frame, such that, during rotation of the impeller, the gap between the outer edge of the impeller and the inner lining is maintained and is substantially constant. For some applications, the impeller is configured to reduce a risk of hemolysis, by being stabilized with respect to the frame, relative to if the impeller were not stabilized with respect to the frame.

For some applications, proximal and distal radial bearings are disposed, respectively, at proximal and distal ends of the frame, and an axial shaft passes through the proximal and distal radial bearings. Typically, the impeller is stabilized with respect to the frame by the impeller being held in a radially-fixed position with respect to the axial shaft and the axial shaft being rigid. For some applications, the impeller includes bushings that are disposed around the axial shaft, and at least one of the bushings is configured to be slidable with respect to the axial shaft. For some applications, the impeller being stabilized with respect to the frame by a region along the axial shaft over which the at least one bushing is configured to be slidable with respect to the axial shaft being coated, such as to substantially prevent the impeller from vibrating, by reducing a gap between the at least one bushing and the impeller. For example, the region may be coated in a diamond-like-carbon coating, a polytetrafluoroethylene coating, and/or a polymeric sleeve.

For some applications, the frame defines struts having a structure that is such that, as the frame transitions from a proximal end of the frame toward a center of the frame, the struts pass through junctions, at which pairs of struts branch from a single strut, in a Y-shape. The structure of the struts of the frame is typically configured such that, in response to a distal end of the delivery catheter and the frame being moved into overlapping positions with respect to each other (e.g., by the distal end of the delivery catheter being advanced over the frame, or by the frame being retracted into the distal end of the delivery catheter), the frame is configured to assume its radially-constrained configuration by becoming axially elongated, and is configured to cause the impeller to assume its radially constrained configuration by becoming axially elongated (e.g., by the pairs of struts that branch from each of junctions being configured to pivot about the junction and move closer to each other such as to close in response to a distal end of the delivery catheter and the frame being moved into overlapping positions with respect to each other).

For some applications, a housing for an impeller of a blood pump is manufactured by performing the following steps. An inner lining is placed around a mandrel. A cylindrical portion of a frame is placed around the inner lining, the cylindrical portion of the frame including struts that define a generally cylindrical shape. A distal portion of an elongate tube is placed around at least a portion of the frame, the tube including a proximal portion that defines at least one blood outlet opening. While the distal portion is disposed around at least the portion of the frame, the inner lining, the frame and the distal portion of the elongate tube are heated, via the mandrel. While heating the inner lining, the frame and the distal portion of the elongate tube, pressure is applied from outside the distal portion of the elongate tube, such as to cause the distal portion of the elongate tube to conform with a structure of the struts of the frame, and such as to cause the inner lining and the distal portion of the elongate tube to become coupled to the frame. For example, the pressure may be applied by means of a silicone tube that is placed outside the distal portion of the elongate tube. For some applications, the inner lining and the elongate tube include an inner lining and elongate tube that are made from different materials from each other, and a thermoforming temperature of a material from which the inner lining is made is higher than a thermoforming temperature of a material from which the elongate tube is made. For some such applications, the inner lining, the frame and the distal portion of the elongate tube are heated to a temperature that is above the thermoforming temperature of the material from which the elongate tube is made and below the thermoforming temperature of the material from which the inner lining is made.

For some applications, the impeller is manufactured by forming a structure having first and second bushings at proximal and distal ends of the structure, the first and second bushings being connected to one another by at least one elongate element. The at least one elongate element is made to radially expand and form at least one helical elongate element, at least partially by axially compressing the structure. An elastomeric material is coupled to the at least one helical elongate element, such that the at least one helical elongate element with the elastomeric material coupled thereto defines a blade of the impeller. Typically, the coupling is performed such that a layer of the material is disposed around a radially outer edge of the at least one helical elongate element, the layer of material forming the effective edge of the impeller blade (i.e., the edge at which the impeller's blood-pumping functionality substantially ceases to be effective). Further typically, the method includes performing a step to enhance bonding of the elastomeric material to the at least one helical elongate element in a manner that does not cause a protrusion from the effective edge of the impeller blade. For example, sutures may be placed within grooves defined by the at least one helical elongate element, such that the sutures do not protrude from the radially outer edge of the helical elongate element, the sutures being configured to enhance bonding of the elastomeric material to the at least one helical elongate element. Alternatively or additionally, a tightly-wound coil is placed around the at least one helical elongate element, such that the elastomeric material forms a substantially smooth layer along a radially outer edge of the coil, the coil being configured to enhance bonding of the elastomeric material to the at least one helical elongate element. Further alternatively or additionally, a sleeve is placed around the at least one helical elongate element, such that the elastomeric material forms a substantially smooth layer along a radially outer edge of the sleeve, the sleeve being configured to enhance bonding of the elastomeric material to the at least one helical elongate element. For some applications, a rounded cross section is provided to the at least one helical elongate element, such that the elastomeric material forms a layer having a substantially uniform thickness at an interface of the elastomeric material with the helical elongate element.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

The scope of the present invention includes using the apparatus and methods described herein in anatomical locations other than the left ventricle and the aorta. Therefore, the ventricular assist device and/or portions thereof are sometimes referred to herein (in the specification and the claims) as a blood pump.

There is therefore provided, in accordance with some applications of the present invention, apparatus including:

a left-ventricular assist device configured to assist left-ventricular functioning of a subject, the left-ventricular assist device including:

a tube configured such that a proximal portion of the tube traverses an aortic valve of the subject, and a distal portion of the tube is disposed within a left ventricle of the subject;

a frame disposed within at least the distal portion of the tube;

a pump disposed within the frame and configured to pump blood through the tube from the subject's left ventricle to the subject's aorta, by pumping the blood into the tube via at least one blood inlet opening that is defined by the tube and that is configured to be disposed within the subject's left ventricle, and by pumping blood out of the tube via at least one blood outlet opening that is defined by the tube and that is configured to be disposed within the subject's aorta; and a distal-tip element configured to define a straight proximal portion that defines a longitudinal axis, and a curved distal portion that is shaped such as to curve in a first direction with respect to the longitudinal axis of the straight proximal portion before passing through an inflection point and curving in a second direction with respect to the longitudinal axis of the straight proximal portion, such that the curved distal portion defines a bulge on one side of the longitudinal axis of the straight proximal portion.

For some applications, the distal-tip element is configured to separate the at least one blood inlet opening from a posterior wall of the subject's left ventricle when the distal-tip element is placed against an apex of the subject's left ventricle.

For some applications, the distal-tip element has a question-mark shape. For some applications, the distal-tip element has a tennis-racket shape.

For some applications, the curved distal portion of the distal-tip element is shaped such that, after passing through the inflection point, the curved distal portion continues to curve such that the curved distal portion crosses back over the longitudinal axis defined by the straight proximal portion. For some applications, the curved distal portion of the distal-tip element is shaped such that after passing through the inflection point the curved distal portion does not cross back over the longitudinal axis defined by the straight proximal portion.

For some applications, the blood pump includes an impeller disposed on an axial shaft, and the distal-tip element includes an axial-shaft-receiving tube configured to receive the axial shaft of the blood pump, and a distal-tip portion configured to define the curved distal portion of the distal-tip element.

For some applications, the distal-tip element is configured to separate the at least one blood inlet opening from a septal wall of the subject's left ventricle as the distal-tip element contacts an apex of the subject's left ventricle. For some applications, the distal-tip element is configured such that, when distal-tip element is inserted into the left ventricle such that the bulge bulges toward the septal wall, then in response to the distal-tip element being pushed against the apex of the subject's left ventricle, the blood inlet opening gets pushed away from the septal wall and toward a free wall of the subject's left ventricle. For some applications, the distal-tip element is configured such that, in response to the distal-tip element being pushed against the apex of the subject's left ventricle, the blood inlet opening gets pushed away from the septal wall and toward the free wall of the subject's left ventricle by the straight proximal portion of the distal-tip element pivoting about the curved distal portion of the distal-tip element.

For some applications, the distal-tip element is configured such that, upon being deployed within a descending aorta of the subject, the distal-tip element centers itself with respect to an aortic valve of the subject. For some applications, the curved distal portion is shaped that after curving in the first direction the curved distal portion defines an elongated straight portion, before curving the in the second direction, such that the elongated straight portion protrudes at an angle with respect to the longitudinal axis of the proximal straight portion of the distal-tip element.

For some applications, a duckbill valve is disposed within a distal-most 10 mm of the distal-tip element. For some applications, the duckbill valve defines a wide inlet and a narrow tip that defines a slit therethrough, the duckbill valve being proximally facing, such that the wide inlet faces a distal end of the distal-tip element and such that the narrow tip faces away from the distal end of the distal-tip element.

For some applications:
the left-ventricular assist device is configured for use with a guidewire;
the distal-tip element defines a guidewire lumen; and
the left-ventricular assist device further includes a guidewire guide disposed within the guidewire lumen at a location that is proximal to the duckbill valve, the guidewire guide shaped to define a hole therethrough, which narrows in diameter from a proximal end of the guidewire guide to a distal end of the guidewire guide, the shape of the guidewire guide being configured to guide a tip of the guidewire toward the slit at the narrow, proximal end of the duckbill valve, when the guidewire is inserted from a proximal end of the left-ventricular assist device.

For some applications, the duckbill valve is shaped to define a converging guide portion at its proximal end, the converging guide portion converging toward the slit, such that the guide portion is configured to further guide the tip of the guidewire toward the slit.

There is further provided, in accordance with some applications of the present invention, apparatus including:

a blood pump configured to be placed inside a body of subject, the blood pump including:
an impeller;
a frame configured to be disposed around the impeller;
a distal-tip portion disposed distally with respect to the frame; and
a duckbill valve disposed entirely within a distal most 10 mm of the distal-tip portion,
the duckbill valve defining a wide inlet and a narrow tip that defines a slit therethrough, the duckbill valve being proximally facing, such that the
wide inlet faces a distal end of the distal-tip portion and
such that the narrow tip faces away from the distal end
of distal-tip portion.

There is further provided, in accordance with some applications of the present invention, apparatus for use with a guidewire, including:

a percutaneous medical device defining a guidewire lumen that extends from a proximal end of the device to a distal end of the device;

a duckbill valve disposed within a distal portion of the guidewire lumen, the duckbill valve defining a wide inlet and a narrow tip that defines a slit therethrough, the duckbill valve being proximally facing, such that the wide inlet faces a distal end of guidewire lumen and such that the narrow tip faces away from the distal end of guidewire lumen; and a guidewire guide disposed within the guidewire lumen at a location that is proximal to the duckbill valve, the guidewire guide shaped to define a hole therethrough, which narrows in diameter from a proximal end of the guidewire guide to a distal end of the guidewire guide, the shape of the guidewire guide being configured to guide a tip of the guidewire toward the slit at the narrow, proximal end of the duckbill valve, when the guidewire is inserted from the proximal end of the percutaneous medical device.

For some applications, the duckbill valve is shaped to define a converging guide portion at its proximal end, the converging guide portion converging toward the slit, such that the guide portion is configured to further guide the tip of the guidewire toward the slit.

There is further provided, in accordance with some applications of the present invention, apparatus including:

a left-ventricular assist device configured to assist left-ventricular functioning of a subject, the left-ventricular assist device including:

a tube configured to traverse an aortic valve of a subject, such that a proximal end of the tube is disposed within an aorta of the subject and a distal end of the tube is disposed within a left ventricle of the subject;

a frame disposed within at least a portion of the tube, the frame defining a plurality of cells, the frame being configured such that, in a non-radially-constrained configuration of the frame, the frame includes a generally cylindrical portion, a width of each of the cells within the cylindrical portion as measured around a circumference of the cylindrical portion being less than 2 mm;

an inner lining that lines at least some of the cylindrical portion of the frame; and an impeller disposed inside the frame such that, in a non-radially-constrained configuration of the impeller, at a location at which a span of the impeller is at its maximum, the impeller is disposed within the cylindrical portion of the frame, such that a gap between an outer edge of the impeller and the inner lining is less than 1 mm, the impeller being configured:
to rotate such as to pump blood from the left ventricle to the aorta, and
to be stabilized with respect to the frame, such that, during rotation of the impeller, the gap between the outer edge of the impeller and the inner lining is maintained and is substantially constant.

For some applications, the impeller is configured to reduce a risk of hemolysis by being stabilized with respect to the frame, relative to if the impeller were not stabilized with respect to the frame.

For some applications, the width of each of the cells within the cylindrical portion as measured around the circumference of the cylindrical portion is between 1.4 mm and 1.6 mm.

For some applications, the width of each of the cells within the cylindrical portion as measured around the circumference of the cylindrical portion is between 1.6 mm and 1.8 mm.

For some applications, the impeller is configured such that the gap between the outer edge of the impeller and the inner lining is less than 0.4 mm.

For some applications:

the left-ventricular assist device further includes an axial shaft and proximal and distal radial bearings disposed, respectively, at proximal and distal ends of the frame, the axial shaft passing through the proximal and distal radial bearings;

the impeller is coupled to the axial shaft; and the impeller is stabilized with respect to the frame by the impeller being held in a radially-fixed position with respect to the axial shaft and the axial shaft being rigid.

For some applications, the impeller includes bushings that are disposed around the axial shaft, at least one of the bushings is configured to be slidable with respect to the axial shaft, and the impeller is stabilized with respect to the frame by a region along the axial shaft over which the at least one bushing is configured to be slidable with respect to the axial shaft being coated such as to substantially prevent the impeller from vibrating, by reducing a gap between the at least one bushing and the axial shaft.

For some applications, the impeller is stabilized with respect to the frame by substantially preventing vibration of the frame with respect to the axial shaft by a ratio of a length of the cylindrical portion of the frame to a total length of the frame being more than 1:2.

For some applications, the ratio of the length of the cylindrical portion of the frame to the total length of the frame is more than 2:3.

There is further provided, in accordance with some applications of the present invention, apparatus including:

a left-ventricular assist device configured to assist left-ventricular functioning of a subject, the left-ventricular assist device including:

a tube configured to traverse an aortic valve of a subject, such that a proximal end of the tube is disposed within an aorta of the subject and a distal end of the tube is disposed within a left ventricle of the subject;

a frame disposed within at least a portion of the tube the frame defining a plurality of cells, the frame being configured such that in a non-radially-constrained configuration of the frame, the frame includes a generally cylindrical portion;

proximal and distal radial bearings disposed, respectively, at proximal and distal ends of the frame;

an axial shaft that passes through the proximal and distal radial bearings;

an inner lining that lines at least some of the cylindrical portion of the frame; and an impeller coupled to the axial shaft inside the frame such that, in a non-radially-constrained configuration of the impeller, at a location at which a span of the impeller is at its maximum, the impeller is disposed within the cylindrical portion of the frame, such that a gap between an outer edge of the impeller and the inner lining is less than 1 mm, the impeller including bushings that are disposed around the axial shaft, at least one of the bushings being configured to be slidable with respect to the axial shaft, and the impeller being stabilized with respect to the frame by a region along the axial shaft over which the at least one bushing is configured to be slidable with respect to the axial shaft being coated such as to substantially prevent the impeller from vibrating, by reducing a gap between the at least one bushing and the impeller.

For some applications, the region along the axial shaft over which the at least one bushing is configured to be slidable with respect to the axial shaft is coated with a diamond-like-carbon coating. For some applications, the region along the axial shaft over which the at least one bushing is configured to be slidable with respect to the axial shaft is coated with a polytetrafluoroethylene coating. For some applications, the region along the axial shaft over which the at least one bushing is configured to be slidable with respect to the axial shaft is coated with a polymeric sleeve. For some applications, the impeller is configured to reduce a risk of hemolysis by being stabilized with respect to the frame, relative to if the impeller were not stabilized with respect to the frame.

There is further provided, in accordance with some applications of the present invention, apparatus including:

a left-ventricular assist device configured to assist left-ventricular functioning of a subject, the left-ventricular assist device including:

a tube configured to traverse an aortic valve of a subject, such that a proximal end of the tube is disposed within an aorta of the subject and a distal end of the tube is disposed within a left ventricle of the subject;

a frame disposed within at least a portion of the tube the frame defining a plurality of cells, the frame being configured such that in a non-radially-constrained configuration of the frame, the frame includes a generally cylindrical portion;

proximal and distal radial bearings disposed, respectively, at proximal and distal ends of the frame;

an axial shaft that passes through the proximal and distal radial bearings;

an inner lining that lines at least some of the cylindrical portion of the frame; and an impeller coupled to the axial shaft inside the frame such that, in a non-radially-constrained configuration of the impeller, at a location at which a span of the impeller is at its maximum, the impeller is disposed within the cylindrical portion of the frame such that a gap between an outer edge of the impeller and the inner lining is less than 1 mm, the impeller being stabilized with respect to the frame by substantially preventing vibration of the frame with respect to the axial shaft, by a ratio of a length of the cylindrical portion of the frame to a total length of the frame being more than 1:2.

For some applications, the ratio of the length of the cylindrical portion of the frame to the total length of the frame is more than 2:3.

For some applications, the impeller is configured to reduce a risk of hemolysis by being stabilized with respect to the frame, relative to if the impeller were not stabilized with respect to the frame.

There is further provided, in accordance with some applications of the present invention, a method, including:

manufacturing an impeller by:

forming a structure having first and second bushings at proximal and distal ends of the structure, the first and second bushings being connected to one another by at least one elongate element;

causing the at least one elongate element to radially expand and form at least one helical elongate element, at least partially by axially compressing the structure; and coupling an elastomeric material to the at least one helical elongate element, such that the at least one helical elongate element with the elastomeric material coupled thereto defines a blade of the impeller, the coupling being performed such that a layer of the material is disposed around a radially outer edge of the at least one helical elongate element, the layer of material forming the effective edge of the impeller blade;

the method including performing a step to enhance bonding of the elastomeric material to the at least one helical elongate element in a manner that does not cause a protrusion from the effective edge of the impeller blade.

For some applications, manufacturing the impeller further includes placing a spring within the structure such that the spring extends from the first bushing to the second bushing, and coupling the elastomeric material to the at least one helical elongate element includes forming a film of the elastomeric material that extends from the at least one helical elongate element to the spring.

For some applications:

forming the structure includes forming a structure having first and second bushings at proximal and distal ends of the structure, the end portions being connected to one another by two elongate elements;

causing the at least one elongate element to radially expand and form at least one helical elongate element includes causing the two elongate elements to radially expand and form two helical elongate elements; and coupling the elastomeric material to the at least one helical elongate element includes coupling the elastomeric material to the two helical elongate elements, such that the two helical elongate elements with the elastomeric material coupled thereto define a blade of the impeller.

For some applications:

forming the structure includes forming a structure having first and second bushings at proximal and distal ends of the structure, the end portions being connected to one another by three or more elongate elements;

causing the at least one elongate element to radially expand and form at least one helical elongate element includes causing the three elongate elements to radially expand and form three or more helical elongate elements; and coupling the elastomeric material to the at least one helical elongate element includes coupling the elastomeric material to the three or more helical elongate elements, such that each of the three or more helical elongate elements with the elastomeric material coupled thereto defines a respective blade of the impeller.

For some applications, causing the at least one elongate element to radially expand and form at least one helical elongate element further includes twisting the structure.

For some applications, performing the step to enhance bonding of the elastomeric material to the at least one helical elongate element includes placing sutures within grooves defined by the at least one helical elongate element, such that the sutures do not protrude from the radially outer edge of the helical elongate element, the sutures being configured to enhance bonding of the elastomeric material to the at least one helical elongate element.

For some applications, performing the step to enhance bonding of the elastomeric material to the at least one helical elongate element includes placing a tightly-wound coil around the at least one helical elongate element, such that the elastomeric material forms a substantially smooth layer along a radially outer edge of the coil, the coil being configured to enhance bonding of the elastomeric material to the at least one helical elongate element.

For some applications, performing the step to enhance bonding of the elastomeric material to the at least one helical elongate element includes placing a sleeve around the at least one helical elongate element, such that the elastomeric material forms a substantially smooth layer along a radially outer edge of the sleeve, the sleeve being configured to enhance bonding of the elastomeric material to the at least one helical elongate element.

For some applications, performing the step to enhance bonding of the elastomeric material to the at least one helical elongate element includes providing a rounded cross section to the at least one helical elongate element, such that the elastomeric material forms a layer having a substantially uniform thickness at an interface between the elastomeric material and the helical elongate element.

There is further provided, in accordance with some applications of the present invention, apparatus for use with a delivery catheter including:
  a blood pump including:
    an impeller configured to pump blood through a subject's body;
    a frame disposed around the impeller,
    the impeller and frame defining non-radially-constrained configurations in which the impeller is configured to pump blood within the subject's body, and defining radially-constrained configurations in which the impeller and frame are inserted and removed from the subject's body using a delivery catheter,
    the frame defining struts having a structure that is such that, as the frame transitions from a proximal end of the frame toward a center of the frame, the struts pass through junctions, at which the two struts branch from a single strut, in a Y-shape;
    the structure of the struts of the frame being configured such that, in response to a distal end of the delivery catheter and the frame being moved into overlapping positions with respect to each other, the frame is configured to assume its radially-constrained configuration by becoming axially elongated, and is configured to cause the impeller to assume its radially constrained configuration by becoming axially elongated.

For some applications, the structure of the struts of the frame is configured such that, in response to a distal end of the delivery catheter and the frame being moved into overlapping positions with respect to each other, the frame is configured to assume its radially-constrained configuration by becoming axially elongated, and is configured to cause the impeller to assume its radially constrained configuration by becoming axially elongated, by the pairs of struts that branch from the junctions being configured to pivot about the junction and move closer to each other such as to close.

For some applications, in its radially-non-constrained configuration, the frame defines a proximal conical portion, a distal conical portion, and a cylindrical portion between the proximal conical portion and the distal conical portion.

For some applications, within the cylindrical portion of the frame, a strut density of the frame is constant.

For some applications, a density of the struts increases from the proximal conical portion to the cylindrical portion, and from the distal conical portion to the cylindrical portion.

For some applications, during operation of the blood pump, the impeller is configured to move with respect to the frame, and a range of movement of the impeller is such that at least a portion of the impeller is disposed within the proximal conical portion of the frame during at least some of the operation of the blood pump, and at least a portion of the impeller is disposed within the cylindrical portion of the frame during at least some of the operation of the blood pump.

For some applications, throughout the operation of the blood pump, at a location at which a span of the impeller is at its maximum, the impeller is configured to be disposed within the cylindrical portion of the frame.

For some applications, a width of each of the cells within the cylindrical portion as measured around a circumference of the cylindrical portion is less than 2 mm.

For some applications, the width of each of the cells within the cylindrical portion as measured around the circumference of the cylindrical portion is between 1.4 mm and 1.6 mm.

For some applications, the width of each of the cells within the cylindrical portion as measured around the circumference of the cylindrical portion is between 1.6 mm and 1.8 mm.

There is further provided, in accordance with some applications of the present invention, a method, including:
  manufacturing a housing for an impeller of a blood pump by:
    placing an inner lining around a mandrel;
    placing, around the inner lining, a cylindrical portion of a frame, the cylindrical portion of the frame including struts that define a generally cylindrical shape;
    placing a distal portion of an elongate tube around at least a portion of the frame, the tube including a proximal portion that defines at least one blood outlet opening;
    while the distal portion is disposed around at least the portion of the frame, heating the inner lining, the frame and the distal portion of the elongate tube via the mandrel; and
    while heating the inner lining, the frame and the distal portion of the elongate tube, applying pressure from outside the distal portion of the elongate tube, such as to cause the distal portion of the elongate tube to conform with a structure of the struts of the frame, and such as to cause the inner lining and the distal portion of the elongate tube to become coupled to the frame.

For some applications, the method further includes, subsequent to causing the inner lining and the distal portion of the elongate tube to become coupled to the frame, shaping a distal end of the frame to define a widened inlet.

For some applications, the method further includes, subsequent to causing the inner lining and the distal portion of the elongate tube to become coupled to the frame, shaping a portion of the frame to form a converging region, such that the frame defines a narrowing in a vicinity of a location within the frame that is configured to house the impeller.

For some applications, placing the distal portion of the elongate tube around at least a portion of the frame includes placing the distal portion of the elongate tube around the entire cylindrical portion of the frame, such the distal portion of the elongate tube overlaps with the entire inner lining.

For some applications:

the inner lining and the elongate tube include an inner lining and elongate tube that are made from different materials from each other, and a thermoforming temperature of a material from which the inner lining is made is higher than a thermoforming temperature of a material from which the elongate tube is made, and heating the inner lining, the frame and the distal portion of the elongate tube includes heating the inner lining, the frame and the distal portion of the elongate tube to a temperature that is above the thermoforming temperature of the material from which the elongate tube is made and below the thermoforming temperature of the material from which the inner lining is made.

For some applications, applying pressure from outside the distal portion of the elongate tube includes applying pressure from outside the distal portion of the elongate tube using an outer tube that is made of silicone.

For some applications, applying pressure from outside the distal portion of the elongate tube, such as to cause the inner lining and the distal portion of the elongate tube to become coupled to the frame, includes coupling the inner lining to an inner surface of the cylindrical portion of the frame, such that the inner lining forms a substantially cylindrical tube.

For some applications, the struts within the cylindrical portion of the frame are shaped to define cells, and a width of each of the cells as measured around a circumference of the cylindrical portion is less than 2 mm.

For some applications, placing the distal portion of the elongate tube around at least a portion of the frame includes placing the distal portion of the elongate tube around only a portion of the cylindrical portion of the frame, such the distal portion of the elongate tube does not overlap with the entire inner lining.

For some applications, placing the distal portion of the elongate tube around only a portion of the cylindrical portion of the frame includes preventing radial expansion of the portion of the cylindrical portion of the frame around which the distal portion of the elongate tube is placed, thereby causing the portion of the cylindrical portion of the frame around which the distal portion of the elongate tube is placed to be narrower than a portion of the cylindrical portion of the frame around which the elongate tube is not placed.

There is further provided, in accordance with some applications of the present invention, apparatus including:

a blood pump configured to be placed inside a body of subject, the blood pump including:
an impeller;
a frame configured to be disposed around the impeller, the frame including struts;
an inner lining disposed inside the frame;
an outer covering material coupled to the inner coupling material from outside the frame at discrete coupling regions along a length of the frame,
a density of the struts of the frame at the coupling regions being less than a density of the struts of the frame at other regions along the length of the frame.

There is further provided, in accordance with some applications of the present invention, apparatus including:

a blood pump configured to be placed inside a body of subject, the blood pump including:
an impeller;
a frame configured to be disposed around the impeller, the frame including struts, and a cylindrical portion of the frame being shaped to define a cylindrical cross-section;
an inner lining disposed inside the frame;
an outer covering material coupled to the inner coupling material from outside the frame, the outer covering material being disposed around only a portion of the cylindrical portion of the frame and the outer covering material being configured to restrict radial expansion of the portion of the cylindrical portion of the frame around which the outer covering material is placed, such that the portion of the cylindrical region of the frame around which the distal portion of the outer covering material is placed is narrower than a portion of the cylindrical region of the frame around which the outer covering material is not placed.

There is further provided, in accordance with some applications of the present invention, apparatus including:

a blood pump configured to be placed inside a body of subject, the blood pump including:
an impeller;
a frame configured to be disposed around the impeller, the frame being configured to define a cylindrical portion that has a substantially cylindrical cross-section;
a covering material that is coupled to the cylindrical portion of the frame, such that a distal end of the cylindrical portion of the frame defines a blood inlet opening, the impeller being configured to be disposed within 15 mm of the blood inlet opening throughout operation of the impeller,
a portion of the frame being shaped such as to reduce turbulence that is generated as blood flows from the blood inlet opening toward the impeller.

For some applications, the portion of the frame includes a widened portion of the frame.

For some applications, the portion of the frame includes a portion of the frame that is shaped to converge toward the impeller.

The present invention will be more fully understood from the following detailed description of embodiments thereof, taken together with the drawings, in which:

BRIEF DESCRIPTION OF THE DRAWINGS

FIGS. 2A, 2B, 2C, 2D, 2E, and 2F are schematic illustrations of a frame that houses an impeller of a ventricular assist device, in accordance with some applications of the present invention;

FIGS. 5A and 5B are schematic illustrations of the impeller and the frame of the ventricular assist device, respectively in non-radially-constrained and radially-constrained states thereof, in accordance with some applications of the present invention;

FIGS. 6A and 6B are schematic illustrations of a ventricular assist device at respective stages of a motion cycle of the impeller of the ventricular assist device with respect to the frame of the ventricular assist device, in accordance with some applications of the present invention;

FIG. 6C is a schematic illustration of a distal-tip element that includes an axial-shaft-receiving tube and a distal-tip portion of a ventricular assist device, in accordance with some applications of the present invention;

FIG. 6D is a schematic illustration of an axial shaft of a ventricular assist device that is at least partially covered or coated, such as to reduce a gap between the axial shaft and a bushing of an impeller that slides over the axial shaft, in accordance with some applications of the present invention;

FIG. 6E is a schematic illustration of an axial shaft of a ventricular assist device and a bushing of an impeller that slides over the axial shaft, the axial shaft and the impeller bushing being configured to prevent rotational motion of the impeller bushing with respect to the axial shaft, in accordance with some applications of the present invention;

FIGS. 6F and 6G are schematic illustrations of an impeller housing configured to provide a gap between the impeller and the housing that varies over the course of a subject's cardiac cycle, in accordance with some applications of the present invention;

FIGS. 15A, 15B, 15C, 15D, and 15E are schematic illustration of a stator that is built into a tube of a ventricular assist device, in accordance with some applications of the present invention;

FIGS. 16A and 16B are schematic illustrations of a ventricular assist device that includes one or more ventricular blood-pressure-measurement tubes, in accordance with some applications of the present invention;

FIGS. 17A, 17B, 17C, and 17D are schematic illustrations of a ventricular assist device that includes a pitot tube that is configured to measure blood flow through a tube of the device, in accordance with some applications of the present invention;

FIGS. 19A, 19B, 19C, 19D, 19E, 19F, 19G, and 19H are schematic illustrations of a ventricular assist device that includes an inner lining on the inside of the frame that houses the impeller, in accordance with some applications of the present invention;

FIGS. 20A, 20B, and 20C are schematic illustrations of a ventricular assist device that includes an inflatable portion (e.g., a balloon) disposed around its distal-tip portion, in accordance with some applications of the present invention;

FIGS. 27A, 27B, and 27C are schematic illustrations of an atraumatic projection that includes a closed ellipse or a closed circle and that is configured to extend distally from a distal-tip element of a ventricular assist device, in accordance with some applications of the present invention;

DETAILED DESCRIPTION OF EMBODIMENTS

Figure 1A:
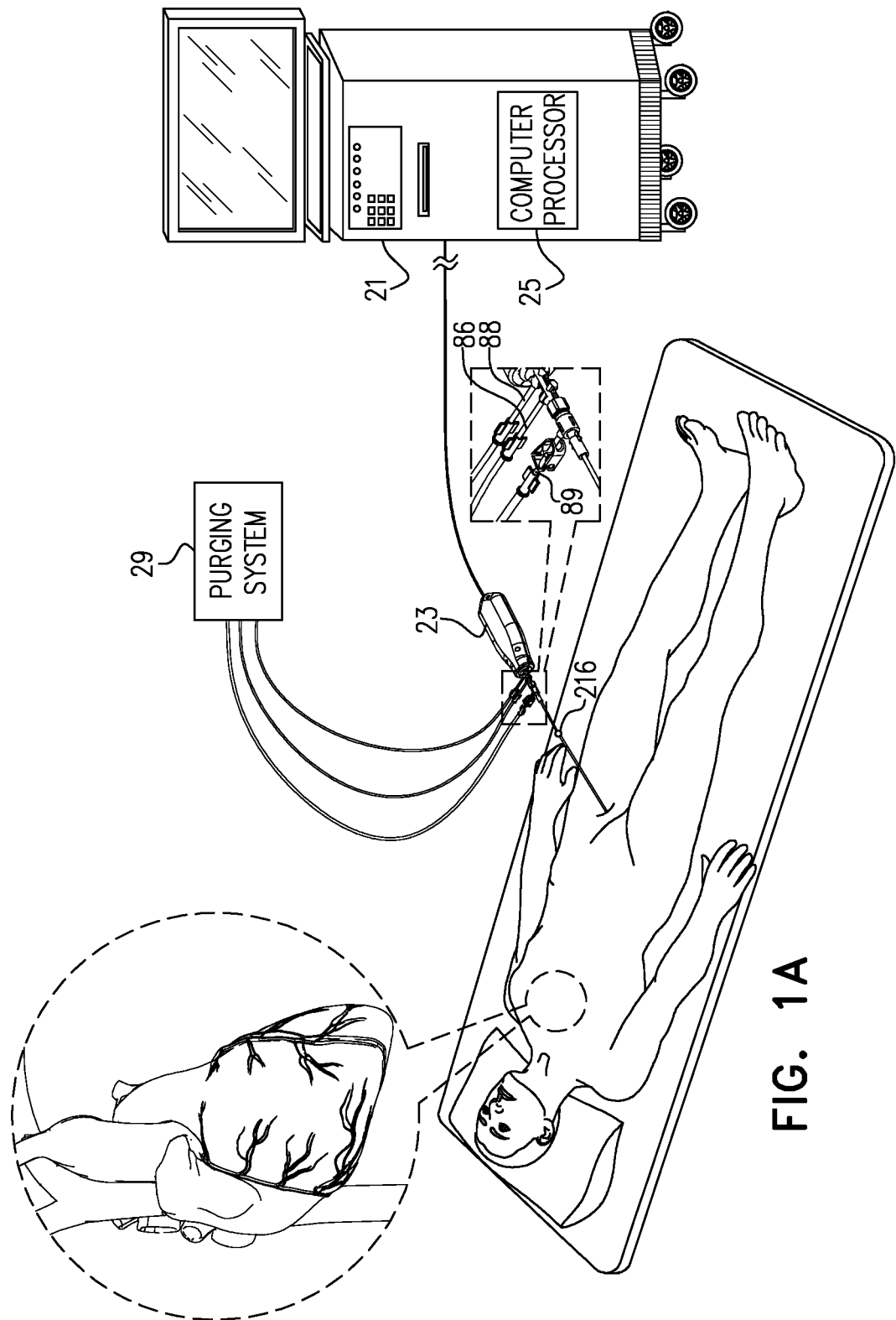
FIGS. 1A, 1B, and 1C are schematic illustrations of a ventricular assist device, a distal end of which is configured to be placed in a subject's left ventricle, in accordance with some applications of the present invention.
Figure 1B:
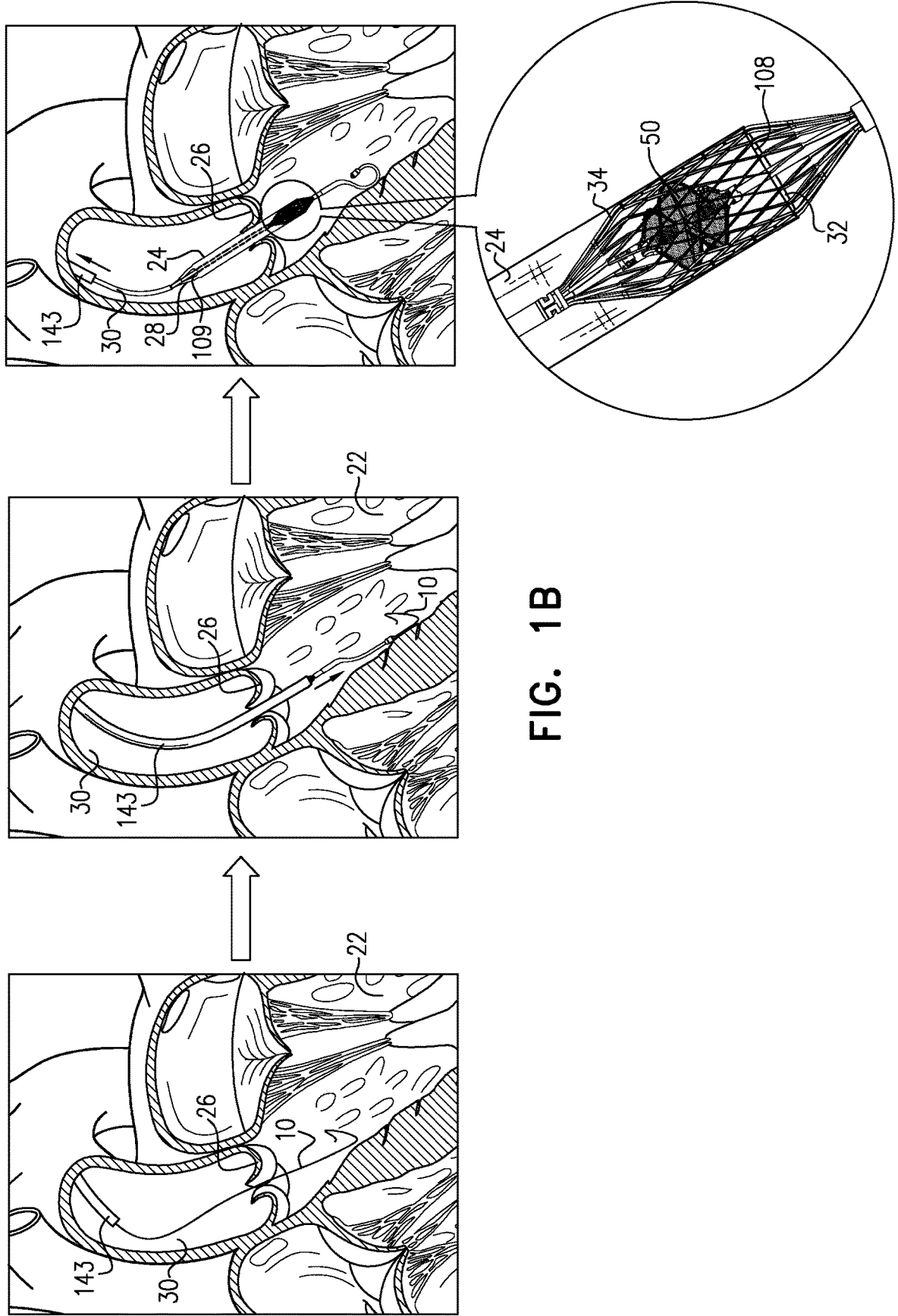
Figure 1C:
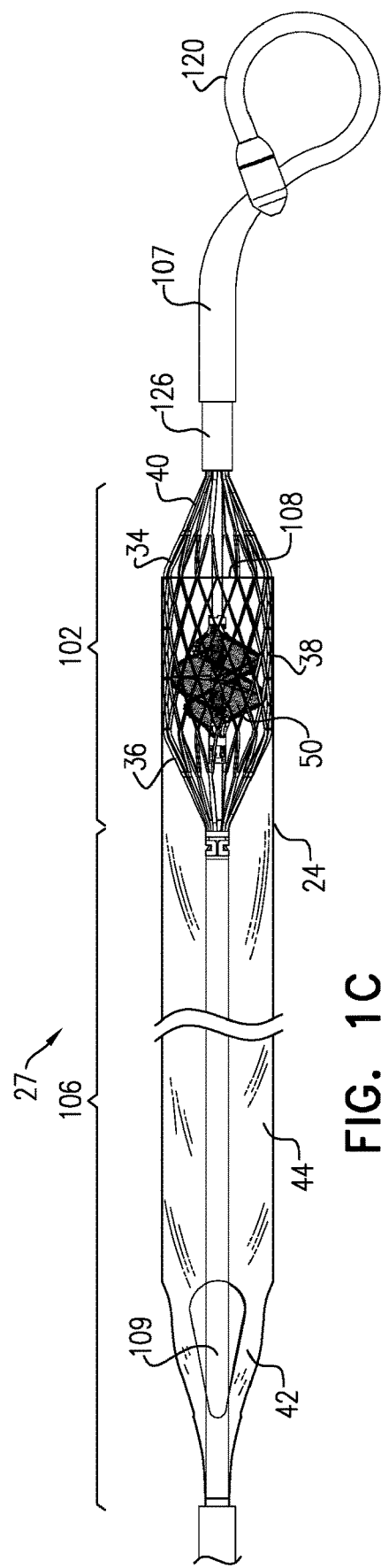

Reference is now made to FIGS. 1A, 1B, and 1C, which are schematic illustrations of a ventricular assist device 20, a distal end of which is configured to be disposed in a subject's left ventricle 22, in accordance with some applications of the present invention. FIG. 1A shows an overview of the ventricular assist device system including a control console 21, and a motor unit 23, FIG. 1B shows the ventricular assist device being inserted into the subject's left ventricle, and FIG. 1C shows a pump portion 27 of the ventricular assist device in greater detail. The ventricular assist device includes a tube 24, which traverses an aortic valve 26 of the subject, such that a proximal end 28 of the tube is disposed in an aorta 30 of the subject and a distal end 32 of the tube is disposed within left ventricle 22. Tube 24 (which is sometimes referred to herein as a "blood-pump tube") is typically an elongate tube, an axial length of the tube typically being substantially larger than its diameter. The scope of the present invention includes using the apparatus and methods described herein in anatomical locations other than the left ventricle and the aorta. Therefore, the ventricular assist device and/or portions thereof are sometimes referred to herein (in the specification and the claims) as a blood pump.

For some applications, the ventricular assist device is used to assist the functioning of a subject's left ventricle during a percutaneous coronary intervention. In such cases, the ventricular assist device is typically used for a period of up to 10 hours (e.g., up to six hours), during a period in which there is risk of developing hemodynamic instability (e.g., during or immediately following the percutaneous coronary intervention). Alternatively or additionally, the ventricular assist device is used to assist the functioning of a subject's left ventricle for a longer period (e.g., for example, 2-20 days, e.g., 4-14 days) upon a patient suffering from cardiogenic shock, which may include any low-cardiac-output state (e.g., acute myocardial infarction, myocarditis, cardiomyopathy, post-partum, etc.). For some applications, the ventricular assist device is used to assist the functioning of a subject's left ventricle for yet a longer period (e.g., several weeks or months), e.g., in a "bridge to recovery" treatment. For some such applications, the ventricular assist device is permanently or semi-permanently implanted, and the impeller of the ventricular assist device is powered transcutaneously, e.g., using an external antenna that is magnetically coupled to the impeller.

As shown in FIG. 1B, which shows steps in the deployment of the ventricular assist device in the left ventricle, typically the distal end of the ventricular assist device is guided to the left ventricle over a guidewire 10. During the insertion of the distal end of the device to the left ventricle, a delivery catheter 143 is disposed over the distal end of the device. Once the distal end of the device is disposed in the left ventricle, the delivery catheter is typically retracted to the aorta, and the guidewire is withdrawn from the subject's body. The retraction of the delivery catheter typically causes self-expandable components of the distal end of the device to assume non-radially-constrained configurations, as described in further detail hereinbelow. Typically, the ventricular assist device is inserted into the subject's body in order to provide an acute treatment to the subject. For some applications, in order to withdraw the left ventricular device from the subject's body at the end of the treatment, the delivery catheter is advanced over the distal end of the device, which causes the self-expandable components of the distal end of the device to assume radially-constrained configurations. Alternatively or additionally, the distal end of the device is retracted into the delivery catheter which causes the self-expandable components of the distal end of the device to assume radially-constrained configurations.

For some applications (not shown), the ventricular assist device and/or delivery catheter 143 includes an ultrasound transducer at its distal end and the ventricular assist device is advanced toward the subject's ventricle under ultrasound guidance.

Referring now to FIG. 1C, which shows pump portion 27 of ventricular assist device 20 in greater detail, typically, an impeller 50 is disposed within a distal portion 102 of tube 24 and is configured to pump blood from the left ventricle into the aorta by rotating. The tube typically defines one or more blood inlet openings 108 at the distal end of the tube, via which blood flows into the tube from the left ventricle, during operation of the impeller. For some applications, proximal portion 106 of the tube defines one or more blood outlet openings 109, via which blood flows from the tube into the ascending aorta, during operation of the impeller.

For some applications, control console 21 (shown in FIG. 1A), which typically includes a computer processor 25, drives the impeller to rotate. For example, the computer processor may control a motor 74 (shown in FIG. 7), which is disposed within motor unit 23 (shown in FIG. 1A) and which drives the impeller to rotate via a drive cable 130 (shown in FIG. 7). For some applications, the computer processor is configured to detect a physiological parameter of the subject (such as left-ventricular pressure, cardiac afterload, rate of change of left-ventricular pressure, etc.) and to control rotation of the impeller in response thereto, as described in further detail hereinbelow. Typically, the operations described herein that are performed by the computer processor, transform the physical state of a memory, which is a real physical article that is in communication with the computer processor, to have a different magnetic polarity, electrical charge, or the like, depending on the technology of the memory that is used. Computer processor 25 is typically a hardware device programmed with computer program instructions to produce a special-purpose computer. For example, when programmed to perform the techniques described herein, computer processor 25 typically acts as a special-purpose, ventricular-assist computer processor and/or a special-purpose, blood-pump computer processor.

For some applications, a purging system 29 (shown in FIG. 1A) drives a fluid (e.g., a glucose solution) to pass through portions of ventricular assist device 20, for example, in order to cool portions of the device and/or in order to wash debris from portions of the device. Purging system 29 is described in further detail hereinbelow.

Typically, along distal portion 102 of tube 24, a frame 34 is disposed within the tube around impeller 50. The frame is typically made of a shape-memory alloy, such as nitinol. For some applications, the shape-memory alloy of the frame is shape set such that at least a portion of the frame (and thereby distal portion 102 of tube 24) assumes a generally circular, elliptical, or polygonal cross-sectional shape in the absence of any forces being applied to distal portion 102 of tube 24. By assuming its generally circular, elliptical, or polygonal cross-sectional shape, the frame is configured to hold the distal portion of the tube in an open state. Typically, during operation of the ventricular assist device, the distal portion of the tube is configured to be placed within the subject's body, such that the distal portion of the tube is disposed at least partially within the left ventricle.

For some applications, along proximal portion 106 of tube 24, the frame is not disposed within the tube, and the tube is therefore not supported in an open state by frame 34. Tube 24 is typically made of a blood-impermeable collapsible material. For example, tube 24 may include polyurethane, polyester, and/or silicone. Alternatively or additionally, the tube is made of polyethylene terephthalate (PET) and/or polyether block amide (e.g., PEBAX®). For some applications (not shown), the tube is reinforced with a reinforcement structure, e.g., a braided reinforcement structure, such as a braided nitinol tube. Typically, the proximal portion of the tube is configured to be placed such that it is at least partially disposed within the subject's ascending aorta. For some applications, the proximal portion of the tube traverses the subject's aortic valve, passing from the subject's left ventricle into the subject's ascending aorta, as shown in FIG. 1B. As described hereinabove, the tube typically defines one or more blood inlet openings 108 at the distal end of the tube, via which blood flows into the tube from the left ventricle, during operation of the impeller. For some applications, the proximal portion of the tube defines one or more blood outlet openings 109, via which blood flows from the tube into the ascending aorta, during operation of the impeller. Typically, the tube defines a plurality of blood outlet openings 109, for example, between two and eight blood outlet openings (e.g., between two and four blood outlet openings). During operation of the impeller, the pressure of the blood flow through the tube typically maintains the proximal portion of the tube in an open state. For some applications, in the event that, for example, the impeller malfunctions, the proximal portion of the tube is configured to collapse inwardly, in response to pressure outside of the proximal portion of the tube exceeding pressure inside the proximal portion of the tube. In this manner, the proximal portion of the tube acts as a safety valve, preventing retrograde blood flow into the left ventricle from the aorta.

Referring again to FIG. 1C, for some applications, frame 34 is shaped such that the frame defines a proximal conical portion 36, a central cylindrical portion 38, and a distal conical portion 40. Typically, the proximal conical portion is such that the narrow end of the cone is proximal with respect to the wide end of the cone. Further typically, the distal conical portion is such that the narrow end of the cone is distal with respect to the wide end of the cone. For some applications, tube 24 extends to the end of cylindrical portion 38 (or slightly proximal or distal thereof), such that the distal end of the tube defines a single axially-facing blood inlet opening 108, as shown in FIG. 1C. For some applications, within at least a portion of frame 34, an inner lining 39 lines the frame, as described hereinbelow with reference to FIGS. 19A-H. In accordance with respective applications, the inner lining partially overlaps or fully overlaps with tube 24 over the portion of the frame that the inner lining lines. For such applications, the distal end of the inner lining defines a single axially-facing blood inlet opening 108. For some applications (not shown), tube 24 extends to the end of distal conical portion 40, and the tube defines one or more lateral blood inlet openings (not shown), e.g., as described in US 2019/0209758 to Tuval, which is incorporated herein by reference. For such applications, the tube typically defines two to four lateral blood inlet openings.

Typically, tube 24 includes a conical proximal portion 42 and a cylindrical central portion 44. The proximal conical portion is typically such that the narrow end of the cone is proximal with respect to the wide end of the cone. Typically, blood outlet openings 109 are defined by tube 24, such that the openings extend at least partially along the proximal conical section of tube 24. For some such applications, the blood outlet openings are teardrop-shaped, as shown in FIG. 1C. Typically, the teardrop-shaped nature of the blood outlet openings in combination with the openings extending at least partially along the proximal conical section of tube 24 causes blood to flow out of the blood outlet openings along flow lines that are substantially parallel with the longitudinal axis of tube 24 at the location of the blood outlet openings.

As described hereinabove, for some applications (not shown), the tube extends to the end of distal conical portion 40 of frame 34. For such applications, the tube typically defines a distal conical portion, with the narrow end of the cone being distal with respect to the wide end of the cone. For some applications (not shown), the diameter of tube 24 changes along the length of the central portion of the tube, such that the central portion of the tube has a frustoconical shape. For example, the central portion of the tube may widen from its proximal end to is distal end, or may narrow from its proximal end to its distal end. For some applications, at its proximal end, the central portion of the tube has a diameter of between 5 and 7 mm, and at its distal end, the central portion of the tube has a diameter of between 8 and 12 mm.

Again referring to FIG. 1C, the ventricular assist device typically includes a distal-tip element 107 that is disposed distally with respect to frame 34 and that includes an axial-shaft-receiving tube 126 and a distal-tip portion 120, both of which are described in further detail hereinbelow.

Reference is now made to FIGS. 2A, 2B, 2C, 2D, 2E, and 2F, which are schematic illustrations of frame 34 that houses an impeller of ventricular assist device 20, in accordance with some applications of the present invention. As described hereinabove, frame 34 is typically made of a shape-memory alloy, such as nitinol, and the shape-memory alloy of the frame is shape set such that the frame (and thereby tube 24) assumes a generally circular, elliptical, or polygonal cross-sectional shape in the absence of any forces being applied to tube 24. By assuming its generally circular, elliptical, or polygonal cross-sectional shape, the frame is configured to hold the distal portion of the tube in an open state.

Typically, the frame is a stent-like frame, in that it comprises struts that, in turn, define cells. Further typically, the frame is covered with tube 24, and/or covered with an inner lining 39, described hereinbelow, with reference to FIGS. 19A-H. As described hereinbelow, for some applications impeller 50 undergoes axial back-and-forth motion with respect to frame 34. Typically over the course of the motion of the impeller with respect to the frame the location of the portion of the impeller that defines the maximum span of the impeller is disposed within cylindrical portion 38 of frame 34. In some cases, if the cells of the cylindrical portion 38 of frame 34 are too large, then tube 24, and/or inner lining 39 gets stretched between edges of the cells, such that the tube 24, and/or inner lining 39 does not define a circular cross-section. For some applications, if this occurs in the region in which the portion of the impeller that defines the maximum span of the impeller is disposed, this results in a non-constant gap between the edges of the impeller blades and tube 24 (and/or inner lining) at that location, over the course of a rotation cycle of the impeller. For some applications, this may lead to increased hemolysis relative to if there were a constant gap between the edges of the impeller blades and tube 24 (and/or inner lining) at that location, over the course of the rotation cycle of the impeller.

Referring to FIG. 2A, at least partially in view of the issues described in the above paragraph, within cylindrical portion 38 of frame 34, the frame defines a large number of relatively small cells. Typically, when the frame is disposed in its non-radially-constrained configuration, the maximum cell width CW of the each of the cells (i.e., the distance from the inner edge of the strut at the central junction on one side of the cell to the inner edge of the strut at the central junction on the other side of the cell, as measured around the circumference of cylindrical portion 38) within the cylindrical portion of the frame is less than 2 mm, e.g., between 1.4 mm and 1.6 mm, or between 1.6 and 1.8 mm. Since the cells are relatively small, the tube 24 (and/or inner lining) defines a substantially circular cross-section within the cylindrical portion of the frame.

Still referring to FIG. 2A, and starting from the proximal end of the frame (which is to the left of the figure), typically the frame defines the following portions (a) coupling portion 31 via which the frame is coupled to a proximal bearing 116 (shown in FIG. 4) of the ventricular assist device, (b) proximal conical portion 36, (c) cylindrical portion 38, (d) distal conical portion 40, and (e) distal strut junctions 33. As illustrated, as the frame transitions from a proximal end of the frame toward the center of the frame (e.g., as the frame transitions through coupling portion 31, through proximal conical portion 36, and to cylindrical portion 38), struts 37 of the frame pass through junctions 35, at which the two struts branch from a single strut, in a Y-shape. As described in further detail hereinbelow, typically frame 34 is placed in a radially-constrained (i.e., crimped) configuration within delivery catheter 143 by the frame being axially elongated. Moreover, the frame typically transmits its radial narrowing to the impeller, and the impeller becomes radially constrained by becoming axially elongated within the frame. For some applications, the struts of the frame being configured in the manner described above facilitates transmission of axial elongation from the delivery catheter (or other device that is configured to crimp the frame) to the frame, which in turn facilitates transmission of axial elongation to the impeller. This is because the pairs of struts that branch from each of junctions 35 are configured to pivot about the junction and move closer to each other such as to close.

Still referring to FIG. 2A, for some applications distal strut junctions 33 are maintained in open states when the frame is coupled to axial shaft 92 (shown in FIG. 2D), in order for the impeller to be placed within the frame via the distal end of the frame. Subsequently, the distal strut portions are closed around the outside of a distal bearing 118, as described in further detail hereinbelow with reference to FIGS. 5A-B. For some applications, a proximal end of distal-tip element 107 (shown in FIG. 1C) holds the distal strut portions in their closed configurations around the outside of distal bearing 118.

Typically, when disposed in its non-radially constrained configuration, frame 34 has a total length of more than 25 mm (e.g., more than 30 mm), and/or less than 50 mm (e.g., less than 45 mm), e.g., 25-50 mm, or 30-45 mm. Typically, when disposed in its radially-constrained configuration (within delivery catheter 143), the length of the frame increases by between 2 and 5 mm. Typically, when disposed in its non-radially constrained configuration, the cylindrical portion of frame 34 has a length of more than 10 mm (e.g., more than 12 mm), and/or less than 25 mm (e.g., less than 20 mm), e.g., 10-25 mm, or 12-20 mm. For some applications, a ratio of the length of the cylindrical portion of the frame to the total length of the frame is more than 1:4 and/or less than 1:2, e.g., between 1:4 and 1:2.

Reference is now made to FIG. 2B, which is a schematic illustration of a pump portion of ventricular assist device 20, at least a portion of cylindrical portion 38 of frame 34 of the ventricular assist device having a helical structure 55, in accordance with some applications of the present invention. For some applications, at least a portion of cylindrical portion 38 of frame 34 of the ventricular assist device has a helical structure 55, in order for the tube 24 (and/or inner lining) to define a substantially circular cross-section within the cylindrical portion of the frame, e.g., for the reasons provided hereinabove.

Figure 2C:
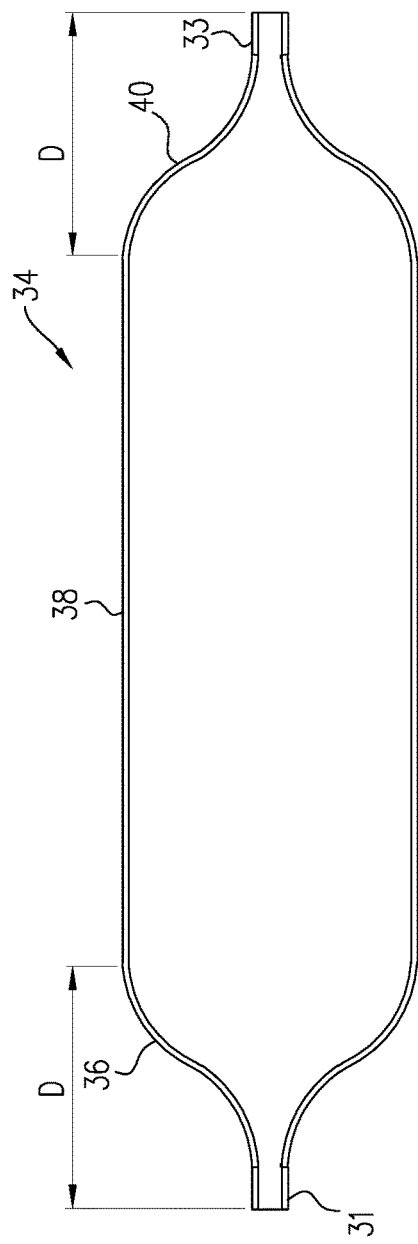

Reference is now made to FIG. 2C, which is a schematic illustration of frame 34, the frame transitioning from its ends to its maximum diameter (i.e., the cylindrical portion of the frame) over a relatively short distance D. Typically, this results in the ratio of the cylindrical portion of the frame to the total length of the frame being greater than that described hereinabove. For example, the ratio of the cylindrical portion of the frame to the total length of the frame may be more than 1:2 or more than 2:3. Further typically, this results in the angle at which the frame widens within the conical portion being greater than if the cylindrical portion has a shorter relative length, ceteris paribus. For some applications, in turn, this reduces vibration of the frame during rotation of the impeller. As described hereinabove, in order to reduce hemolysis, it is typically desirable to maintain a constant gap between the edges of the impeller blades and tube 24 (and/or inner lining 39). Therefore, it is typically desirable to reduce vibration of the frame with respect to the impeller.

Figure 2D:
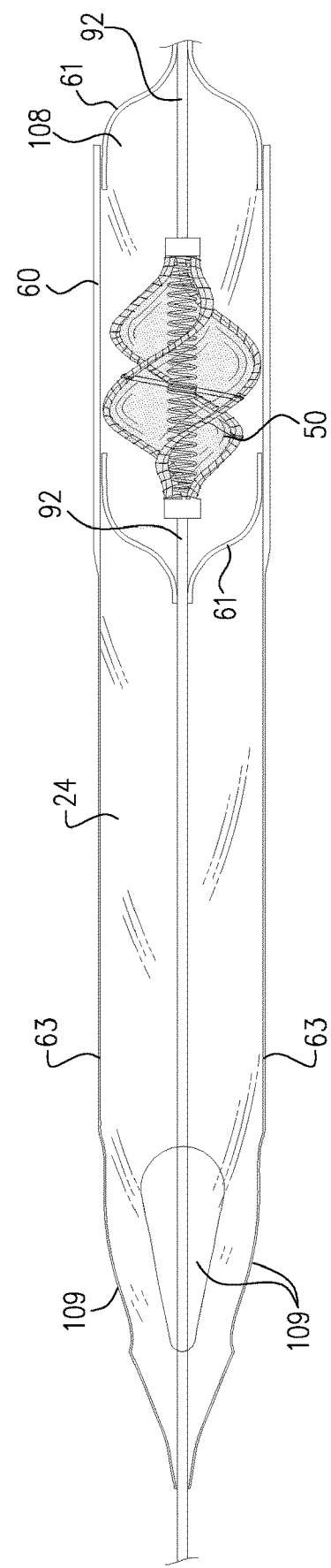

Reference is now made to FIG. 2D, which is a schematic illustration of a pump portion of a ventricular assist device that includes an inflatable impeller housing 60, in accordance with some applications of the present invention. For some applications, rather than having frame 34 surrounding the impeller, the inflatable housing surrounds the impeller. For some applications, at least in the region of the housing that surrounds the impeller, the frame is configured to define an inner circular cross-section, such that there is a constant gap between the edges of the impeller blades and the inner wall of the housing, over the course of the rotation cycle of the impeller.

Typically, for applications as shown in FIG. 2D, proximal and distal bearing frames 61 are disposed inside the inflatable impeller housing. The bearing frames are configured to act as radial bearings with respect to axial shaft 92 (described hereinbelow) to which impeller 50 is coupled. For some applications, the impeller housing is made of a flexible and inflatable material. The impeller housing is typically inserted into the left ventricle in a deflated state, and is inflated once disposed inside the left ventricle, such as to assume its deployed shape. Tube 24 typically extends proximally from the inflatable impeller housing. For some applications, tubes 63 pass along tube 24 (e.g., an inner surface or an outer surface of the tube), and the inflatable housing is inflated via the tubes. For some applications, the impeller housing is inflated with saline and/or a different solution (e.g., a glucose solution). For some applications, the inflatable impeller housing defines one or more blood inlet openings 108.

Figure 2E:
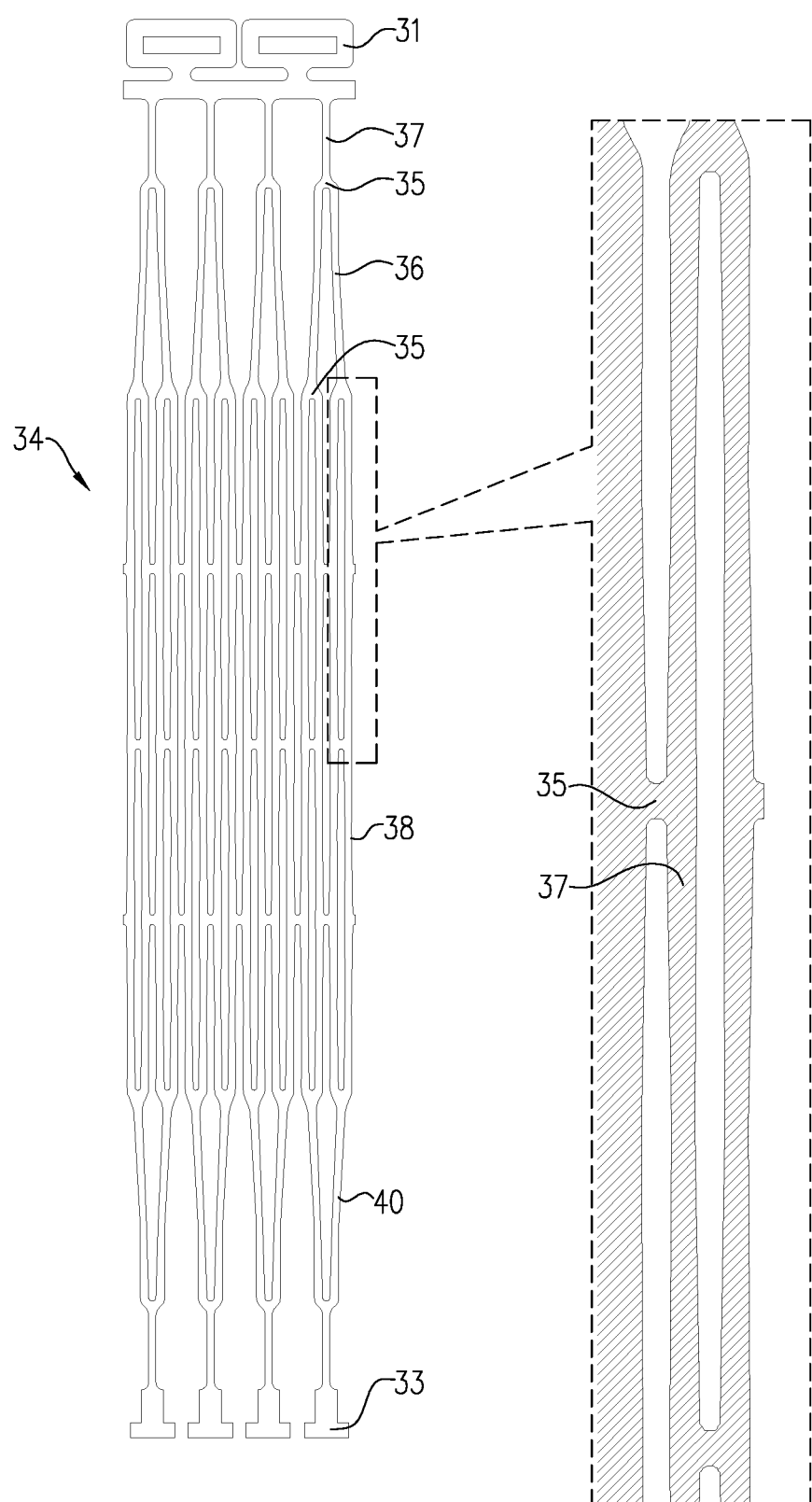
Figure 2F:
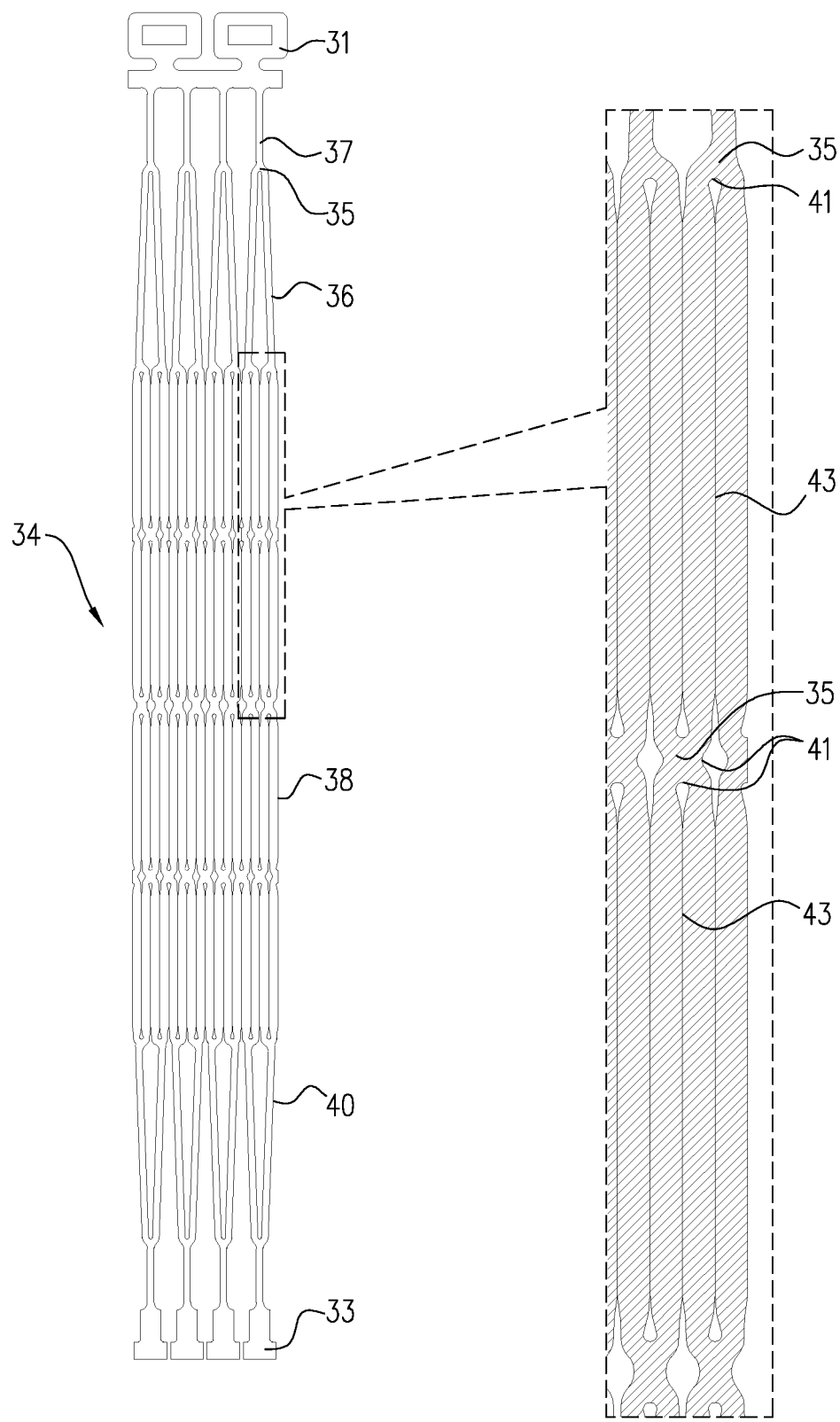

Reference is now made to FIGS. 2E and 2F, which are schematic illustrations of flattened profiles of frame 34, the frame being generally configured as shown in FIG. 2A, in accordance with some applications of the present invention. Frame 34 is typically laser cut from a tube of a shape memory alloy, such as nitinol. The profiles shown in FIGS. 2E and 2F depict (for illustrative purposes) how the frame of the device would appear if, prior to shape setting the frame, a longitudinal incision were to be made along the length of the frame at a given circumferential location of the frame, and the frame were to then be laid out flat upon a surface. For some applications, within cylindrical portion 38 of the frame, the cells are cut by passing a laser along the outlines of the perimeter of the cells, as indicated by the enlarged portion of FIG. 2E. As described hereinabove, typically, within the cylindrical portion the cells are relatively small, which means that a relatively large number of cells are cut within the circumference of the frame. Due to the size of the laser that is used for cutting the cells, it can be challenging passing the laser around the full perimeter of the cells. However, in the vicinity of the junctions it is desirable for the cells to be rounded, in order to reduce strain at the junctions. Therefore, for some applications, the cylindrical portion of the frame is cut as generally shown in FIG. 2F. Namely, at junctions 35, the laser cuts rounded edges 41. However, between the junctions, the laser cuts a single slit 43, rather than cutting around the perimeter of the cell.

Figure 3A:
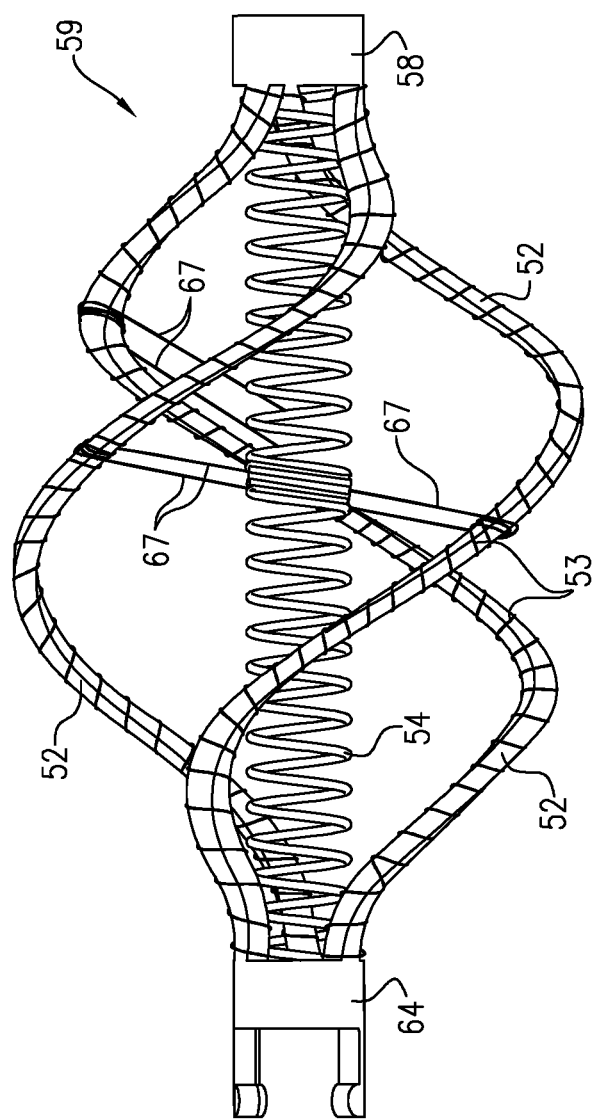
FIGS. 3A, 3B, 3C, 3D, 3E, 3F, 3G, 3H, 3I, 3J, and 3K are schematic illustrations of an impeller of a ventricular assist device or a portion thereof, in accordance with some applications of the present invention.
Figures 3B, 3C:
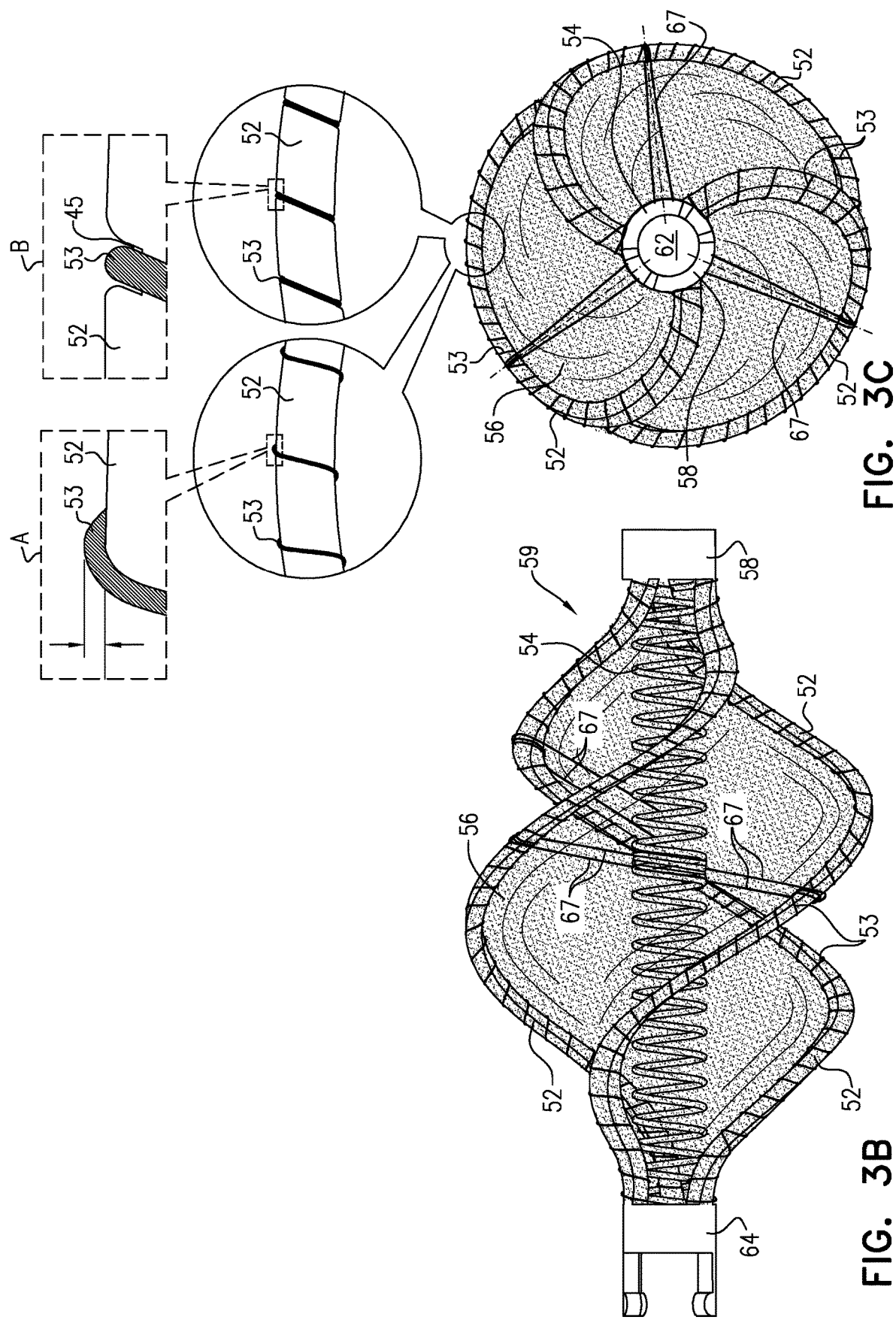

Reference is now made to FIGS. 3A-C, which are schematic illustrations of impeller 50 or portions thereof, in accordance with some applications of the present invention. Typically, the impeller includes at least one outer helical elongate element 52, which winds around a central axial spring 54, such that the helix defined by the helical elongate element is coaxial with the central axial spring. Typically, the impeller includes two or more helical elongate elements (e.g., three helical elongate elements, as shown in FIGS. 3A-C). For some applications, the helical elongate elements and the central axial spring are made of a shape-memory material, e.g., a shape-memory alloy such as nitinol. Typically, each of the helical elongate elements and the central axial spring support a film 56 of a material (e.g., an elastomer, such as polyurethane, and/or silicone) therebetween. For some applications, the film of material includes pieces of nitinol embedded therein, for example in order to strengthen the film of material. For illustrative purposes, the impeller is shown in the absence of the material in FIG. 3A. FIGS. 3B and 3C show respective views of the impeller with the material supported between the helical elongate elements and the spring.

Each of the helical elongate elements, together with the film extending from the helical elongate element to the spring, defines a respective impeller blade, with the helical elongate elements defining the outer edges of the blades, and the axial spring defining the axis of the impeller. Typically, the film of material extends along and coats the spring. For some applications, sutures 53 (e.g., polyester sutures, shown in FIGS. 3B and 3C) are wound around the helical elongate elements, e.g., as described in US 2016/0022890 to Schwammenthal, which is incorporated herein by reference. Typically, the sutures are configured to facilitate bonding between the film of material (which is typically an elastomer, such as polyurethane, or silicone) and the helical elongate element (which is typically a shape-memory alloy, such as nitinol). For some applications, sutures (e.g., polyester sutures, not shown) are wound around spring 54. Typically, the sutures are configured to facilitate bonding between the film of material (which is typically an elastomer, such as polyurethane, or silicone) and the spring (which is typically a shape-memory alloy, such as nitinol).

Enlargements A and B of FIG. 3C show two alternative ways in which the sutures are tied around helical elongate elements 52. For some applications, the sutures are tied around the outer surface of the helical elongate elements, as shown in enlargement A. Alternatively, the helical elongate elements define grooves 45 on their outer surfaces, and the sutures are embedded within the grooves, as shown in enlargement B. By embedding the sutures within the grooves, the sutures typically do not add to the outer profile of the impeller, and the outer profile of the impeller is defined by the outer surfaces of the helical elongate elements.

Typically, proximal ends of spring 54 and helical elongate elements 52 extend from a proximal bushing (i.e., sleeve bearing) 64 of the impeller, such that the proximal ends of spring 54 and helical elongate elements 52 are disposed at a similar radial distance from the longitudinal axis of the impeller, as each other. Similarly, typically, distal ends of spring 54 and helical elongate elements 52 extend from a distal bushing 58 of the impeller, such that the distal ends of spring 54 and helical elongate elements 52 are disposed at a similar radial distance from the longitudinal axis of the impeller, as each other. Typically, spring 54, as well as proximal bushing 64 and distal bushing 58 of the impeller, define a lumen 62 therethrough (shown in FIG. 3C).

Figure 4:
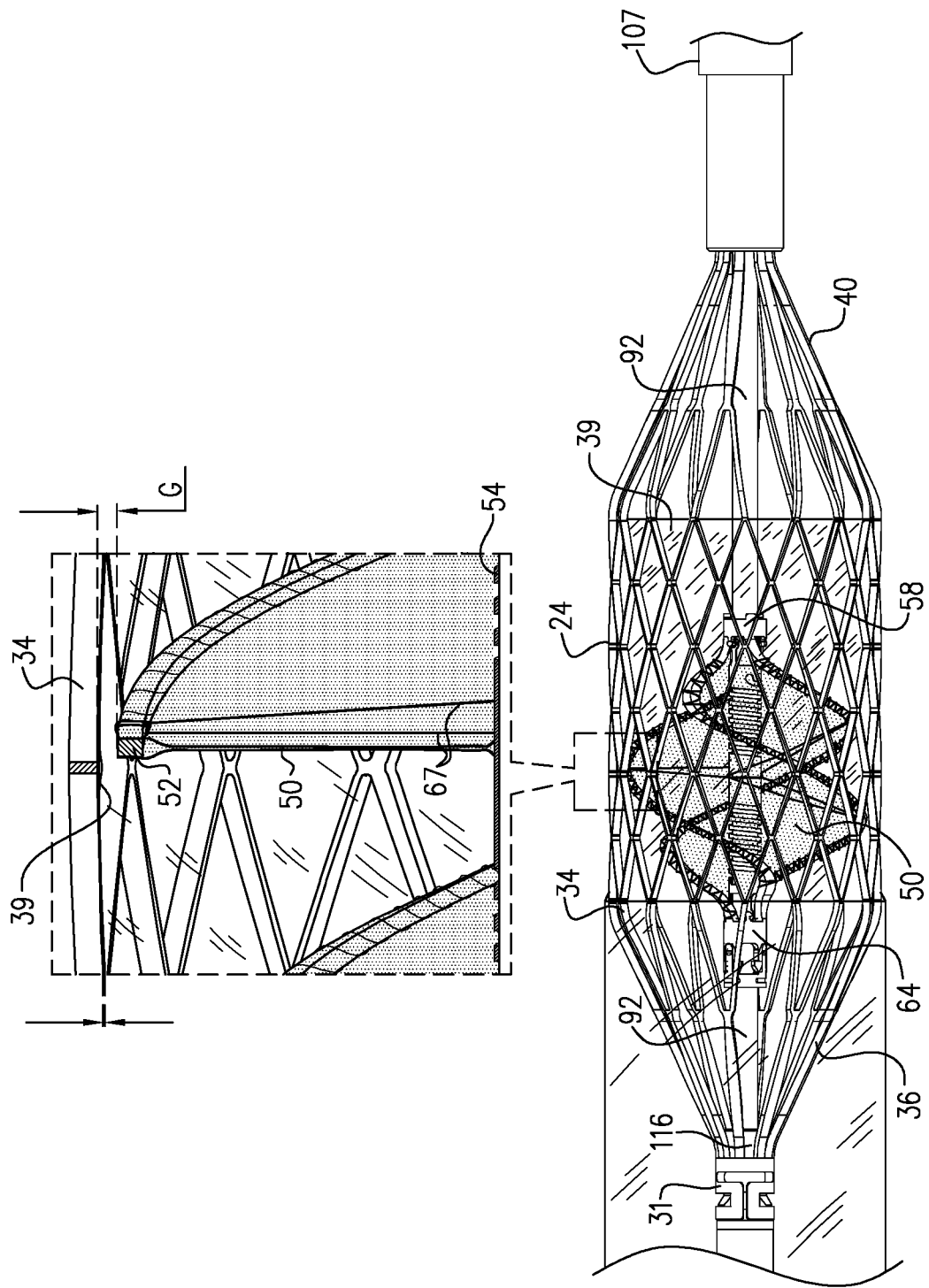
FIG. 4 is a schematic illustration of an impeller disposed inside a frame of a ventricular assist device, in accordance with some applications of the present invention.

Reference is now made to FIG. 4, which is a schematic illustration of impeller 50 disposed inside frame 34 of ventricular assist device 20, in accordance with some applications of the present invention. For some applications, within at least a portion of frame 34, an inner lining 39 lines the frame, as described hereinbelow with reference to FIGS. 19A-H. In accordance with respective applications, the inner lining partially overlaps or fully overlaps with tube 24 over the portion of the frame that the inner lining lines. In the application shown in FIG. 4, the inner lining lines the inside of the cylindrical portion of the frame and tube 24 does not cover the cylindrical portion of the frame. However, the scope of the present application includes applying the apparatus and methods described with reference to FIG. 4 to any one of the applications described hereinbelow with reference to FIGS. 19A-H.

As shown in FIG. 4, typically there is a gap G, between the outer edge of impeller 50 and inner lining 39, even at a location at which the span of the impeller is at its maximum. For some applications, it is desirable that the gap between the outer edge of the blade of the impeller and the inner lining 39 be relatively small, in order for the impeller to efficiently pump blood from the subject's left ventricle into the subject's aorta. However, it is also desirable that a gap between the outer edge of the blade of the impeller and the inner surface of frame 34 be maintained substantially constant throughout the rotation of the impeller within frame 34, for example, in order to reduce the risk of hemolysis.

For some applications, when the impeller and frame 34 are both disposed in non-radially-constrained configurations, gap G between the outer edge of the impeller and the inner lining 39, at the location at which the span of the impeller is at its maximum, is greater than 0.05 mm (e.g., greater than 0.1 mm), and/or less than 1 mm (e.g., less than 0.4 mm), e.g., 0.05-1 mm, or 0.1-0.4 mm. For some applications, when the impeller is disposed in its non-radially-constrained configurations, the outer diameter of the impeller at the location at which the outer diameter of the impeller is at its maximum is more than 7 mm (e.g., more than 8 mm), and/or less than 10 mm (e.g., less than 9 mm), e.g., 7-10 mm, or 8-9 mm. For some applications, when frame 34 is disposed in its non-radially-constrained configuration, the inner diameter of frame 34 (as measured from the inside of inner lining 39 on one side of the frame to the inside of inner lining on the opposite side of the frame) is greater than 7.5 mm (e.g., greater than 8.5 mm), and/or less than 10.5 mm (e.g., less than 9.5 mm), e.g., 7.5-10.5 mm, or 8.5-9.5 mm. For some applications, when the frame is disposed in its non-radially-constrained configuration, the outer diameter of frame 34 is greater than 8 mm (e.g., greater than 9 mm), and/or less than 13 mm (e.g., less than 12 mm), e.g., 8-13 mm, or 9-12 mm.

Typically, an axial shaft 92 passes through the axis of impeller 50, via lumen 62 of the impeller. Further typically, the axial shaft is rigid, e.g., a rigid tube. For some applications, proximal bushing 64 of the impeller is coupled to the shaft such that the axial position of the proximal bushing with respect to the shaft is fixed, and distal bushing 58 of the impeller is slidable with respect to the shaft. The axial shaft itself is radially stabilized via a proximal radial bearing 116 and a distal radial bearing 118. In turn, the axial shaft, by passing through lumen 62 defined by the impeller, radially stabilizes the impeller with respect to the inner surface of frame 34, such that even a relatively small gap between the outer edge of the blade of the impeller and the inner surface of frame 34 (e.g., a gap that is as described above) is maintained, during rotation of the impeller.

Referring again to FIGS. 3A-C, for some applications, the impeller includes a plurality of elongate elements 67 extending radially from central axial spring 54 to outer helical elongate elements 52. The elongate elements are typically flexible but are substantially non-stretchable along the axis defined by the elongate elements. Further typically, each of the elongate elements is configured not to exert force upon the helical elongate element, unless force is acting upon the impeller that is causing the helical elongate element to move radially outward, such that (in the absence of the elongate element) a separation between the helical elongate element and the central axial spring would be greater than a length of the elongate element. For example, the elongate elements may include strings (such as polyester, and/or another polymer or a natural material that contains fibers) and/or wires (such as nitinol wires, and/or wires made of a different alloy, or a metal).

For some applications, the elongate elements 67 maintain the helical elongate element (which defines the outer edge of the impeller blade) within a given distance with respect to the central axial spring. In this manner, the elongate elements are configured to prevent the outer edge of the impeller from being forced radially outward due to forces exerted upon the impeller during the rotation of the impeller. The elongate elements are thereby configured to maintain the gap between the outer edge of the blade of the impeller and the inner surface of frame 34, during rotation of the impeller. Typically, more than one (e.g., more than two) and/or fewer than eight (e.g., fewer than four) elongate elements 67 are used in the impeller, with each of the elongate elements typically being doubled (i.e., extending radially from central axial spring 54 to an outer helical elongate element 52, and then returning from the helical elongate element back to the central axial spring). For some applications, a plurality of elongate elements, each of which extends from the spring to a respective helical elongate element and back to the spring, are formed from a single piece of string or a single wire, as described in further detail hereinbelow.

For some applications, the impeller is manufactured in the following manner. Proximal bushing 64, distal bushing 58, and helical elongate elements 52 are cut from a tube of shape-memory material, such as nitinol. The cutting of the tube, as well as the shape setting of the shape-memory material, is typically performed such that the helical elongate elements are defined by the shape-memory material, e.g., using generally similar techniques to those described in US 2016/0022890 to Schwammenthal. Typically, spring 54 is inserted into the cut and shape-set tube, such that the spring extends along the length of the tube from at least the proximal bushing to the distal bushing. For some applications, the spring is inserted into the cut and shape-set tube while the spring is in an axially compressed state, and the spring is configured to be held in position with respect to the tube, by exerting a radial force upon the proximal and distal bushings. Alternatively or additionally, portions of the spring are welded to the proximal and distal bushings. For some applications, the spring is cut from a tube of a shape-memory material, such as nitinol. For some such applications, the spring is configured such that, when the spring is disposed in a non-radially-constrained configuration (in which the spring is typically disposed during operation of the impeller), there are substantially no gaps between windings of the spring and adjacent windings thereto.

For some applications, subsequent to spring 54 being inserted into the cut and shape-set tube, elongate elements 67, as described hereinabove, are placed such as to extend between the spring and one or more of the helical elongate elements, for example, in the following manner. A mandrel (e.g., a polyether ether ketone (PEEK) and/or a polytetrafluoroethylene (PTFE) mandrel) is inserted through the lumen defined by the spring and the bushings. A string or a wire is then threaded such that it passes (a) from the mandrel to a first one of the helical elongate elements, (b) back from the first of the helical elongate elements to the mandrel, (c) around the mandrel, and to a second one of the helical elongate elements, (d) back from the second one of the helical elongate elements to the mandrel, etc. Once the string or the wire has been threaded from the mandrel to each of the helical elongate elements and back again, the ends of the string or the wire are coupled to each other, e.g., by tying them to each other. For some applications, sutures 53 (e.g., polyester sutures) are wound around the helical elongate elements, in order to facilitate bonding between the film of material (which is typically an elastomer, such as polyurethane, or silicone) and the helical elongate elements (which is typically a shape-memory alloy, such as nitinol), in a subsequent stage of the manufacture of the impeller. For some applications, sutures (e.g., polyester sutures, not shown) are wound around spring 54. Typically, the sutures are configured to facilitate bonding between the film of material (which is typically an elastomer, such as polyurethane, or silicone) and the spring (which is typically a shape-memory alloy, such as nitinol), in the subsequent stage of the manufacture of the impeller.

Typically, at this stage, a structure 59 has been assembled that is as shown in FIG. 3A. The structure includes the cut and shape-set tube that defines the proximal and distal bushings, the helical elongate elements, and the spring (and, optionally, the elongate elements, and the sutures). This structure is dipped into the material that defines film 56. For some applications, the assembled structure is dipped into the material with the mandrel disposed through the lumen defined by the spring and the bushings, although it is noted that the mandrel is not shown in FIG. 3A. Typically, the material from which the film is made is silicone and/or polyurethane (and/or a similar elastomer), and the assembled structure is dipped into the material, while the material is in an uncured, liquid state. Subsequently, the material is cured such that it solidifies, e.g., by being left to dry. Once the material has dried, the mandrel is typically removed from the lumen defined by the bushings and the spring.

The result of the process described above is typically that there is a continuous film of material extending between each of the helical elongate elements to the spring, and also extending along the length of the spring, such as to define a tube, with the spring embedded within the tube. The portions of the film that extend from each of the helical elongate elements to the spring define the impeller blades. For applications in which the impeller includes elongate elements 67, the elongate elements are typically embedded within these portions of film.

Typically, impeller 50 is inserted into the left ventricle transcatheterally, while impeller 50 is in a radially-constrained configuration. In the radially-constrained configuration, both helical elongate elements 52 and central axial spring 54 become axially elongated, and radially constrained. Typically film 56 of the material (e.g., silicone and/or polyurethane) changes shape to conform to the shape changes of the helical elongate elements and the axial support spring, both of which support the film of material. Typically, using a spring to support the inner edge of the film allows the film to change shape without the film becoming broken or collapsing, due to the spring providing a large surface area to which the inner edge of the film bonds. For some applications, using a spring to support the inner edge of the film reduces a diameter to which the impeller can be radially constrained, relative to if, for example, a rigid shaft were to be used to support the inner edge of the film, since the diameter of the spring itself can be reduced by axially elongating the spring.

As described hereinabove, for some applications, proximal bushing 64 of impeller 50 is coupled to axial shaft 92 such that the axial position of the proximal bushing with respect to the shaft is fixed, and distal bushing 58 of the impeller is slidable with respect to the shaft. For some applications, when the impeller is radially constrained for the purpose of inserting the impeller into the ventricle or for the purpose of withdrawing the impeller from the subject's body, the impeller axially elongates by the distal bushing sliding along the axial shaft distally. Subsequent to being released inside the subject's body, the impeller assumes its non-radially-constrained configuration (in which the impeller is typically disposed during operation of the impeller), as shown in FIGS. 3A-C.

It is noted that, for illustrative purposes, in some of the figures, impeller 50 is shown without including all of the features of the impeller as shown and described with respect to FIGS. 3A-C. For example, some of the figures show the impeller not including sutures 53 and/or elongate elements 67. The scope of the present application includes using an impeller with any of the features shown and described with respect to FIGS. 3A-C in combination with any of the apparatus and methods described herein.

Figure 3D:
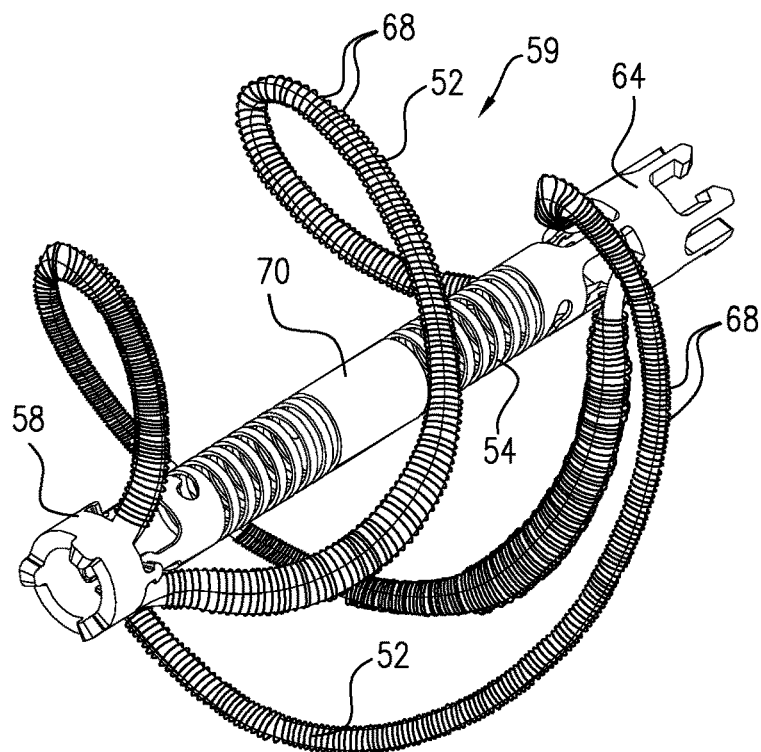
Figure 3E:
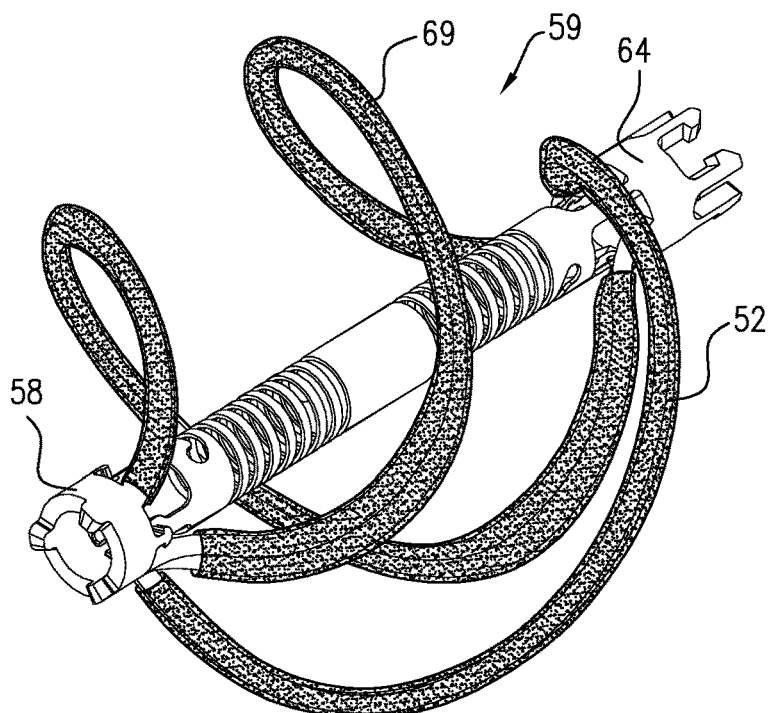
Figure 3F:
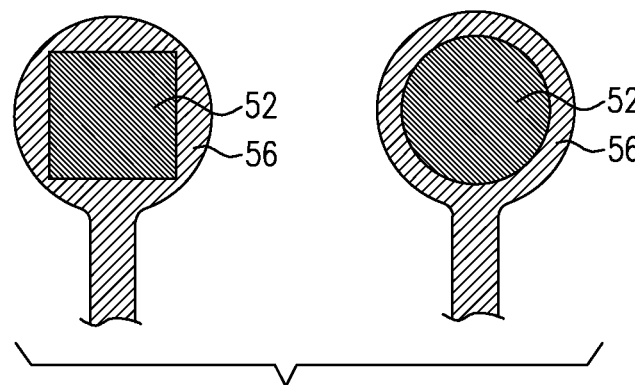

Reference is now made to FIGS. 3D, 3E, and 3F, which are schematic illustration of impeller 50 or portions thereof, in accordance with some applications of the present invention. As described hereinabove, for some applications, impeller 50 includes sutures 53. Sutures 53 are wound around the helical elongate elements 52 and are configured to facilitate bonding between the film of material (which is typically an elastomer, such as polyurethane, or silicone) and the helical elongate element (which is typically a shape-memory alloy, such as nitinol).

As an alternative or in addition to sutures 53, for some applications, coils 68 are wound around (or placed over) the helical elongate elements, as shown in FIG. 3D. For example, a tightly-wound coil (e.g., a tightly-wound nitinol coil) may be wound around (or placed around) each of the helical elongate elements. The coil typically facilitates bonding between the film of material and the helical elongate element by increasing the surface area to which the material bonds at the interface between the material and the helical elongate element. For some applications, structure 59 is formed modularly (e.g., as described hereinbelow with reference to FIG. 3F.) For some such applications, the coils are placed around each of the elongate elements 52 (e.g., by sliding the entire coil over the elongate element in a single action), prior to the elongate elements being coupled to the proximal and distal bushings of the impeller.

As a further alternative to or in addition to sutures 53, for some applications, sleeves 69 are placed around the helical elongate elements, as shown in FIG. 3E. For example, such sleeves may be made of a polymer, such as polyester. The sleeves typically facilitate bonding between the film of material and the helical elongate elements by increasing the surface area to which the material bonds at the interfaces between the material and the helical elongate elements. For some applications, the sleeve acts as a mediator between a material from which the elongate elements are made, which typically has a relatively high stiffness (and is typically nitinol), and the material from which film 56 is made, which is typically an elastomer having a relatively low stiffness. The sleeve thereby enhances the strength of the coupling between the material and the helical elongate elements, when the material dries. For some applications, sleeves 69 are applied to structure 59. For some such applications, longitudinal slits are formed in the sleeves in order to allow the sleeves to be placed around the helical elongate elements 52. Subsequent to being placed around helical elongate elements 52 the slits are closed (e.g., by suturing or adhering the slits closed). For some applications, structure 59 is formed modularly (e.g., as described hereinbelow with reference to FIG. 3F.) For some such applications, the sleeves are placed around elongate elements 52, prior to the elongate elements being coupled to the proximal and distal bushings of the impeller.

As yet a further alternative to or in addition to sutures 53, for some applications, elongate elements 52 are shaped to have a rounded (e.g., a circular) cross section, as shown in the right portion of FIG. 3F (which shows a cross-sectional view of an elongate element having a rounded cross-section). The left portion of FIG. 3F shows a cross-sectional view of elongate element 52 with material of film 56 coupled to the elongate element, in a case in which the elongate element has a non-rounded cross section (e.g., a square or a rectangular cross section). As shown, it is sometimes the case that the material (e.g., the silicone and/or the polyurethane) from which the film is made forms a thinner layer at the corners of an elongate element having a non-rounded cross-section. By contrast as shown in the left portion of FIG. 3F, when the elongate element has a rounded cross section, the material typically forms a layer having a substantially uniform thickness at the interface with the elongate element. Therefore, for some applications, the elongate elements have rounded cross sections.

For some applications, proximal and distal bushings 64, 58 and elongate elements 52 are cut from an alloy tube, e.g., as described hereinabove. For such applications, after the tube is cut, the elongate elements typically have non-rounded edges. Therefore for some applications, subsequent to the tube being cut, the edges of the elongate elements are rounded, for example, using grinding, sandblasting, tumble finishing, etching, plasma, surface-charging, and/or by adding rounded edges to the elongate elements. Alternatively, the proximal and distal bushings and the elongate elements may be formed in a modular manner, and may subsequently be coupled to each other (e.g., via welding, and/or swaging). For some such applications, the elongate elements that are coupled to the proximal and distal bushings have rounded cross sections. As described hereinabove with reference to FIG. 3E, for some applications, sleeves 69 are placed on the elongate elements prior to the elongate elements being coupled to the proximal bushing and/or prior to the elongate elements being coupled to the distal bushing.

For some applications, alternative or additional techniques are used to facilitate bonding between the film of material and the helical elongate elements. For example, the helical elongate elements may be treated using a surface treatment (such as, grinding, sandblasting, tumble finishing, etching, plasma, surface-charging, etc.), in order to roughen the outer surface of the helical elongate elements.

In accordance with the above description of FIGS. 3A-F, for some applications of the present invention, impeller 50 is manufactured by forming a structure having first and second bushings 64, 58 at proximal and distal ends of the structure, the first and second bushings being connected to one another by at least one elongate element 52. The at least one elongate element is made to radially expand and form at least one helical elongate element, at least partially by axially compressing the structure. An elastomeric material is coupled to the at least one helical elongate element, such that the at least one helical elongate element with the elastomeric material coupled thereto defines a blade of the impeller. Typically, the coupling is performed such that a layer of the material is disposed around a radially outer edge of the at least one helical elongate element, the layer of material forming the effective edge of the impeller blade (i.e., the edge at which the impeller's blood-pumping functionality substantially ceases to be effective). Further typically, the method includes performing a step to enhance bonding of the elastomeric material to the at least one helical elongate element in a manner that does not cause a protrusion from the effective edge of the impeller blade. For example, sutures 53 may be placed within grooves defined by the at least one helical elongate element, such that the sutures do not protrude from the radially outer edge of the helical elongate element, the sutures being configured to enhance bonding of the elastomeric material to the at least one helical elongate element. Alternatively or additionally, tightly-wound coil 68 may be placed around the at least one helical elongate element, such that the elastomeric material forms a substantially smooth layer along a radially outer edge of the coil, the coil being configured to enhance bonding of the elastomeric material to the at least one helical elongate element. Further alternatively or additionally, sleeve 69 may be placed around the at least one helical elongate element, such that the elastomeric material forms a substantially smooth layer along a radially outer edge of the sleeve, the sleeve being configured to enhance bonding of the elastomeric material to the at least one helical elongate element. For some applications, a rounded cross section is provided to the at least one helical elongate element, such that the elastomeric material forms a layer having a substantially uniform thickness at an interface of the elastomeric material with the helical elongate element. As noted hereinabove, it is typically desirable that gap G between the outer edge of the blade of the impeller and the inner lining 39 (shown in FIG. 4) be relatively small. Therefore, it is desirable that there be no protrusion from the effective edge of the impeller blade, since this would occupy some of the gap between the outer edge of the impeller blade (thereby requiring a larger gap), without increasing the effectiveness of the blood-pumping functionality of the impeller.

Figure 3G:
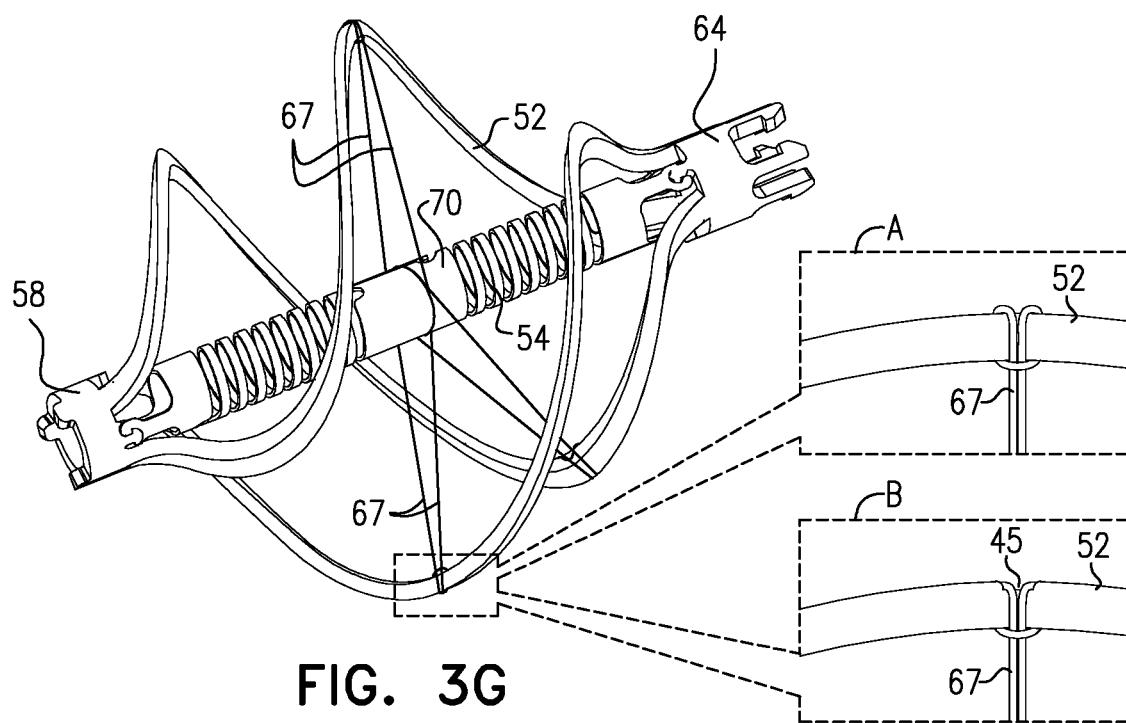
Figure 3H:
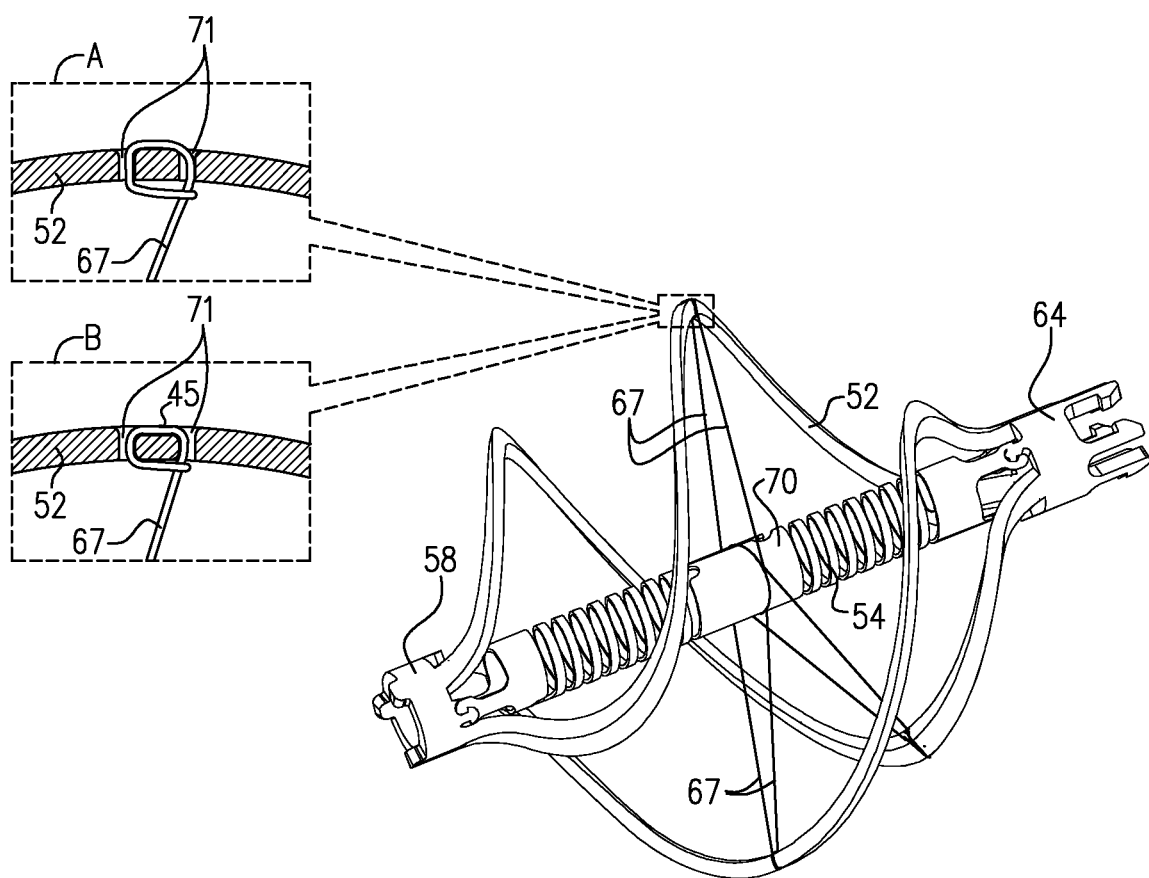

Reference is now made to FIGS. 3G and 3H, which are schematic illustrations of elongate elements 67 extending between each of the helical elongate elements 52 and spring 54, in accordance with some applications of the present invention. For some applications, a respective looped elongate element 67 extends between each of the helical elongate elements and the spring. Typically, the looped elongate elements are closed loops that have predefined lengths and are (substantially) non-stretchable. The lengths of the looped elongate elements are typically predefined, such as to maintain the helical elongate element (which defines the outer edge of the impeller blade) within a given distance with respect to the central axial spring, and to thereby maintain the gap between the outer edge of the blade of the impeller and the inner surface of frame 34, during rotation of the impeller, as described hereinabove. For some applications, the impeller is formed by looping first ends of the looped elongate elements around each of the helical elongate elements as indicated in the enlarged portions of FIGS. 3G and 3H. Subsequently, spring 54 is inserted through proximal and distal bushings 64, 58, and through second ends of the looped helical elongate elements.

For some applications, at a longitudinally-central location of spring 54, the spring is shaped to define a tube 70 (i.e., without windings), as shown in FIGS. 3G and 3H. Typically, the second ends of the looped elongate elements loop around the tube at the longitudinally-central location of the spring. Typically, this reduces a risk of the looped elongate elements tearing, relative to if the second ends of the looped elongate elements were to loop around windings of the spring. For some applications (not shown), the tube defines a groove therein and the second ends of the looped elongate elements are configured to be held within the groove.

For some applications, the looped elongate element is looped around the body of the helical elongate element, as shown in the enlarged portions of FIG. 3G. Enlargements A and B of FIG. 3G show two alternative ways in which the looped elongate element is looped around the body of the helical elongate element. For some applications, looped elongate element is looped around the outer surface of the helical elongate element, as shown in enlargement A. Alternatively, the helical elongate elements define grooves 45 on their outer surfaces, and the looped elongate element is looped around a groove 45 (such as to become embedded within the groove), as shown in enlargement B. By embedding the looped elongate element within the grooves, the looped elongate element typically does not add to the outer profile of the impeller, and the outer profile of the impeller is defined by the outer surfaces of the helical elongate elements.

For some applications, the helical elongate element is shaped to define two holes 71 disposed in close proximity to each other, and the looped elongate element may be looped through the holes, as shown in the enlarged portions of FIG. 3H. Enlargements A and B of FIG. 3H show two alternative ways in which the looped elongate element is looped through holes 71. For some applications, the looped elongate element is looped around the outer surface of the helical elongate element and through holes 71, as shown in enlargement A. Alternatively, the helical elongate elements define grooves 45 on their outer surfaces, and the looped elongate element is looped around groove 45 and through holes 71 (such as to become embedded within the groove), as shown in enlargement B. By embedding the looped elongate element within the grooves, the looped elongate element typically does not add to the outer profile of the impeller, and the outer profile of the impeller is defined by the outer surfaces of the helical elongate elements.

Figure 3I:
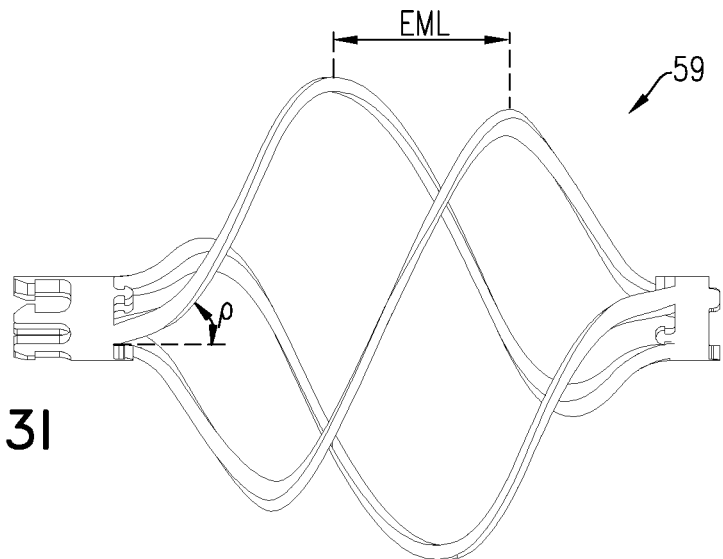
Figure 3J:
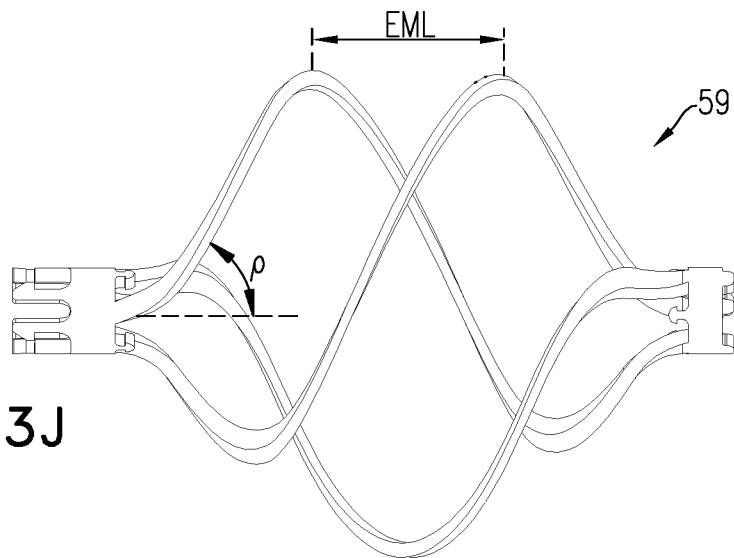
Figure 3K:
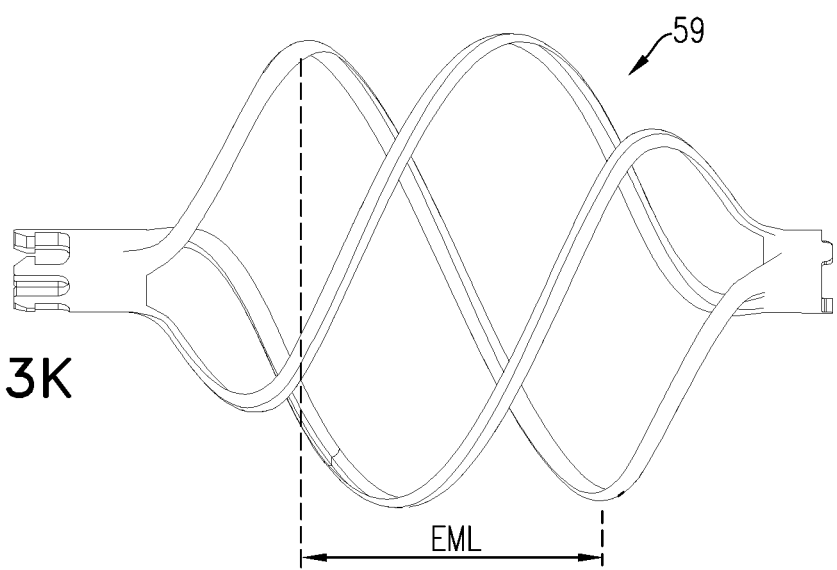

Referring now to FIGS. 3I, 3J, and 3K, for some applications, structure 59 is configured to provide a relatively long effective maximum-span length EML, the effective maximum-span length EML being defined as the axial length along which the span of the impeller is at its maximum. Typically, increasing the effective maximum-span length EML of the impeller increases the efficiency of the impeller (i.e., the amount of flow generated by the impeller at a given rotation rate). For some applications, the angle rho that the leading edge of the impeller blade makes with respect to the longitudinal axis of the impeller is greater than 45 degrees, e.g., between 45 degrees and 70 degrees. As may be observed by comparing FIG. 3J to FIG. 3I, ceteris paribus, increasing angle rho increases the effective maximum-span length EML, even if the overall length of the impeller is not increased. Alternatively, the effective maximum-span length EML of the impeller is increased by making the impeller longer, as shown in FIG. 3K.

Reference is now made to FIGS. 5A and 5B, which are schematic illustrations of impeller 50 and frame 34 of ventricular assist device 20, respectively in non-radially-constrained and radially-constrained states thereof, in accordance with some applications of the present invention. The impeller and the frame are typically disposed in the radially-constrained states during the transcatheteral insertion of the impeller and the frame into the subject's body, and are disposed in the non-radially-constrained states during operation of the impeller inside the subject's left ventricle. As described hereinabove, typically tube 24 is disposed over at least some of the frame and extends proximally therefrom. However, for illustrative purposes, the frame and the impeller are shown in the absence of tube 24 in FIGS. 5A-B.

As indicated in FIG. 5B, the frame and the impeller are typically maintained in radially-constrained configurations by delivery catheter 143. Typically, in the radially-constrained configuration of the impeller the impeller has a total length of more than 15 mm (e.g., more than 20 mm), and/or less than 30 mm (e.g., less than 25 mm), e.g., 15-30 mm, or 20-25 mm. Further typically, in the non-radially constrained configuration of the impeller, the impeller has a length of more than 8 mm (e.g., more than 10 mm), and/or less than 18 mm (e.g., less than 15 mm), e.g., 8-18 mm, or 10-15 mm. Still further typically, when the impeller and frame 34 are disposed in radially constrained configurations (as shown in FIG. 5B), the impeller has an outer diameter of less than 2 mm (e.g., less than 1.6 mm) and the frame has an outer diameter of less than 2.5 mm (e.g., less than 2.1 mm).

Figure 5C:
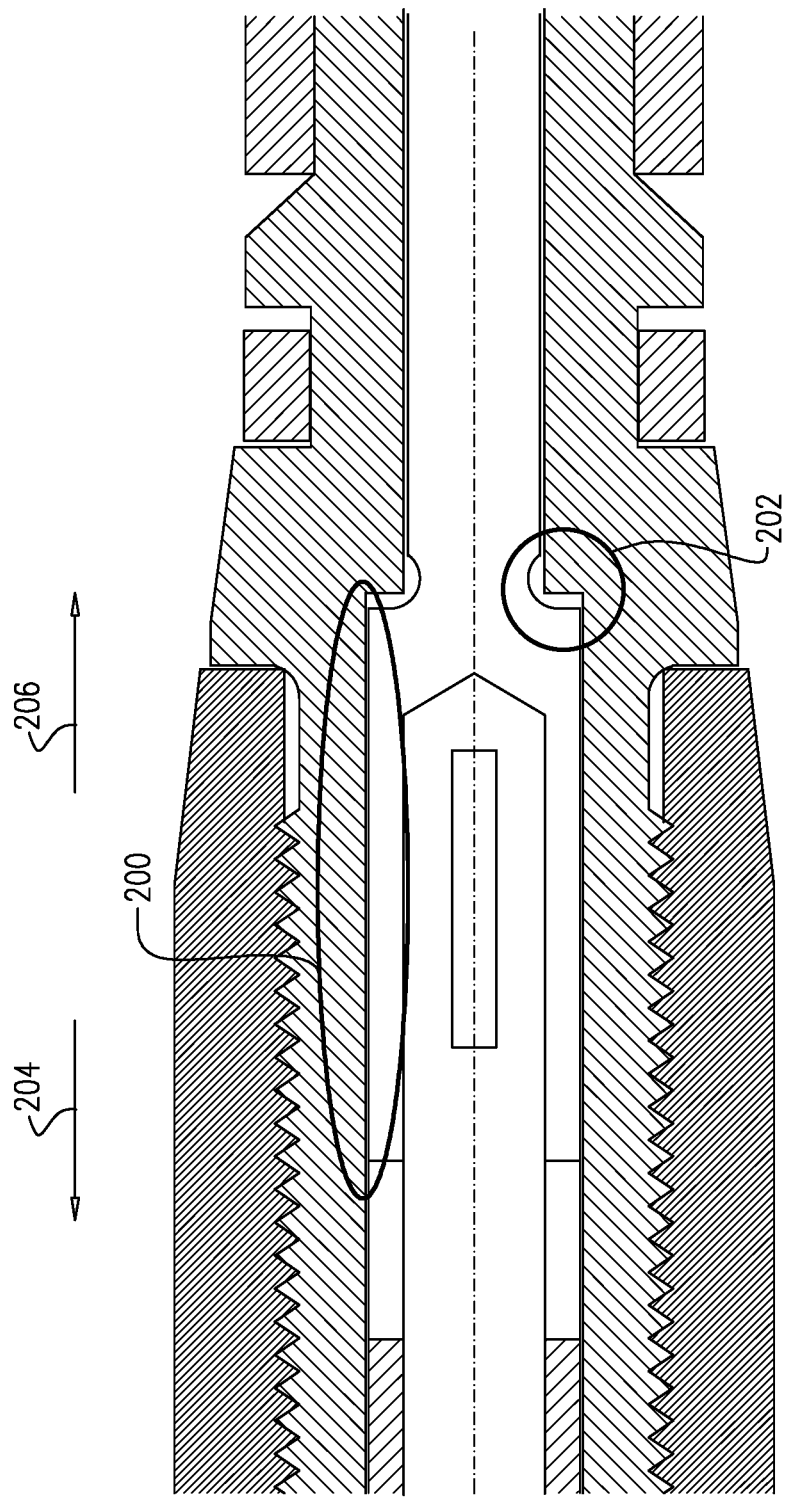
FIG. 5C is a schematic illustration of a typical bearing assembly that is used in prior art axial impeller-based blood pumps.

Reference is also made to FIG. 5C, which shows a typical bearing assembly that is used in prior art axial impeller-based blood pumps. FIG. 5C is shown for the purpose of acting as a point of reference for some of the applications of the invention described herein. As shown in FIG. 5C, a bearing assembly typically includes a radial bearing (indicated by ellipse 200) and a thrust bearing (indicated by circle 202). The radial bearing is configured to reduce radial motion of the impeller, by maintaining the axis of the impeller at a given radial position. In response to an impeller pumping blood in a first direction, forces acting upon the impeller typically push the impeller to move in the opposite direction to the first direction. The purpose of a thrust bearing is to oppose such motion of the impeller and to maintain the axial position of the impeller. In the example shown in FIG. 5C, in response to the impeller pumping blood in the direction of arrow 204, the impeller gets pushed in the direction of arrow 206, and the thrust bearing opposes this motion. Typically, due to the frictional forces that are exerted upon them, bearings undergo a substantial amount of heating and wear. Thrust bearings are typically exposed to substantial heating and wear, due to the fact that the frictional forces that are exerted upon them are typically spread over opposing surfaces having a smaller contact area between them, than is the case for radial bearings.

As described hereinabove, typically, axial shaft 92 passes through the axis of impeller 50, via lumen 62 of the impeller. Typically, proximal bushing 64 of the impeller is coupled to the shaft via a coupling element 65 such that the axial position of the proximal bushing with respect to the shaft is fixed, and distal bushing 58 of the impeller is slidable with respect to the shaft. The axial shaft itself is radially stabilized via a proximal radial bearing 116 and a distal radial bearing 118.

Typically, coupling portion 31 of frame 34 is coupled to proximal radial bearing 116, for example, via snap-fit coupling, and/or via welding. Typically, at the distal end of frame 34 distal strut junctions 33 are placed into grooves defined by the outer surface of distal radial bearing 118, the grooves being shaped to conform with the shapes of the distal strut portions. The proximal end of distal-tip element 107 (which defines distal-tip portion 120) typically holds the distal strut portions in their closed configurations around the outside of distal radial bearing 118, as shown. For some applications, the device includes a distal extension 121 that extends distally from the distal radial bearing. Typically, the extension is configured to stiffen a region of the distal-tip element into which the distal end of shaft 92 moves (e.g., an axial-shaft-receiving tube 126, described hereinbelow, or a portion thereof).

As described above, axial shaft 92 is radially stabilized via proximal radial bearing 116 and distal radial bearing 118. In turn, the axial shaft, by passing through lumen 62 defined by the impeller, radially stabilizes the impeller with respect to the inner surface of frame 34, such that even a relatively small gap between the outer edge of the blade of the impeller and the inner surface of frame 34 (e.g., a gap that is as described above) is maintained, during rotation of the impeller, as described hereinabove. For some applications, axial shaft 92 is made of stainless steel, and proximal bearing 116 and/or distal bearing 118 are made of hardened steel. Typically, when crimping (i.e., radially constraining) the impeller and the frame for the purpose of inserting the impeller and the frame into the subject's body, distal bushing 58 of the impeller is configured to slide along the axial shaft in the distal direction, such that the impeller becomes axially elongated, while the proximal bushing remains in an axially fixed position with respect to the axial shaft. More generally, the impeller changes from its radially-constrained configuration to its non-radially-constrained configuration, and vice versa, by the distal bushing sliding over the axial shaft, while the proximal bushing remains in an axially fixed position with respect to the axial shaft. (For some applications, distal bushing 58 of the impeller is coupled to the shaft via coupling element 65 such that the axial position of the distal bushing with respect to the shaft is fixed, and proximal bushing 64 of the impeller is slidable with respect to the shaft. Such applications are described hereinbelow with reference to FIGS. 11A-C.)

Typically, the impeller itself is not directly disposed within any radial bearings or thrust bearings. Rather, bearings 116 and 118 act as radial bearings with respect to the axial shaft. Typically, pump portion 27 (and more generally ventricular assist device 20) does not include any thrust bearing that is configured to be disposed within the subject's body and that is configured to oppose thrust generated by the rotation of the impeller. For some applications, one or more thrust bearings are disposed outside the subject's body (e.g., within motor unit 23, shown in FIGS. 1A, 7, and 8A-B), and opposition to thrust generated by the rotation of the impeller is provided solely by the one or more thrust bearings disposed outside the subject's body. For some applications, a mechanical element and/or a magnetic element is configured to maintain the impeller within a given range of axial positions. For example, a magnet (e.g., magnet 82, described hereinbelow with reference to FIG. 7) that is disposed at the proximal end of the drive cable (e.g., outside the subject's body) may be configured to impart axial motion to the impeller, and/or to maintain the impeller within a given range of axial positions.

Reference is now made to FIGS. 6A and 6B, which are schematic illustrations of ventricular assist device 20 at respective stages of a motion cycle of impeller 50 of the ventricular assist device with respect to frame 34 of the ventricular assist device, in accordance with some applications of the present invention. For some applications, while the impeller is pumping blood through tube 24 by rotating, axial shaft 92 (to which the impeller is fixated) is driven to move the impeller axially back-and-forth within frame 34, by the axial shaft moving in an axial back-and-forth motion, as described in further detail hereinbelow with reference to FIG. 7. Alternatively or additionally, the impeller and the axial shaft are configured to move axially back-and-forth within frame 34 in response to forces that are acting upon the impeller, and without requiring the axial shaft to be actively driven to move in the axial back-and-forth motion. Typically, over the course of the subject's cardiac cycle, the pressure difference between the left ventricle and the aorta varies from being approximately zero during ventricular systole (hereinafter "systole") to a relatively large pressure difference (e.g., 50-70 mmHg) during ventricular diastole (hereinafter "diastole"). For some applications, due to the increased pressure difference that the impeller is pumping against during diastole (and due to the fact that drive cable 130 is stretchable), the impeller is pushed distally with respect to frame 34 during diastole, relative to the location of the impeller with respect to frame 34 during systole. In turn, since the impeller is connected to the axial shaft, the axial shaft is moved forward. During systole, the impeller (and, in turn, the axial shaft) move back to their systolic positions. In this manner, the axial back-and-forth motion of the impeller and the axial shaft is generated in a passive manner, i.e., without requiring active driving of the axial shaft and the impeller, in order to cause them to undergo this motion. This passive axial back-and-forth motion of the impeller is described in further detail hereinbelow, for example, with reference to FIG. 9. FIG. 6A shows the impeller and axial shaft disposed at their typical systolic positions and FIG. 6B shows the impeller and axial shaft disposed at their typical diastolic positions.

For some applications, by moving in the axial back-and-forth motion, the portions of the axial shaft that are in contact with proximal bearing 116 and distal bearing 118 are constantly changing. For some such applications, in this manner, the frictional force that is exerted upon the axial shaft by the bearings is spread over a larger area of the axial shaft than if the axial shaft were not to move relative to the bearings, thereby reducing wear upon the axial shaft, ceteris paribus. Alternatively or additionally, by moving in the back-and-forth motion with respect to the bearing, the axial shaft cleans the interface between the axial shaft and the bearings from any residues, such as blood residues.

For some applications, when frame 34 and impeller 50 are in non-radially-constrained configurations thereof (e.g., when the frame and the impeller are deployed within the left ventricle), the length of the frame exceeds the length of the impeller by at least 2 mm (e.g., at least 4 mm, or at least 8 mm). Typically, the proximal bearing 116 and distal bearing 118 are each 2-4 mm (e.g., 2-3 mm) in length. Further typically, the impeller and the axial shaft are configured to move axially within the frame in the back-and-forth motion at least along the length of each of the proximal and distal bearings, or at least along twice the length of each of the bearings. Thus, during the back-and-forth axial movement of the axial shaft, the axial shaft is wiped clean on either side of each of the bearings.

For some applications, the range of the impeller motion is as indicated in FIGS. 6A-B, with 6A indicating the proximal-most disposition of the impeller over the course of the cardiac cycle (at which the impeller is typically disposed during systole) and FIG. 6B indicating the distal-most disposition of the impeller over the course of the cardiac cycle (at which the impeller is typically disposed during diastole). As shown in FIG. 6A, for some applications, at its proximal-most position the proximal end of the impeller is disposed at location Ip, which is within the proximal conical section of frame 34. As shown in FIG. 6B, for some applications, at its distal-most position the distal end of the impeller is disposed at location Id, which is at the distal end of the cylindrical section of frame 34. For the purpose of the present application, the entire section of the frame from Ip to Id may be considered as housing the impeller, since this entire section of the frame typically houses at least a portion of the impeller over at least a portion of the cardiac cycle. Typically, over the course of the entire cardiac cycle, the section of the impeller at which the span of the impeller is at its maximum is disposed within the cylindrical portion of the frame 34. However, a proximal portion of the impeller is typically disposed within the proximal conical section of the frame during at least a portion of the cardiac cycle.

Reference is again made to FIGS. 6A and 6B, and reference is also made to FIG. 6C, which is an enlarged schematic illustration of distal-tip element 107, which includes axial-shaft-receiving tube 126 and distal-tip portion 120 of ventricular assist device 20, in accordance with some applications of the present invention. Typically, distal-tip element 107 is a single integrated element that includes both axial-shaft-receiving tube 126 and distal-tip portion 120. For some applications, distal-tip element 107 is configured to be soft, such that the distal-tip portion is configured not to injure tissue of the subject, even if the distal-tip portion comes into contact with the tissue (e.g., tissue of the left ventricle). For example, distal-tip element 107 may be made of silicone, polyethylene terephthalate (PET) and/or polyether block amide (e.g., PEBAX®). For some applications, the distal-tip portion defines a lumen 122 therethrough. For some such applications, during insertion of the ventricular assist device into the left ventricle, guidewire 10 (FIG. 1B) is first inserted into the left ventricle, for example, in accordance with known techniques. The distal-tip portion of the ventricular assist device is then guided to the left ventricle by advancing the distal-tip portion over the guidewire, with the guidewire disposed inside lumen 122. For some applications, a duckbill valve 390 (or a different type of hemostasis valve) is disposed at the distal end of lumen 122 of distal-tip portion 120, as described in further detail hereinbelow.

Typically, during the insertion of the ventricular assist device into the subject's ventricle, delivery catheter 143 is placed over impeller 50 and frame 34 and maintains the impeller and the frame in their radially-constrained configurations. For some applications, distal-tip element 107 extends distally from the delivery catheter during the insertion of the delivery catheter into the subject's ventricle. For some applications, at the proximal end of the distal-tip element, the distal-tip element has a flared portion 124 that acts as a stopper and prevents the delivery catheter from advancing beyond the flared portion.

It is noted that the external shape of distal-tip portion in FIGS. 6A-C (as well as in some other figures) is shown as defining a complete loop, with the distal end of the distal-tip portion (within which duckbill valve 390 is disposed) crossing over a more proximal portion of the distal-tip portion. Typically, as a result of having had a guidewire inserted therethrough (during insertion of the ventricular assist device into the left ventricle), the distal-tip portion remains partially straightened, even after the removal of the guidewire from the distal-tip portion. Typically, the partial straightening of the distal-tip portion is such that, when the distal-tip portion is disposed within the left ventricle, in the absence of external forces acting upon the distal-tip portion, the distal-tip portion does not define a complete loop, e.g., as shown in FIG. 1B, and in FIG. 23A. Other aspects of the shape of the distal-tip portion are described in further detail hereinbelow.

Referring again to FIG. 6C, for some applications, axial-shaft-receiving tube 126 extends proximally from distal-tip portion 120 of distal-tip element 107. As described hereinabove, typically, the axial shaft undergoes axial back-and-forth motion during the operation of impeller 50. Axial-shaft-receiving tube 126 defines lumen 127, which is configured to receive the axial shaft when the axial shaft extends beyond distal bearing 118. For some applications, the shaft-receiving tube defines a stopper 128 at its distal end, the stopper being configured to prevent advancement of the axial shaft beyond the stopper. For some applications, the stopper comprises a rigid component that is inserted (e.g., embedded) into the distal end of the shaft-receiving tube. Alternatively, the stopper comprises a shoulder between lumen 127 of the axial-shaft-receiving tube and lumen 122 of distal-tip portion 120. Typically, such a shoulder is present since lumen 122 of tip portion 120 is narrower than lumen 127. This is because lumen 127 is typically configured to accommodate the axial shaft, while lumen 122 is configured to accommodate guidewire 10, and the axial shaft is typically wider than guidewire 10, since the axial shaft is itself configured to accommodate guidewire 10 within internal lumen 132 (shown in FIGS. 10B and 10C) of the axial shaft.

Typically, during normal operation of the impeller, the axial shaft does not extend to stopper 128, even when drive cable 130 (shown in FIG. 7) is maximally elongated (e.g., during diastole). However, stopper 128 is configured to prevent the axial shaft from protruding into the tip portion when the delivery catheter is advanced over impeller 50 and frame 34, during retraction of ventricular assist device 20 from the subject's ventricle. In some cases, during the advancement of the delivery catheter over the frame and the impeller, the drive cable is at risk of snapping. In the absence of stopper 128, in such cases the axial shaft may protrude into the tip portion. Stopper 128 prevents this from happening, even in the event that the drive cable snaps.

Typically, during operation of the ventricular assist device, and throughout the axial back-and-forth motion cycle of the impeller, the impeller is disposed in relatively close proximity to the distal-tip portion. For example, the distance of the impeller to the distal-tip portion may be within the distal-most 50 percent, e.g., the distal-most 30 percent (or the distal-most 20 percent) of tube 24, throughout the back-and-forth motion axial cycle of the impeller.

Reference is now made to FIG. 6D, which is a schematic illustration of impeller 50 and axial shaft 92 of ventricular assist device 20, a region of the axial shaft being coated with a coating or a covering material 95, in accordance with some applications of the present invention. As described hereinabove, typically, distal bushing 58 of the impeller is not fixedly coupled to the shaft. Also as described hereinabove, in order to reduce hemolysis, it is typically desirable to maintain a constant gap between the edges of the impeller blades and tube 24 (and/or inner lining 39). Therefore, it is typically desirable to reduce vibration of the impeller. For some applications, the impeller is stabilized with respect to the frame by a region along the axial shaft over which the distal bushing is configured to be slidable with respect to the axial shaft being coated such as to substantially prevent the impeller from vibrating, by reducing a gap (e.g., by substantially filling the gap) between the at least one bushing and the impeller. For example, the region of the axial shaft may be coated in polytetrafluoroethylene (e.g., Teflon®) and/or diamond-like-carbon (DLC) coating or may be covered with a sleeve (which is typically a polymer, such as polyester). By substantially filling the gap between the between the inner surface of distal bushing 58 and the outer surface of axial shaft 92, vibration of the impeller is typically reduced relative to if the region of the axial shaft were not coated. For some applications, the gap between the distal bushing and the axial shaft is less than 40 micrometers, e.g., less than 30 micrometers, whether or not the axial shaft is coated. For some applications, the proximal bushing of the impeller is configured to be slidable with respect to the axial shaft (for example, as described with reference to FIGS. 11A-C), and similar techniques to those described above are applied to the proximal bushing.

Reference is now made to FIG. 6E, which is a schematic illustration of impeller 50 and axial shaft 92 of ventricular assist device 20, distal bushing 58 of the impeller including a protrusion 96 from its inner surface that is configured to slide within a slot 97 defined by an outer surface of the axial shaft, in accordance with some applications of the present invention. As described hereinabove, typically, distal bushing 58 of the impeller is not fixedly coupled to the shaft. For some applications, protrusion 96 and slot 97 are configured to prevent the distal end of the impeller rotating with respect to the axial shaft, as the impeller undergoes axial motion with respect to the axial shaft. Typically, at its proximal end, slot 97 defines a stopper 98. The stopper is configured to prevent the distal bushing from sliding proximally beyond the stopper, by preventing axial motion of protrusion 96 proximally beyond the stopper. Typically, by preventing the distal bushing from sliding proximally beyond the stopper, a minimum length of the impeller is maintained. In turn, this typically prevents the span of the impeller from increasing beyond a given maximum span, which maintains the gap between the edges of the impeller blades and tube 24 (and/or inner lining 39).

In accordance with the above description of FIGS. 6A-E (as well as the description of additional figures), the scope of the present invention includes one or more techniques for reducing hemolysis that is caused by the pumping of blood by the impeller. Typically, frame 34, which is disposed around the impeller defines a plurality of cells, and the frame is configured such that, in a non-radially-constrained configuration of the frame, the frame comprises generally cylindrical portion 38. Further typically, a cell width CW of each of the cells within the cylindrical portion as measured around a circumference of the cylindrical portion being less than 2 mm (e.g., 1.4-1.6 mm, or 1.6-1.8 mm). For some applications, inner lining 39 lines at least the cylindrical portion of the frame, and the impeller is disposed inside the frame such that, in a non-radially-constrained configuration of the impeller, at a location at which a span of the impeller is at its maximum, the impeller is disposed within the cylindrical portion of the frame, such that gap G between an outer edge of the impeller and the inner lining is less than 1 mm (e.g., less than 0.4 mm). Typically, the impeller is configured to rotate such as to pump blood from the left ventricle to the aorta, and to be stabilized with respect to the frame, such that, during rotation of the impeller, the gap between the outer edge of the impeller and the inner lining is maintained and is substantially constant. Typically, the impeller is configured to reduce a risk of hemolysis by being stabilized with respect to the frame (such that, during rotation of the impeller, the gap between the outer edge of the impeller and the inner lining is maintained and is substantially constant), relative to if the impeller were not stabilized with respect to the frame.

For some applications, proximal and distal radial bearings 116 and 118 are disposed, respectively, at proximal and distal ends of the frame, and axial shaft 92 passes through the proximal and distal radial bearings. Typically, the impeller is stabilized with respect to the frame by the impeller being held in a radially-fixed position with respect to the axial shaft and the axial shaft being rigid. For some applications, a gap between each of the axial bearings and the axial shaft is less than 15 micrometers, e.g., between 2 micrometers and 13 micrometers. For some applications, the impeller includes bushings 64, 58 that are disposed around the axial shaft, and at least one of the bushings (e.g., distal bushing 58) is configured to be slidable with respect to the axial shaft. For some applications, the impeller is stabilized with respect to the frame by a region along the axial shaft over which the at least one bushing is configured to be slidable with respect to the axial shaft being coated such as to substantially prevent the impeller from vibrating, by reducing a gap between the at least one bushing and the impeller. For example, the region may be coated in a diamond-like-carbon coating, a polytetrafluoroethylene coating, and/or a polymeric sleeve. For some applications, the gap between the distal bushing and the axial shaft is less than 40 micrometers, e.g., less than 30 micrometers, whether or not the axial shaft is coated.

Reference is now made to FIGS. 6F and 6G, which are schematic illustrations of ventricular assist device 20, cylindrical portion 38 of frame 34 tapering from a proximal end of the cylindrical portion to a distal end of the cylindrical portion, in accordance with some applications of the present invention. As described hereinabove, for some applications, impeller 50 and axial shaft 92 are configured to move axially back-and-forth within frame 34 in response to forces that are acting upon the impeller, and without requiring the axial shaft to be actively driven to move in the axial back-and-forth motion. Typically, over the course of the subject's cardiac cycle, the pressure difference between the left ventricle and the aorta varies from being approximately zero during systole to a relatively large pressure difference (e.g., 50-70 mmHg) during diastole. For some applications, due to the increased pressure difference that the impeller is pumping against during diastole (and due to drive cable 130 being stretchable), the impeller is pushed distally with respect to frame 34 during diastole, relative to the location of the impeller with respect to frame 34 during systole. In turn, since the impeller is connected to the axial shaft, the axial shaft is moved forward. During systole, the impeller (and, in turn, the axial shaft) move back to their systolic positions. In this manner, the axial back-and-forth motion of the impeller and the axial shaft is generated in a passive manner, i.e., without requiring active driving of the axial shaft and the impeller, in order to cause them to undergo this motion. FIG. 6F shows the impeller disposed at its typical systolic position and FIG. 6G shows the impeller disposed at its typical diastolic position.

For some applications, by virtue of the cylindrical portion of frame 34 being tapered from the proximal end to the distal end of the cylindrical portion, the gap between the edges of the impeller blades and tube 24 (and/or inner lining 39) is less during diastole than during systole. Due to the smaller gap between the edges of the impeller blades and tube 24 (and/or inner lining 39), the pumping efficiency of the impeller is typically greater during diastole than during systole. For some applications, it is desirable for the pumping efficiency to be greater during diastole than during systole, since the impeller is pumping against an increased pressure gradient during diastole versus during systole, as described above.

Notwithstanding the description of the FIGS. 6E and 6F, it is typically the case that throughout the axial motion cycle of the impeller the gap between the edges of the impeller blades and tube 24 (and/or inner lining 39) is constant.

Figure 7:
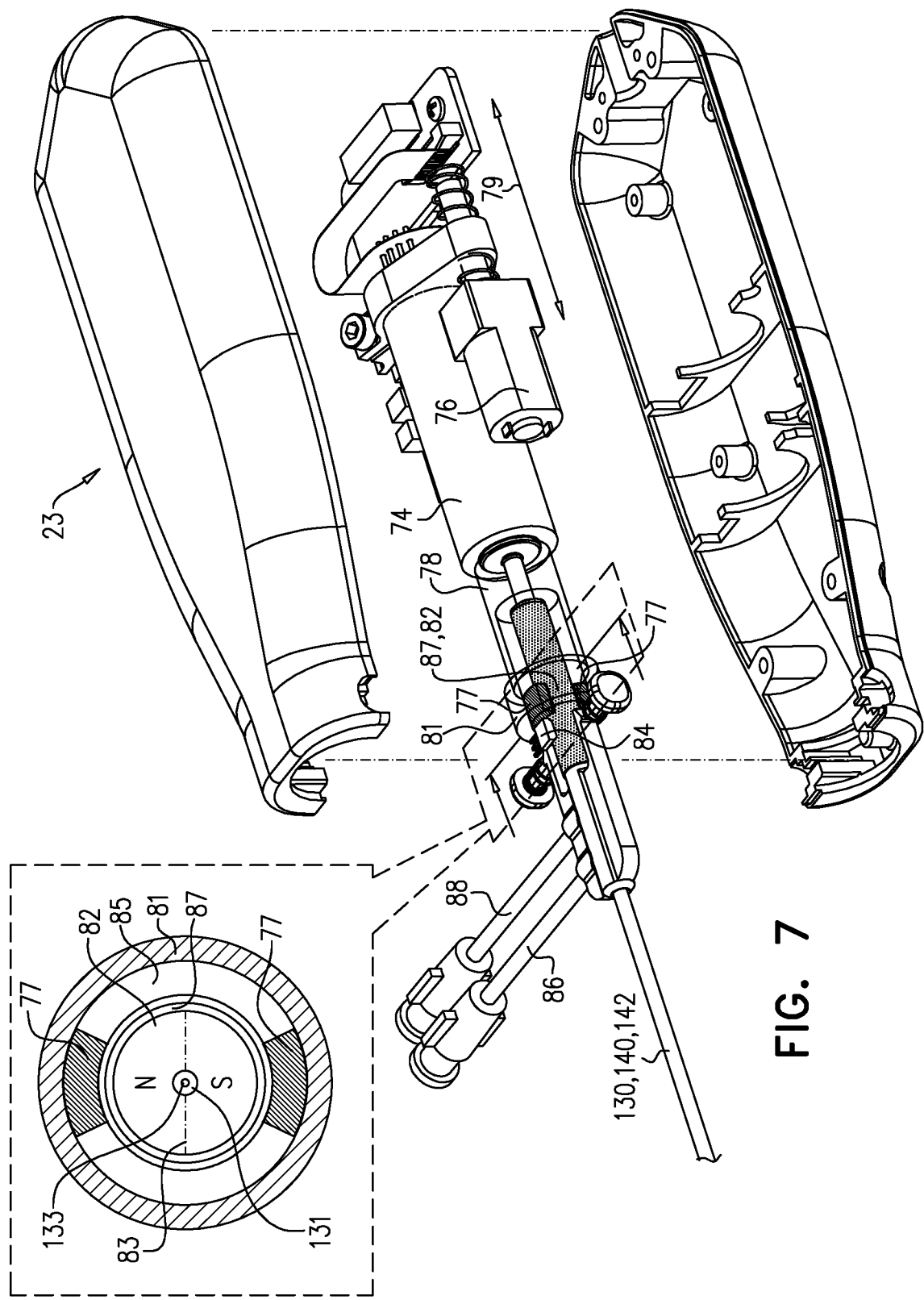
FIG. 7 is a schematic illustration of a motor unit of a ventricular assist device, in accordance with some applications of the present invention.
Figure 8:
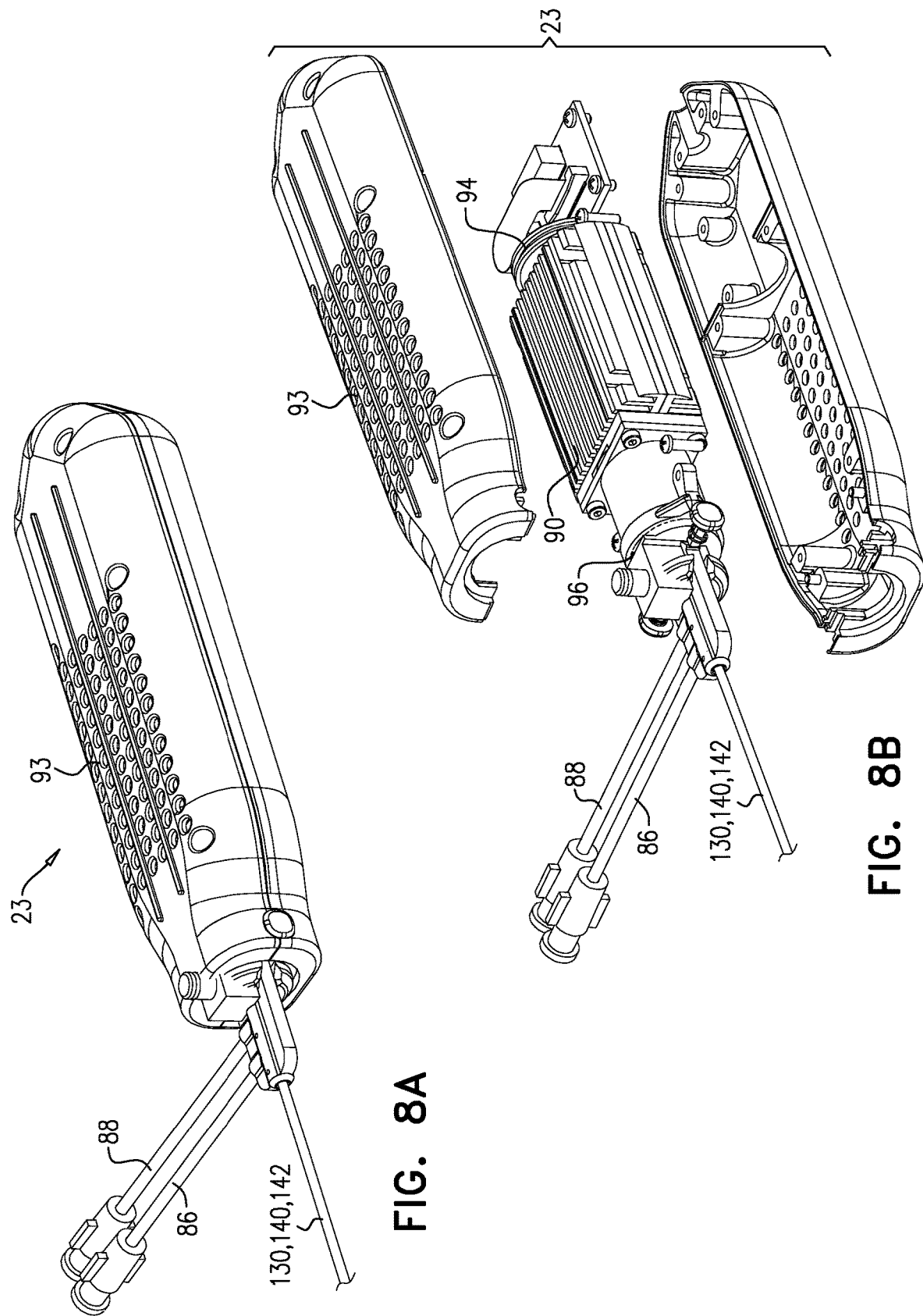
FIGS. 8A and 8B are schematic illustrations of a motor unit of a ventricular assist device, in accordance with some applications of the present invention.

Reference is now made to FIG. 7, which is a schematic illustration of an exploded view of motor unit 23 of ventricular assist device 20, in accordance with some applications of the present invention. For some applications, computer processor 25 of control console 21 (FIG. 1A) that controls the rotation of impeller 50 is also configured to control the back-and-forth motion of the axial shaft. Typically, both types of motion are generated using motor unit 23. The scope of the present invention includes controlling the back-and-forth motion at any frequency. For some applications, an indication of the subject's cardiac cycle is detected (e.g., by detecting the subject's ECG), and the back-and-forth motion of the axial shaft is synchronized to the subject's cardiac cycle.

Typically, motor unit 23 includes a motor 74 that is configured to impart rotational motion to impeller 50, via drive cable 130. As described in further detail hereinbelow, typically, the motor is magnetically coupled to the drive cable. For some applications, an axial motion driver 76 is configured to drive the motor to move in an axial back-and-forth motion, as indicated by double-headed arrow 79. Typically, by virtue of the magnetic coupling of the motor to the drive cable, the motor imparts the back-and-forth motion to the drive cable, which it turn imparts this motion to the impeller. As described hereinabove and hereinbelow, for some applications, the drive cable, the impeller, and/or the axial shaft undergo axial back-and-forth motion in a passive manner, e.g., due to cyclical changes in the pressure gradient against which the impeller is pumping blood. Typically, for such applications, motor unit 23 does not include axial motion driver 76.

For some applications, the magnetic coupling of the motor to the drive cable is as shown in FIG. 7. As shown in FIG. 7, a set of driving magnets 77 are coupled to the motor via a driving magnet housing 78. For some applications, the driving magnet housing includes ring 81 (e.g., a steel ring), and the driving magnets are adhered to an inner surface of the ring. For some applications a spacer 85 is adhered to the inner surface of ring 81, between the two driving magnets, as shown. A driven magnet 82 is disposed between the driving magnets such that there is axial overlap between the driving magnets and the driven magnet. The driven magnet is coupled to a pin 131, which extends to beyond the distal end of driven magnet 82, where the pin is coupled to the proximal end of drive cable 130. For example, the driven magnet may be cylindrical and define a hole therethrough, and pin 131 may be adhered to an inner surface of the driven magnet that defines the hole. For some applications, the driven magnet is cylindrical, and the magnet includes a North pole and a South pole, which are divided from each other along the length of the cylinder along a line 83 that bisects the cylinder, as shown. For some applications, the driven magnet is housed inside a cylindrical housing 87. Typically, pin 131 defines a guidewire lumen 133, which is described in further detail hereinbelow with reference to FIGS. 10B-C.

It is noted that in the application shown in FIG. 7, the driving magnets are disposed outside the driven magnet. However, the scope of the present application includes reversing the configurations of the driving magnets and the driven magnet, mutatis mutandis. For example, the proximal end of the drive cable may be coupled to two or more driven magnets, which are disposed around a driving magnet, such that there is axial overlap between the driven magnets and the driving magnet.

As described hereinabove, typically purging system 29 (shown in FIG. 1A) is used with ventricular assist device 20. Typically, motor unit 23 includes an inlet port 86 and an outlet port 88, for use with the purging system. For some applications, a purging fluid is continuously or periodically pumped into the ventricular assist device via inlet port 86 and out of the ventricular assist device via outlet port 88. Additional aspects of the purging system are described hereinbelow.

Typically, magnet 82 and pin 131 are held in axially fixed positions within motor unit 23. The proximal end of the drive cable is typically coupled to pin 131 and is thereby held in an axially fixed position by the pin. Typically, drive cable 130 extends from pin 131 to axial shaft 92 and thereby at least partially fixes the axial position of the axial shaft, and in turn impeller 50. For some applications, the drive cable is somewhat stretchable. For example, the drive cable may be made of coiled wires that are stretchable. The drive cable typically allows the axial shaft (and in turn the impeller) to assume a range of axial positions (by the drive cable becoming more or less stretched), but limits the axial motion of the axial shaft and the impeller to being within a certain range of motion (by virtue of the proximal end of the drive cable being held in an axially fixed position, and the stretchability of the drive cable being limited).

Reference is now made to FIGS. 8A and 8B, which are schematic illustrations of motor unit 23, in accordance with some applications of the present invention. In general, motor unit 23 as shown in FIGS. 8A and 8B is similar to that shown in FIG. 7, and, unless described otherwise, motor unit 23 as shown in FIGS. 8A and 8B contains similar components to motor unit 23 as shown in FIG. 7. For some applications, the motor unit includes a heat sink 90 that is configured to dissipate heat that is generated by the motor. Alternatively or additionally, the motor unit includes ventilation ports 93 that are configured to facilitate the dissipation of heat that is generated by the motor. For some applications, the motor unit includes vibration dampeners 94 and 96 that are configured to dampen vibration of the motor unit that is caused by rotational motion and/or axial back-and-forth motion of components of the ventricular assist device.

As described hereinabove, for some applications, impeller 50 and axial shaft 92 are configured to move axially back-and-forth within frame 34 in response to forces that act upon the impeller, and without requiring the axial shaft to be actively driven to move in the axial back-and-forth motion. Typically, over the course of the subject's cardiac cycle, the pressure difference between the left ventricle and the aorta varies from being approximately zero during systole to a relatively large pressure difference (e.g., 50-70 mmHg) during diastole. For some applications, due to the increased pressure difference that the impeller is pumping against during diastole (and due to the drive cable being stretchable), the impeller is pushed distally with respect to frame 34 during diastole, relative to the location of the impeller with respect to frame 34 during systole. In turn, since the impeller is connected to the axial shaft, the axial shaft is moved forward. During systole, the impeller (and, in turn, the axial shaft) move back to their systolic positions. In this manner, the axial back-and-forth motion of the impeller and the axial shaft is generated in a passive manner, i.e., without requiring active driving of the axial shaft and the impeller, in order to cause them to undergo this motion.

Figure 9:
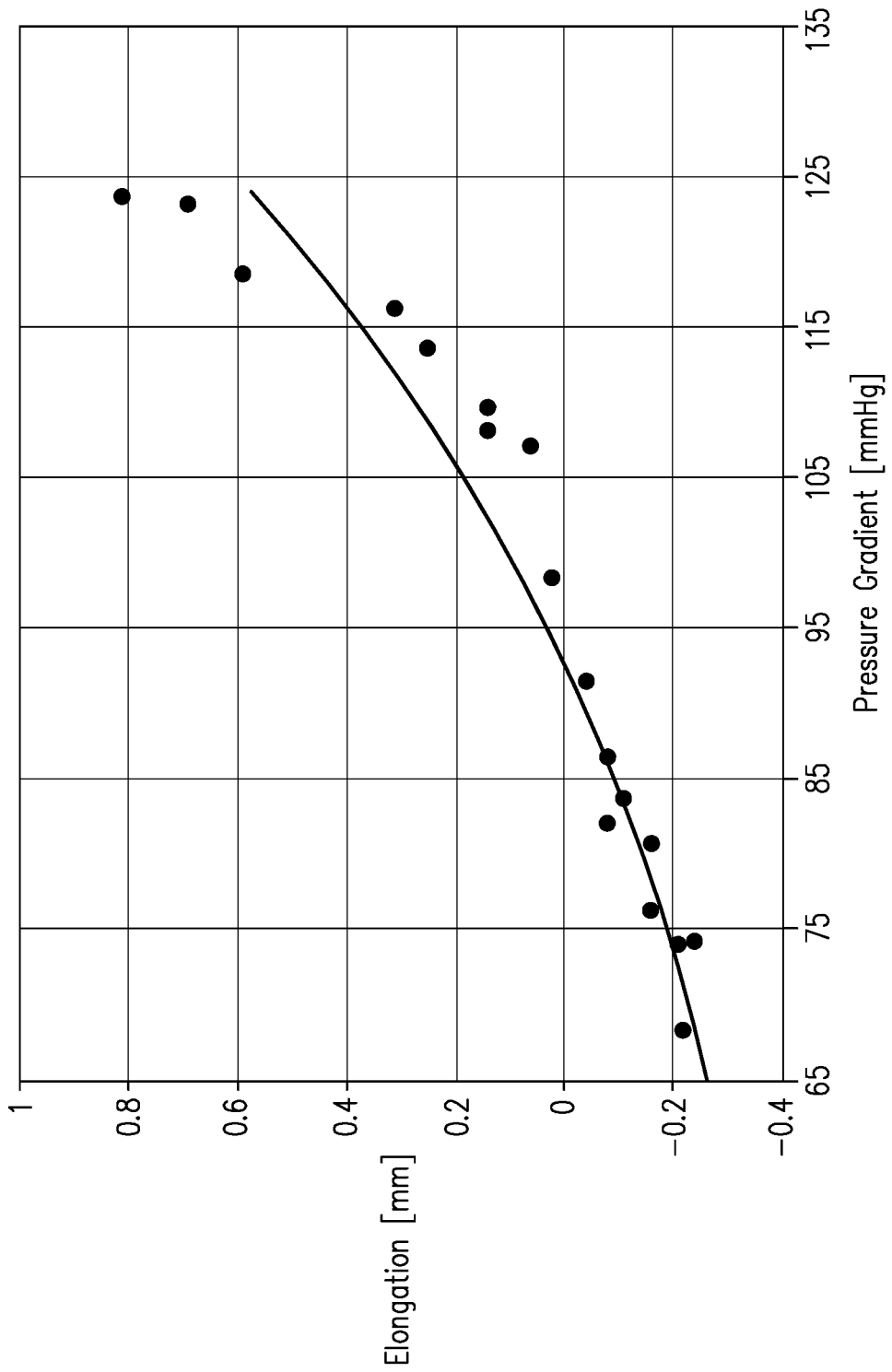
FIG. 9 is a graph indicating variations in the length of a drive cable of a ventricular assist device as a pressure gradient against which the impeller of the blood pump varies, as measured in experiments performed by the inventors of the present application.

Reference is now made to FIG. 9, which is a graph indicating variations in the length of a drive cable of a ventricular assist device, as a pressure gradient against which the impeller of the ventricular assist device varies, as measured in experiments performed by inventors of the present application. An impeller and a drive cable as described herein were used to pump a glycerin-based solution through chambers, with the chambers set up to replicate the left ventricle and the aorta, and the solution having properties (such as, density and viscosity) similar to those of blood. The pressure gradient against which the impeller was pumping varied, due to an increasing volume of fluid being disposed within the chamber into which the impeller was pumping. At the same time, movement of the drive cable was imaged and changes in the length of the drive cable were determined via machine-vision analysis of the images. The graph shown in FIG. 9 indicates the changes in the length of the drive cable that were measured, as a function of the pressure gradient. The y-axis of the graph shown in FIG. 9 is such that 0 mm elongation represents the length of the drive cable when the impeller is at rest. It is noted that the graph starts at a pressure gradient value of 65 mmHg, and that at this pressure the elongation is negative (at approximately −0.25 mm), i.e., the drive cable is shortened relative to the length of the drive cable prior to initiation of rotation of the impeller. This is because the drive cable was configured such that, when the impeller first started pumping, the drive cable shortened (relative to the length of the drive cable before the impeller was activated), due to coils within the drive cable unwinding. As seen in the section of the curve that is shown in FIG. 9, after the initial shortening of the drive cable that resulted from the aforementioned effect, it was then the case that as the pressure gradient increased, the drive cable became increasingly elongated.

As indicated by the results shown in FIG. 9 and as described hereinabove, it is typically the case that, in response to variations in the pressure against which the impeller is pumping blood (e.g., the pressure difference between the left ventricle and the aorta), the impeller moves back and forth with respect to frame 34. In turn, the movement of the impeller causes drive cable 130 to become more or less elongated.

For some applications, during operation of the ventricular assist device, computer processor 25 of control console 21 (FIG. 1A) is configured to measure an indication of the pressure exerted upon the impeller (which is indicative of the pressure difference between the left ventricle and the aorta), by measuring an indication of tension in drive cable 130, and/or axial motion of the drive cable. For some applications, based upon the measured indication, the computer processor detects events in the subject's cardiac cycle, determines the subject's left-ventricular pressure, and/or determines the subject's cardiac afterload. For some applications, the computer processor controls the rotation of the impeller, and/or the axial back-and-forth motion of the axial shaft in response thereto.

Referring again to FIG. 7, for some applications, ventricular assist device 20 includes a sensor 84. For example, the sensor may include a Hall sensor that is disposed within motor unit 23, as shown in FIG. 7. For some applications, the Hall sensor measures variations in the magnetic field that is generated by one of the magnets in order to measure the axial motion of drive cable 130, and, in turn, to determine the pressure against which the impeller is pumping. For example, the inner, driven magnet 82 may be axially longer than the outer, driving magnets 77. Due to the inner magnet being longer than the outer magnets, there are magnetic field lines that emanate from the inner magnet that do not pass to the outer magnets, and the magnetic flux generated by those field lines, as measured by the Hall sensor, varies as the drive cable, and, in turn, the inner magnet moves axially. During operation, motor 74 rotates, creating an AC signal in the Hall sensor, which typically has a frequency of between 200 Hz and 800 Hz. Typically, as the tension in the drive cable changes due to the subject's cardiac cycle, this gives rise to a low frequency envelope in the signal measured by the Hall sensor, the low frequency envelope typically having a frequency of 0.5-2 Hz. For some applications, the computer processor measures the low frequency envelope, and derives the subject's cardiac cycle from the measured envelope. It is noted that typically the axial motion of the magnet is substantially less than that of the impeller, since the full range of motion of the impeller isn't transmitted along the length of the drive cable. However, it is typically the case that the axial back-and-forth motion of the impeller gives rise to a measurable back-and-forth motion of the magnet.

For some applications, the Hall sensor measurements are initially calibrated, such that the change in magnetic flux per unit change in pressure against which the impeller is pumping (i.e., per unit change in the pressure difference between the left ventricle and the aorta) is known. It is known that, in most subjects, at systole, the left-ventricular pressure is equal to the aortic pressure. Therefore, for some applications, the subject's aortic pressure is measured (e.g., using techniques as described hereinbelow with reference to FIGS. 16A-D), and the subject's left-ventricular pressure at a given time is then calculated by the computer processor, based upon (a) the measured aortic pressure, and (b) the difference between the magnetic flux measured by the Hall sensor at that time, and the magnetic flux measured by the Hall sensor during systole (when the pressure in the left ventricle is assumed to be equal to that of the aorta).

For some applications, generally similar techniques to those described in the above paragraph are used, but rather than utilizing Hall sensor measurements, a different parameter is measured in order to determine left ventricular blood pressure at a given time. For example, it is typically the case that there is a relationship between the amount of power that is required to power the rotation of the impeller at a given rotation rate and the pressure difference that is generated by the impeller. (It is noted that some of the pressure difference that is generated by the impeller is used to overcome the pressure gradient against which the impeller is pumping, and some of the pressure difference that is generated by the impeller is used to actively pump the blood from the left ventricle to the aorta, by generating a positive pressure difference between the left ventricle and the aorta. Moreover, the relationship between the aforementioned components typically varies over the course of the cardiac cycle.) For some applications, calibration measurements are performed, such that the relationship between (a) power consumption by the motor that is required to rotate the impeller at a given rotation rate and (b) the pressure difference that is generated by the impeller, is known. For some applications, the subject's aortic pressure is measured (e.g., using techniques as described hereinbelow with reference to FIGS. 16A-D), and the subject's left-ventricular pressure at a given time is then calculated by the computer processor, based upon (a) the measured aortic pressure, (b) the power consumption by the motor that is required to rotate the impeller at a given rotation rate at that time, and (c) the predetermined relationship between power consumption by the motor that is required to rotate the impeller at a given rotation rate and the pressure difference that is generated by the impeller. For some applications, the above-described technique is performed while maintaining the rotation rate of the impeller at a constant rate. Alternatively or additionally, the rotation rate of the impeller is varied, and the variation of the rotation rate of the impeller is accounted for in the above-described calculations.

Typically, tube 24 has a known cross-sectional area (when the tube is in an open state due to blood flow through the tube). For some applications, the flow through tube 24 that is generated by the impeller is determined based on the determined pressure difference that is generated by the impeller, and the known cross-sectional area of the tube. For some applications, such flow calculations incorporate calibration parameters in order to account for factors such as flow resistance that are specific to the ventricular assist device (or type of ventricular assist device) upon which the calculations are performed. For some applications, the ventricular pressure-volume loop is derived, based upon the determined ventricular pressure.

Figure 10A:
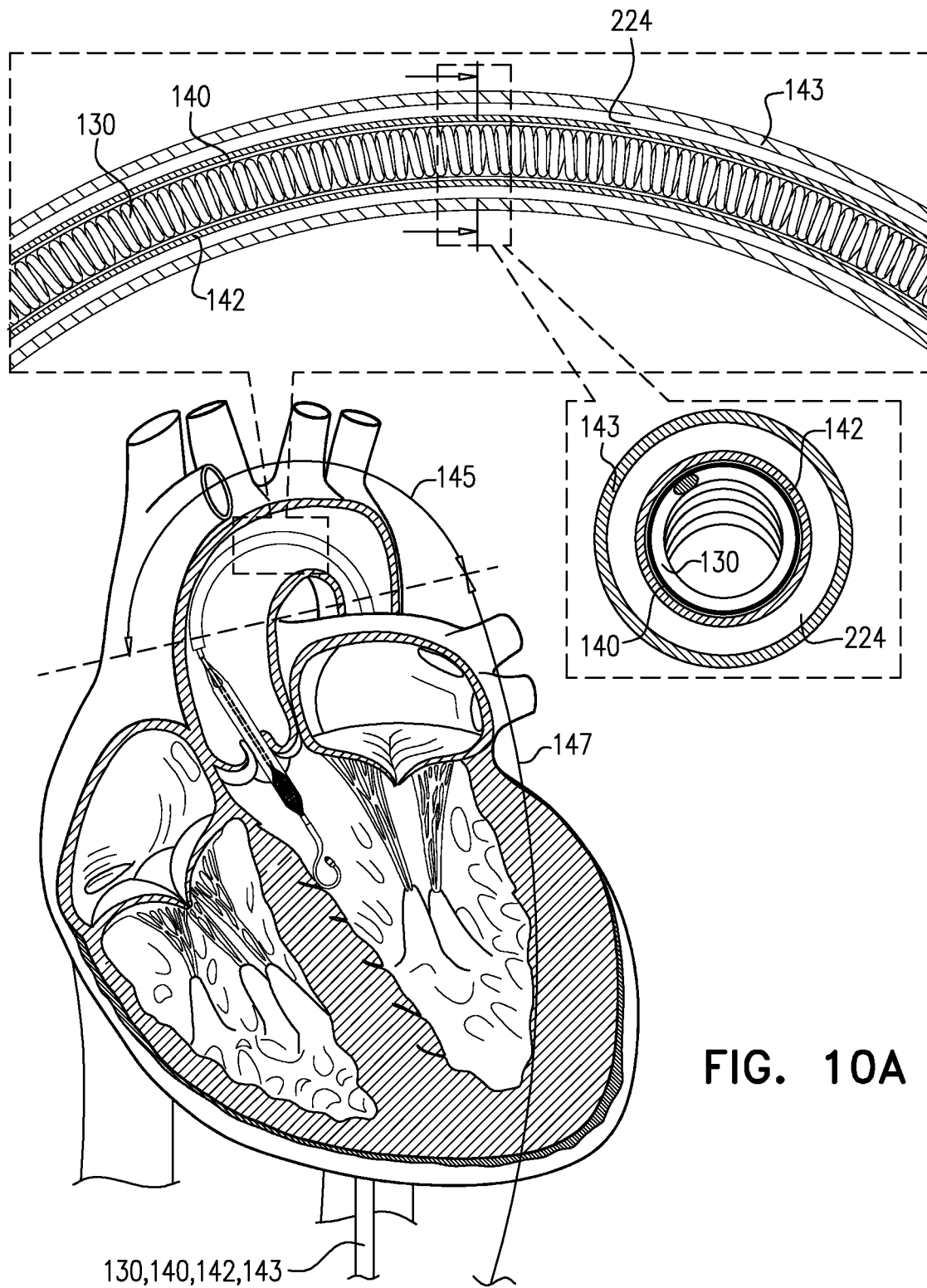
FIGS. 10A, 10B, and 10C are schematic illustrations of a drive cable of a ventricular assist device, in accordance with some applications of the present invention.
Figure 10B:
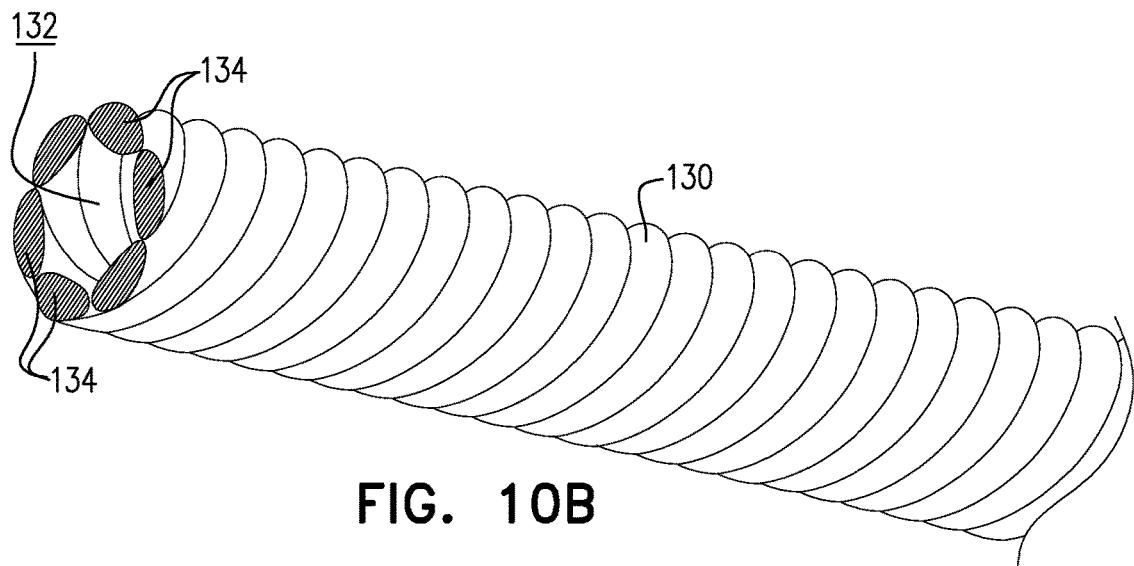
Figure 10C:
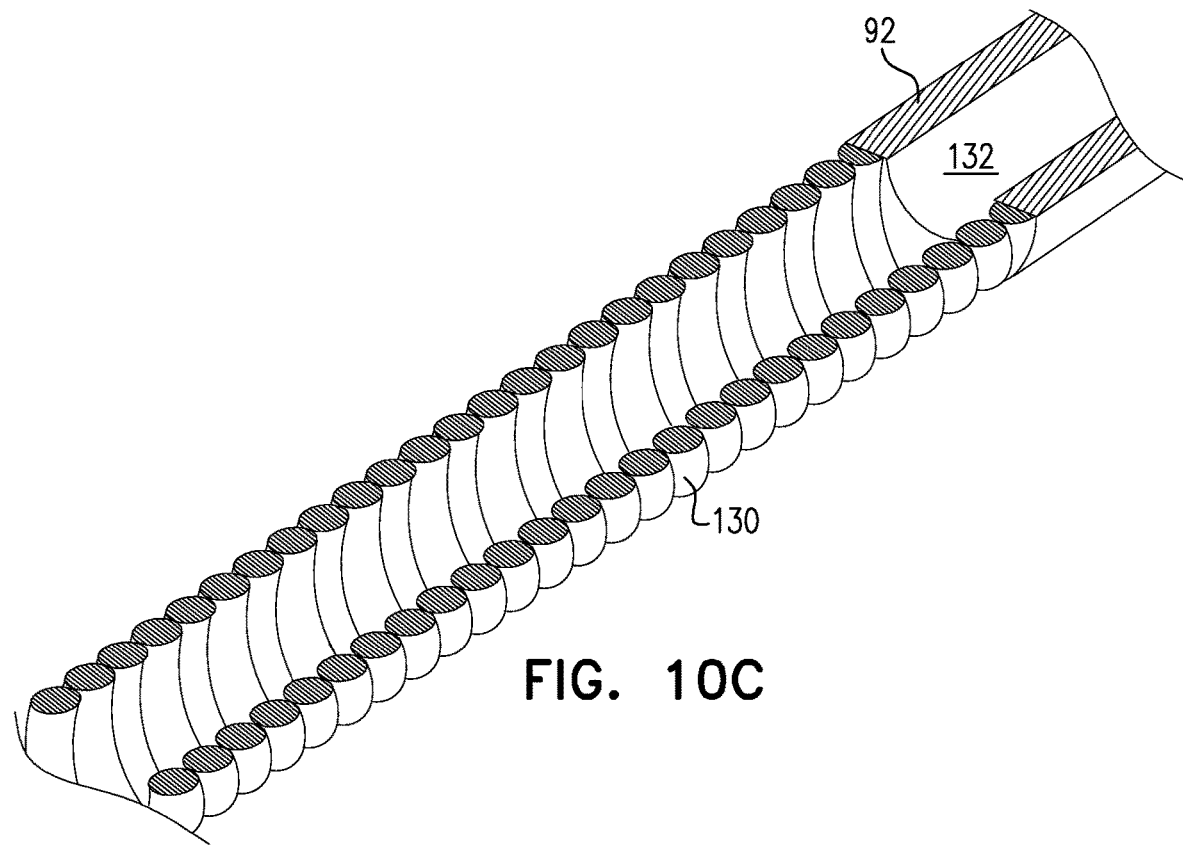

Reference is now made to FIGS. 10A, 10B, and 10C, which are schematic illustrations of drive cable 130 of ventricular assist device 20, in accordance with some applications of the present invention. Typically, the rotational motion of the impeller (which is imparted via the axial shaft), as well as the axial back-and-forth motion of the axial shaft described hereinabove, is transmitted to the axial shaft via the drive cable, as described hereinabove. Typically, the drive cable extends from motor unit 23 (which is typically disposed outside the subject's body) to the proximal end of axial shaft 92 (as shown in FIG. 10C, which shows the connection between the distal end of the drive cable and the proximal end of the axial shaft). For some applications, the drive cable includes a plurality of wires 134 (as shown in FIG. 10B) that are disposed in a tightly-coiled configuration in order to impart sufficient strength and flexibility to the drive cable, such that a portion of the cable is able to be maintained within the aortic arch (the portion corresponding to arrow 145 in FIG. 10A), while the cable is rotating and moving in the axial back-and-forth motion. The drive cable is typically disposed within a first outer tube 140, which is configured to remain stationary while the drive cable undergoes rotational and/or axial back-and-forth motion. The first outer tube is configured to effectively act as a bearing along the length of the drive cable. Typically, the first outer tube is made of a polymer (such as, polyether ether ketone) that is configured to be highly resistant to fatigue even under the frictional forces that are generated by the relative motion between the drive cable and the first outer tube. However, since such polymers are typically relatively rigid, only a thin layer of the polymer is typically used in the first outer tube. For some applications, the first outer tube is disposed within a second outer tube 142, which is made of a material having greater flexibility than that of the first outer tube (e.g., nylon, and/or polyether block amide), and the thickness of the second outer tube is greater than that of the first outer tube.

Typically, during insertion of the impeller and the cage into the left ventricle, impeller 50 and frame 34 are maintained in a radially-constrained configuration by delivery catheter 143. As described hereinabove, in order for the impeller and the frame to assume non-radially-constrained configurations, the delivery catheter is retracted. For some applications, as shown in FIG. 10A, the delivery catheter remains in the subject's aorta during operation of the left ventricular device, and outer tube 142 is disposed inside the delivery catheter. For some applications, during operation of the left ventricular device, a channel 224 is defined between delivery catheter 143 and outer tube 142. (It is noted that the channel as shown in FIG. 10A is not to scale, for illustrative purposes.) Channel 224 is described in further detail hereinbelow. In order to retract the left ventricular device from the subject's body, the delivery catheter is advanced over the impeller and the frame, such that the impeller and the frame assume their radially-constrained configurations. The catheter is then withdrawn from the subject's body.

Referring to FIG. 10C (which shows a cross-sectional view of drive cable 130 and axial shaft 92), typically, the axial shaft and the drive cable define a continuous lumen 132 therethrough. For some applications, the left ventricular device is guided to the aorta and to the left ventricle by placing the axial shaft and the cable over guidewire 10 (described hereinabove), such that the guidewire is disposed inside lumen 132. Typically, the guidewire is inserted through duckbill valve 390 (or other hemostasis valve) disposed at the distal end of distal tip portion of distal-tip element 107. The guidewire passes through guidewire lumen 122 (of the distal-tip portion), and then passes into lumen 132 which is defined by the axial shaft at that point. The guidewire then continues to pass through lumen 132 all the way until the proximal end of the drive cable. From the proximal end of the drive cable, the guidewire passes through guidewire lumen 133 defined by pin 131, which is disposed outside of the subject's body even after insertion of the distal end of ventricular assist device 20 into the subject's left ventricle. Typically, when the distal end of the ventricular assist device is disposed inside the subject's left ventricle, the guidewire is retracted from the subject's body by pulling the guidewire out of the proximal end of guidewire lumen 133. Subsequently, the axial position of driven magnet 82 (within which pin 131 is disposed) is fixed such as to be disposed between driving magnets 77, as shown in FIG. 7. For example, a portion of motor unit 23 in which the driven magnet is disposed may be coupled to a portion of the motor unit in which driving magnets 77 are disposed using click-lock element 150 (shown in FIG. 13B).

For some applications, by using lumen 132 of the axial shaft and the cable in the above-described manner, it is not necessary to provide an additional guidewire guide to be used during insertion of left-ventricular assist device 20. For some applications, the axial shaft and the cable each have outer diameters of more than 0.6 mm (e.g., more than 0.8 mm), and/or less than 1.2 mm (e.g., less than 1 mm), e.g., 0.6-1.2 mm, or 0.8-1 mm. For some applications, the diameter of lumen 132, defined by the shaft and the cable, is more than 0.3 mm (e.g., more than 0.4 mm), and/or less than 0.7 mm (e.g., less than 0.6 mm), e.g., 0.3-0.7 mm, or 0.4-0.6 mm. For some applications, drive cable 130 has a total length of more than 1 m (e.g., more than 1.1 m), and/or less than 1.4 m (e.g., less than 1.3 m), e.g., 1-1.4 m, or 1.1-1.3 m. Typically, the diameters of guidewire lumen 122 and guidewire lumen 133 are generally similar to that of lumen 132.

Figure 10D:
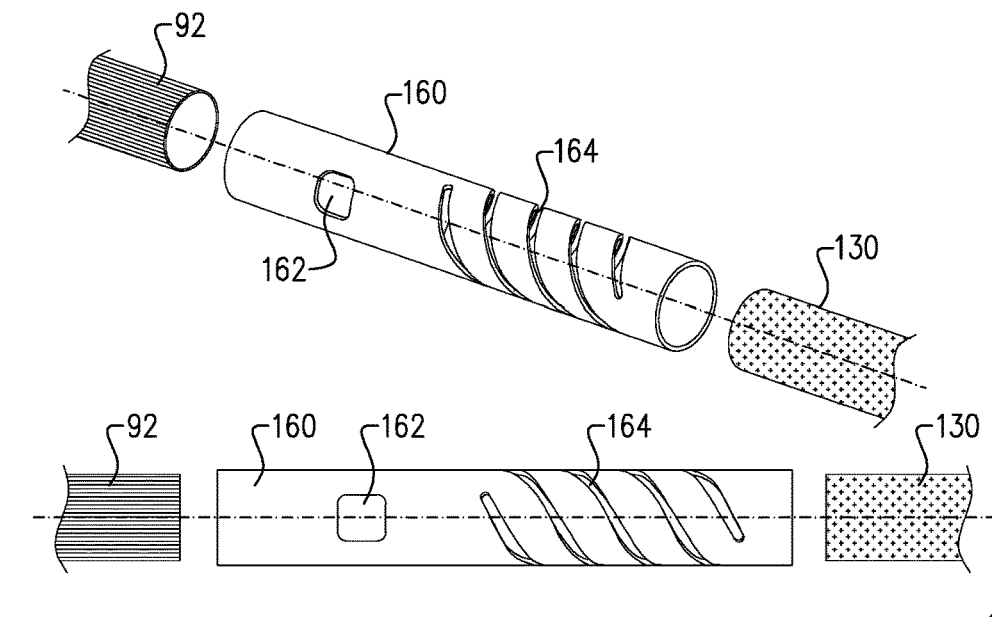
FIGS. 10D, 10E, and 10F are schematic illustrations of the drive cable and an axial shaft of the ventricular assist device, in accordance with some applications of the present invention.
Figure 10E:
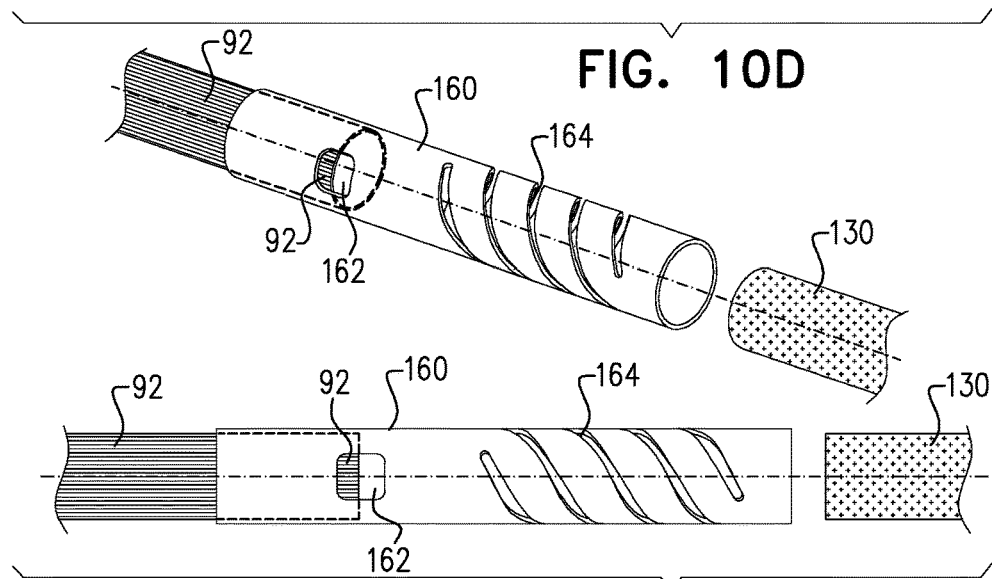
Figure 10F:
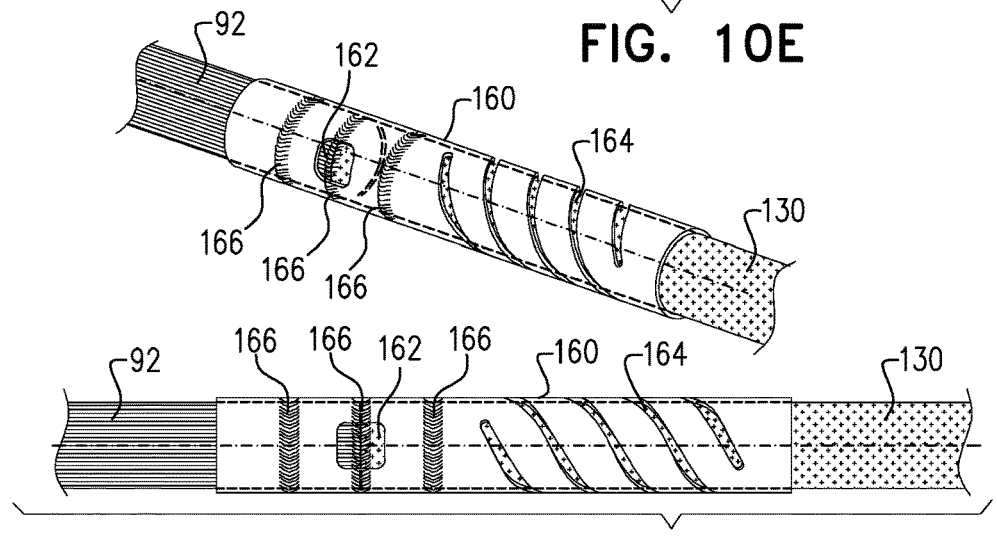

Reference is now made to FIGS. 10D, 10E, and 10F, which are schematic illustrations of respective steps of a technique for coupling drive cable 130 to axial shaft 92 using a butt-welding overtube 160, in accordance with some applications of the present invention. Typically, butt-welding overtube defines a window 162, and a helical groove 164. For some applications, axial shaft is inserted into a first end of butt-welding overtube, such that the proximal end of axial shaft 92 is visible at a given location across window 162, e.g., at the halfway point across the width of the window, as shown in the transition from FIG. 10D to FIG. 10E. Subsequently, drive cable 130 is inserted into the other end of the butt-welding overtube, until the distal end of the drive cable is also disposed at the given location across window 162 (e.g., at the halfway point across the width of the window), and is typically touching the proximal end of the axial shaft, as shown in the transition from FIGS. 10E and 10F.

It is noted that the insertion of the axial shaft and the drive cable into butt-welding overtube 160 may be in the reverse order to that shown. Namely, the drive cable may be inserted first, followed by the axial shaft. It is further noted that, for illustrative purposes, drive cable is shown as a tube in FIGS. 10D-F. However, the drive cable typically includes a plurality of coiled wires, e.g., as shown in FIG. 10B.

Typically, once both the axial shaft and the drive cable have been inserted into butt-welding overtube 160, a plurality of welding rings 166 are welded into the butt-welding overtube. Typically, one ring is welded at the given location across window 162, e.g., at the halfway point across the width of the window. Further typically, an additional ring is welded on either side of window 162, but at a location that is spaced from the ends of the butt-welding overtube. In this manner, the additional welding rings weld the butt-welding overtube to the axial shaft and drive cable without the additional welding rings being welded directly onto the outer surfaces of the axial shaft and the drive cable. For some applications, this places less strain on the welding rings relative to if the additional welding rings were to be welded at ends of the butt-welding overtube, such that the additional welding rings were to be welded directly onto the outer surfaces of the axial shaft and the drive cable. Typically, the welding rings are welded to a depth that is such that the butt-welding overtube is welded to the axial shaft and the drive cable, without reducing the diameter of guidewire lumen 132. As shown, typically, the drive cable is inserted into the butt-welding overtube, such that the helical groove is disposed around the drive cable. Typically, the helical groove provides flexibility to the portion of the butt-welding overtube that is disposed over drive cable 130.

For some applications, generally similar techniques to those described for welding the distal end of drive cable 130 to axial shaft 92, are used for welding the proximal end of the drive cable to pin 131 (described hereinabove with reference to FIG. 7), mutatis mutandis. For some applications, the drive cable comprises portions having respective characteristics (e.g., respective numbers of wires in the set of coiled wires that comprise the portions of the drive cable). For some such applications, generally similar techniques to those described for welding the distal end of drive cable 130 to axial shaft 92, are used for welding the respective portions of the drive cable to each other, mutatis mutandis.

For some applications, certain features of butt-welding overtube 160 and the techniques for use therewith are practiced in the absence of others of the features. For example, the butt-welding overtube may include the window, and the welding rings may be welded in the above-described manner, even in the absence of the helical groove.

Figure 11A:
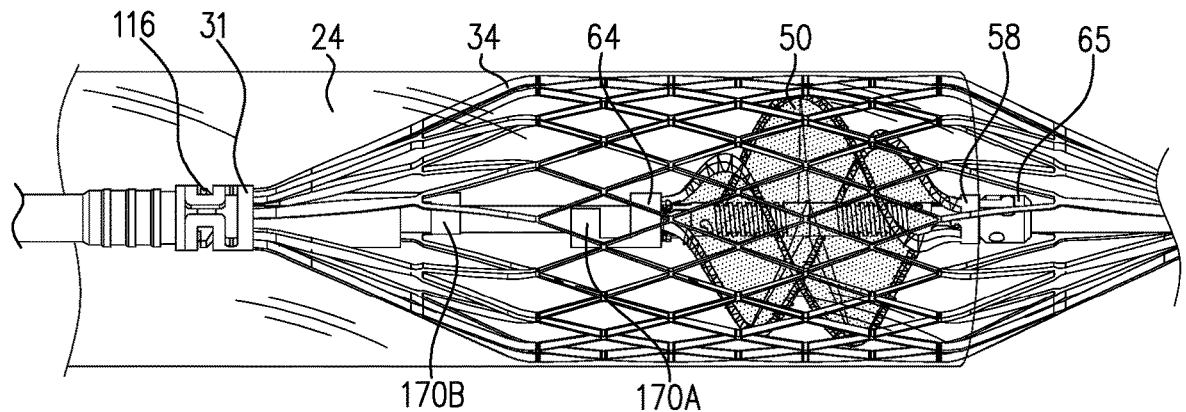
FIGS. 11A and 11B are schematic illustrations of an impeller that is coupled to an axial shaft at the distal end of the impeller and that is not coupled to the axial shaft at the proximal end of the impeller, in accordance with some applications of the present invention.
Figure 11B:
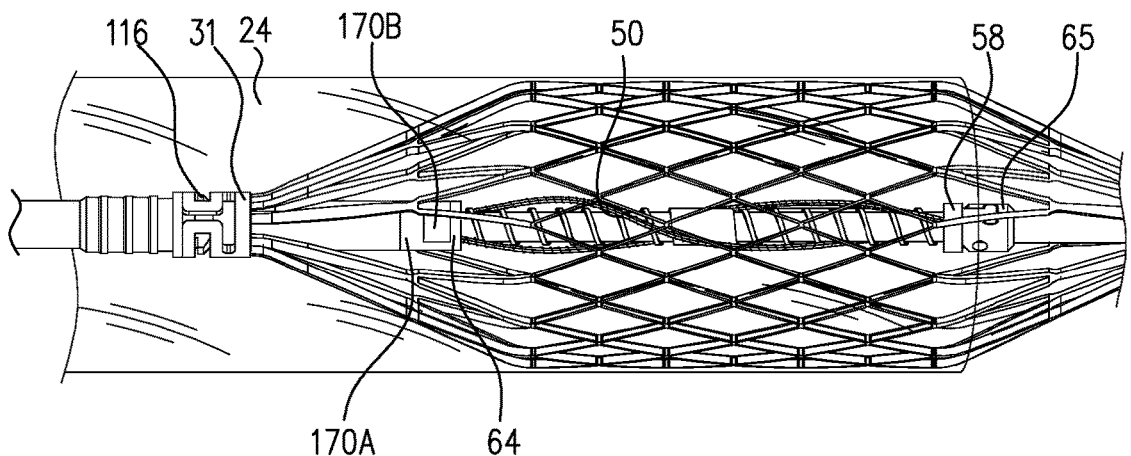

Reference is now made to FIGS. 11A and 11B, which are schematic illustrations of impeller 50, the impeller being coupled to axial shaft 92 at the distal end of the impeller and not being coupled to the axial shaft at the proximal end of the impeller, in accordance with some applications of the present invention. As described hereinabove, typically, axial shaft 92 passes through the axis of impeller 50, via lumen 62 of the impeller. For some applications, distal bushing 58 of the impeller is coupled to the shaft via coupling element 65 such that the axial position of the distal bushing with respect to the axial shaft is fixed, and proximal bushing 64 of the impeller is slidable with respect to the axial shaft. The axial shaft itself is radially stabilized via proximal radial bearing 116 and distal radial bearing 118. Proximal and distal ends of frame 34 are rigidly coupled to the proximal and distal bearings, as described hereinabove. In turn, the axial shaft, by passing through lumen 62 defined by the impeller, radially stabilizes the impeller with respect to the inner surface of frame 34, such that even a relatively small gap between the outer edge of the blade of the impeller and the inner surface of frame 34 (e.g., a gap that is as described above) is maintained, during rotation of the impeller, as described hereinabove. For such applications, typically, when crimping (i.e., radially constraining) the impeller and the frame for the purpose of inserting the impeller and the frame into the subject's body, proximal bushing 64 of the impeller is configured to slide along the axial shaft in the distal direction, such that the impeller becomes axially elongated, while the distal bushing remains in an axially fixed position with respect to the axial shaft. More generally, the impeller changes from its radially-constrained configuration to its non-radially-constrained configuration, and vice versa, by the proximal bushing sliding over the axial shaft, while the distal bushing remains in an axially fixed position with respect to the axial shaft.

Figure 11C:
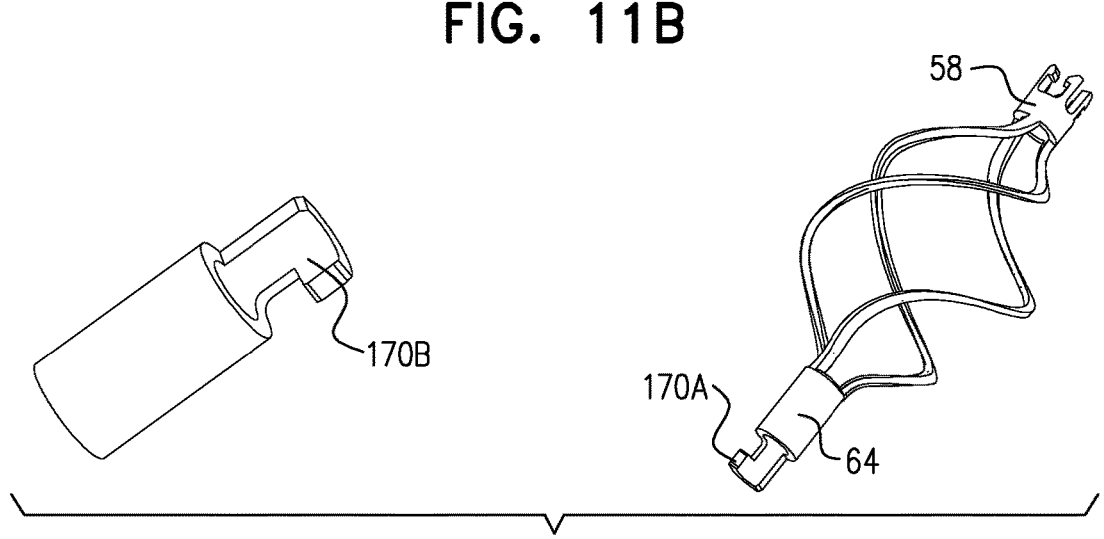
FIG. 11C is a schematic illustration of coupling portions for facilitating the crimping of the impeller of FIGS. 11A and 11B.

Reference is now made to FIG. 11C, which is a schematic illustration of first and second coupling portions 170A and 170B for facilitating the crimping of the impeller of FIGS. 11A-B, independently of other components of frame 34, in accordance with some applications of the present invention. First and second portions 170A and 170B are configured to become engaged with each other. The first portion is disposed on the impeller, and the second portion is coupled to frame 34 and/or proximal bearing 116. Referring again to FIGS. 11A and 11B, for some applications, prior to crimping frame 34, the impeller is radially constricted, by engaging portions 170A and 170B with each other and axially elongating the impeller, such as to radially constrict the impeller. Subsequently, frame 34 is crimped. Typically, when the impeller and the frame are disposed in the subject's left ventricle, the first and second coupling portions are decoupled from each other, such that the proximal end of impeller is able to move with respect to frame 34 and proximal bearing 116.

Figure 12A:
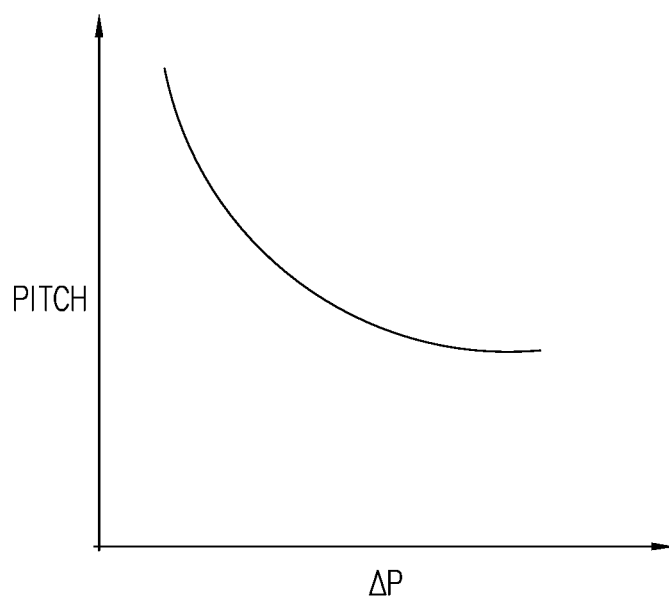
FIG. 12A is a graph showing the relationship between the pressure gradient against which the impeller is pumping and the pitch of the impeller when the impeller is configured as shown in FIG. 11A.
Figure 12B:
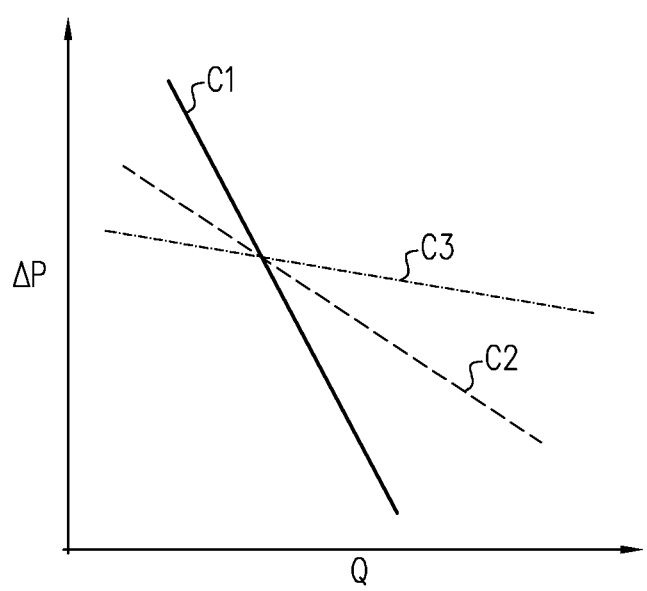
FIG. 12B is a graph showing pressure-flow curves for impellers having respective pitches, in accordance with some applications of the present invention.

Reference is now made to FIG. 12A, which is a graph showing the relationship between the pressure gradient against which the impeller is pumping and the pitch of the impeller when the impeller is configured as shown in FIGS. 11A-B. As shown, since the proximal end of the impeller is slidable, as the pressure gradient against which the impeller is pumping increases, the pitch of the impeller decreases, due to the impeller blades being axially compressed by the pressure against which the impeller is pumping. Reference is also made to FIG. 12B, which is a graph showing pressure-flow curves for impellers as described herein having respective pitches. Curve C1 corresponds to an impeller having a relatively small pitch, C2 corresponds to an impeller having a medium pitch, and C3 corresponds to an impeller having a relatively large pitch. As shown, the smaller the pitch of the impeller, the greater the gradient of the pressure-flow curve, ceteris paribus. Moreover, at relatively high pressure gradients, an impeller having a smaller pitch generates greater flow than an impeller having a greater pitch, whereas at relatively low pressure gradients, an impeller having a larger pitch generates greater flow than an impeller having a smaller pitch, ceteris paribus. In accordance with FIGS. 12A-B, for some applications, by virtue of the impeller being coupled to the axial shaft at its distal end and being slidable with respect to the axial shaft at its proximal end, as the pressure gradient against which the impeller pumps increases, the pitch of the impeller decreases. Thus, at higher pressure gradients (at which a smaller pitch typically generates greater flow), the impeller has a smaller pitch, while at lower pressure gradients (at which a larger pitch typically generates greater flow), the impeller has a greater pitch.

With reference to the curves shown in FIG. 12B and with respect to the impeller as it is typically configured in the context of the present application (i.e., with the proximal bearing coupled to the axial shaft and not as shown in FIGS. 11A-B), it is typically desirable that the impeller has the following characteristics:

1) At a rotation rate of less than 20,000 RPM (e.g., less than 19,000 RPM), when pumping against a pressure gradient of 100-120 mmHg, the impeller provides positive or at least zero flow. This is so that, even in the eventuality that there is unusually high backpressure from the aorta to the left ventricle, there is no blood flow in this direction.

2) At a rotation rate of less than 20,000 RPM (e.g., less than 19,000 RPM), when pumping against a pressure gradient of more than 50 mmHg (e.g., more than 60 mmHg), for example, 50-70 mmHg, the impeller provides flow of more than 3.5 L/min (e.g., more than 4.5 L/min), for example 3.5-5 L/min. Under normal physiological conditions, the pressure gradient between the left ventricle and the aorta at diastole is within the aforementioned range, and it is desirable to provide a flow rate as described even during diastole.

As indicated in the curves shown in 12B, in order to provide the first characteristic an impeller having a smaller pitch (corresponding to curve C1) is preferable, but in order to provide the second characteristic an impeller having a larger pitch (corresponding to curve C3) is preferable. With this background in mind, the inventors of the present application have found that, in order to satisfy the first and second characteristics in an optimum manner, it is typically desirable for the impeller to have a pitch that is such that, when the impeller is in its non-radially-constrained configuration, the helical elongate elements of the impeller (and therefore the impeller blades) undergo a complete revolution of 360 degrees (or would undergo a complete revolution if they were long enough) over an axial length of more than 8 mm (e.g., more than 9 mm), and/or less than 14 mm (e.g., less than 13 mm), e.g., 8-14 mm, 9-13 mm, or 10-12 mm. Typically, when the impeller has a pitch that is as described, and at a rotation rate of less than 20,000 RPM (e.g., less than 19,000 RPM) the impeller provides zero or positive flow at a pressure gradient of more than 100 mmHg, e.g., more than 110 mmHg, and a flow of more than 3 L/min (e.g., more than 4.5 L/min), for example 3.5-5 L/min, at a pressure gradient of more than 50 mmHg (e.g., more than 60 mmHg), for example, 50-70 mmHg. Typically, the impeller is configured to provide the aforementioned flow rates by virtue of the impeller having a maximum diameter of more than 7 mm (e.g. more than 8 mm), when the impeller is in its non-radially-constrained configuration.

For some applications, the pitch of helical elongate elements 52 of the impeller (and therefore the impeller blade) varies along the lengths of the helical elongate elements, at least when the impeller is in a non-radially-constrained configuration. Typically, for such applications, the pitch increases from the distal end of the impeller (i.e., the end that is inserted further into the subject's body, and that is placed upstream with respect to the direction of antegrade blood flow) to the proximal end of the impeller (i.e., the end that is placed downstream with respect to the direction of antegrade blood flow), such that the pitch increases in the direction of the blood flow. Typically, the blood flow velocity increases along the impeller, along the direction of blood flow. Therefore, the pitch is increased along the direction of the blood flow, such as to further accelerate the blood.

Figure 13A:
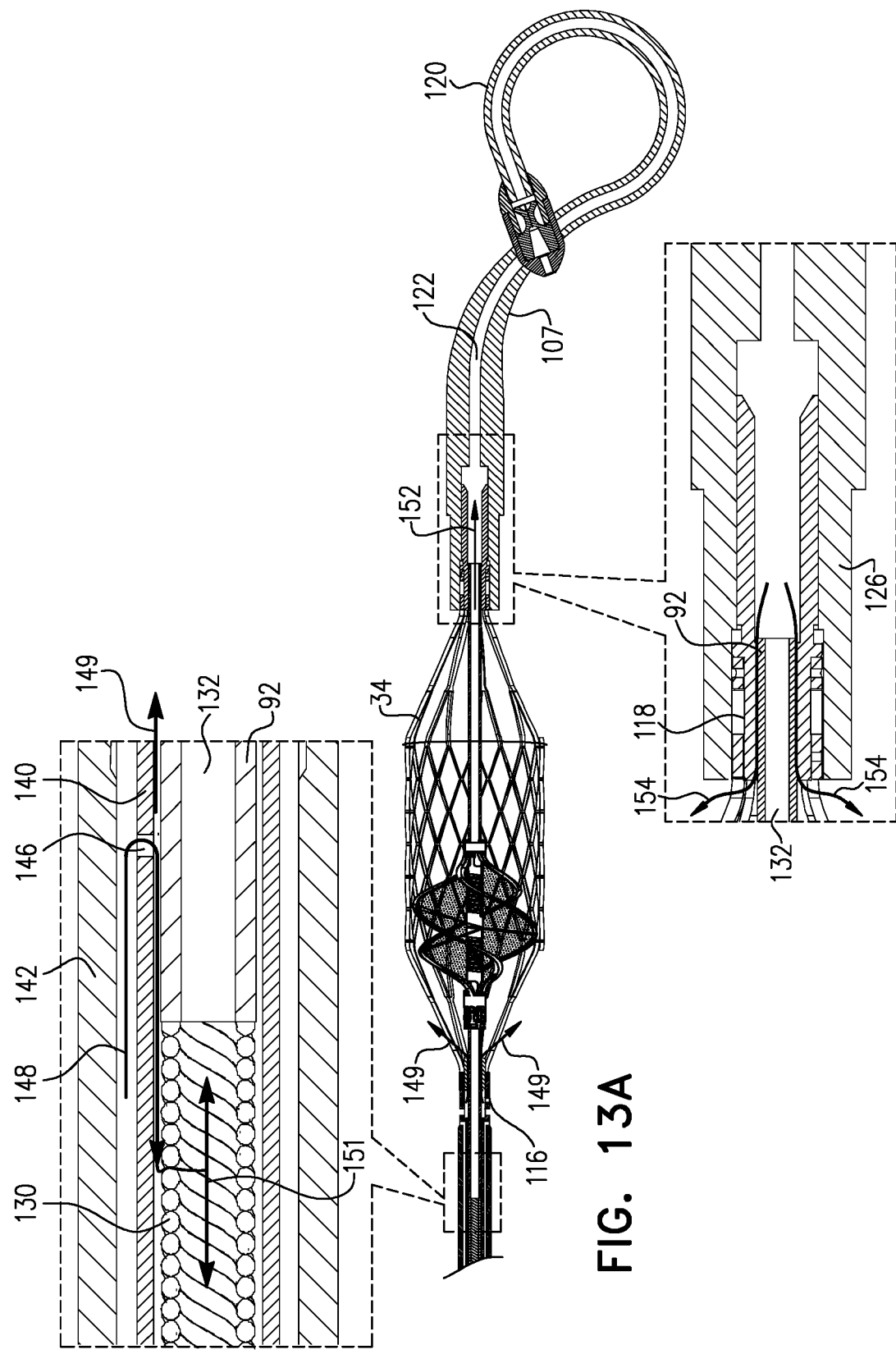
FIGS. 13A, 13B, and 13C are schematic illustrations of a procedure for purging a drive cable and/or radial bearings of a ventricular assist device, in accordance with some applications of the present invention.
Figure 13B:
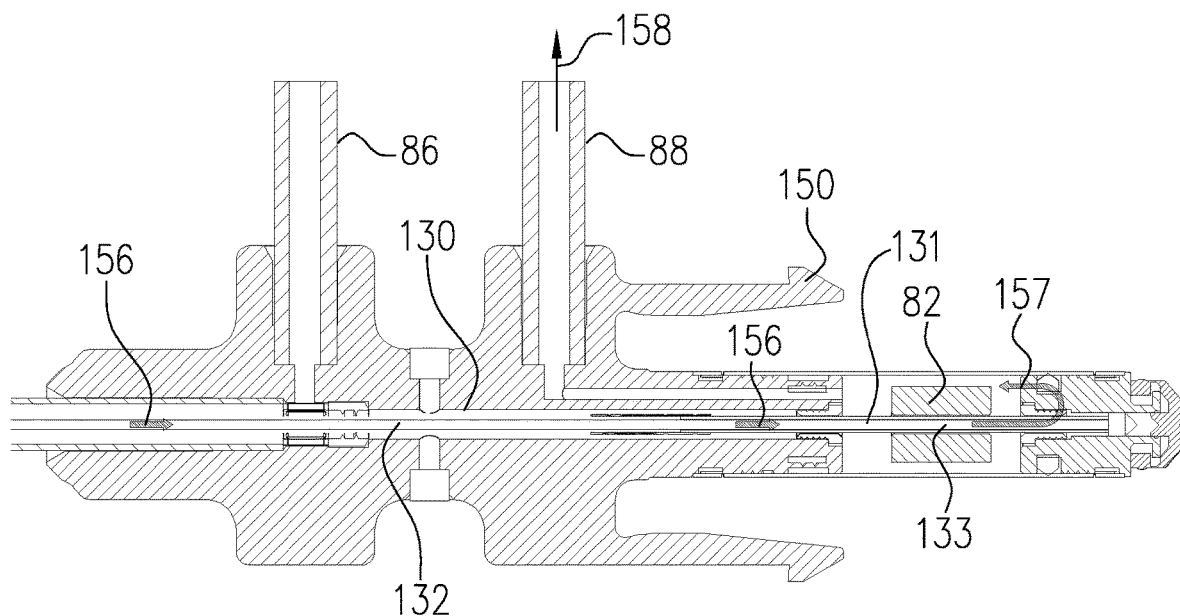
Figure 13C:
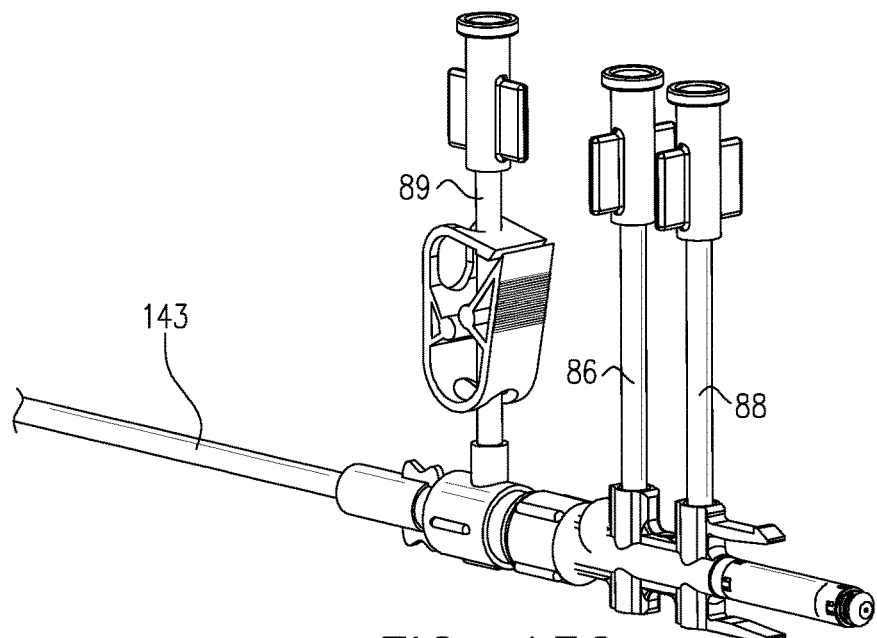

Reference is now made to FIGS. 13A, 13B, and 13C, which are schematic illustrations of a procedure for purging drive cable 130 of ventricular assist device 20, in accordance with some applications of the present invention. For some applications, proximal to proximal bearing 116, axial shaft 92 and cable 130 are surrounded by first and second outer tubes 140 and 142, as described hereinabove. Typically, both the first and second outer tubes remain stationary, during rotation of the drive cable. For some applications, purging system 29 (shown in FIG. 1A) controls the flow of a purging fluid (e.g., a fluid containing glucose or dextrose) via inlet port 86 and outlet port 88 (shown in FIGS. 7, 8A, 8B, 13B, and 13C). The fluid is configured to remove air from the space between the drive cable and the outer tube, and/or to reduce frictional forces between drive cable 130 (which rotates), and outer tube 140 (which remains stationary, during rotation of the drive cable), and/or to reduce frictional forces between axial shaft 92 and proximal bearing 116 and/or distal bearing 118.

Referring to FIG. 13A, for some applications, the purging fluid is pumped between the first and second outer tubes, and there is an opening 146 within the first outer tube in the vicinity of the proximal bearing. For some applications, the purging fluid flows between first outer tube 140 and drive cable 130 via opening 146, as indicated by purging-fluid-flow arrow 148 in FIG. 13A. In this manner, the interface between drive cable 130 (which rotates), and outer tube 140 (which remains stationary, during rotation of the drive cable) is purged. For some applications, some of the purging fluid additionally flows to the interface between the axial shaft and proximal bearing 116, thereby purging the interface (and/or reducing frictional forces at the interface), as indicated by purging-fluid-flow arrows 149 in FIG. 13A. Typically, the flow of the purging fluid in the direction of arrows 149 also prevents blood from flowing into the interface between the axial shaft and the proximal bearing.

As described hereinabove (with reference to FIG. 10B) typically the drive cable includes a plurality of coiled wire. For some applications, purging fluid passes into lumen 132 defined by the drive cable via gaps in the coiled wires. Once the purging fluid is disposed within lumen 132 it flows in both proximal and distal directions, as indicated by arrow 151 of FIG. 13A. The purging fluid that flows in the distal direction typically flows out of the distal end of lumen 132 and toward lumen 122 defined by distal-tip portion, as indicated by arrow 152 of FIG. 13A. At the end of distal-tip portion, the purging fluid is typically prevented from flowing out of the distal-tip portion by duckbill valve 390. Therefore, some of the purging fluid typically flows to the interface between the axial shaft and distal bearing 118, thereby purging the interface (and/or reducing frictional forces at the interface), as indicated by purging-fluid-flow arrows 154 in FIG. 13A. Typically, the flow of the purging fluid in the direction of arrows 154 also prevents blood from flowing into the interface between the axial shaft and the distal bearing.

As described above, once the purging fluid is disposed within lumen 132 it flows in both proximal and distal directions, as indicated by arrow 151 of FIG. 13A. Referring now to FIG. 13B, typically, at the proximal end of ventricular assist device 20, the purging fluid flows in the direction of arrows 156 out of the proximal end of lumen 132 and then out of the proximal end of lumen 133 defined by pin 131. For some applications, the purging fluid then flows in the direction of arrow 157 and around driven magnet, such as to reduce frictional forces that the driven magnet is exposed to. For some applications, the purging fluid then flows out of outlet port 88, in the direction of arrow 158. Typically, the purging fluid is then disposed of. Alternatively, the purging fluid is pumped back into the device, via inlet port 86.

With reference to the above description of the purging procedure that is typically used with ventricular assist device 20, it is noted that guidewire lumens 122, 132, and 133 (which were previously used to facilitate insertion of the device over guidewire 10, as described hereinabove), are typically used as flow channels for purging fluid, during use of the ventricular assist device.

Referring now to FIG. 13C, for some applications, ventricular assist device includes an additional purging fluid inlet port 89, which is typically used to pump purging fluid into channel 224 between delivery catheter 143 and outer tube 142. For some applications, the purging fluid is pumped into this channel at a low enough pressure, that it is still possible to detect aortic blood pressure via this channel, as described in further detail hereinbelow. For some applications, rather than continuously pumping purging fluid into channel 224, fluid is pumped into this channel periodically in order to flush the channel. For some applications, port 89 and channel 224 are used for aortic pressure sensing, as described in further detail hereinbelow.

Figure 13D:
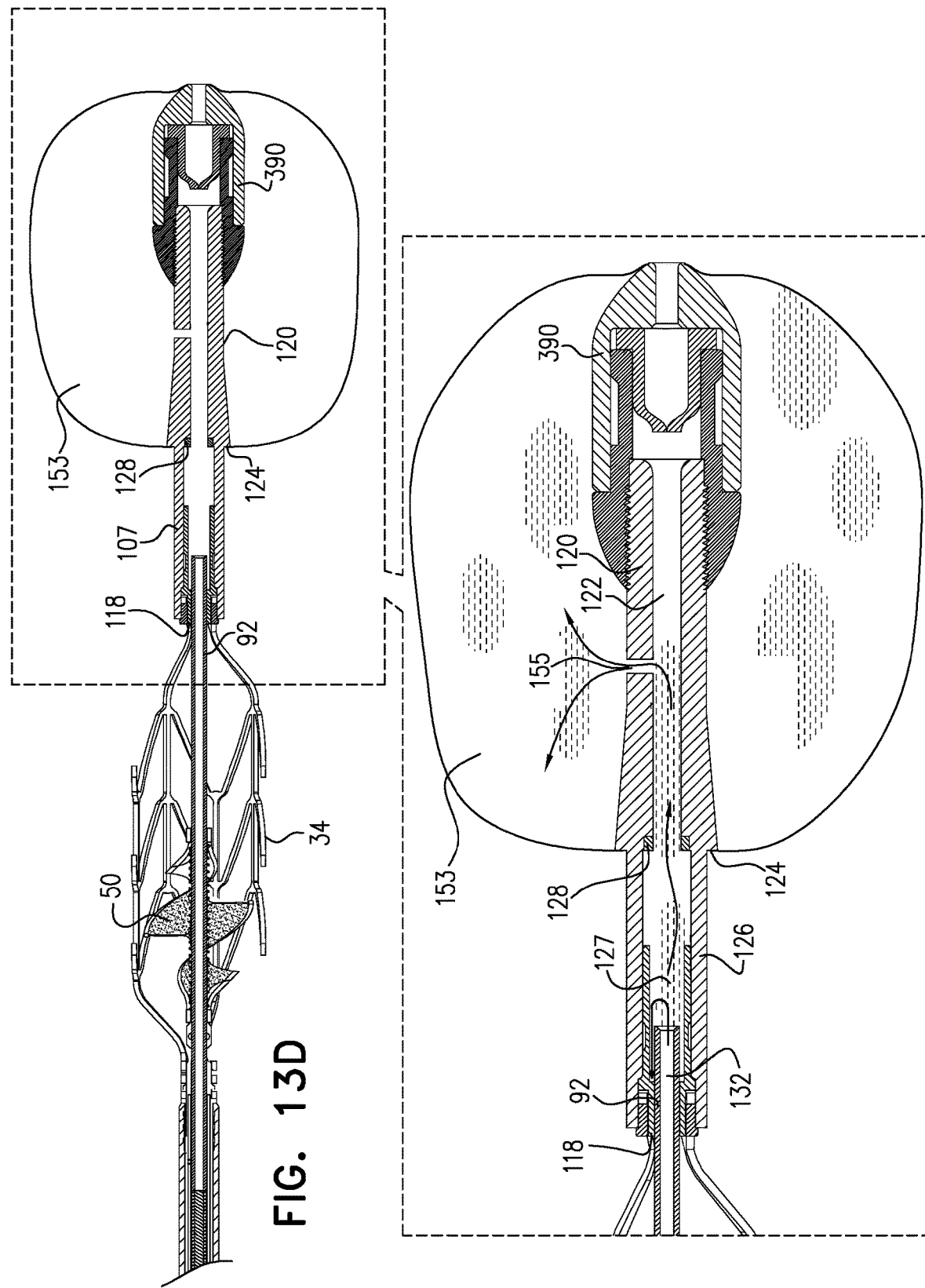
FIG. 13D is a schematic illustration of a ventricular assist device that includes an inflatable portion (e.g., a balloon) disposed around its distal-tip portion, the inflatable portion being configured to be inflated by a fluid that is used for purging the drive cable of the device, in accordance with some applications of the present invention.

Reference is now made to FIG. 13D, which is a schematic illustration of ventricular assist device 20 that includes an inflatable portion 153 (e.g., a balloon) on its distal tip, the inflatable portion being configured to be inflated by a fluid that is used for purging the drive cable of the device, in accordance with some applications of the present invention. As described hereinabove, with reference to FIG. 13A, for some applications, purging fluid is pumped through lumen 132 defined by drive cable 130 and axial shaft 92, such that at least some fluid flows all the way to the distal end of the axial shaft. Typically, for such applications, the purging fluid continues to flow into lumen 122 of distal-tip portion 120. For some applications, inflatable portion 153 is disposed around the distal-tip portion, and a there is an opening 155 between lumen 122 and the interior of the inflatable portion. The inflatable portion is inflated by the purging fluid entering the interior of the inflatable portion, via opening 155. For some applications, by controlling the pressure at which the purging fluid is pumped into ventricular assist device 20, the inflation of the inflatable portion is controlled.

It is noted that, in accordance with some applications of the present invention, the shape of distal-tip element 107 as shown in FIG. 13D (as well as in FIGS. 16A, 16B, 16E, 17D, 30, and 31, for example) is generally as described in US 2019/0209758 to Tuval, which is incorporated herein by reference. The scope of the present invention includes combining the apparatus and methods described with respect to any one of the figures with any of the shapes of the distal-tip element described herein. It is further noted that, in accordance with some applications of the present invention, the configuration of frame 34 as shown in FIG. 13D is generally as described in US 2019/0209758 to Tuval, which is incorporated herein by reference. The scope of the present invention includes combining the apparatus and methods described with respect to any one of the figures with any of the shapes of the distal-tip portion and/or configurations of frame 34 described herein.

Figure 13E:
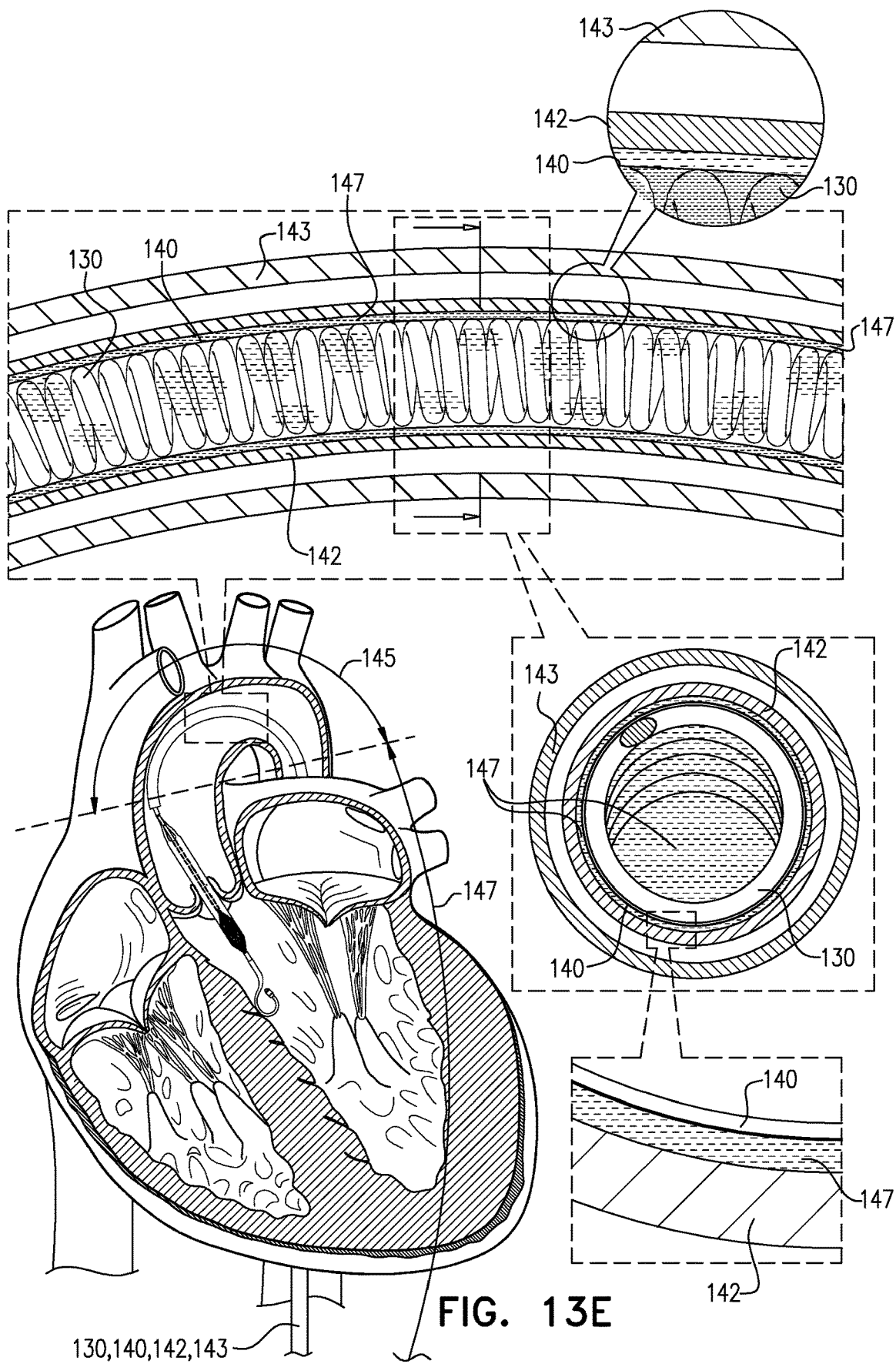
FIG. 13E is a schematic illustration of a technique for reducing frictional forces between a drive cable and an outer tube in which the drive cable rotates and/or for reducing frictional forces at radial bearings of a ventricular assist device, in accordance with some applications of the present invention.

Referring to FIG. 13E, for some applications, as an alternative to pumping a purging fluid through the ventricular assist device throughout the operation of the ventricular assist device, fluid 147 is initially released into the space between drive cable 130 (which rotates), and outer tube 140 (which remains stationary, during rotation of the drive cable), such that the fluid fills the space between the drive cable and outer tube 140, as well as lumen 132. The fluid is then kept in place, between the drive cable and outer tube 140, and within lumen 132, typically, throughout the operation of the ventricular assist device. The fluid is configured to remove air from the space between the drive cable and the outer tube, and/or to reduce frictional forces between drive cable 130 (which rotates), and outer tube 140 (which remains stationary, during rotation of the drive cable), and/or to reduce frictional forces between axial shaft and proximal bearing 116 and/or distal bearing 118. For some applications, the fluid is additionally configured to fill the space between tube 140 and tube 142, e.g., by passing through holes defined by tube 140. For some such applications, heat conducting elements are disposed within the first outer tube and/or the second outer tube, in order to dissipate heat from regions at which a large amount of heat is generated by frictional forces.

For some applications, the fluid has a relatively high viscosity, e.g. a viscosity of more than 100 mPa·s (e.g., more than 500 mPa·s), for example, between 100 mPa·s and 1000 mPa·s, such that the fluid remains substantially in place, during operation of the ventricular assist device. For example, petroleum jelly and/or ultrasound coupling gel may be used as the fluid. For some applications, in order to pump the fluid toward the distal end of the ventricular assist device, the fluid is initially heated, in order to temporarily decrease its viscosity.

Figure 14A:
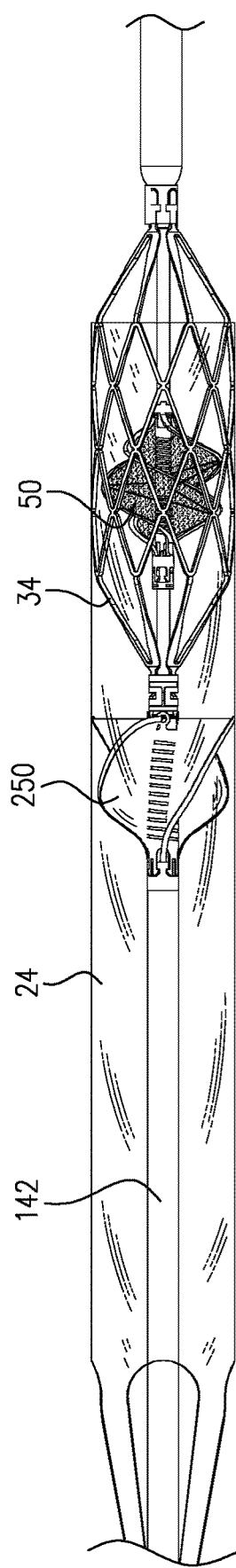
FIGS. 14A, 14B, and 14C are schematic illustrations of a stator configured to be disposed inside a tube of a ventricular assist device, proximal to a frame in which the impeller of the ventricular assist device is disposed, in accordance with some applications of the present invention.
Figure 14C:
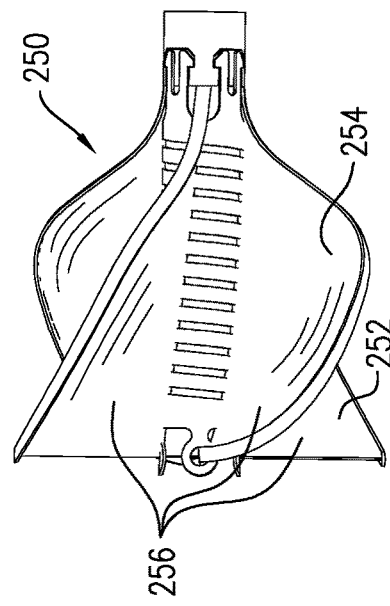
Figure 14B:
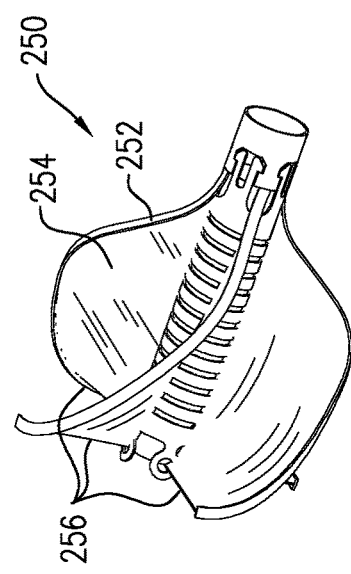

Reference is now made to FIGS. 14A, 14B, and 14C, which are schematic illustrations of a stator 250 configured to be disposed inside tube 24 of ventricular assist device 20, proximal to frame 34 and impeller 50, in accordance with some applications of the present invention. For some applications, the stator is made of a frame 252 that is coupled to outer tube 142, and a flexible material 254 (e.g. polyurethane, polyester, silicone, polyethylene terephthalate (PET), and/or polyether block amide (PEBAX®) that is coupled to the frame. Typically, the stator is shaped to define a plurality of curved projections 256 (e.g., more than 2, and/or less than 8 curved projections) that extend radially from outer tube 142, when device 20 is in a non-radially-constrained configuration. The curvature of the curved projections is typically such as to oppose the direction of rotation of the impeller. The stator is typically configured to reduce rotational flow components from the blood flow prior to the blood flowing from outlet openings 109 of tube 24. For some applications, the projections of stator 250 are not curved.

Typically, during the insertion of tube 24 to the left ventricle, the curved projections of the stator are radially constrained by delivery catheter 143. Upon being released from the delivery catheter, the curved projections are configured to automatically assume their curved configurations.

Figure 15C:
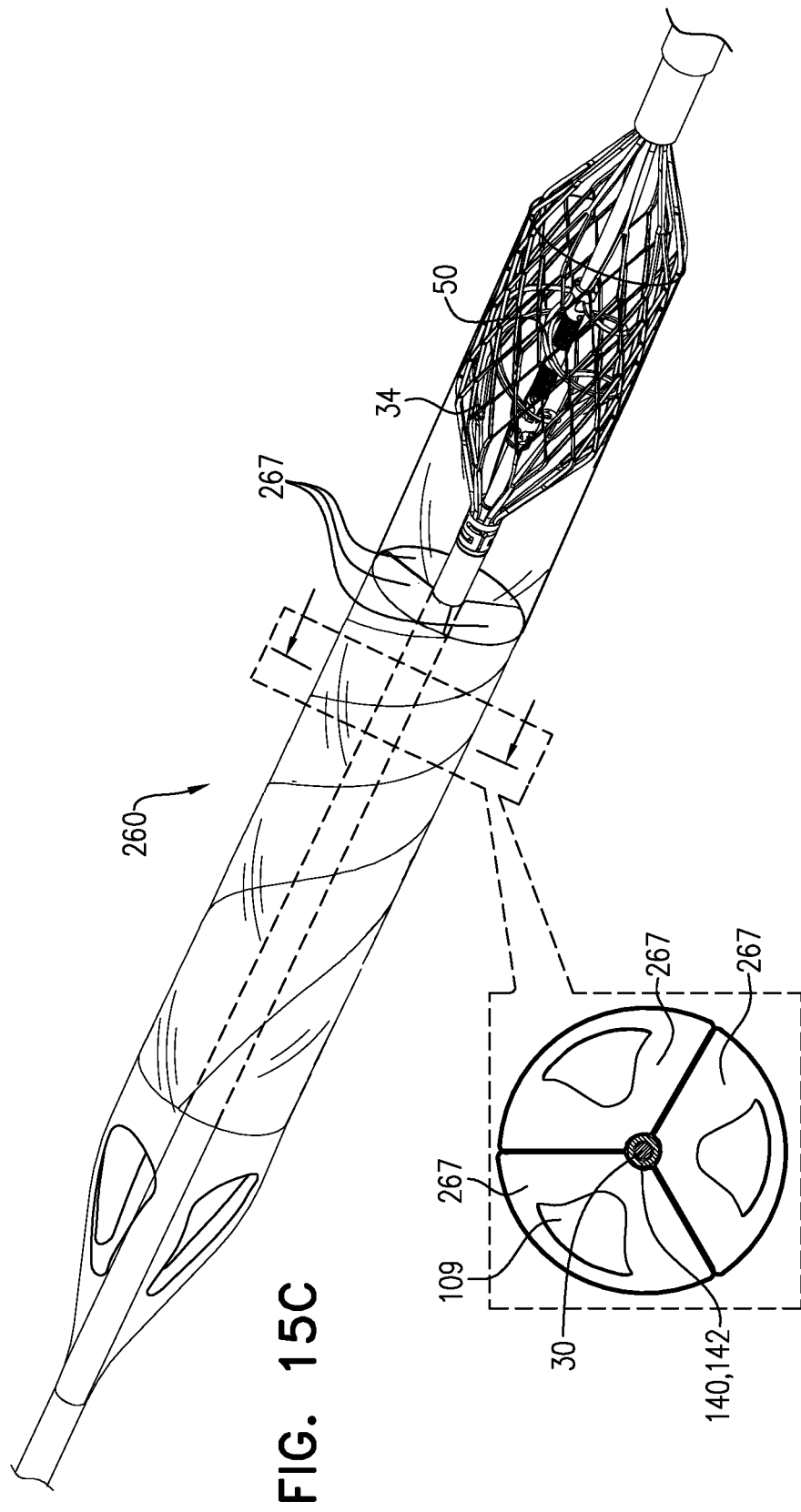

Reference is now made to FIGS. 15A, 15B, 15C, 15D, and 15E, which are schematic illustration of a stator 260 that is defined by tube 24 of ventricular assist device 20, in accordance with some applications of the present invention. Typically, stator 260 defined by a portion of tube 24 that is disposed proximally with respect to frame 34 and impeller 50, and is configured to reduce rotational flow components from the blood flow prior to the blood flowing from outlet openings 109 of tube 24. For some applications, stator 260 is made up of one or more curved ribbons 262 that curve around outer tube 142 within tube 24, as shown in FIG. 15A. Alternatively or additionally, stator 260 comprises a portion 266 of tube 24, which is twisted, such that the walls of the tube itself define folds that are such as to reduce rotational flow components from the blood flow prior to the blood flowing from outlet openings 109 of tube 24, as shown in FIG. 15B.

Figure 15D:
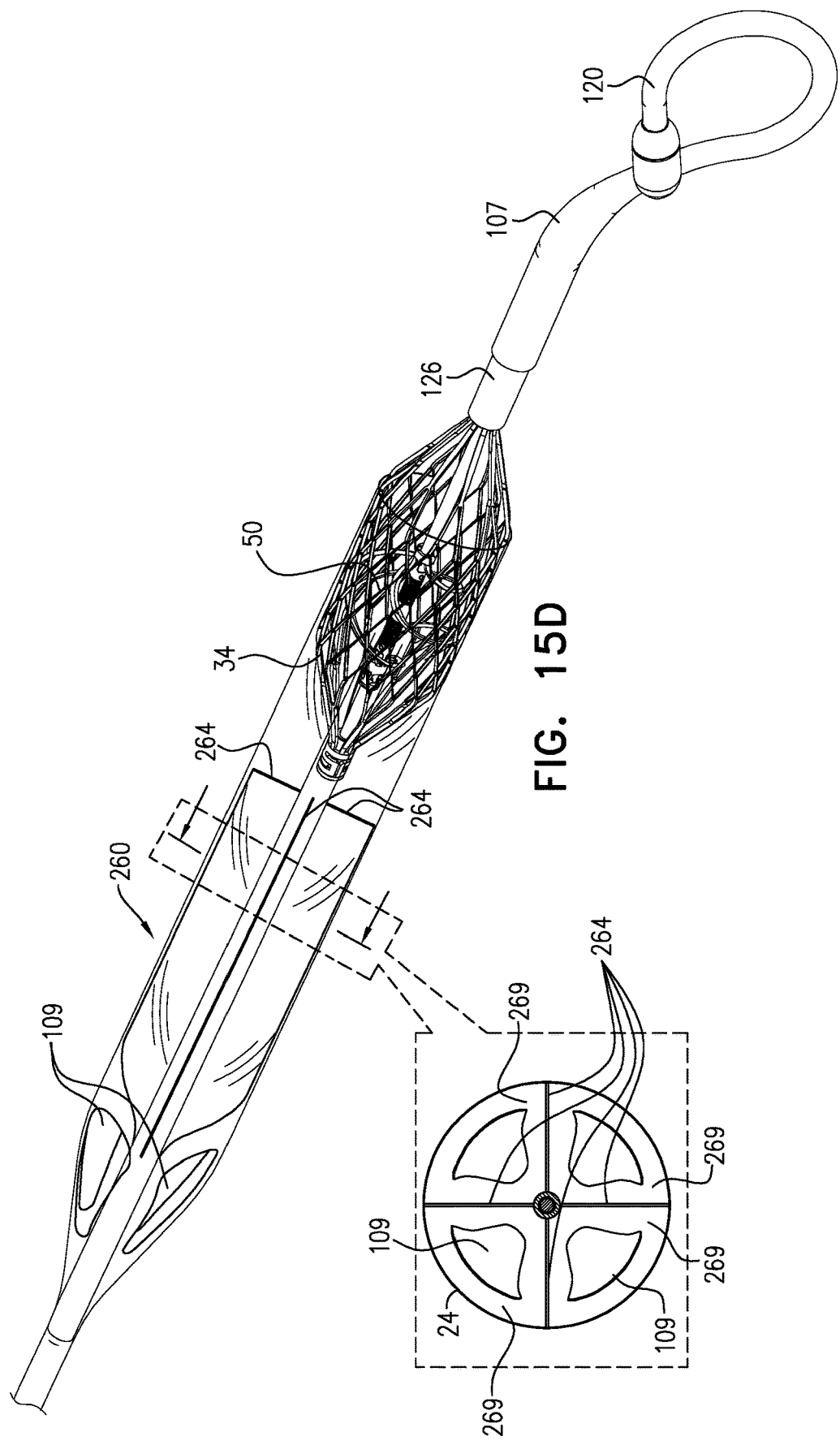
Figure 15E:
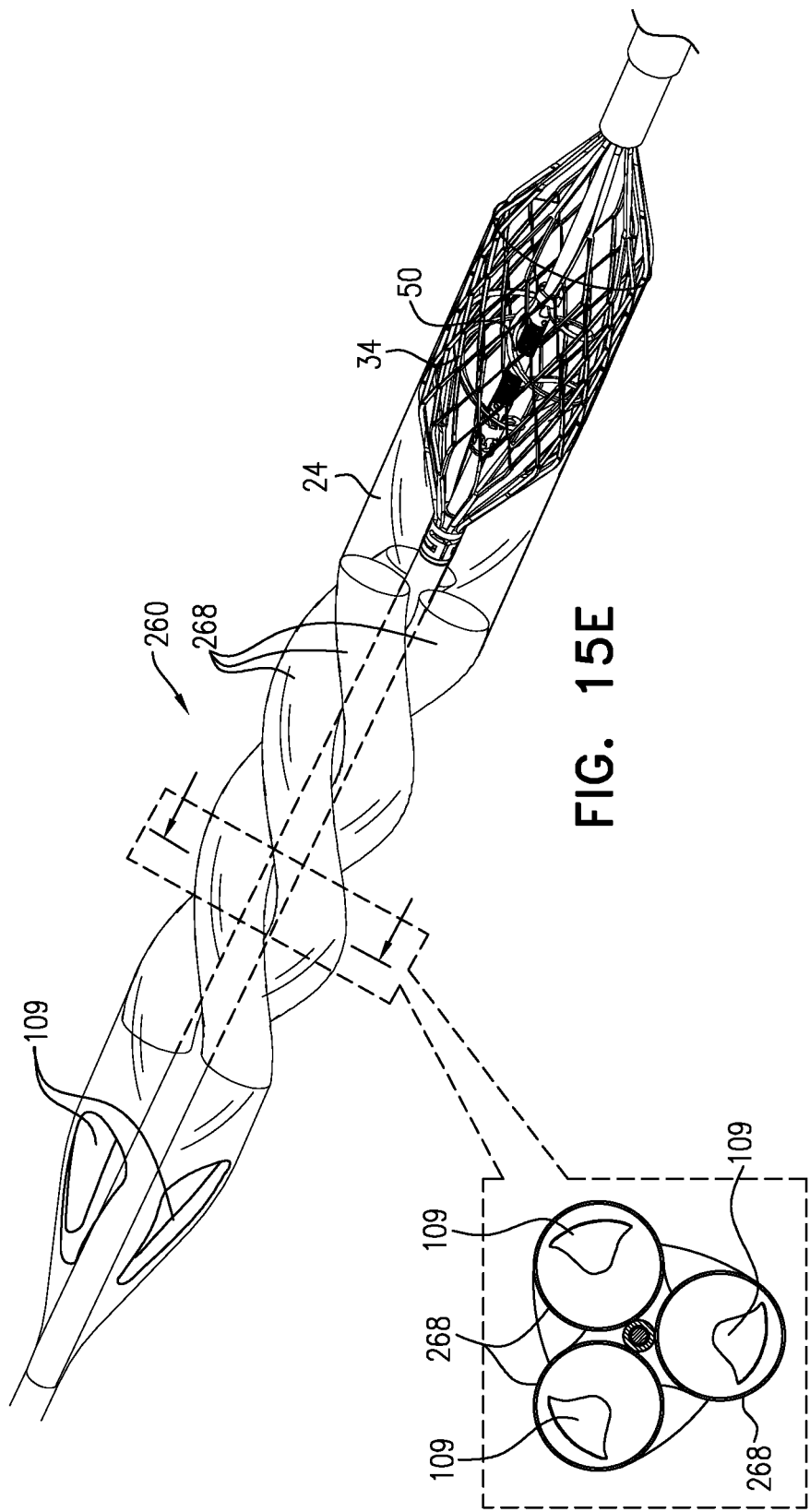

For some applications, along a portion of tube 24 between the proximal end of frame 34 and outlet openings 109, the tube is split into a plurality of compartments 267 by a plurality of curved ribbons 262, such that the compartments define intertwined helices along the length of the portion of the tube, as shown in FIG. 15C. Alternatively, along a portion of tube 24 between the proximal end of frame 34 and outlet openings 109, the tube is split into a plurality of compartments 269 by a plurality of ribbons 264 that are parallel with the longitudinal axis of tube 24, as shown in FIG. 15D. For some applications, within a portion of tube 24 between the proximal end of frame 34 and outlet openings 109, tube 24 includes a plurality of helical tubes 268 that are configured to function as stator 260. For some applications, the helical tubes are twisted around each other, as shown. Typically, each of the examples of stator 260 shown in FIGS. 15A, 15B, 15C, 15D, and 15E is configured to reduce rotational flow components from the blood flow prior to the blood flowing from outlet openings 109 of tube 24.

Figure 16B:
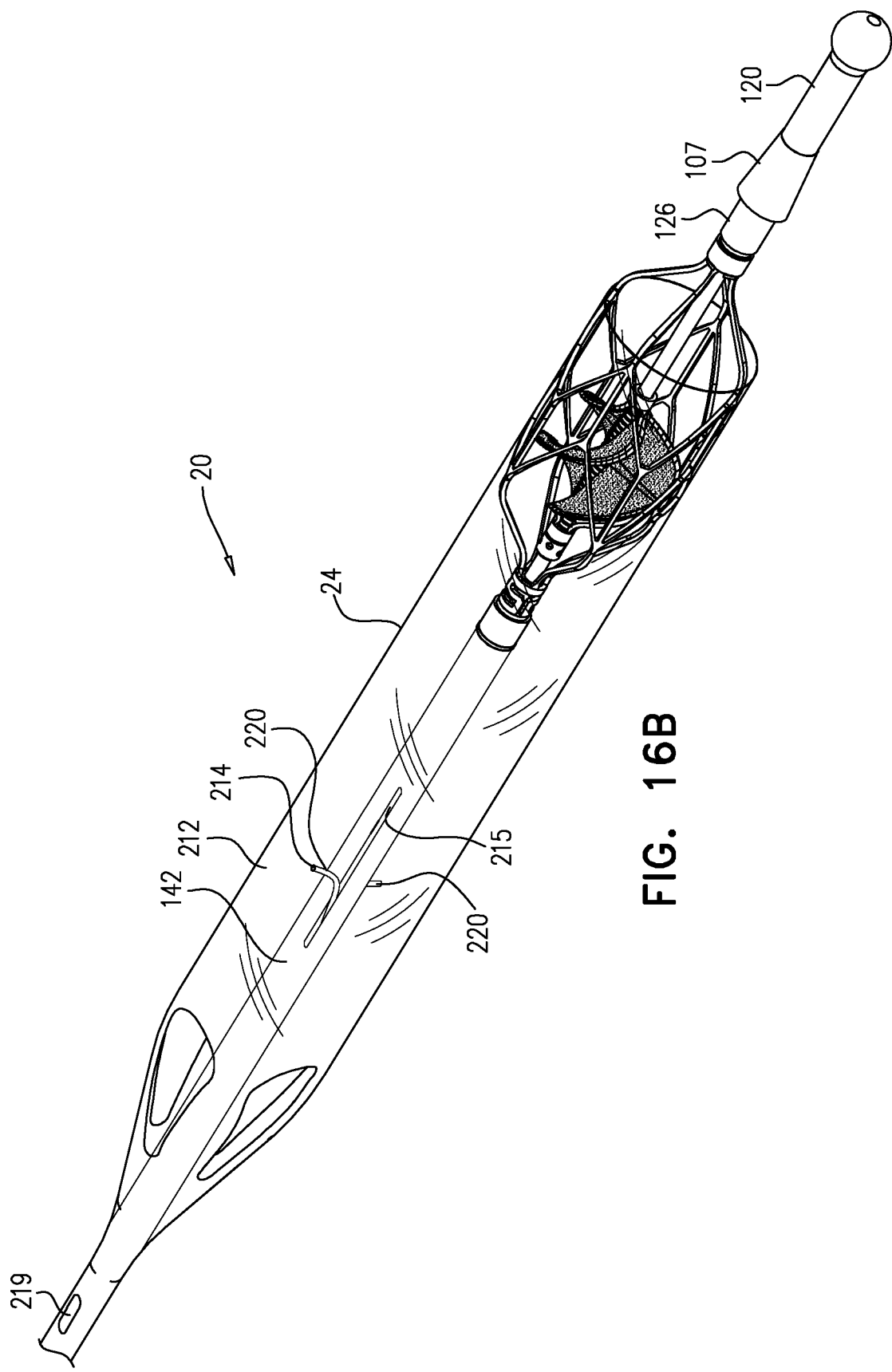

Reference is now made to FIGS. 16A and 16B, which are schematic illustrations of ventricular assist device 20, the ventricular assist device including one or more ventricular blood-pressure-measurement tubes 220, in accordance with some applications of the present invention. As described hereinabove, typically, the ventricular assist device includes tube 24, which traverses the subject's aortic valve, such that a proximal end of the tube is disposed within the subject's aorta and a distal end of the tube is disposed within the subject's left ventricle. Typically, a blood pump (which typically includes impeller 50), is disposed within the subject's left ventricle within tube 24, and is configured to pump blood through tube 24 from the left ventricle into the subject's aorta. For some applications, ventricular blood-pressure-measurement tube 220 is configured to extend to at least an outer surface 212 of tube 24, such that an opening 214 at the distal end of the blood-pressure-measurement tube is in direct fluid communication with the patient's bloodstream outside tube 24. Typically, opening 214 is configured to be within the subject's left ventricle proximal to the blood pump (e.g., proximal to impeller 50). A pressure sensor 216 (illustrated schematically in FIG. 1A) measures pressure of blood within the ventricular blood-pressure-measurement tube. Typically, by measuring pressure of blood within the left ventricular blood-pressure-measurement tube, the pressure sensor thereby measures the subject's blood pressure outside tube 24 (i.e., left ventricular blood pressure). Typically, blood-pressure-measurement tube 210 extends from outside the subject's body to opening 214 at the distal end of the tube, and pressure sensor 216 is disposed toward a proximal end of the tube, e.g., outside the subject's body. For some applications, computer processor 25 (FIG. 1A), receives an indication of the measured blood pressure and controls the pumping of blood by the impeller, in response to the measured blood pressure.

For some applications, the ventricular assist device includes two or more such ventricular blood-pressure-measurement tubes 220, e.g., as shown in FIGS. 16A and 16B. For some applications, based upon the blood pressure as measured within each of the left ventricular blood-pressure-measurement tubes, computer processor 25 determines whether the opening of one of the two or more ventricular blood-pressure-measurement tubes is occluded. This may occur, for example, due to the opening coming into contact with the wall of the interventricular septum, and/or a different intraventricular portion. Typically, in response to determining that the opening of one of the two or more ventricular blood-pressure-measurement tubes is occluded, the computer processor determines the subject's left-ventricular pressure based upon the blood pressure measured within a different one of the two or more ventricular blood-pressure-measurement tubes.

Referring to FIG. 16A, as described hereinabove, for some applications, drive cable 130 extends from a motor outside the subject's body to axial shaft 92 upon which impeller 50 is disposed. Typically, the drive cable is disposed within outer tube 142. For some applications, the drive cable is disposed within first outer tube 140 and second outer tube 142, as described hereinabove. For some applications, aortic blood pressure is measured using at least one aortic blood-pressure-measurement tube 222 that defines an opening 219 in outer tube 142 at its distal end. The aortic blood-pressure-measurement tube is configured to extend from outside the subject's body to an outer surface of outer tube 142 within the subject's aorta, such that the opening at the distal end of the aortic blood-pressure-measurement tube is in direct fluid communication with the subject's aortic bloodstream. Blood pressure sensor 216 is configured to measure the subject's aortic blood pressure by measuring blood pressure within the aortic blood-pressure-measurement tube.

For some applications, the one or more ventricular blood-pressure measurement tubes 220 and/or one or more aortic blood-pressure measurement tubes 222 are disposed within outer tube 142, surrounding the drive cable. For some applications, portions of the one or more blood-pressure-measurement tubes are defined by the walls of outer tube 142, as shown in the cross-sections of FIGS. 16A and 16B. For some applications, within outer tube 142, the blood pressure measurement tubes have elliptical cross-sections (as shown). Typically, this increases the cross-sectional areas of the tubes, relative to if they were to have circular cross-sections. Typically, within a distal portion of each of the ventricular blood-pressure measurement tubes 220 (which extends to opening 214), the tube has a circular cross-section. For some applications, the diameter of the distal portion of the tube is more than 0.2 mm, and/or less than 0.5 mm (e.g., 0.2-0.5 mm).

As shown in FIGS. 16A and 16B, for some applications, outer tube 142 defines a groove 215 in a portion of the outer surface of the outer tube that is configured to be disposed within tube 24. Typically, during insertion of the ventricular assist device into the subject's body, the portion of ventricular blood-pressure-measurement tube 220 that extends from within tube 24 to at least an outer surface of tube 24, is configured to be disposed within the groove, such that the portion of the ventricular blood-pressure-measurement tube does not protrude from the outer surface of the outer tube.

Figure 16C:
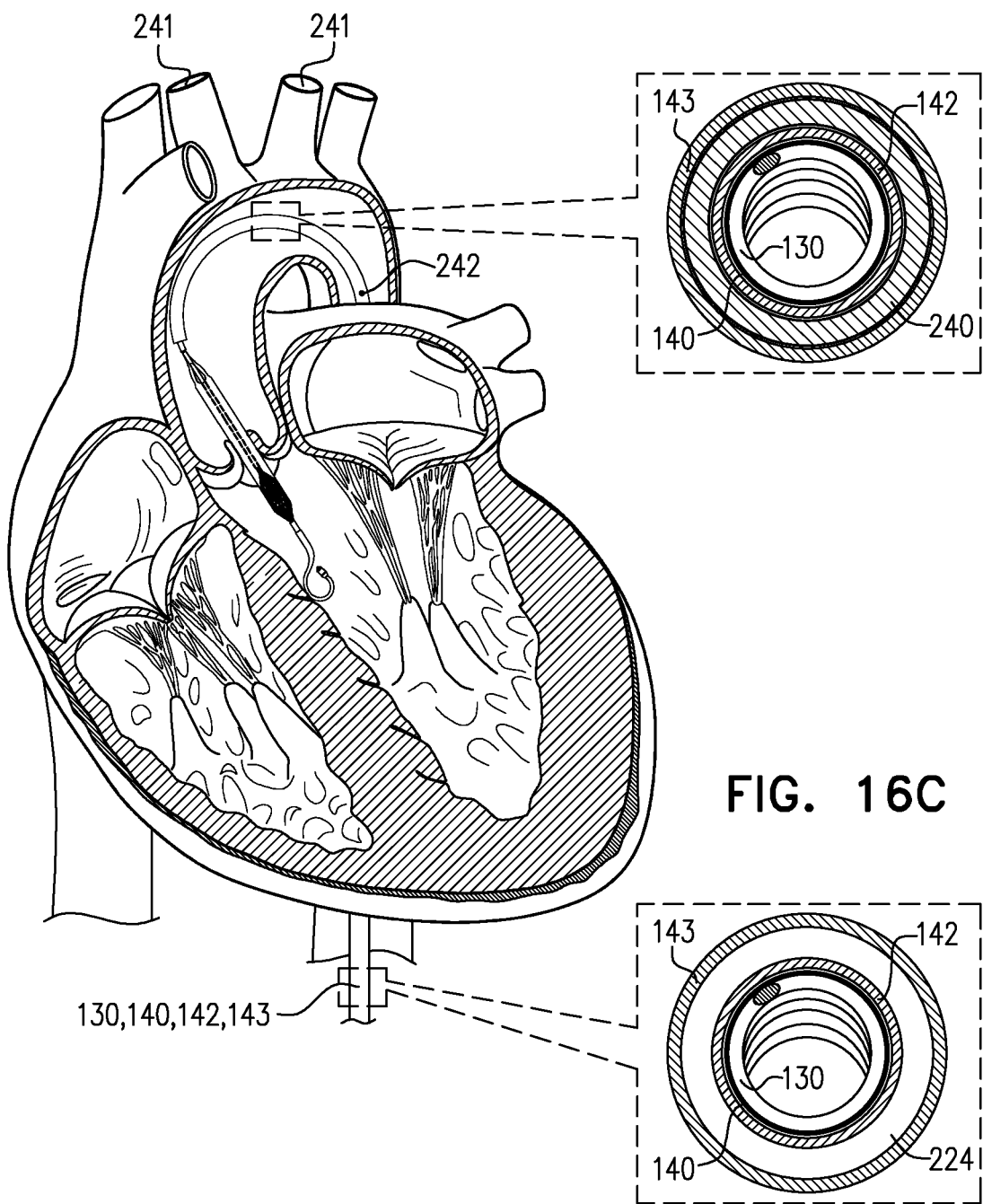
FIGS. 16C and 16D are schematic illustrations of a ventricular assist device having an aortic blood pressure measurement channel within a delivery catheter, in accordance with some applications of the present invention.
Figure 16D:
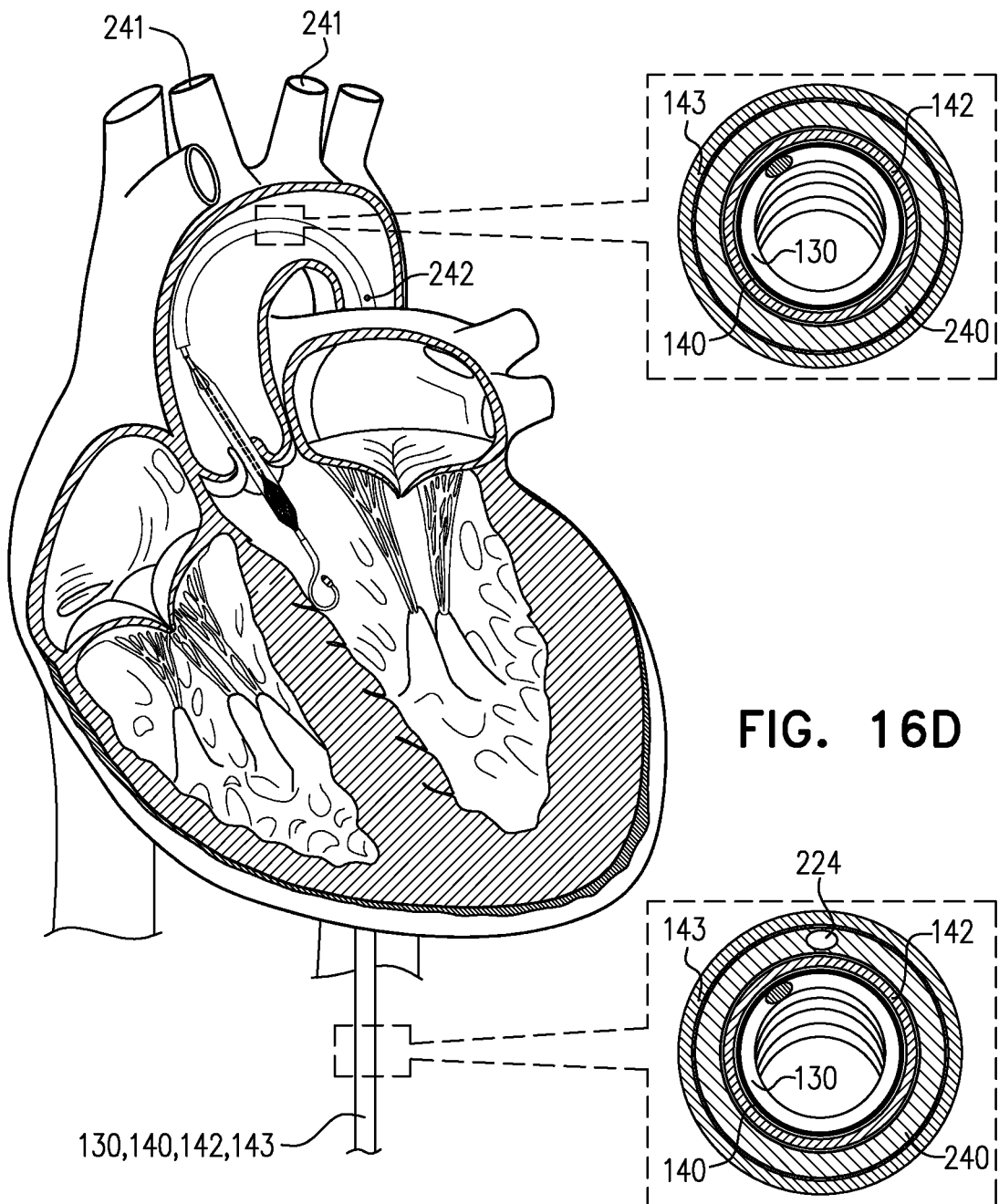

Reference is now made to FIGS. 16C and 16D, which are schematic illustrations of ventricular assist device 20, the device having an aortic blood pressure measurement channel 224 within delivery catheter 143, in accordance with some applications of the present invention. For some applications, during operation of the ventricular assist device, channel 224 is defined between delivery catheter 143 and outer tube 142 that extends from the distal end of the delivery catheter to the proximal end of the delivery catheter. For example, FIG. 10A shows a gap between the outside of outer tube 142 and the inside of delivery catheter 143, which can function as the aforementioned channel. (It is noted that the scale of the channel as shown in FIG. 10A is not to scale, for illustrative purposes.) Typically, during operation of the ventricular assist device, the distal end of the delivery catheter is disposed within the subject's aorta, and the proximal end of the delivery catheter is disposed outside the subject's body. Therefore, by sensing pressure within the channel between delivery catheter 143 and outer tube 142, blood pressure sensor 216 (which is shown in FIG. 1A and which is typically disposed outside the subject's body) is able to detect aortic pressure. For some applications, the pressure sensor senses aortic pressure via port 89, shown in FIG. 13C. As noted hereinabove, with reference to FIG. 13C, purging fluid is typically pumped into the channel between delivery catheter 143 and outer tube 142. For some applications, the purging fluid is pumped into this channel at a low enough pressure, that it is still possible to detect aortic blood pressure via the channel, in the above-described manner.

For some applications, a spacing tube 240 is placed between outer tube 142 and delivery catheter 143 along at least a distal portion of delivery catheter 143, such as to fill the gap between the outer tube and the delivery catheter. For some applications, the spacing tube is configured to prevent debris, emboli, and/or other matter from flowing out of the distal end of the delivery catheter from where they could flow into carotid arteries 241. For some applications, the delivery catheter defines a lateral hole 242, which is exposed to the aortic blood stream. For some such applications, proximal of hole 242, the spacing tube is not disposed between the delivery catheter and the outer tube, as shown in FIG. 16C. Thus, proximal of hole 242, channel 224 is defined between the delivery catheter and outer tube 142, such that the subject's aortic blood pressure is detected via channel 224, in the manner described hereinabove. Alternatively, proximal of hole 242, the spacing tube is disposed between the delivery catheter and the outer tube, but the spacing tube defines channel 224 which extends from the hole to the proximal end of the delivery catheter, as shown in FIG. 16D. Typically, the subject's aortic blood pressure is detected via channel 224, in the manner described hereinabove (e.g., via port 89).

Figure 16E:
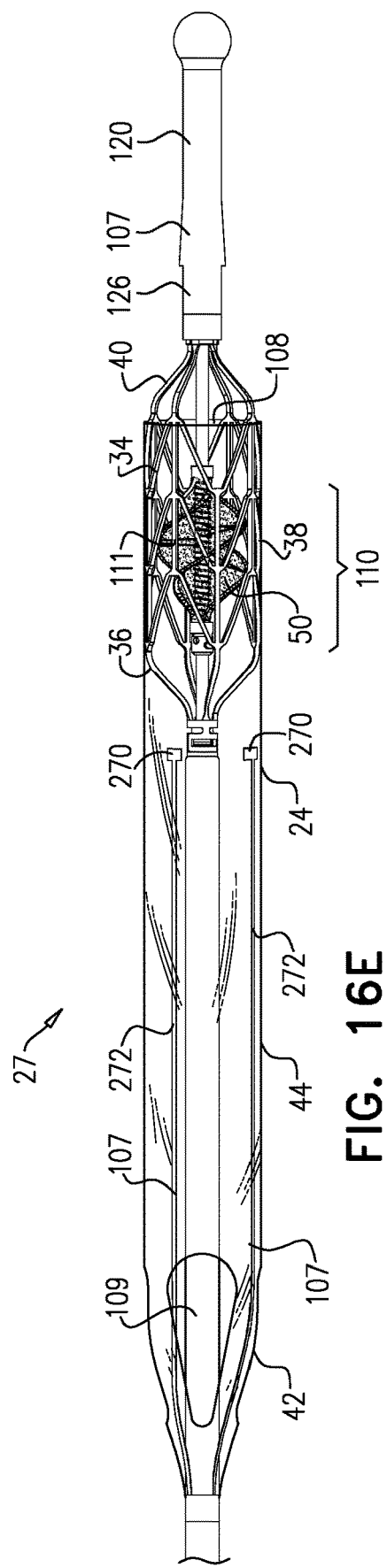
FIG. 16E is a schematic illustration of a ventricular assist device that includes one or more sensors that are disposed on an outer surface of a tube of the device, in accordance with some applications of the present invention.

Reference is now made to FIG. 16E, which is a schematic illustration of ventricular assist device 20, the device including one or more blood-pressure-measurement sensors 270 that are disposed on an outer surface of tube 24, in accordance with some applications of the present invention. For some applications, generally similar techniques to those described with reference to ventricular blood-pressure-measurement tube 220 are performed using an electrical wire 272 that extends along blood-pump tube 24 (and that typically extends from outside the subject's body) to the outer surface of tube 24. Blood-pressure-measurement sensor 270 is disposed at a tip of the wire in electrical communication with the subject's bloodstream outside of tube 24. The subject's blood pressure outside tube 24 (e.g., the subject's ventricular blood pressure and/or the subject's aortic blood pressure) is measured by detecting an electrical parameter using the sensor. For some applications, wire 272 and/or sensor 270 is printed onto the outer surface of tube 24.

For some applications, sensor 270 is configured to perform conductance measurements. For some applications, conductance sensors are disposed inside tube 24 (rather than on the outer surface of tube 24), but are configured to sense conductance using frequency that is substantially not attenuated by tube 24. For some applications, additional conductance sensors are disposed on the left-ventricular assist device, for example, on distal-tip element 107. For some such applications, computer processor 25 (FIG. 1A) applies a current between the most distal electrode, which is typically configured to be disposed near the apex of the heart, and the most proximal electrode, which is typically configured to be disposed above the aortic valve. Conductance of that current between each pair of the electrodes is then measured by the computer processor. For some applications, the application of the current, and the conductance measurements, are performed using generally similar techniques to those described in an article entitled "The Conductance Volume Catheter Technique for Measurement of Left Ventricular Volume in Young Piglets," by Cassidy et al. (Pediatric Research, Vol. 31, No. 1, 1992, pp. 85-90). For some applications, the computer processor is configured to derive the subject's real-time left-ventricular pressure-volume loop based upon the conductance measurements. For some applications, the computer processor controls a rate of rotation of the impeller responsively to the derived pressure-volume loop.

For some applications, the subject's ventricular blood pressure is derived from the conductance measurements. For some such applications, the subject's aortic blood pressure is measured (e.g., as described hereinabove). The subject's left ventricular pressure is derived by measuring conductance measurements over the course of the subject's cardiac cycle, and determining the difference between the left ventricular pressure and the aortic pressure at any given point within the cardiac cycle, based upon having previously calibrated the conductance measurements with left-ventricular/aortic pressure gradients. For some applications, the computer processor is configured to calculate the first derivative of the left-ventricular pressure measurements. Typically, such changes are indicative of the rate of change of pressure within the left ventricle, which itself is an important clinical parameter. It is noted that the first derivative of the left-ventricular pressure is typically unaffected by changes in aortic pressure, since the aortic pressure curve is relatively flat as the left-ventricular pressure curve undergoes changes that are of clinical importance.

Figure 17B:
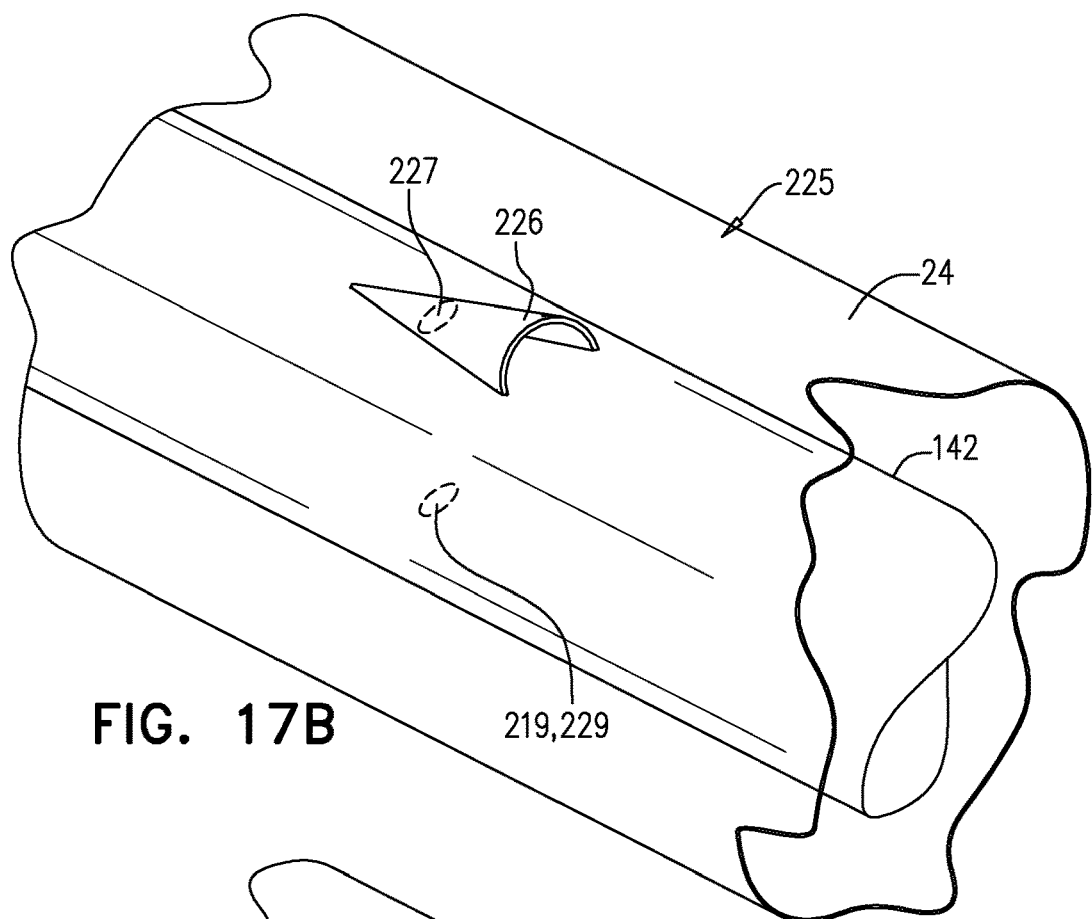
Figure 17C:
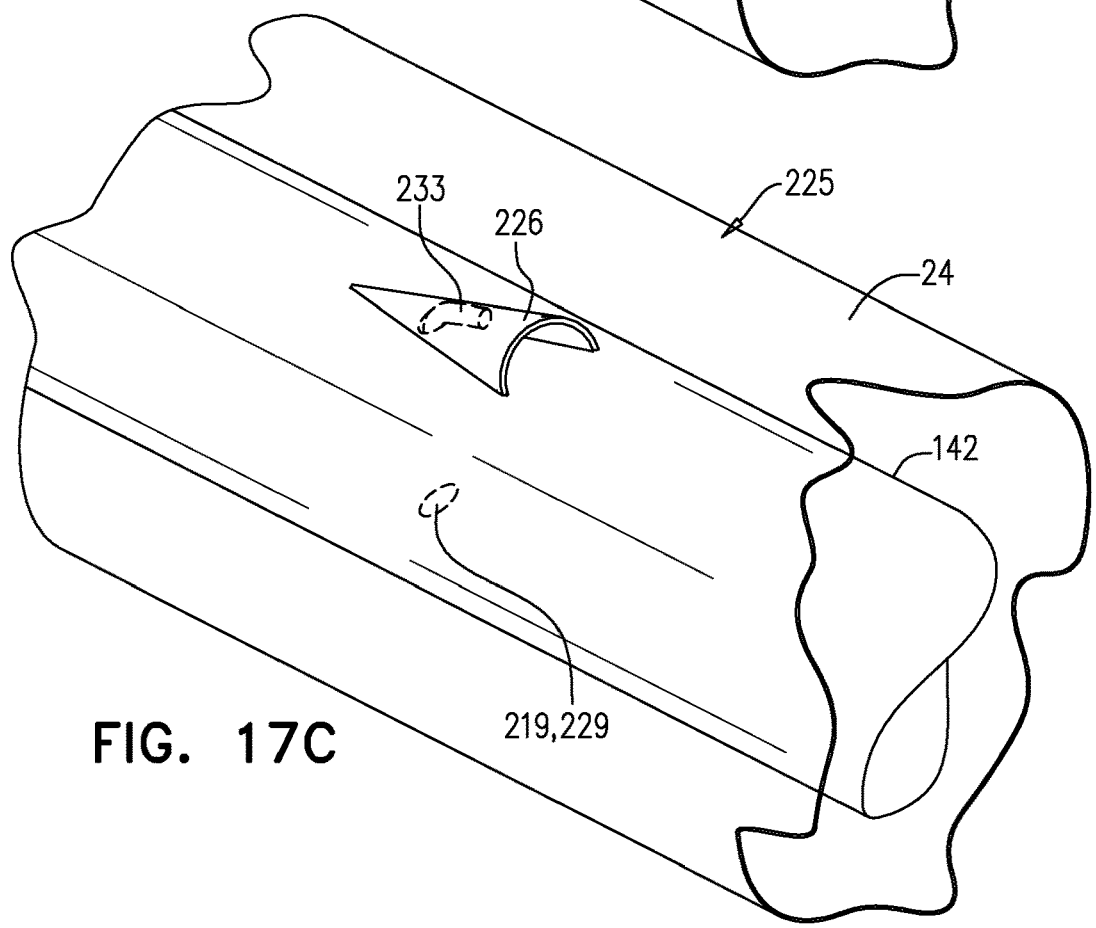

Reference is now made to FIGS. 17A, 17B, 17C, and 17D, which are schematic illustrations of outer tube 142 of ventricular assist device 20, the outer tube including a pitot tube 225 that is configured to measure blood flow through tube 24 of the device, in accordance with some applications of the present invention. The portion of outer tube 142 shown in FIGS. 17A-D is typically disposed within tube 24. For some applications, a flow obstacle 226 (which is typically funnel shaped) is configured to create a stagnation region near a stagnation pressure tap 227. For some applications, flow straighteners 228 are added to the outer surface of tube 142, in order remove any swirling component of the flow (which does not contribute to the axial flow rate), as shown in FIG. 17A. Alternatively, the stagnation pressure tap is disposed sufficiently proximally within funnel-shaped flow obstacle 226 that the flow obstacle itself acts to remove the swirling components of the flow, prior to the blood reaching the stagnation pressure tap, as shown in FIG. 17B. For some applications, the stagnation pressure tap includes a short tube 233 that protrudes from outer tube 142 within funnel-shaped flow obstacle 226, such that the opening of short tube 233 faces the direction of axial blood flow through tube 24, as shown in FIG. 17C. Outer tube 142 additionally defines opening 219, which functions as a static pressure tap 229. The pressure within stagnation pressure tap 227 and within static pressure tap 229 is measured using a pressure sensor, e.g., a pressure sensors that are disposed outside the subject's body, as described hereinabove with reference to FIGS. 16A-D.

In some applications, flow through tube 24 is calculated based upon the pressure measurements. For example, flow through tube 24 may be calculated using the following equation:

$$Q = C \cdot A \cdot \sqrt{\frac{2\Delta P}{\rho}}$$

in which:

Q is the flow through tube 24,

C is a calibration constant that is empirically determined and accounts for factors such as impeller velocity and the geometries of pressure taps 227 and 229, A is the cross-sectional area of tube 24 (not including the area that outer tube 142 occupies), ΔP is the difference between the stagnation pressure (measured via pressure tap 227), and the static pressure (measured via pressure tap 229)

ρ is the fluid density of blood.

Figure 17D:
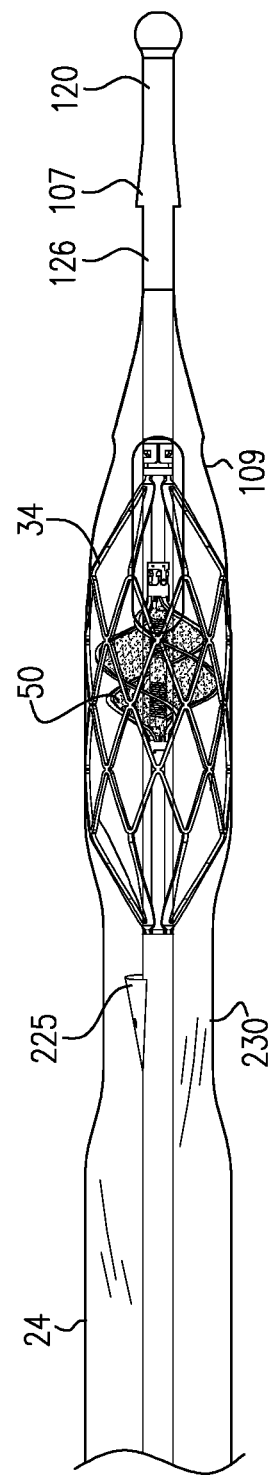

Referring to FIG. 17D, for some applications a region 230 of tube 24 within which pitot tube 225 is disposed is narrowed with respect to the rest of the cylindrical portion of tube 24. For some applications, the narrowing of the region facilitates more accurate measurements being made using the pitot tube. For some applications, narrow region 230 of tube 24 is configured to be placed within the subject's aortic valve. Typically, the narrowing of the tube at region 230 is configured to facilitate placement of region 230 at the aortic valve. For some applications, tube 24 includes narrow region 230 even in the absence of pitot tube 225, in order to facilitate placement of this region of the tube at the aortic valve, in the above-described manner.

Figure 18:
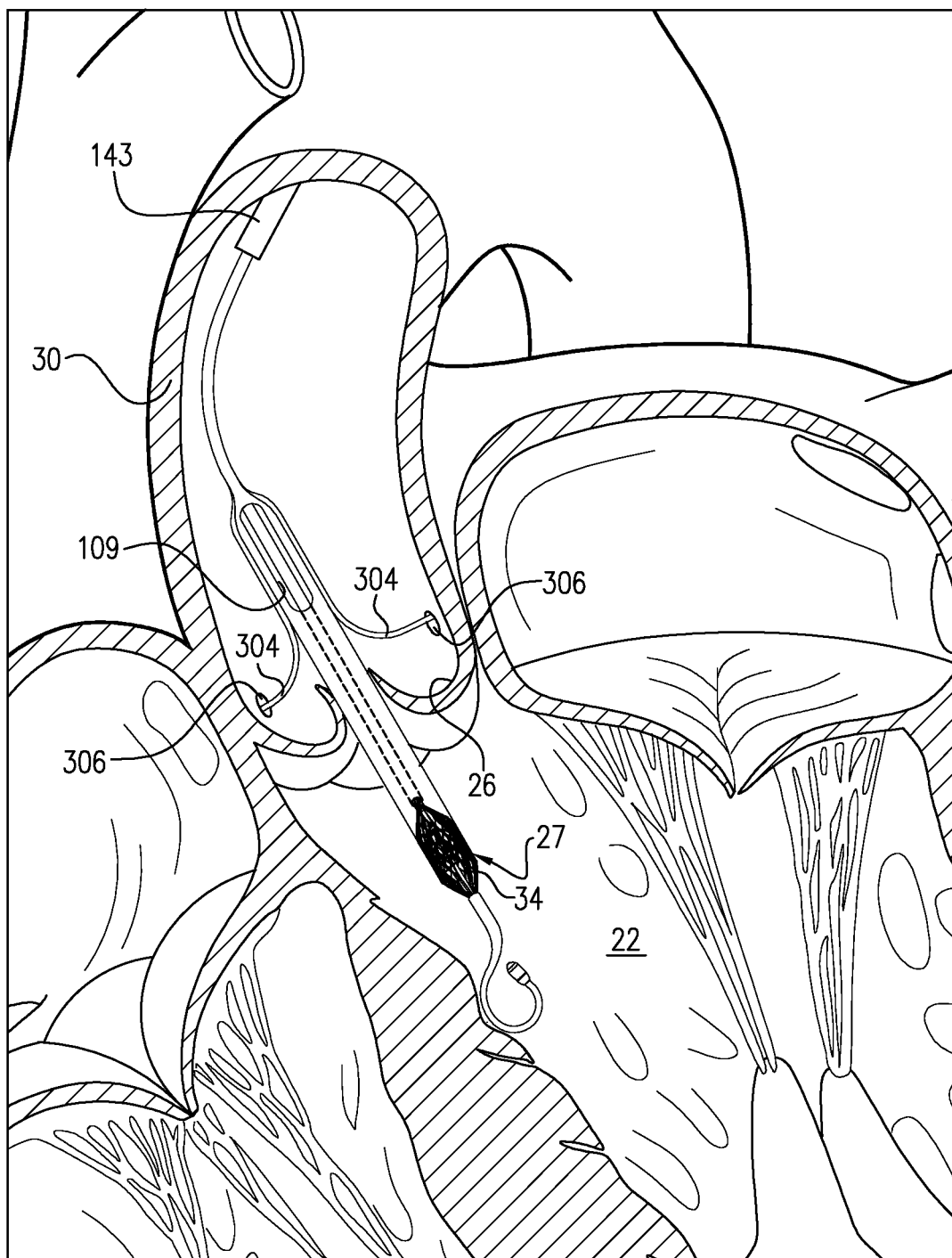
FIG. 18 is a schematic illustration of a ventricular assist device that includes coronary artery tubes and/or wires, in accordance with some applications of the present invention.

Reference is now made to FIG. 18, which is a schematic illustration of ventricular assist device 20, the ventricular assist device including coronary artery tubes and/or wires 304, in accordance with some applications of the present invention. For some applications, one or more tubes and/or wires extend along the outside or the inside of a proximal portion of tube 24. The tubes and/or wires are shape set, such that in non-radially-constrained configurations of the tubes and/or wires, distal ends of the tubes and/or wires extend radially from the outer surface of tube 24. The tubes and/or wires are positioned to extend radially from an axial location along tube 24 such that, when the distal ends of the tubes and/or wires are positioned at the subject's coronary arteries 306, pump portion 27 of the device is correctly positioned within the subject's left ventricle 22. For some applications, a medical professional who is deploying ventricular assist device 20, ensures that pump portion 27 of the device is correctly positioned within the subject's left ventricle 22, by inserting the distal ends of the tubes and/or wires into the coronary arteries 306. For some applications, tubes are used in the above-described embodiments, and the tubes extend proximally to the proximal end of the ventricular assist device (e.g., via outer tubes 140, 142, and/or via delivery catheter 143). For some such applications, a procedure is performed with respect to one or more of the coronary arteries via the tubes. Alternatively or additionally, contrast agent is injected via the tubes, in order to facilitate imaging of the current location of the device. For some applications, generally similar techniques are performed using ventricular blood-pressure measurement tubes 220, described hereinabove. For example, contrast agent may be injected via the blood-pressure measurement tubes, in order to facilitate imaging of the current location of the device.

Reference is now made to FIGS. 19A, 19B, 19C, 19D, 19E, 19F, 19G, and 19H, which are schematic illustrations of ventricular assist device 20, the device including inner lining 39 that lines the inside of frame 34 that houses impeller 50, in accordance with some applications of the present invention. (For illustrative purposes, inner lining 39 and tube 24 on the side of the device facing out of the page are shown as transparent in FIGS. 19A-E.) For some applications, inner lining 39 is disposed inside frame 34, in order to provide a smooth inner surface through which blood is pumped by impeller. Typically, by providing a smooth surface, the covering material reduces hemolysis that is caused by the pumping of blood by the impeller, relative to if the blood were pumped between the impeller and struts of frame 34. For some applications, inner lining includes polyurethane, polyester, and/or silicone. Alternatively or additionally, the inner lining includes polyethylene terephthalate (PET) and/or polyether block amide (PEBAX®).

Figure 19B:
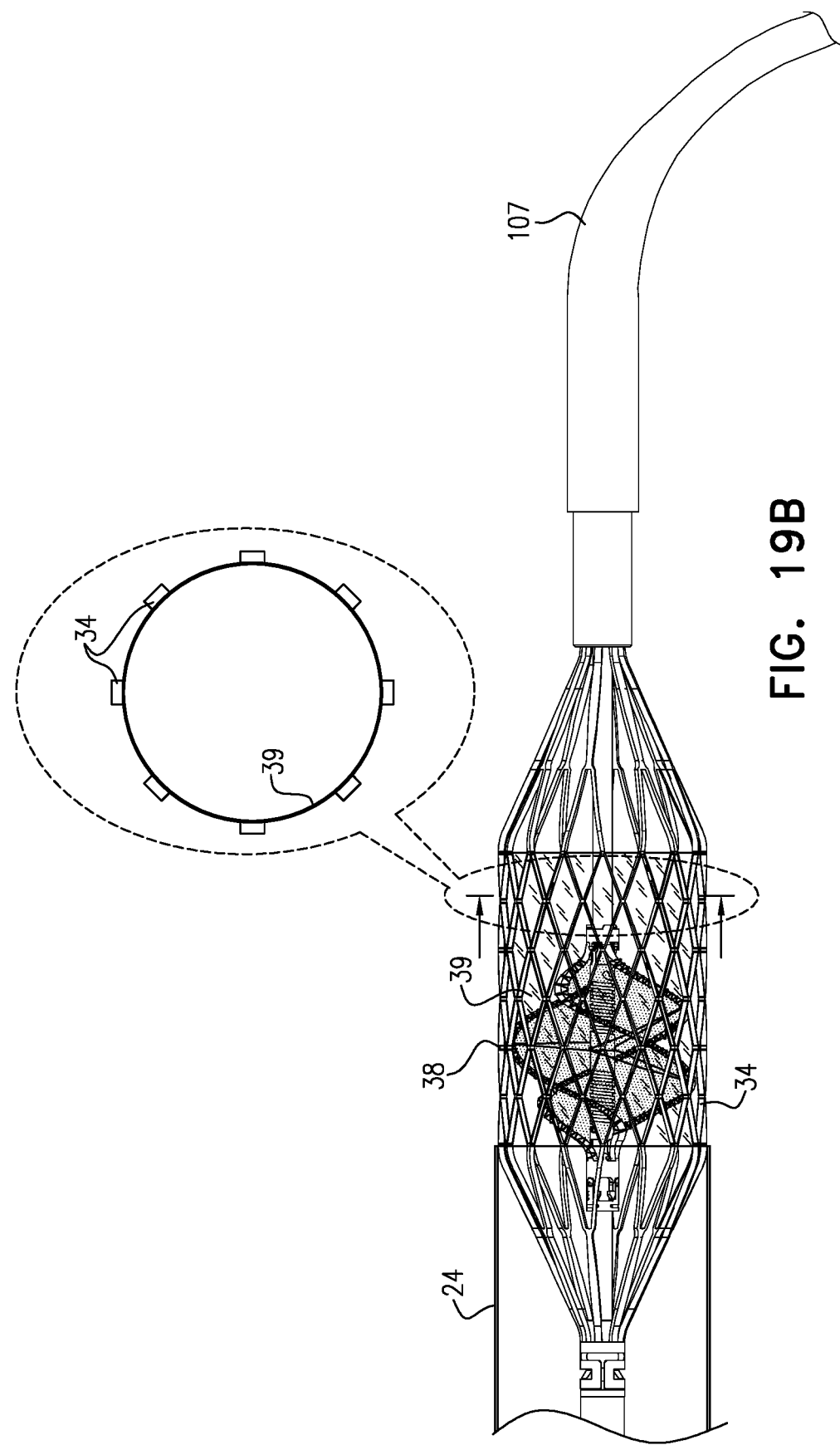

Typically, the inner lining is disposed over at least the inner surface of the cylindrical portion of frame 34 (the cylindrical portion being indicated in FIGS. 2A-C, for example). For some applications, tube 24 also covers the cylindrical portion 38 of frame 34, around the outside of the frame, for example, such that tube 24 and inner lining 39 overlap over at least 50 percent of the length of the inner lining, for example, over the entire length of the cylindrical portion of frame 34, e.g., as shown in FIG. 19A. For some applications, there is only partial overlap between tube 24 and inner lining 39, e.g., as shown in FIG. 19B. For example, tube 24 may overlap with inner lining along less than 50 percent (e.g., along less than 25 percent) of the length of the inner lining. For some such applications, during insertion of ventricular assist device 20 into the subject's body, the impeller is advanced distally within frame 34, such that the impeller is not disposed within the area of overlap between the tube and the inner lining, such that there is no longitudinal location at which the impeller, tube 24, frame 34, and inner lining 39 all overlap with each other.

Typically, for applications as shown in FIGS. 19A and 19B, over the area of overlap between inner lining 39 and tube 24, the inner lining is shaped to form a smooth surface (e.g., in order to reduce hemolysis, as described hereinabove), and tube 24 is shaped to conform with the struts of frame 34 (e.g., as shown in the cross-section in FIG. 19A). Typically, over the area of overlap between inner lining 39 and tube 24, the tube and the inner lining are coupled to each other, e.g., via vacuum, via an adhesive, and/or using a thermoforming procedure, for example as described hereinbelow.

For some applications, inner lining 39 and tube 24 are made of different materials. For example, the inner lining may be made of polyurethane, and the tube may be made of polyether block amide (PEBAX®). Typically, the material from which the inner lining is made has a higher thermoforming temperature than that of the material from which the tube is made. For some applications in which the inner lining and the tube overlap along at least a portion of frame 34 (e.g., along the cylindrical portion of frame 34), the tube and the inner lining are bonded to each other and/or the frame in the following manner. Initially, the inner lining is placed over a mandrel. The frame is then placed over the inner lining. Subsequently, tube 24 is placed around the outside of the frame. For some applications, in order to mold tube 24 to conform with the struts of frame 34, without causing the inner lining to deform, the frame is heated to a temperature that is above the thermoforming temperature of tube 24 but below the thermoforming temperature of inner lining 39.

Typically, the frame is heated from inside the frame, using the mandrel. Typically, while the frame is heated to the aforementioned temperature, an outer tube (which is typically made from silicone) applies pressure to tube 24 that causes tube 24 to be pushed radially inwardly, in order to cause the tube to conform with the shapes of the struts of the frame, as shown in the cross-section of FIG. 19A. For some applications, the combination of the frame, the inner lining, and the portion of tube 24 disposed around the frame is subsequently shape set to a desired shape and dimensions using shape setting techniques that are known in the art.

In accordance with the above description, the scope of the present invention includes a method for manufacturing a housing for an impeller of a blood pump that includes performing the following steps. An inner lining is placed around a mandrel. A cylindrical portion of a frame is placed around the inner lining, the cylindrical portion of the frame including struts that define a generally cylindrical shape. A distal portion of an elongate tube is placed around at least a portion of the frame, the tube including a proximal portion that defines at least one blood outlet opening. While the distal portion is disposed around at least the portion of the frame, the inner lining, the frame and the distal portion of the elongate tube are heated, via the mandrel. While heating the inner lining, the frame and the distal portion of the elongate tube, pressure is applied from outside the distal portion of the elongate tube, such as to cause the distal portion of the elongate tube to conform with a structure of the struts of the frame, and such as to cause the inner lining and the distal portion of the elongate tube to become coupled to the frame. For example, the pressure may be applied by means of a silicone tube that is placed outside the distal portion of the elongate tube. For some applications, the inner lining and the elongate tube include an inner lining and elongate tube that are made from different materials from each other, and a thermoforming temperature of a material from which the inner lining is made is higher than a thermoforming temperature of a material from which the elongate tube is made. For some such applications, the inner lining, the frame and the distal portion of the elongate tube are heated to a temperature that is above the thermoforming temperature of the material from which the elongate tube is made and below the thermoforming temperature of the material from which the inner lining is made.

Figure 19C:
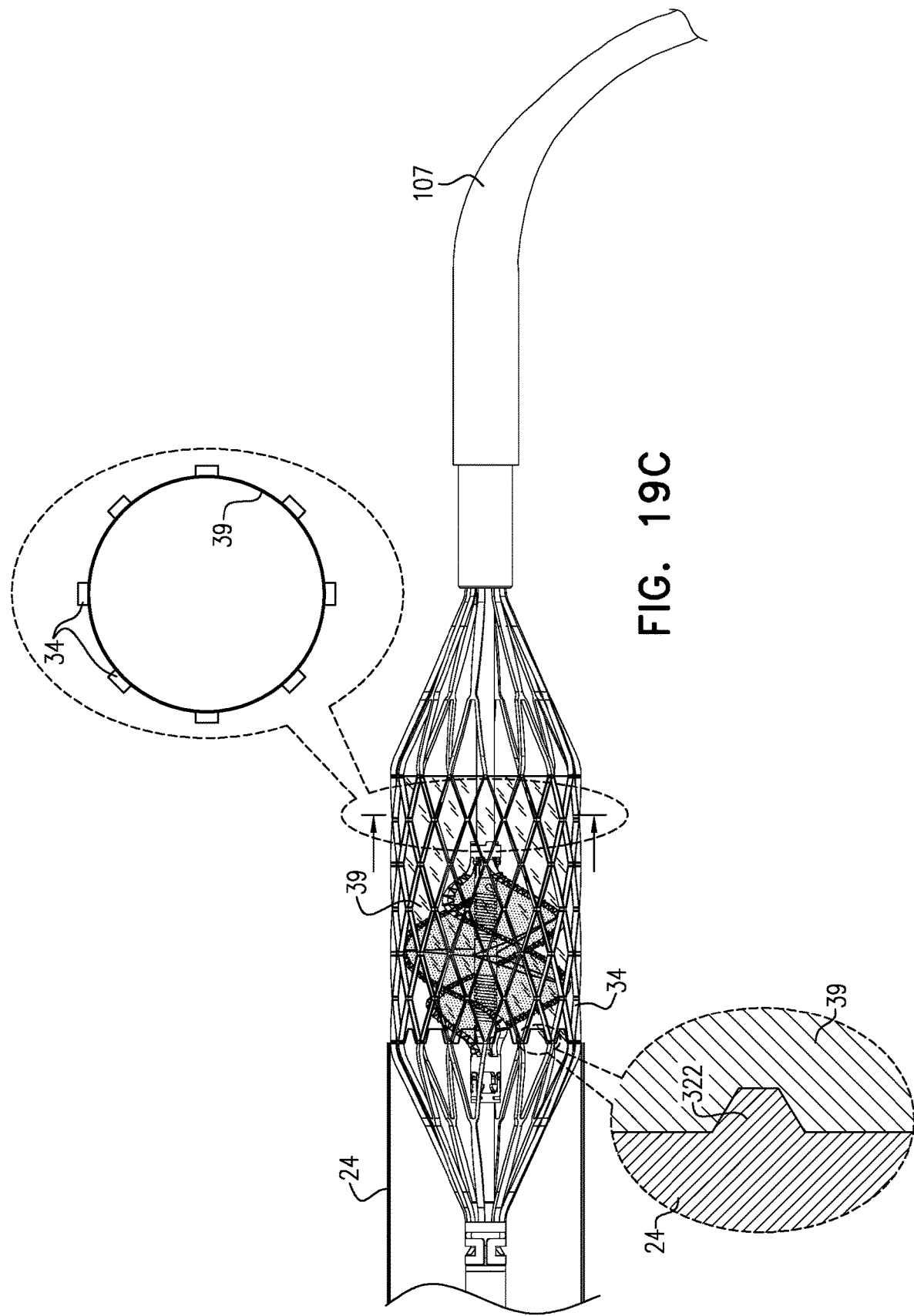

Referring to FIG. 19C, for some applications, tube 24 does not overlap with inner lining 39, but tabs 322 extend through struts of frame 34 from tube 24 to inner lining 39, and are used to sealingly couple the tube to the inner lining (e.g., by being adhered to the inner lining). Alternatively or additionally (not shown), tabs 322 extend from the inner lining to tube 24 and are used to sealingly couple the tube to the inner material (e.g., by being adhered to the tube).

As described hereinabove, for some applications, the combination of the frame, the inner lining, and the portion of tube 24 disposed around the frame is shape set to a desired shape and dimensions using shape setting techniques that are known in the art. Referring to FIG. 19D, for some applications, the combination of the frame, the inner lining, and the portion of tube 24 disposed around the frame is shape set such that a distal portion 330 of cylindrical portion 38 of the frame is widened with respect to the rest of the cylindrical portion of the frame. Typically, the widening of the frame is such that blood inlet opening 108 (which is typically defined by the inner lining at the distal end of the cylindrical portion of the frame) is widened relative to the rest of the cylindrical portion of the frame. Typically, the impeller is disposed in close proximity to the blood inlet opening throughout operation (and the axial back-and-forth motion) of the impeller, with the distal end of the impeller typically being disposed within 15 mm of the blood inlet opening throughout operation of the impeller. For some applications, having a widened blood inlet opening in close proximity to the impeller reduces turbulence that is generated as blood flows into the blood inlet opening. The reduction of turbulence typically increases blood flow and/or reduces hemolysis that is generated by the impeller relative to if the frame were to define a non-widened blood inlet opening.

Referring to FIG. 19E, for some applications, the combination of the frame, the inner lining, and the portion of tube 24 disposed around the frame is shape set such that a distal portion 332 of cylindrical portion 38 of the frame converges from the distal end of the cylindrical portion of the frame and toward the impeller (such as to define a portion of the frame that is narrower than the rest of the cylindrical portion of the frame in the vicinity of the impeller (e.g., in the vicinity of the distal end of the impeller)). For some applications, having a portion of the frame that converges toward the impeller reduces turbulence that is generated as blood flows from the blood inlet opening toward the impeller. The reduction of turbulence typically increases blood flow and/or reduces hemolysis that is generated by the impeller relative to if the frame were not to define the converging portion.

Figure 19F:
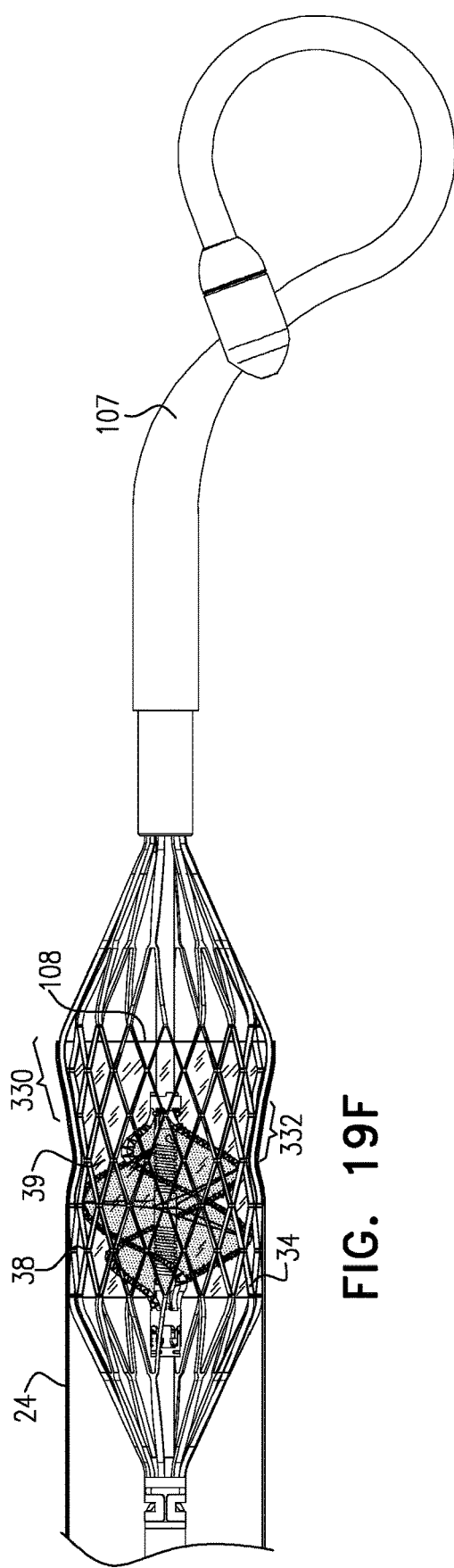

Referring to FIG. 19F, for some applications the combination of the frame, the inner lining, and the portion of tube 24 disposed around the frame is shape set such that the features described, respectively, with reference to FIGS. 19D and 19E are combined. That is to say that a first distal portion 330 of the cylindrical portion of the frame is widened with respect to the rest of cylindrical portion 38 of the frame, and a second portion 332 of the cylindrical portion of the frame converges toward the impeller.

Figure 19G:
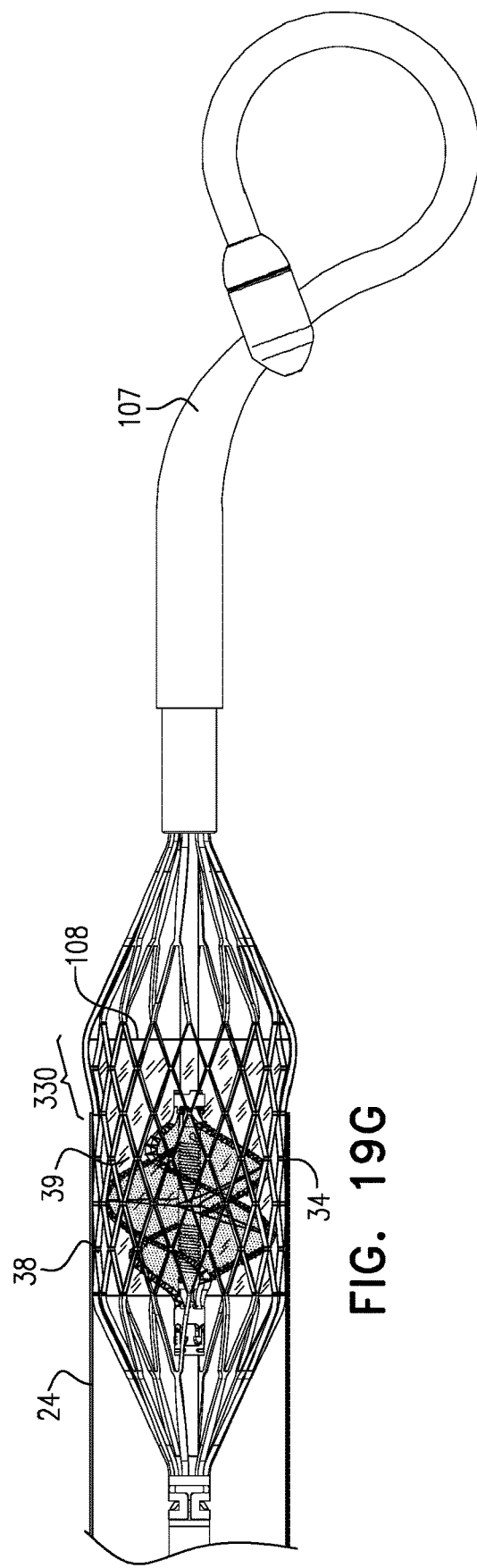

Referring to FIG. 19G, for some applications, tube 24 does not extend to the distal end of cylindrical portion 38 of frame 34. For some such applications, along the portion of the frame along which the tube does extend, the tube is configured to limit the radial expansion of the frame. Along the distal portion of the cylindrical portion of the frame (over which the tube does not extend), the expansion of the frame is not limited by tube 24. Therefore, the distal portion of the cylindrical portion of the frame is widened with respect to the portion of the cylindrical portion of the frame that is proximal thereto (over which tube 24 does extend). For some applications, this results in blood inlet opening 108 being wider than it would be if tube 24 were to extend along the full length of the cylindrical portion of the frame. As described with reference to FIG. 19D, typically, the impeller is disposed in close proximity to the blood inlet opening throughout operation (and the axial back-and-forth motion) of the impeller, with the distal end of the impeller typically being disposed within 15 mm of the blood inlet opening throughout operation of the impeller. For some applications, having a widened blood inlet opening in close proximity to the impeller reduces turbulence that is generated as blood flows into the blood inlet opening. The reduction of turbulence typically increases blood flow and/or reduces hemolysis that is generated by the impeller relative to if the frame were to define a non-widened blood inlet opening.

Referring to FIG. 19H, for some applications, in order to facilitate coupling of inner lining 39 to frame 34, an outer covering material is coupled (e.g., using adhesive, vacuum and/or a thermoforming procedure) to the inner lining from outside frame 34 at certain discrete coupling regions 326 along the length of the frame. (It is noted that in FIG. 19, tube 24 and frame 34 are shown in the absence of other components of the ventricular assist device (such as the impeller and the axial shaft), for illustrative purposes.) For some applications, at at least one of these coupling regions, tube 24 comprises the outer covering material, as shown in the proximal-most coupling region, to the right of FIG. 19G. Alternatively or additionally, an additional outer covering material 328 is placed around frame 34 at one or more of the coupling regions. For example, the additional coupling material may be made from similar materials to those used for inner lining 39 and/or tube 24. For some applications, at the coupling regions, frame 34 has a lower density of struts relative to the density of struts of the frame (i.e., the ratio of the surface area occupied by the struts to the areas of open spaces between the struts) at other locations along the length of the frame. For example, as shown in FIG. 19G, along cylindrical portion 38 of the frame, at the coupling regions that frame has straight axial struts 329, whereas at other regions within the cylindrical portion of the frame, the frame defines zigzag struts, and there is a ratio of two zigzag struts to each straight strut. Typically, the reduced density of struts at the coupling regions allows the outer covering material to be directly coupled to the inner lining over a greater surface area, than if the frame did not have the reduced strut density at the coupling region.

Reference is now made to FIGS. 20A, 20B, and 20C, which are schematic illustrations of ventricular assist device 20 that includes an inflatable portion 331 (e.g., a balloon), the inflatable portion being in respective states of inflation in each of FIGS. 20A, 20B and 20C, in accordance with some applications of the present invention. For some applications (as shown), inflatable portion 331 is inflated in a generally similar manner to that described hereinabove with reference to inflatable portion 153 shown in FIG. 13D. Namely, the inflatable portion is inflated by the purging fluid entering the interior of the inflatable portion, via opening 155. For some applications, by controlling the pressure at which the purging fluid is pumped into ventricular assist device 20, the inflation of the inflatable portion is controlled. Alternatively or additionally, an inflation lumen for inflating the inflatable portion is configured to pass through outer tube 142, and to then pass along the outer surface of tube 24, and to the inflatable portion of the distal-tip portion.

For some applications, the inflatable portion is configured to be in respective states of inflation during respective phases of the deployment of ventricular assist device. For some applications, distal-tip portion 120 has a radially-converging shape (as shown in FIGS. 20A-C) and is configured to act as a dilator, during insertion of ventricular assist device via a puncture in the subject's body, as described hereinabove. In this manner, the delivery catheter 143 and components of the ventricular assist device that are disposed within the delivery catheter can be inserted into the puncture without requiring pre-dilation of the puncture, and without requiring a separate introducer device, for facilitating insertion of the delivery catheter through the puncture. Typically, during the insertion of the distal-tip portion through the puncture in the subject's body, inflatable portion 331 is maintained in a deflated state, as shown in FIG. 20A.

For some applications, subsequent to the distal-tip portion being inserted via the puncture in the subject's body, the distal-tip portion is used to guide the delivery catheter along curved anatomy (e.g., the aortic arch). For some applications, during this stage of the procedure, the inflatable portion is partially inflated, such as to prevent the distal-tip portion from causing trauma to the patient's vasculature. The inflatable portion is shown in the partially inflated state in FIG. 20B.

For some applications, upon ventricular assist device 20 being deployed such that the distal-tip portion is within the subject's left ventricle, inflatable portion 331 is more fully inflated than in the state of the inflatable portion shown in FIG. 20B (e.g., fully inflated). Typically, when the inflatable portion is more fully inflated, the inflatable portion separates one or more blood inlet openings 108 from inner structures of the left ventricle in three dimensions. In this manner, the inflatable portion separates one or more blood inlet openings 108 from the interventricular septum, chordae tendineae, papillary muscles, and/or the apex of the left ventricle. For some applications, the inflatable portion is shaped such as to direct blood flow from the left ventricle into the one or more blood inlet openings.

Typically, a hemostasis valve (e.g., duckbill valve 390) is disposed within lumen 122 of distal-tip portion 120. For some applications, the hemostasis valve prevents blood from flowing into lumen 122, and/or into lumen 132. Typically, the hemostasis valve, by preventing purging fluid from flowing out of the distal end of lumen 122, causes the purging fluid to flow toward the interface between axial shaft 92 and distal bearing 118, as described hereinabove.

Figure 21:
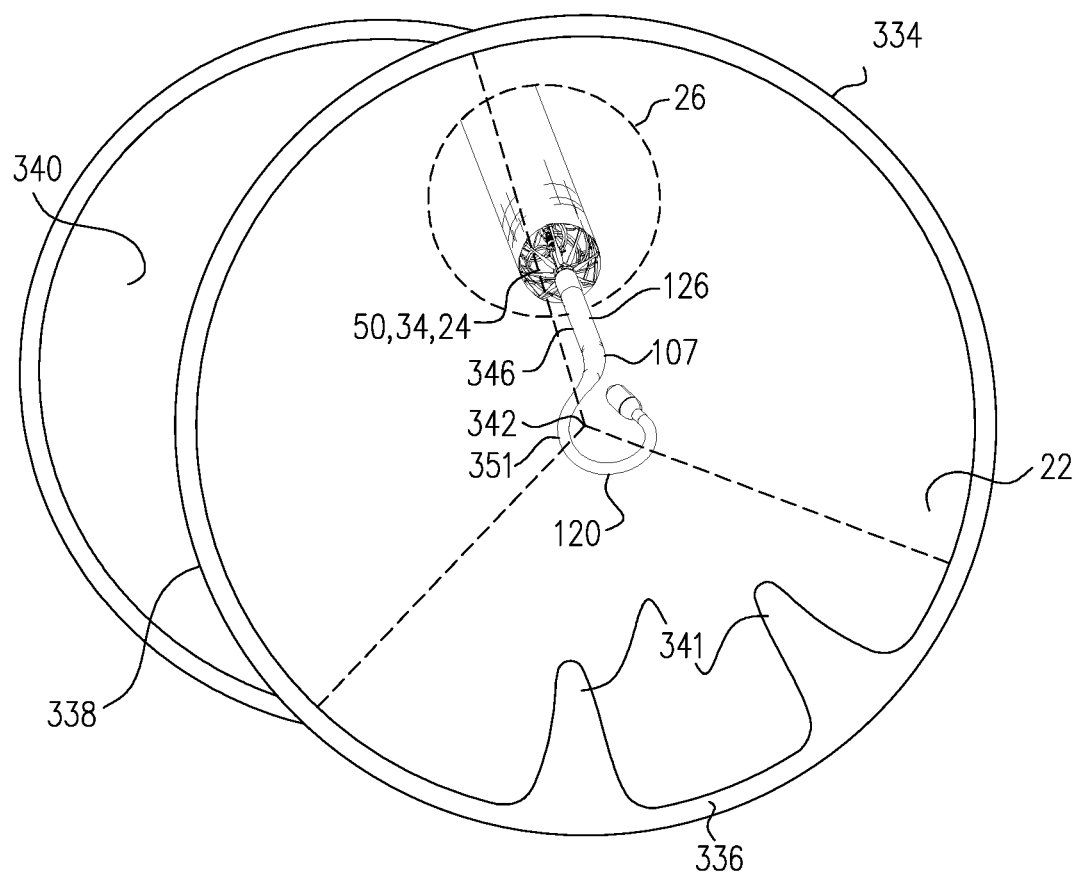
FIG. 21 is a schematic illustration of a ventricular assist device being placed inside a subject's left ventricle, with a transverse cross-sectional view of the left ventricle being illustrated, in accordance with some applications of the present invention.

Reference is now made to FIG. 21, which is a schematic illustration of ventricular assist device 20 being placed inside a subject's left ventricle 22 (a transverse cross-sectional view of the left ventricle being illustrated), in accordance with some applications of the present invention. (FIG. 21 shows aortic valve 26 overlaid on the transverse cross-section of the left ventricle even though the aortic valve lies in a different plane from the plane of the main cross-sectional view, for illustrative purposes.) Reference is also made to FIGS. 22A-D, which are schematic illustrations of distal-tip element 107 of the ventricular assist device that is at least partially curved such as to define a curvature that is similar to that of a question mark, in accordance with some applications of the present invention, and to FIGS. 23A and 23B, which are schematic illustrations of the ventricular assist device of FIGS. 22C-D disposed inside a subject's left ventricle, in accordance with some applications of the present invention.

Figure 23B:
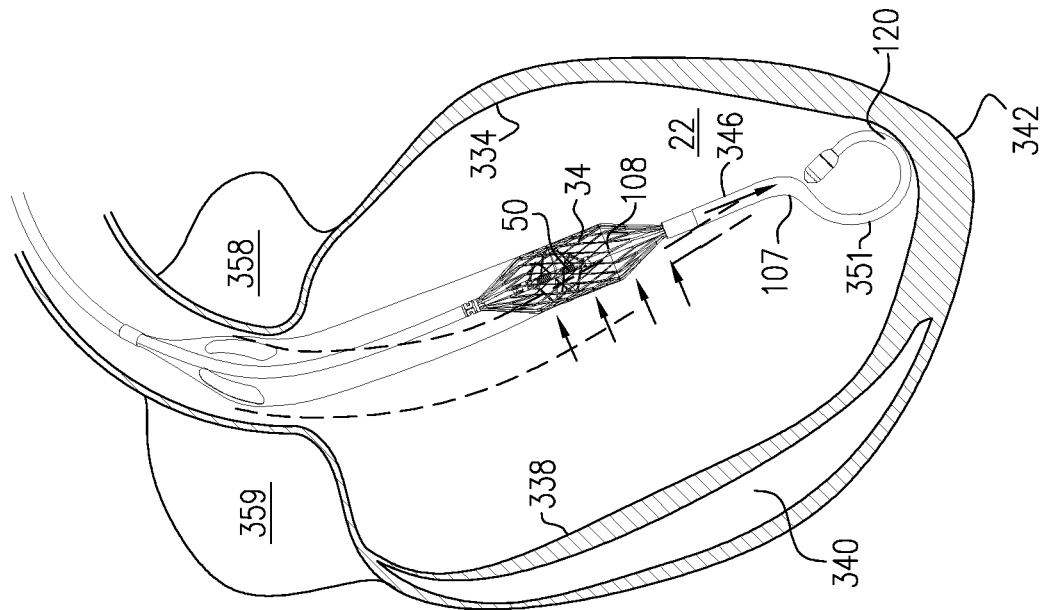
FIGS. 23A and 23B are schematic illustrations of the ventricular assist device of FIG. 22D disposed inside a subject's left ventricle, in accordance with some applications of the present invention.
Figure 23A:
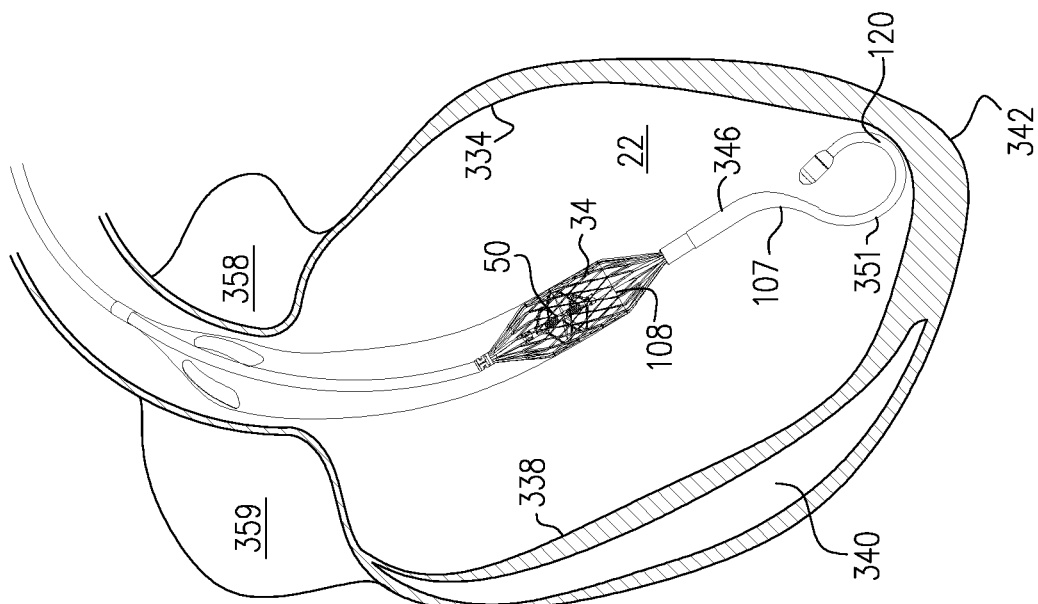

For some applications, the ventricular assist device is guided by the guidewire over which it is inserted toward apex 342 of the left ventricle. The walls of the left ventricle may be thought of as being made up of the septal wall 338 (which separates the left ventricle from the right ventricle 340), the posterior wall 336 (from which the papillary muscles 341 protrude, and above which the mitral valve apparatus is disposed), and the free wall 334, each of these three walls occupying approximately one third of the circumference of the left ventricle (as illustrated by the dashed lines, which trisect the left ventricle in FIG. 21). Typically, it is undesirable for the distal-tip element (or any other portions of the ventricular assist device) to come into contact with the septal wall, since there is a risk that this can give rise to arrythmias. Further typically, it is desirable to maintain a distance between the distal-tip element (and any other portions of the ventricular assist device) from the posterior wall, in order not to interfere with the mitral valve apparatus, and in order to prevent the mitral valve apparatus from interfering with the functioning of the ventricular assist device. Therefore, the ventricular assist device is typically guided toward the apex, in such a manner that, if and when the distal-tip element contacts the inner wall of the left ventricle, it contacts free wall 334, as shown in FIGS. 21 and 23A-B.

Figure 22A:
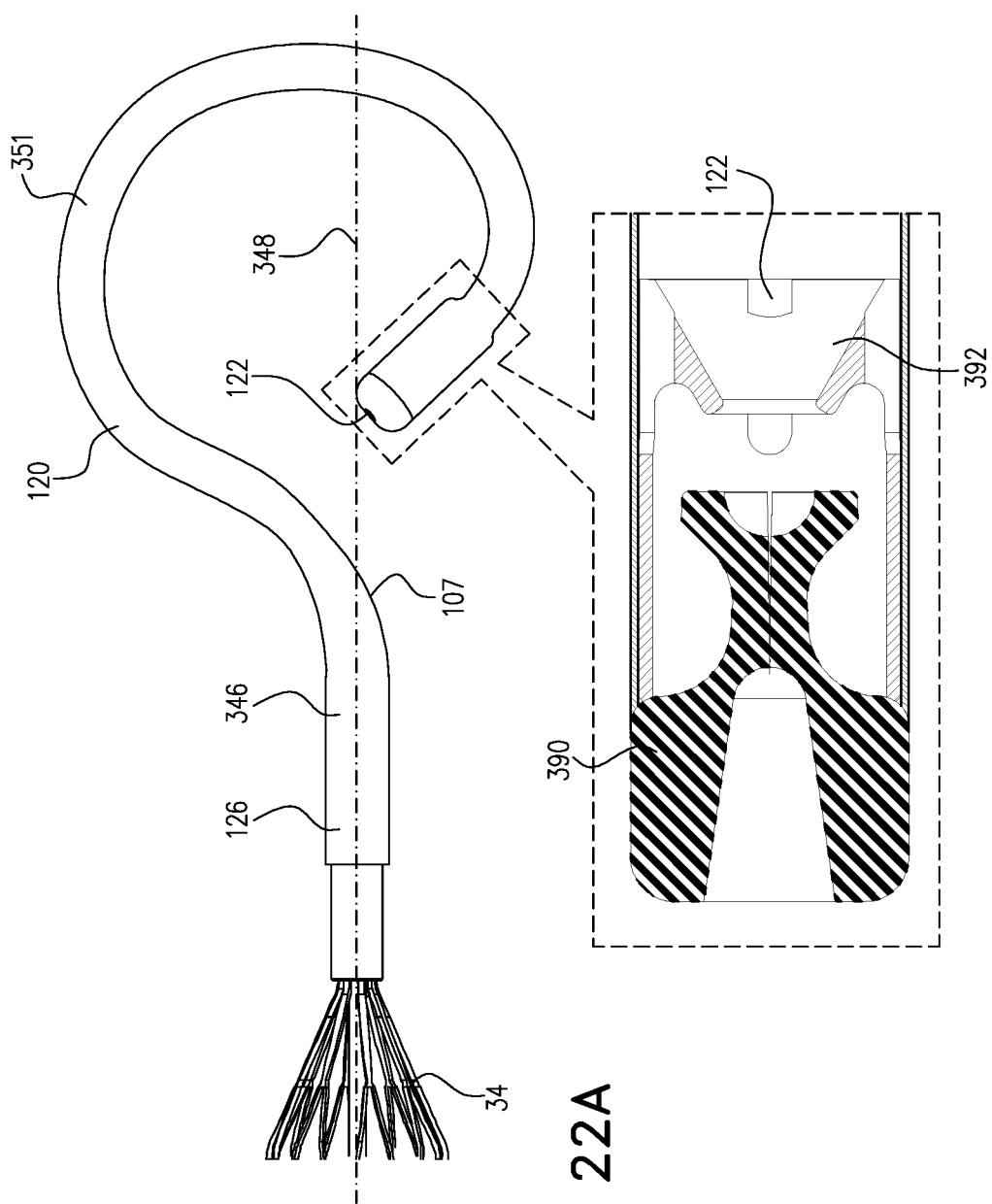
FIGS. 22A, 22B, 22C, and 22D are schematic illustrations of a distal-tip element of a ventricular assist device that is at least partially curved such as to define a question-mark shape or a tennis-racket shape, in accordance with some applications of the present invention.
Figure 22B:
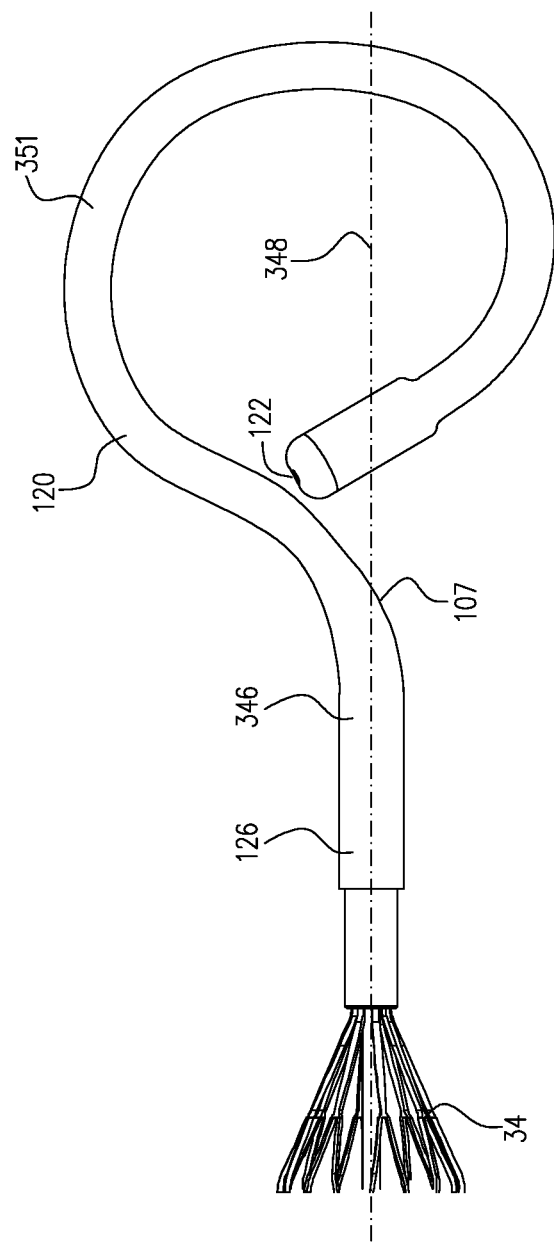
Figure 22C:
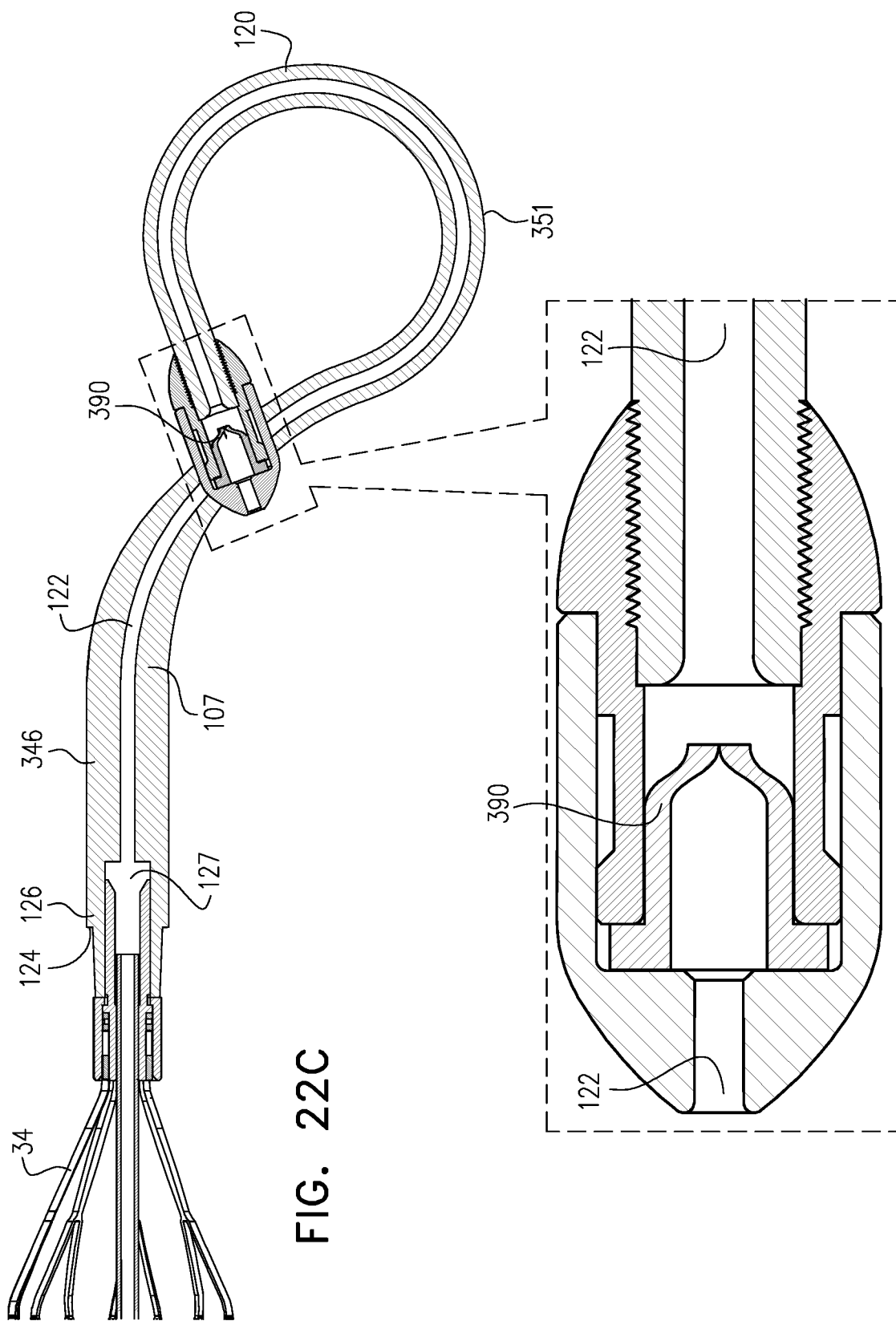
Figure 22D:
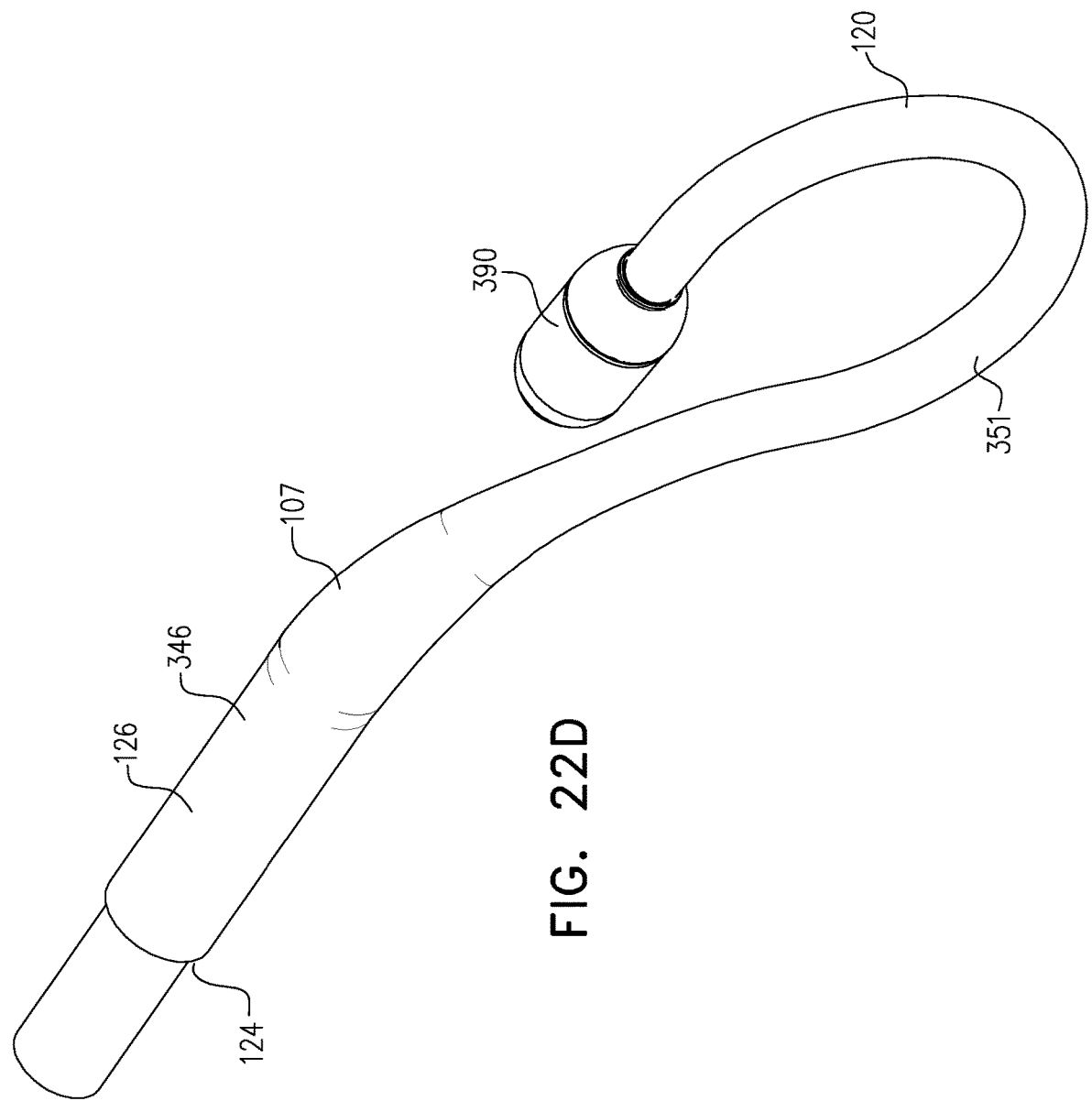

Typically, the ventricular assist device is introduced into the subject's ventricle over a guidewire, as described hereinabove. Distal-tip portion 120 defines guidewire lumen 122, such that the distal-tip portion is held in a straightened configuration during the introduction of the ventricular assist device into the subject's ventricle. For some applications, upon the guidewire being removed, distal-tip portion is configured to assume its curved shape. It is noted that FIGS. 22A-D illustrate the shape of distal-tip portion 120 as it is initially formed. Typically, as a result of having the guidewire inserted through guidewire lumen 122 (thereby temporarily straightening the distal-tip portion), upon being deployed within the subject's left ventricle, the curvature of the distal-tip portion is less than that shown in at least some of FIGS. 22A-D. For example, FIGS. 22C-D show that the curvature of the distal-tip portion is such that the curved portion of the distal-tip portion forms a complete loop. However, the distal-tip portion of FIGS. 22C-D is shown in FIG. 23A within the subject's left ventricle and it does not form a complete loop.

As described hereinabove, distal-tip portion 120 typically forms a portion of distal-tip element 107 which also includes axial-shaft receiving tube 126. Typically, distal-tip element 107 is configured such that in its non-constrained configuration (i.e., in the absence of any forces acting upon the distal-tip portion), the distal-tip element is at least partially curved. For some applications, within a given plane, distal-tip element 107 has a proximal, straight portion 346 (at least a portion of which typically comprises axial-shaft-receiving tube 126). The proximal straight portion of distal-tip element 107 defines a longitudinal axis 348. The curved portion of distal-tip element 107 curves away from longitudinal axis 348 in a first direction, and then passes through an inflection point and curves in the opposite direction with respect to longitudinal axis 348. For example, as shown in FIGS. 22A-B, within the plane of the page, the distal-tip element first curves to the top of the page, then curves to the bottom of the page, and as shown in FIGS. 22C-D, within the plane of the page, the distal-tip element first curves to the bottom of the page, then curves to the top of the page. Typically, when shaped as shown in FIGS. 22A-D, the distal-tip element defines an overall curvature that is similar to that of a question mark or a tennis-racket, the distal-tip element defining a bulge 351 on one side of the longitudinal axis of the straight proximal straight portion of the distal-tip element. For some applications, the bulge is generally shaped as a semi-ellipse. (It is noted that in this context the term "semi-ellipse" includes a semi-circle. It is further noted that is some cases, the tip does not define a precise semi-ellipse, but rather a bulged shape that is substantially similar to a semi-ellipse.)

As shown in FIGS. 22A-B, for some applications, after passing through the inflection point the distal-tip element continues to curve such that the distal-tip element crosses back over longitudinal axis 348. FIG. 22A shows an example in which the end of the distal-tip element does not cross back over the longitudinal axis yet again, and there is a larger gap between the distal end of the distal-tip element and the proximal end of the curved portion. FIG. 22B shows an example in which the end distal-tip element does cross back over the longitudinal axis yet again, and there is a smaller gap between the distal end of the distal-tip element and the proximal end of the curved portion. As shown in FIGS. 22C-D (which are, respectively, cross-sectional and isometric views of the same shaped distal-tip element), for some applications, after passing through the inflection point the tip does not curve such that the distal-tip element crosses back over longitudinal axis 348. Rather, all of the curvature of the curved portion of the distal-tip element occurs on one side of longitudinal axis 348.

Figure 28A:
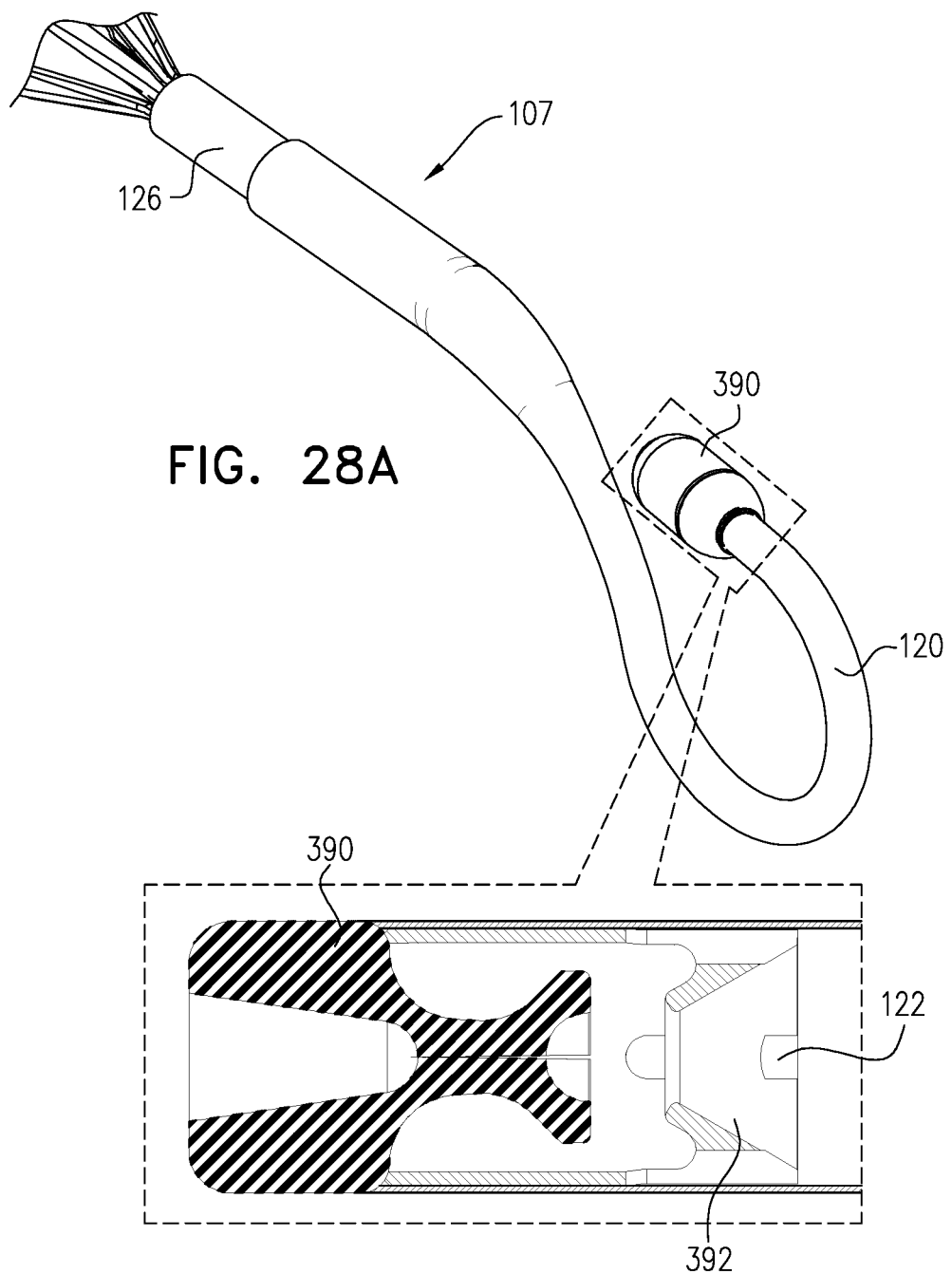
FIG. 28A is a schematic illustration of a duckbill valve and guidewire guide disposed at the distal end of an atraumatic tip, in accordance with some applications of the present invention.
Figure 28B:
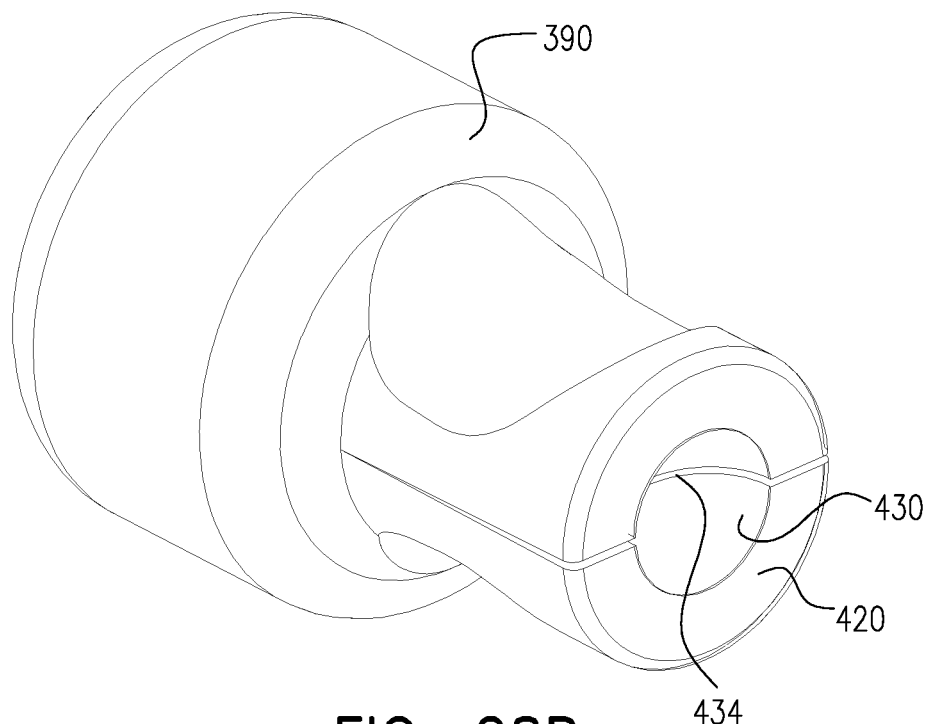
FIGS. 28B and 28C are schematic illustration of respective views of the duckbill valve of FIG. 28A, in accordance with some applications of the present invention.
Figure 28C:
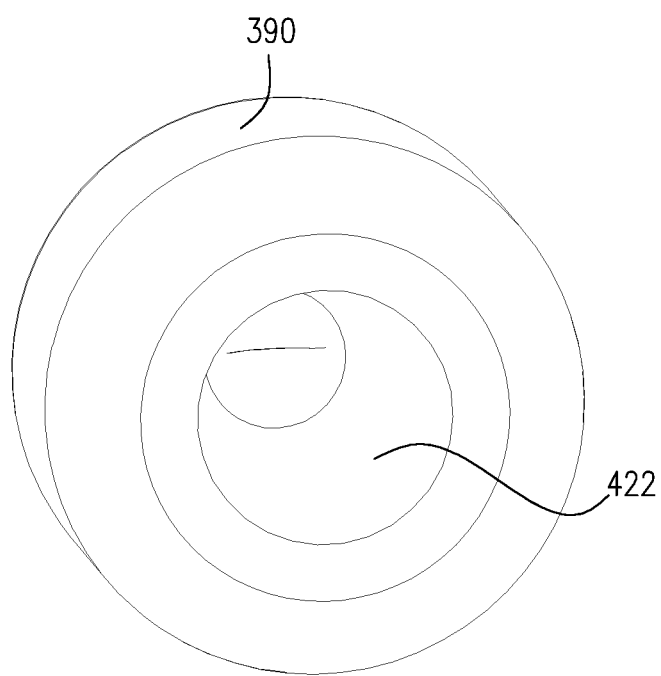

Referring to FIGS. 22A and 22C, typically, a hemostasis valve (e.g., duckbill valve 390) is disposed within a distal section of distal-tip portion 120, and is configured to prevent blood flow into lumen 122. For some applications, the duckbill valve 390 is as described in further detail hereinbelow with reference to FIGS. 28A-C. For example, FIG. 22A shows an example in which the duckbill valve of FIGS. 28A-C is used. Alternatively, a different duckbill valve is used, e.g., as shown in FIG. 22C. Typically, the duckbill valve has a maximum width of less than 3 mm, e.g., less than 2 mm. Typically, the entire duckbill valve is disposed within a distal section of the distal-tip portion that is disposed within the distal-most 10 mm, e.g., the distal most 5 mm of the distal-tip portion. For some applications, the duckbill valve is proximally facing (i.e., such that the wide inlet of the valve faces the distal end of distal-tip portion and such that the narrow tip of the valve faces away from the distal end of distal-tip portion 120), as described in further detail hereinbelow with reference to FIGS. 28A-E. For some applications, a guidewire guide 392 is disposed within distal-tip portion 120 at a location that is proximal to the duckbill valve (e.g., as shown in FIG. 22A). As shown in FIGS. 22A-D, typically, the distal section of the distal portion is widened in order to accommodate the duckbill valve and/or the guidewire guide. For some applications, by virtue of the distal portion being widened, the distal tip of the distal-tip portion (via which a guidewire is inserted into the distal-tip portion) does not have a sharp edge. Rather the edge has a width of more than 1 mm. Typically, the lack of a sharp edge at the distal tip of the distal-tip portion helps to prevent the distal tip of the distal-tip portion from causing trauma to structure within the left ventricle.

Typically, upon being deployed within the subject's left ventricle, the curvature of the curved portion of distal-tip element 107 is configured to provide an atraumatic tip to ventricular assist device 20. Further typically, the distal-tip element is configured to space the inlet openings 108 of the ventricular assist device from walls of the left ventricle.

Referring now to FIGS. 23A and 23B, it is first noted that these figures show a cross-sectional view of the left ventricle 22 in which septal wall 338 is disposed on the left of the page and free wall 334 is disposed on the right of the page. In this view, the left atrium 359, and left atrial appendage 358 are visible above the left ventricle, and right ventricle 340 is visible to the left of the left ventricle. For some applications, distal-tip element 107 is configured to separate the blood inlet opening from a posterior wall of the subject's left ventricle when the distal-tip element is placed against the apex of the subject's left ventricle. Typically, the distal-tip element is configured to separate the blood inlet opening from a septal wall of the subject's left ventricle as the distal-tip element contacts the apex of the subject's left ventricle.

Typically, distal-tip element 107 is inserted into the left ventricle, such that bulge 351 bulges toward the septal wall 338. When disposed in this configuration, in response to distal-tip element 107 being pushed against the apex (e.g., due to a physician advancing the device or in response to movement of the left ventricle), the blood inlet opening typically gets pushed in the direction of free wall 334 and away from the septal wall 338 (in the direction of the arrows shown in FIG. 23B. Typically, this is due to proximal straight portion 346 pivoting about the curved portion of the question mark shape, as shown. By contrast, other shapes of tips, if disposed in a similar orientation may result in the blood inlet opening being pushed toward the septal wall. For example, if the distal-tip element were to have a pigtail tip (in which the tip curves in a single direction of curvature) that is oriented such that the pigtail curve is on the free wall side of the longitudinal axis of the straight portion of the distal-tip element, then pushing the tip distally would typically cause the blood inlet openings toward the septal wall due to the loop of the pigtail curve tightening.

Figure 24A:
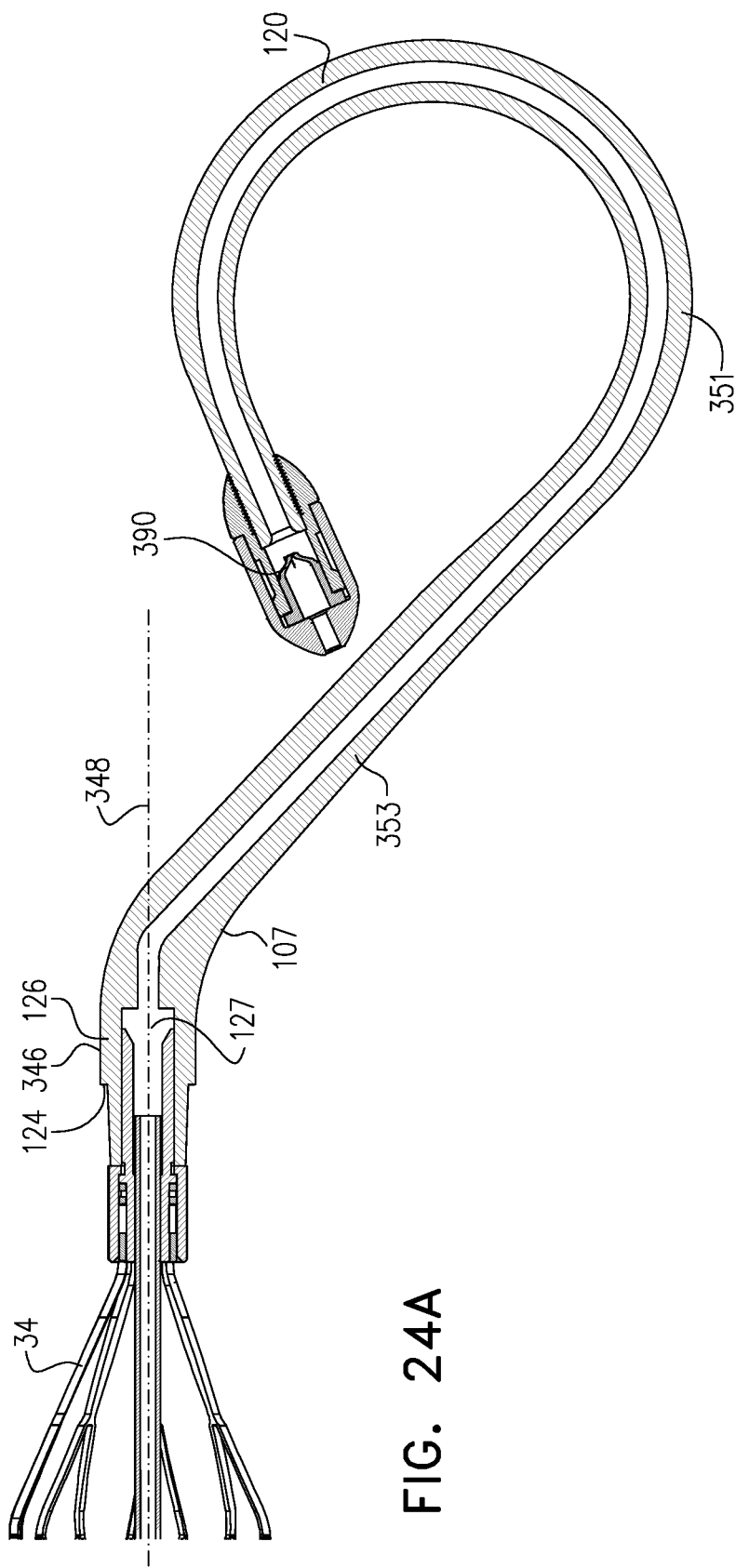
FIGS. 24A, 24B, and 24C are schematic illustrations of a distal-tip element that is configured to center itself with respect to a subject's aortic valve, in accordance with some applications of the present invention.
Figure 24B:
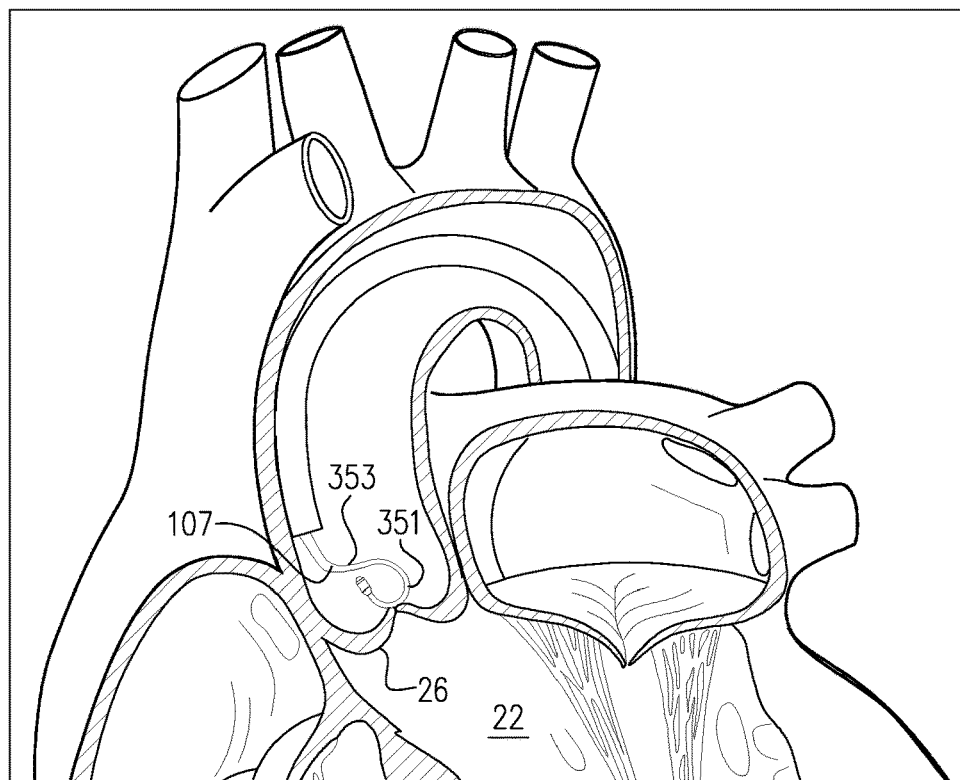
Figure 24C:
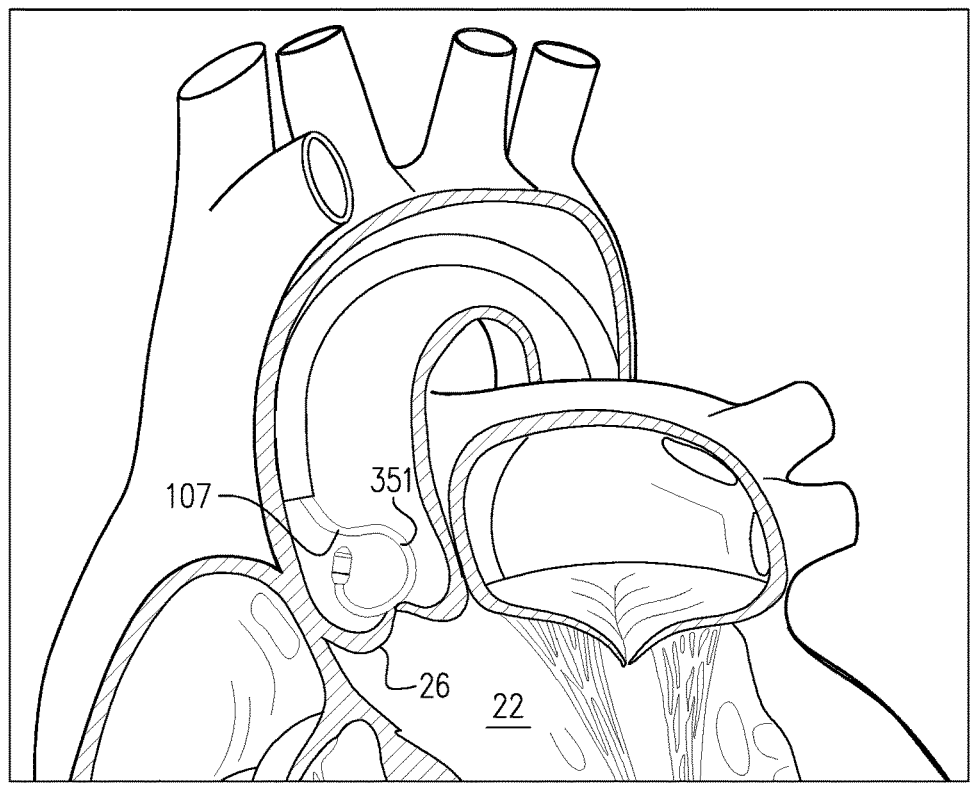

Reference is now made to FIGS. 24A, 24B, 24C, which are schematic illustrations of distal-tip element 107, the distal-tip element being configured to center itself with respect to aortic valve 26, in accordance with some applications of the present invention. As shown in FIG. 24A, for some applications, the curved distal portion is shaped that after curving in the first direction the curved distal portion defines an elongated straight portion 353, before curving in the second direction. As shown in FIG. 24B, the distal-tip element is configured such that upon being released within the subject's aorta, the distal-tip element centers itself with respect to aortic valve 26. Thus, the distal-tip portion may be used to guide ventricular assist device through the aortic valve in an atraumatic manner. This may be desirable, for example, in instances in which the ventricular assist device is mistakenly retracted through the aortic valve from the left ventricle, after the distal-tip element has been released within the left ventricle. Referring to FIG. 24C, an alternative or additional manner in which to configure the distal-tip element to provide the above-described functionality is for the radius of bulge 351 of the distal-tip element to be sufficiently large such as to center the distal-tip element with respect to the aortic valve. For example, the radius of the bulge of the distal-tip element may be greater than 15 mm (e.g., greater than 17 mm).

With reference to all of FIGS. 21-24C it is noted that the scope of the present invention includes using a question-mark or tennis-racket shaped distal-tip element in combination with any ventricular assist device, and even in the absence of other features and/or portions of distal-tip element 107 (such as, axial-shaft-receiving tube 126).

Figure 25A:
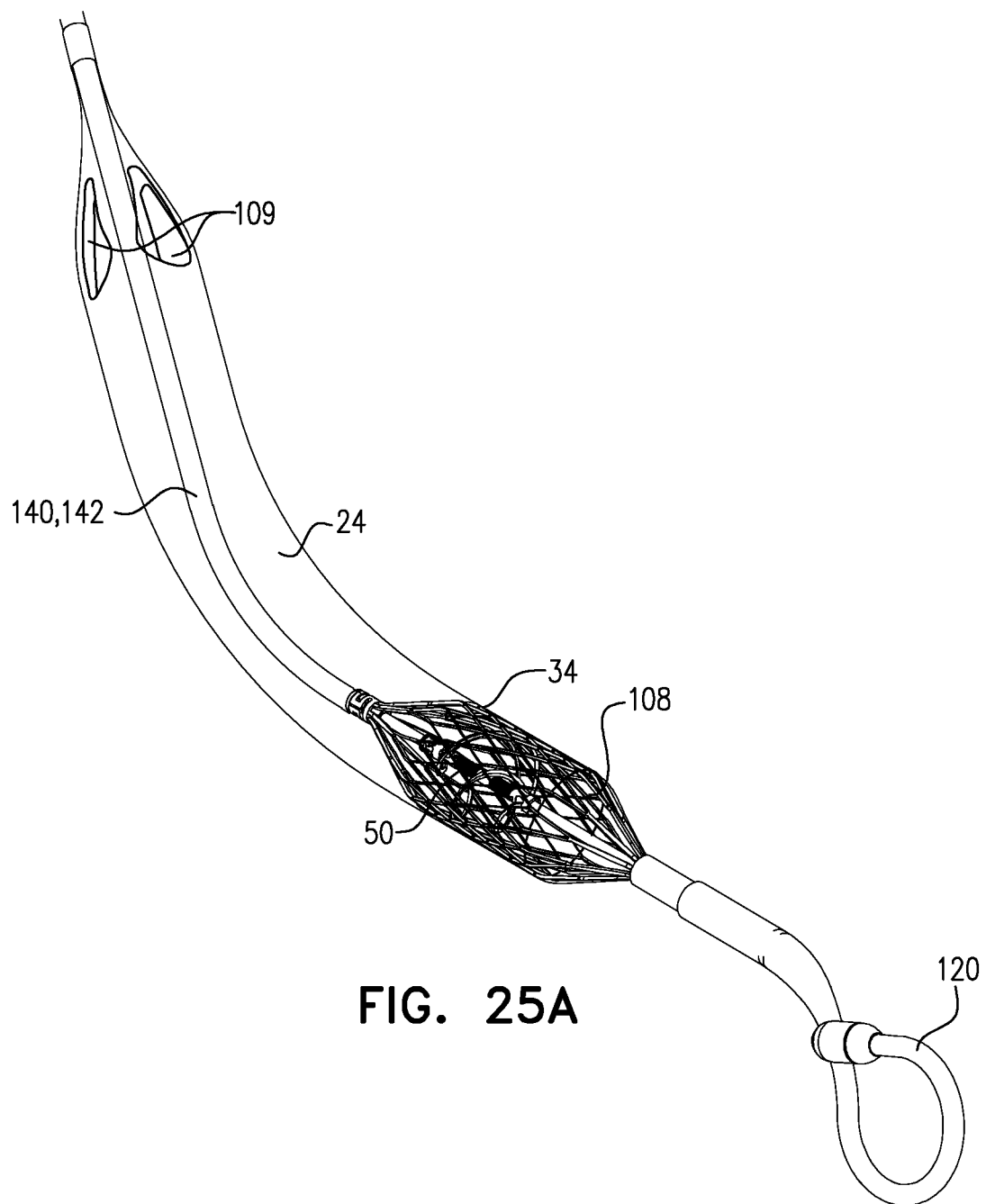
FIGS. 25A, 25B, 25C, 25D, and 25E are schematic illustrations of a ventricular assist device that includes a tube that is configured to become curved when blood is pumped through the tube, in accordance with some applications of the present invention.
Figure 25B:
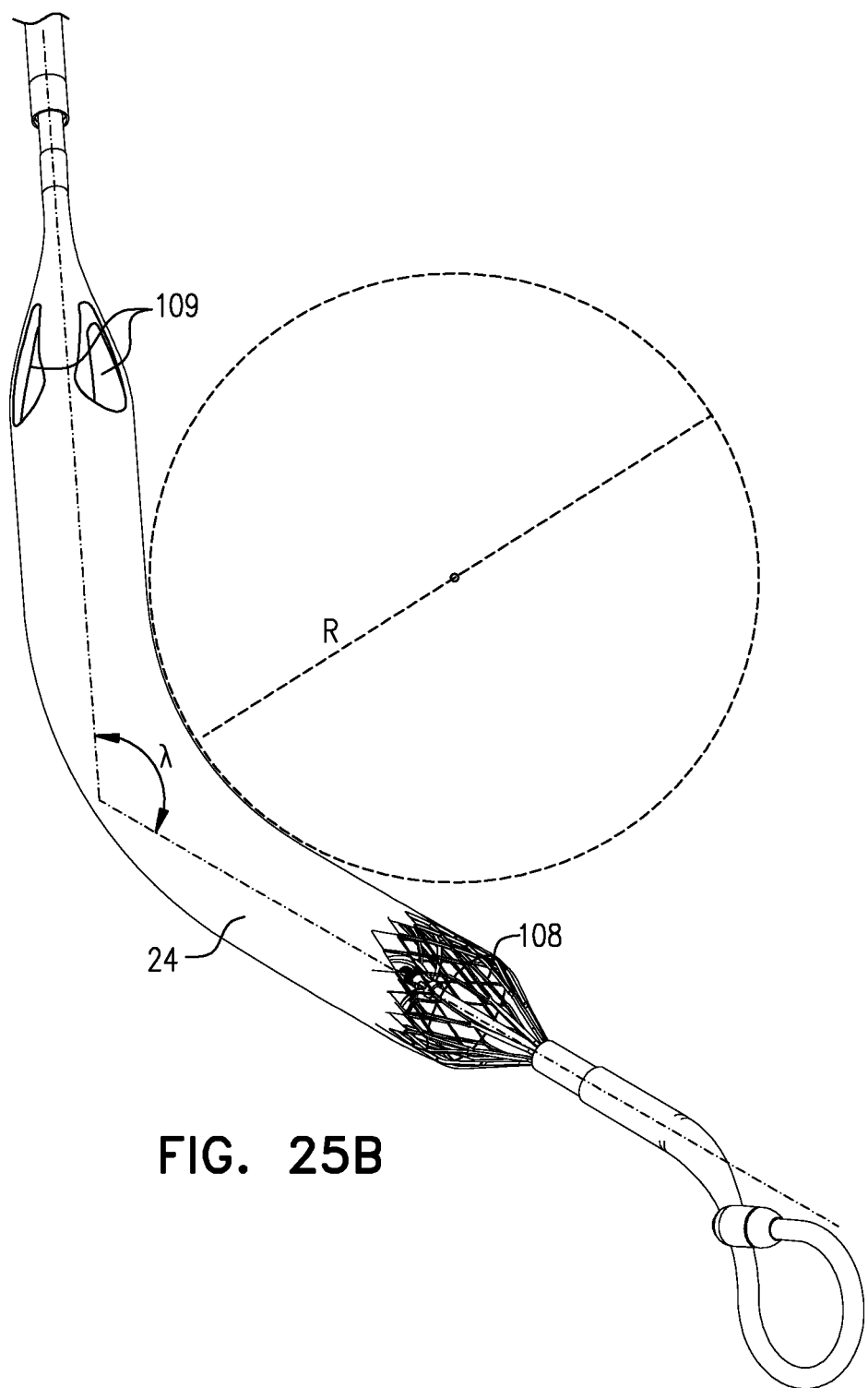
Figure 25C:
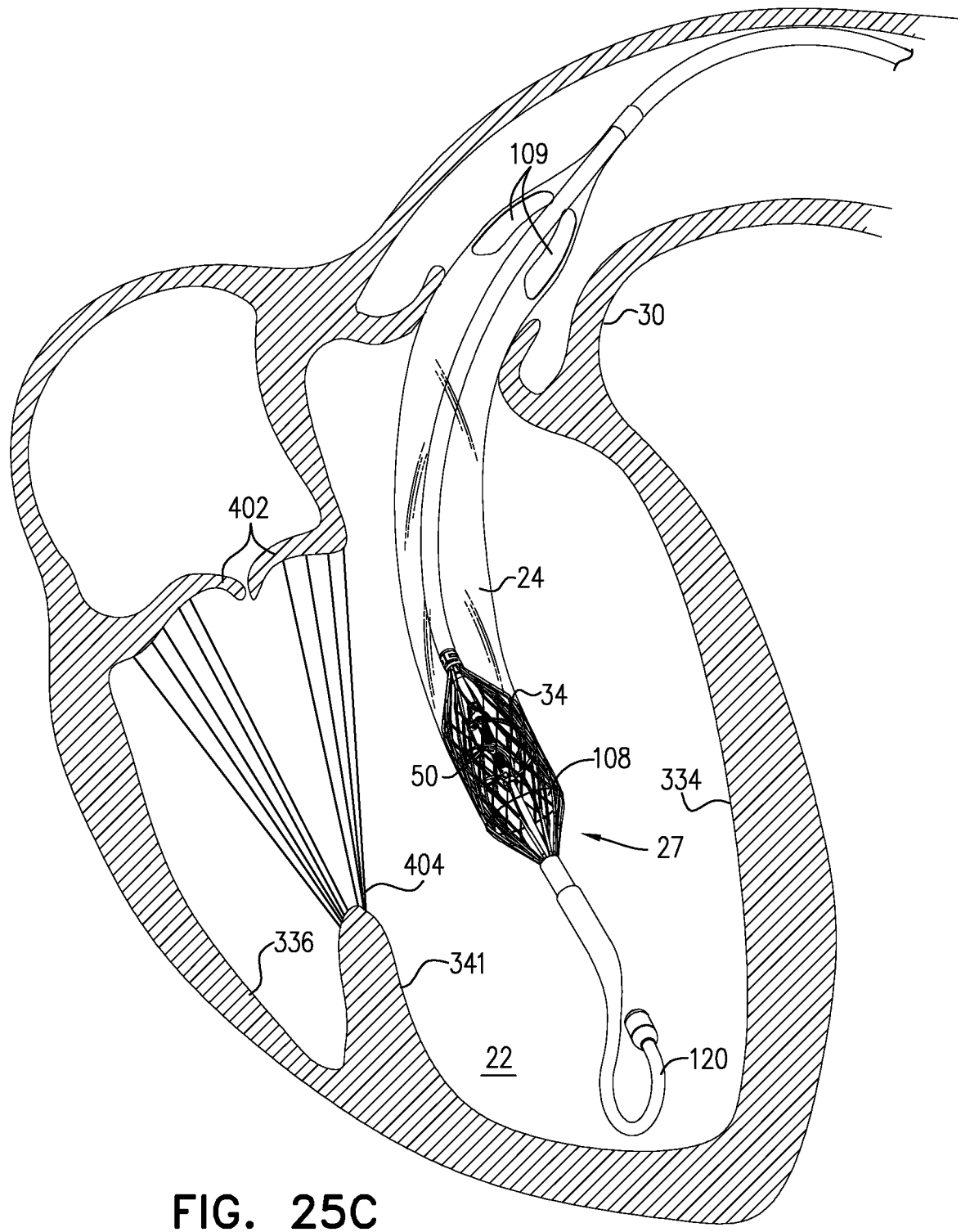

Reference is now made to FIG. 25A, which is a schematic illustration of ventricular assist device 20, tube 24 of the device being configured to become curved when blood is pumped through the tube, in accordance with some applications of the present invention. Reference is also made to FIG. 25B, which is a schematic illustration of tube 24 of FIG. 25A, in the absence of other components of the ventricular assist device, in accordance with some applications of the present invention. Reference is additionally made to FIG. 25C, which is a schematic illustration of ventricular assist device 20 of FIGS. 25A-B disposed inside a subject's aorta 30 and left ventricle 22, in accordance with some applications of the present invention. It is noted that the view of the aorta and the left ventricle as shown in FIG. 25C is different to that shown, for example, in FIG. 1B. FIG. 1B and similar figures are schematic illustrations, provided for illustrative purposes and do not necessarily precisely depict the scale and orientation of the ventricular assist with respect to the anatomy. It is further noted that the view of the aorta and the left ventricle as shown in FIG. 25C is different to that shown, for example, in FIGS. 23A and 23B. FIG. 25C shows a cross-sectional view of the left ventricle in which the posterior wall 336 is disposed on the left of the page and the free wall 334 is disposed on the right of the page.

As described hereinabove, for some applications, along a proximal portion of tube 24, frame 34 is not disposed within the tube, and the tube is therefore not supported in an open state by frame 34. Tube 24 is typically made of a blood-impermeable, collapsible material. For example, tube 24 may include polyurethane, polyester, and/or silicone. Alternatively or additionally, the tube is made of polyethylene terephthalate (PET) and/or polyether block amide (PEBAX®). Typically, the proximal portion of the tube is configured to be placed such that it is at least partially disposed within the subject's ascending aorta. For some applications, the proximal portion of the tube traverses the subject's aortic valve, passing from the subject's left ventricle into the subject's ascending aorta, as shown in FIG. 1B. As described hereinabove, the tube typically defines one or more blood inlet openings 108 at the distal end of the tube, via which blood flows into the tube from the left ventricle, during operation of the impeller. For some applications, the proximal portion of the tube defines one or more blood outlet openings 109, via which blood flows from the tube into the ascending aorta, during operation of the impeller. During operation of the impeller, the pressure of the blood flow through the tube typically maintains the proximal portion of the tube in an open state.

For some applications, tube 24 is pre-shaped such that, during operation of the impeller, when the pressure of the blood flow through the tube maintains the proximal portion of the tube in an open state, the tube is curved. Typically, the curvature is such that when the proximal end of the tube is disposed within the aorta, at least a portion of the tube is disposed within the left ventricle and curving away from the posterior wall of the left ventricle, toward the apex of the left ventricle and/or toward the free wall. Further typically, the curvature is such that when the proximal end of the tube is disposed within the aorta, at least a portion of the tube is disposed within the left ventricle and curving away from the septal wall of the left ventricle, toward the apex of the left ventricle and/or toward the free wall. For some applications, the curvature of the tube is such that a separation is maintained between blood inlet openings 108 and posterior wall 336 of the left ventricle, mitral valve leaflets 402 and/or subvalvular components of the mitral valve (such as chordae tendineae 404 and/or papillary muscles 341), as shown in FIG. 25C.

Typically, tube 24 is pre-shaped using blow molding in a curved mold, or using a shaping mold after a blow-molding process or a dipping process. Typically, the distal portion of the tube, within which frame 34, impeller 50 and axial shaft 92 are disposed, is maintained in a straight and open configuration by frame 34. The portion of the tube, which is proximal to frame 34 and which is disposed within the left ventricle, is typically shaped to define the above-described curvature. For some applications, the curvature is such that an angle gamma between the longitudinal axis of the tube at the proximal end of the tube, and the longitudinal axis of the tube at the distal end of the tube is greater than 90 degrees (e.g., greater than 120 degrees, or greater than 140 degrees), and/or less than 180 degrees (e.g., less than 160 degrees, or less than 150 degrees), e.g., 90-180 degrees, 90-160 degrees, 120-160 degrees, or 140-150 degrees. For some applications, the curvature of the tube is such that the surface of the tube that is at the inside of the curve defines a radius of curvature R that is greater than 10 mm, e.g. greater than 20 mm, and/or less than 200 mm (e.g., 100 mm), e.g., 10-200 mm, or 20-100 mm. (A dashed circle with a dashed line across its diameter is shown in FIG. 25B, in order to indicate how radius of curvature R is measured.)

It is noted that tube 24, as described with reference to FIGS. 25A-C is configured such that (a) in the absence of blood flowing through the tube, the tube typically collapses in response to pressure outside the tube exceeding pressure inside the tube, and (b) when blood flows through the tube at a sufficient rate that pressure within the tube exceeds pressure outside the tube, then the tube assumes its pre-shaped, curved configuration. It is further noted that when tube 24 assumes its curved configuration, the tube typically causes the portion of drive cable 130 that is disposed within the curved portion of the tube to also become curved, as shown in FIGS. 25A and 25C. That is to say that it is the pre-shaping of the tube itself that typically causes the tube and the drive cable to curve, rather than the drive cable (or a different element disposed inside the tube) that causes the tube to curve. Alternatively, outer tube 140 and/or 142 (which is disposed around the drive cable) is shaped to define the curve, and the outer tube causes the drive cable and tube 24 to assume the curved shapes. For some applications, both outer tube 140 and/or 142 and tube 24 are shaped to define curved shapes.

It is noted that tube 24 as shown in FIGS. 25A-C is generally configured as described hereinabove with reference to FIG. 2A (i.e., with a conical distal portion 46, and with a plurality of blood inlet openings 108). However, the scope of the present invention includes combining the curved configuration of the tube, as described with reference to FIGS. 25A-C, with other general configurations of the tube (e.g., as described hereinabove).

Figure 25D:
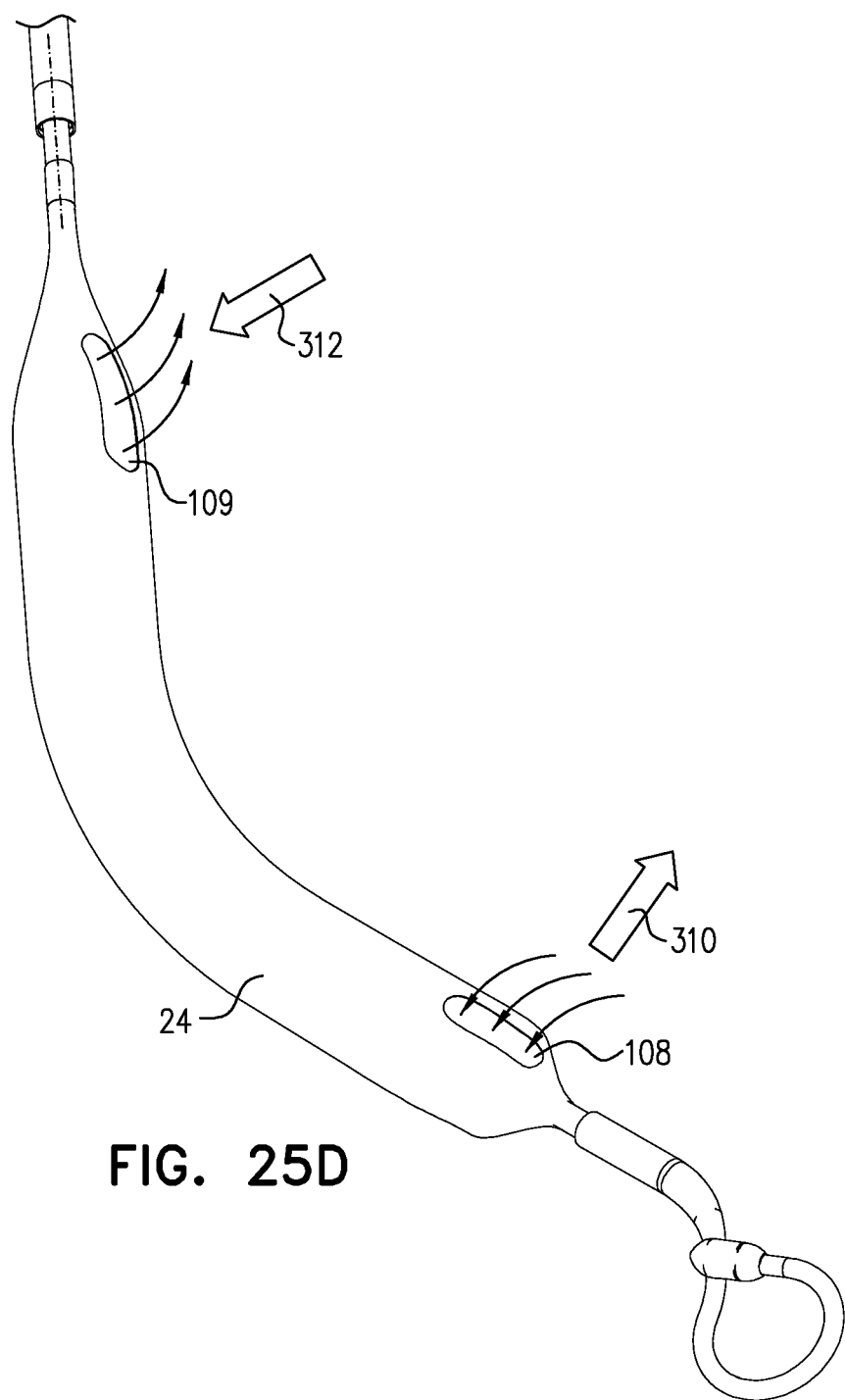
Figure 25E:
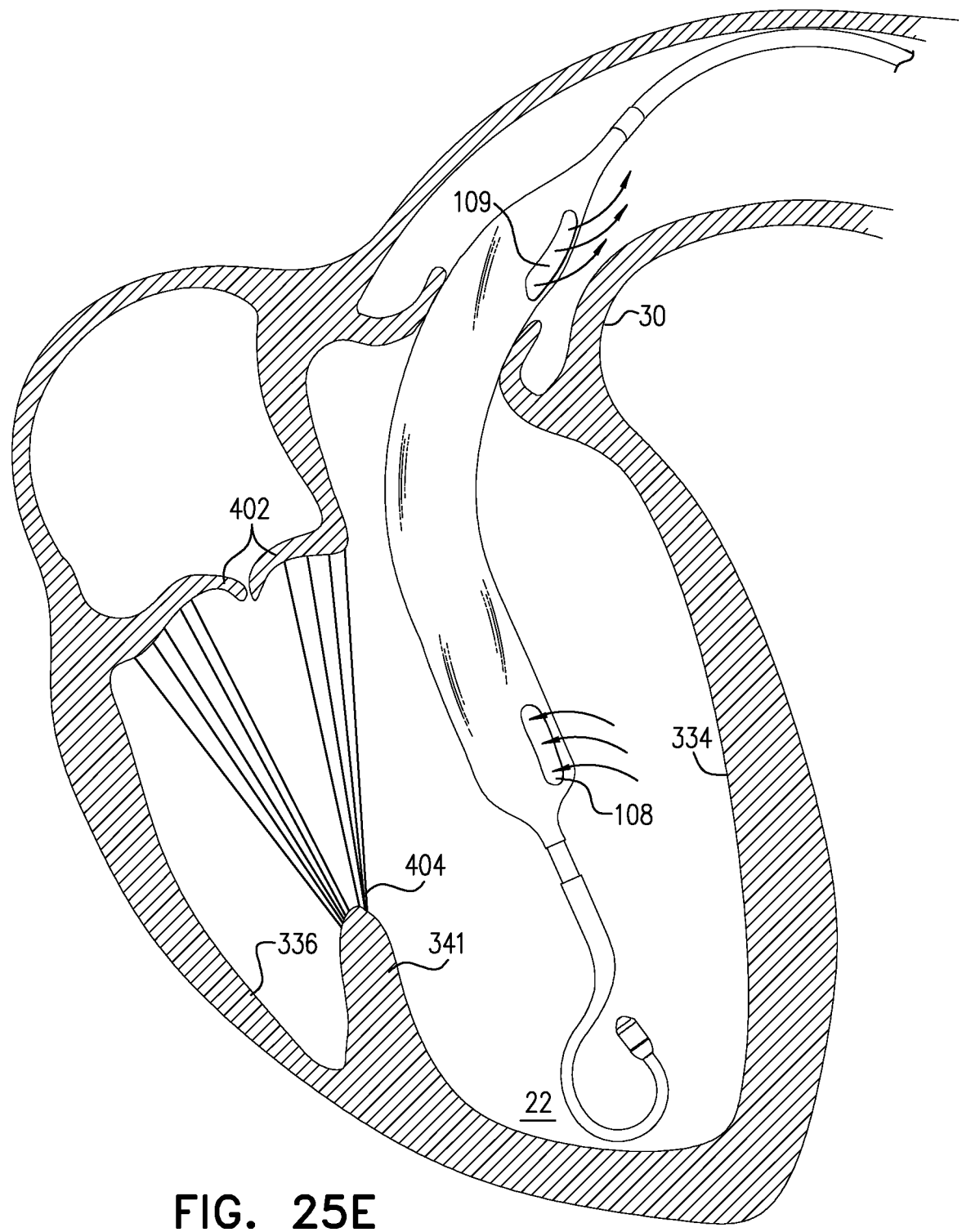

Reference is now made to FIGS. 25D-E, which are schematic illustrations of ventricular assist device 20, tube 24 of the device being configured to become curved when blood is pumped through the tube, in accordance with some applications of the present invention. In FIGS. 25D and 25E, tube 24 is shown in the absence of other components of the ventricular assist device (such as impeller 50, frame 34, etc.), for illustrative purposes. FIG. 25E is a schematic illustration of ventricular assist device 20 of FIG. 25D disposed inside a subject's aorta 30 and left ventricle 22, in accordance with some applications of the present invention. The view of the left ventricle shown in FIG. 25E is similar to that shown in FIG. 25C. For some applications, inlet openings 108 and/or outlet openings 109 are disposed in a non-axisymmetric configuration around tube 24. Typically, tube 24 defines the inlet openings and/or the outlet openings at locations that are such as to cause tube 24 to become curved and/or such as to maintain the curvature of tube 24 as described with reference to FIGS. 25A-C. For example, as shown, the blood inlet holes may be disposed on the side of tube 24 that is at the inside of the curve of the tube (or on the inside of the desired curve of the tube). As blood flows into the blood inlet opening, this lowers the pressure in the region above the blood inlet opening, and the distal end of tube 24 is then pulled toward this region (as indicated by arrow 310). Alternatively or additionally, the blood outlet openings 109 may be disposed on the side of tube 24 that is at the inside of the curve of the tube (or on the inside of the desired curve of the tube). As blood exits the blood outlet openings the blood impacts the wall of the aorta, which causes the proximal end of tube 24 to be pushed in the opposite direction, in the direction of arrow 312.

As described with reference to FIGS. 25A-C, typically, the curvature of the tube is such that a separation is maintained between blood inlet openings 108 and posterior wall 336 of the left ventricle, mitral valve leaflets 402 and/or subvalvular components of the mitral valve (such as chordae tendineae 404 and/or papillary muscles 341), as shown in FIG. 25E. Typically, the curvature is such that when the proximal end of the tube is disposed within the aorta, at least a portion of the tube is disposed within the left ventricle and curving away from the posterior wall of the left ventricle, toward the apex of the left ventricle and/or toward the free wall. Further typically, the curvature is such that when the proximal end of the tube is disposed within the aorta, at least a portion of the tube is disposed within the left ventricle and curving away from the septal wall of the left ventricle, toward the apex of the left ventricle and/or toward the free wall.

Figure 25F:
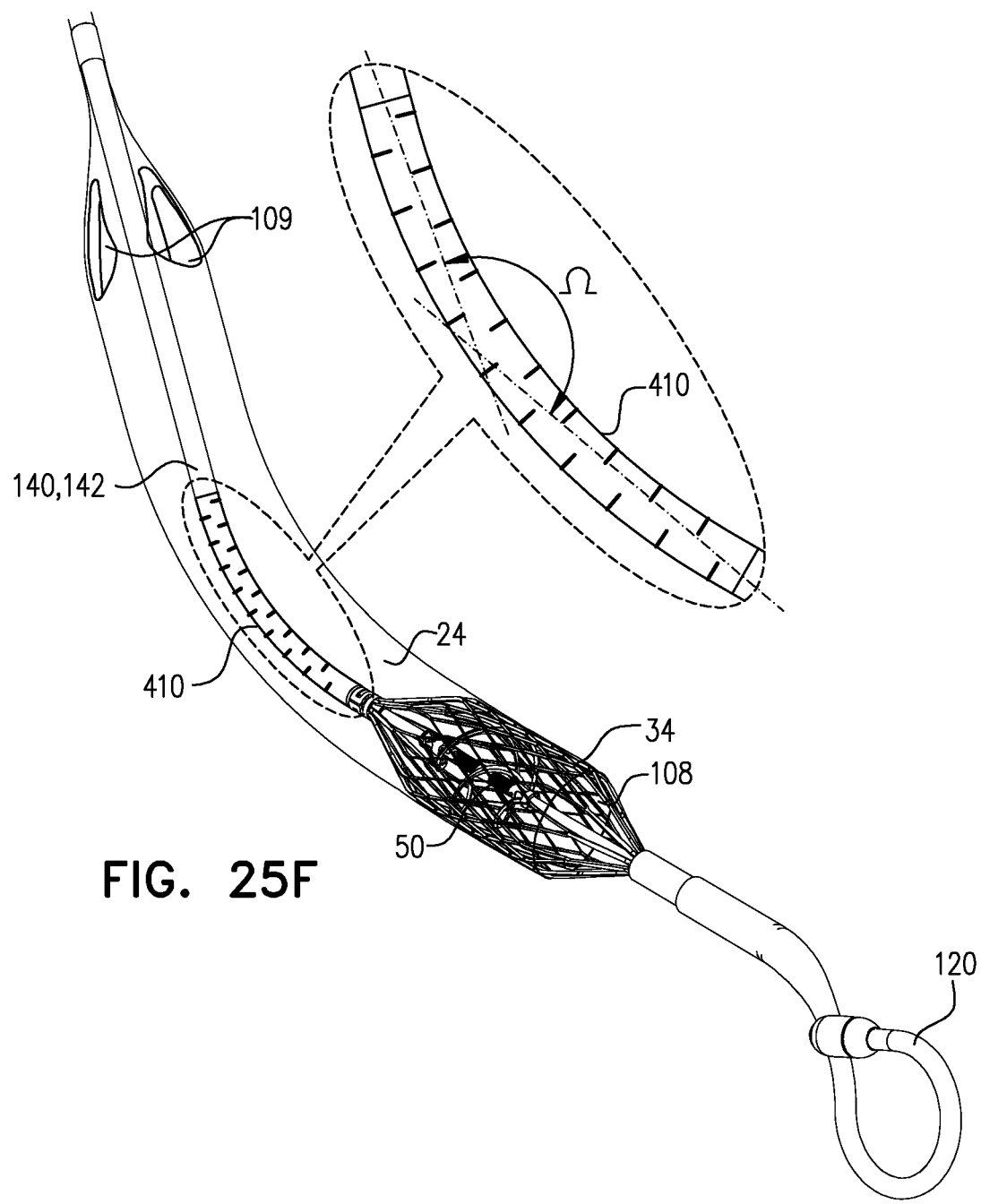
FIG. 25F is a schematic illustration of a ventricular assist device that includes a curved element that is made of a shape-memory material and that is configured to provide a portion of the ventricular assist device with a predefined curvature, in accordance with some applications of the present invention.

Reference is now made to FIG. 25F, which is a schematic illustration of ventricular assist device 20, the ventricular assist device including a curved element 410 that is configured to provide tube 24 with a predefined curvature, in accordance with some applications of the present invention. For some applications, as an alternative or in addition to tube 24 itself being shaped to define a curve (e.g., as described with reference to FIGS. 24A-E), the ventricular assist device includes curved element 410. Typically, the curved element is made of a shape-memory material, e.g., a shape-memory alloy, such as nitinol. For some applications, the curved element is formed from a nitinol tube that is cut to define holes or slits, such that the tube is able to be pre-shaped in the desired curved shape. For example, the nitinol element may be what is known in the art as a nitinol "hypotube" (i.e., a nitinol tube with micro-engineered features along its length). Typically, curved element 410 is disposed around drive cable 130 along a longitudinal section of the drive cable that is proximal to (e.g., immediately proximal to) proximal radial bearing 116. For some applications, along this longitudinal section of the drive cable, the curved element is used in place of outer tube 142.

For some applications, the curved element is shape set to have a curvature that is generally similar to that described with respect to tube 24, with reference to FIGS. 25A-E. For some applications, the curvature is such that angle omega between the longitudinal axis of the curved element at the proximal end of the curved element, and the longitudinal axis of the curved element at the distal end of the curved element is greater than 90 degrees (e.g., greater than 120 degrees, or greater than 140 degrees), and/or less than 180 degrees (e.g., less than 160 degrees, or less than 150 degrees), e.g., 90-180 degrees, 90-160 degrees, 120-160 degrees, or 140-150 degrees. For some applications, the curvature of the tube is such that the surface of the curved element that is at the inside of the curve defines radius of curvature that is greater than 10 mm, e.g. greater than 20 mm, and/or less than 200 mm (e.g., 100 mm), e.g., 10-200 mm, or 20-100 mm. As described with reference to FIGS. 25A-C, typically, the curvature of the tube is such that a separation is maintained between blood inlet openings 108 and posterior wall 336 of the left ventricle, mitral valve leaflets 402 and/or subvalvular components of the mitral valve (such as chordae tendineae 404 and/or papillary muscles 341), as shown in FIG. 25C. Typically, the curvature is such that when the proximal end of the tube is disposed within the aorta, at least a portion of the tube is disposed within the left ventricle and curving away from the posterior wall of the left ventricle, toward the apex of the left ventricle and/or toward the free wall. Further typically, the curvature is such that when the proximal end of the tube is disposed within the aorta, at least a portion of the tube is disposed within the left ventricle and curving away from the septal wall of the left ventricle, toward the apex of the left ventricle and/or toward the free wall.

With reference to FIGS. 25A-F, it is noted that for some applications tube 24 adopts a curved shape by virtue of outer tube 142 becoming anchored to the aorta and distal-tip portion 120 becoming anchored to the inner wall of the left ventricle (e.g., the free wall in the vicinity of the apex), as described hereinabove. It is further noted that the curvature of the tube shown in FIGS. 23A-B is less than that shown in FIGS. 25A-F because FIGS. 23A-B show a different view of the device. In the view shown in FIGS. 23A-B, the curvature is typically less pronounced than in the view shown in FIGS. 25A-F.

Reference is now made to FIGS. 26A, 26B, 26C, 26D, 26E, and 26F, which are schematic illustrations of distal-tip element 107 of ventricular assist device 20, the distal-tip element being at least partially curved, in accordance with respective applications of the present invention. (Distal-tip element 107 is shown in the absence of the distal end of frame 34, in FIGS. 26B-F.) Typically, the ventricular assist device is introduced into the subject's ventricle over a guidewire, as described hereinabove. Distal-tip portion 120 defines a guidewire lumen 122, such that the distal-tip portion is held in a straightened configuration during the introduction of the ventricular assist device into the subject's ventricle. For some applications, upon the guidewire being removed distal-tip portion is configured to assume a shape as shown in one of FIGS. 26A-F.

Figure 26A:
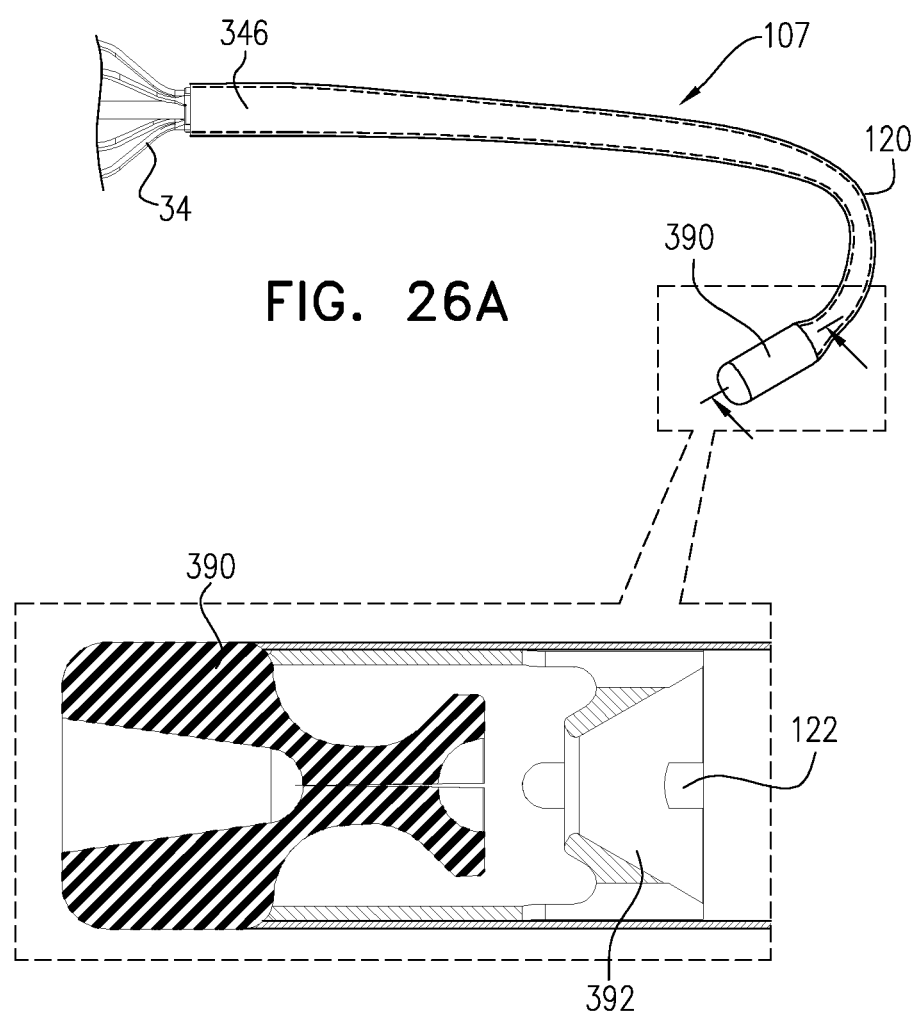
FIGS. 26A, 26B, 26C, 26D, 26E, and 26F are schematic illustrations of a distal-tip element of a ventricular assist device that is at least partially curved, in accordance with some applications of the present invention.

Typically, distal-tip element 107 is configured such that in its non-constrained configuration (i.e., in the absence of any forces acting upon the distal-tip portion), the distal-tip element is at least partially curved. For some applications, the distal-tip element curves around an angle of more than 90 degrees (e.g., more than 120 degrees), and less than 180 degrees (e.g., less than 160 degrees), e.g., 90-180 degrees, 120-180 degrees, or 120-160 degrees, e.g., as shown in FIG. 26A.

Figure 26B:
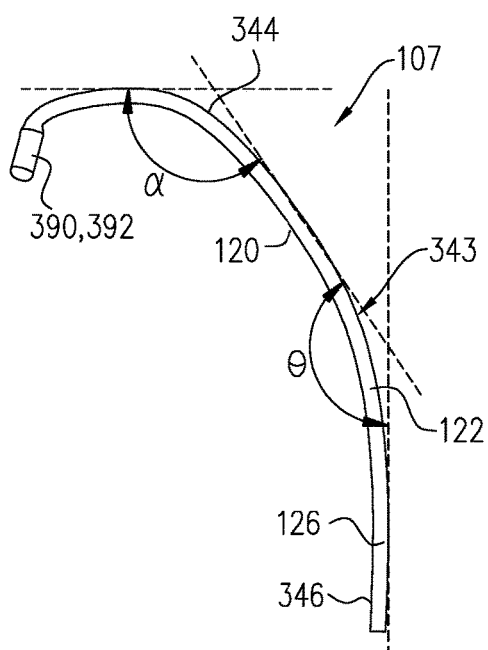

For some applications, the distal-tip element defines a first proximal curved portion 343, and defines a second distal curved portion 344, as shown in FIG. 26B. For some applications, the first curve defines an angle theta of more than 130 degrees (e.g., more than 140 degrees), and/or less than 160 degrees (e.g., less than 150 degrees), e.g., 130-160 degrees, or 140-150 degrees. For some applications, the second curve defines an angle alpha of more than 110 degrees (e.g., more than 120 degrees), and/or less than 140 degrees (e.g., less than 130 degrees), e.g., 110-140 degrees, or 120-130 degrees. Typically, the stiffness of curved portions 343, 344 of the distal-tip element 107 is less than that of a proximal straight portion 346 of the distal-tip element, which is disposed proximally to both curved portions. For some applications, the stiffness of second curved portion 344 is less than that of first proximal curved portion 343.

Figures 26C, 26D:
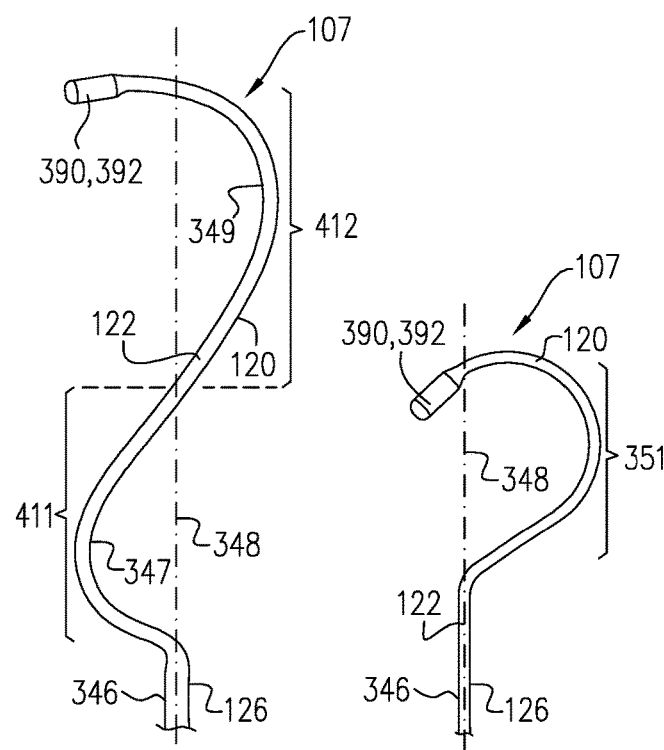

Referring to FIGS. 26C and 26D, for some applications, within a given plane, distal-tip element has proximal, straight portion 346 that defines a longitudinal axis 348, curves away from longitudinal axis 348 in a first direction, and then curves in the opposite direction with respect to longitudinal axis 348. For example, as shown in FIG. 26C, within the plane of the page, the distal-tip element first curves to the left of the page, then curves to the right of the page, and then curves again to the left of the page. Or, as shown in FIG. 26D, within the plane of the page, the distal-tip element first curves to the right of the page and then curves to the left of the page. (The example shown in FIG. 26D is generally similar to that shown in FIG. 22A, except that the portion of the tip disposed distally to where the tip intersects longitudinal axis 348 is shorter in FIG. 26D than in FIG. 22).

It is noted that when shaped as shown in FIG. 26C, distal-tip element 107 typically defines a first turning point 347 which is disposed on a first side of a longitudinal axis 348 of proximal straight portion 346 of distal-tip portion 120 (e.g., the left side of the longitudinal axis, as shown in FIG. 26C), and a second turning point 349, which is disposed on the opposite side of longitudinal axis 348 of proximal straight portion 346 of distal-tip portion 120 (e.g., the right side of the longitudinal axis, as shown in FIG. 26C). For some applications, the distal-tip portion is thereby shaped to defined two bulges on respective sides of longitudinal axis 348. Typically, the distal bulge 412 is larger (e.g., wider) than proximal bulge 411, as shown. For some applications, the bulges are generally shaped as semi-ellipses. Typically, the distal semi-ellipse defines a larger radius than that of the proximal semi-ellipse, as shown. (It is noted that in this context the term "semi-ellipse" includes a semi-circle. It is further noted that is some cases, the tip does not define two precise semi-ellipses, but rather bulged shapes that are substantially similar to semi-ellipses.)

Typically, when shaped as shown in FIG. 26D, the distal-tip element defines an overall curvature that is similar to that of a question mark, the tip portion defining a bulge 351 on one side of the longitudinal axis of the straight proximal straight portion of the distal-tip portion. For some applications, the bulge is generally shaped as a semi-ellipse. (It is noted that in this context the term "semi-ellipse" includes a semi-circle. It is further noted that is some cases, the tip does not define a precise semi-ellipse, but rather a bulged shape that is substantially similar to a semi-ellipse.)

Typically, upon being deployed within the subject's left ventricle, the curvature of portions of distal-tip element 107 is configured to provide atraumaticity to tip portion 120. Further typically, the distal-tip portion is configured to space the inlet openings 108 of the ventricular assist device from walls of the left ventricle.

For some applications, by curving in at least three directions such as to define turning points on respective sides of longitudinal axis 348 (e.g., as shown in FIG. 26C) and/or by curving in at least two directions (e.g., as shown in FIG. 26D), the distal-tip element is configured to absorb forces exerted upon the distal-tip portion by walls of the left ventricle by a greater amount than if the distal-tip element were to curve in a single direction.

Figure 26E:
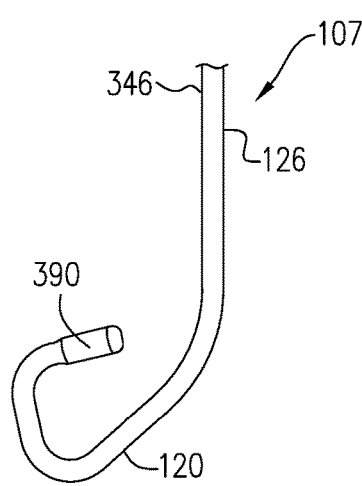
Figure 26F:
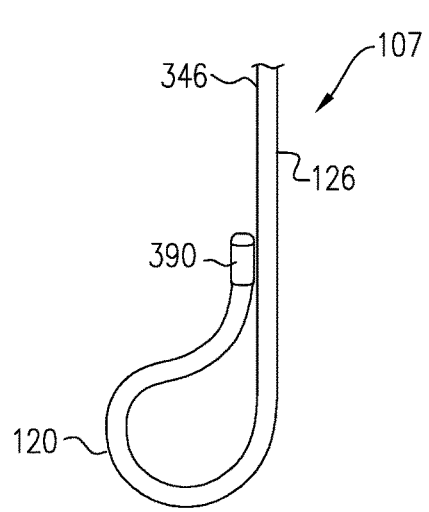

For some applications, distal-tip element 107 defines a plurality of curves each of which defines a different radius of curvature, and/or curves is a respective direction e.g., as shown in FIGS. 26E and 26F.

As described hereinabove, for some applications, duckbill valve 390 is disposed within a distal section of distal-tip portion 120. The duckbill valve is shown and described in further detail hereinbelow with reference to FIGS. 28A-C.

It is noted that for all of the curved distal-tip elements that are described herein (e.g., with reference to FIGS. 21-24C and FIGS. 26A-F), typically, the curvatures of the distal-tip portion are all within a single plane. With reference to all shapes of distal-tip portions that are described herein (e.g., with reference to FIGS. 21-24C) the scope of the present invention includes using a question-mark or tennis-racket shaped distal-tip portion in combination with any ventricular assist device, and even in the absence of other features and/or portions of distal-tip element 107 (such as, axial-shaft-receiving tube 126).

Reference is now made to FIGS. 27A, 27B, and 27C, which are schematic illustrations of atraumatic projections 350 that are configured to extend from the distal end of the distal-tip element 107 of ventricular assist device 20, in accordance with respective applications of the present invention. (Projection 350 is shown in the absence of distal-tip element 107, in FIGS. 27A-C.) For some applications, the atraumatic projection includes a closed ellipse or a closed circle. Typically, the ventricular assist device is introduced into the subject's ventricle over a guidewire, as described hereinabove. Along a proximal portion of atraumatic projection 350, the atraumatic projection defines a guidewire lumen 352. The closed circle or ellipse of the atraumatic projection typically defines holes 354 in its sidewalls, and the guidewire passes through these holes. During insertion of the ventricular assist device into the subject's ventricle, the circle or ellipse is typically elongated axially, by a proximal portion of the circle or the ellipse being held within the delivery catheter. Further typically, a distal portion of the axially-elongated circle or ellipse protrude from the distal tip of the delivery catheter, and acts as an atraumatic tip for the delivery catheter, as the catheter passes through the subject's vasculature.

Typically, upon being deployed within the subject's left ventricle, projection 350 is configured to provide an atraumatic tip to distal-tip element 107. Further typically, the projection is configured to space the inlet openings 108 of the ventricular assist device from walls of the left ventricle.

FIGS. 27A, 27B, and 27C show respective shapes of projection 350, when the projection is in a non-radially-constrained configuration. Typically, projection 350 is configured to assume such shapes when the projection is deployed inside the subject's left ventricle.

Figure 28D:
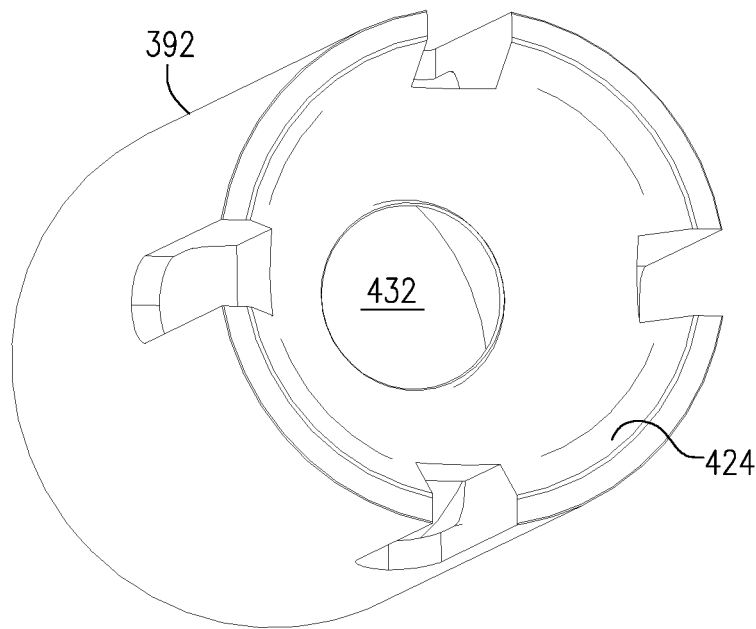
FIGS. 28D and 28E are schematic illustration of respective views of the guidewire guide of FIG. 28A, in accordance with some applications of the present invention.
Figure 28E:
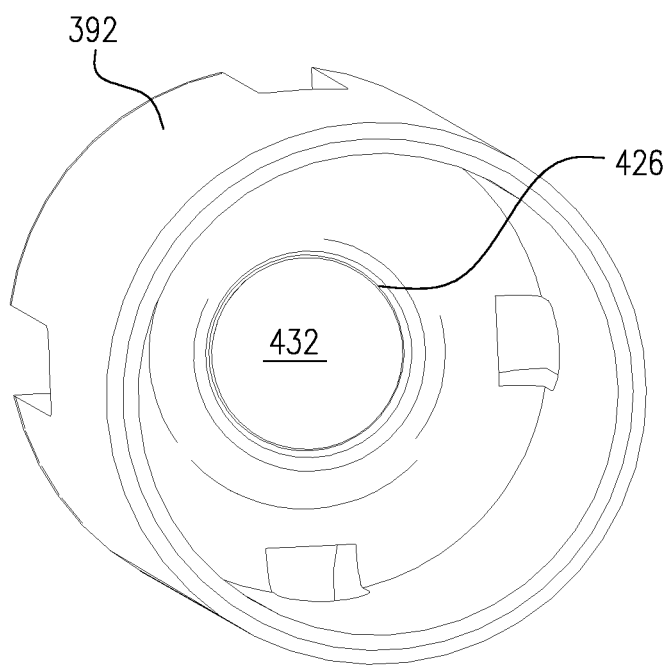

Reference is now made to FIG. 28A, which is a schematic illustration of duckbill valve 390 and guidewire guide 392 disposed at the distal end of distal-tip portion 120 of a ventricular assist device, in accordance with some applications of the present invention. Reference is also made to FIGS. 28B and 28C, which are schematic illustrations of views of, respectively, a proximal, narrow end 420 of duckbill valve 390 and a distal, wide end 422 of duckbill valve 390, in accordance with some applications of the present invention. Reference is additionally made to FIGS. 28D and 28E, which are schematic illustration of a proximal end 424 of guidewire guide 392, and a distal end 426 of guidewire guide 392, in accordance with some applications of the present invention.

It is noted that although duckbill valve 390 and guidewire guide 392 are shown at the distal end of a given example of distal-tip element 107, the scope of the present invention includes combining duckbill valve 390 and guidewire guide 392 with any of the other examples of a distal-tip element described herein. Moreover, the scope of the present invention includes using duckbill valve 390 and guidewire guide 392 within the tip of any percutaneous device and is not limited to using duckbill valve 390 and guidewire guide 392 within a ventricular assist device.

As described hereinabove, typically, duckbill valve 390 has a maximum width of less than 3 mm, e.g., less than 2 mm. Typically, the entire duckbill valve is disposed within a distal section of the distal-tip portion that is disposed within the distal-most 10 mm, e.g., the distal most 5 mm of the distal-tip portion. Further typically, as shown, the duckbill valve is proximally facing (i.e., such that the wide inlet of the duckbill valve faces the distal end of distal-tip portion and such that the narrow tip of the duckbill valve faces away from the distal end of distal-tip portion 120). This is because typically the pressure of the fluid that is pumped into distal-tip portion (e.g., as described hereinabove with reference to FIGS. 13A-C) is greater than the pressure of the blood in the left ventricle. The duckbill valve is proximally facing, so as to prevent the fluid from flowing out of the distal end of the distal portion, such that the fluid flows back toward distal bearing 118, as described hereinabove. Typically, blood does not flow into guidewire lumen 122, since the pressure inside guidewire lumen 122 is greater than the pressure of the blood in the left ventricle, outside the lumen.

Typically, ventricular assist device is advanced to the left ventricle via a guidewire (e.g., guidewire 10, shown in FIG. 1B). The guidewire is typically inserted into guidewire lumen 122 of distal-tip portion 120 via the distal end of the distal-tip portion. Typically, insertion of the guidewire through the distal end of the distal-tip portion is relatively straightforward, since distal, wide end 422 of duckbill valve 390 guides the guidewire through the duckbill valve.

For some applications, when ventricular assist device is disposed inside the subject's body, it is desirable to insert another guidewire from a proximal end of the ventricular assist device to the distal end of the distal-tip portion. For example, if a further procedure is going to be performed with respect to the subject's left ventricle subsequent to the operation of the left ventricular device, then rather than retracting ventricular assist device and having to reinsert a guidewire through a percutaneous puncture, it may be desirable to utilize the existing percutaneous puncture and to insert the guidewire via guidewire lumen 122, before retracting ventricular assist device 20.

Typically, in order to facilitate insertion of a guidewire through guidewire lumen 122 from a proximal end of the ventricular assist device, the ventricular assist device includes guidewire guide 392. Guidewire guide 392 is configured to facilitate insertion of the guidewire through narrow proximal end 420 of duckbill valve 390. Guidewire guide is shaped to define a hole 432 therethrough, which narrows in diameter from proximal end 424 of the guidewire guide to distal end 426 of the guidewire guide. The shape of the guidewire guide is configured to guide the tip of the guidewire toward a slit 434 at the narrow, proximal end of the duckbill valve. For some applications, the duckbill valve is additionally shaped to define a converging guide portion 430 at its proximal end, the converging guide portion converging toward slit 434, such that the guide portion is configured to further guide the tip of the guidewire toward slit 434.

The scope of the present invention includes using duckbill valve 390 and guidewire guide 392 within a guidewire lumen of any percutaneous device and is not limited to using duckbill valve 390 and guidewire guide 392 within a ventricular assist device. Typically, duckbill valve 390 and guidewire guide 392 facilitate insertion of a guidewire via the guidewire lumen from a proximal end of the device to a distal end of the device.

Figure 29:
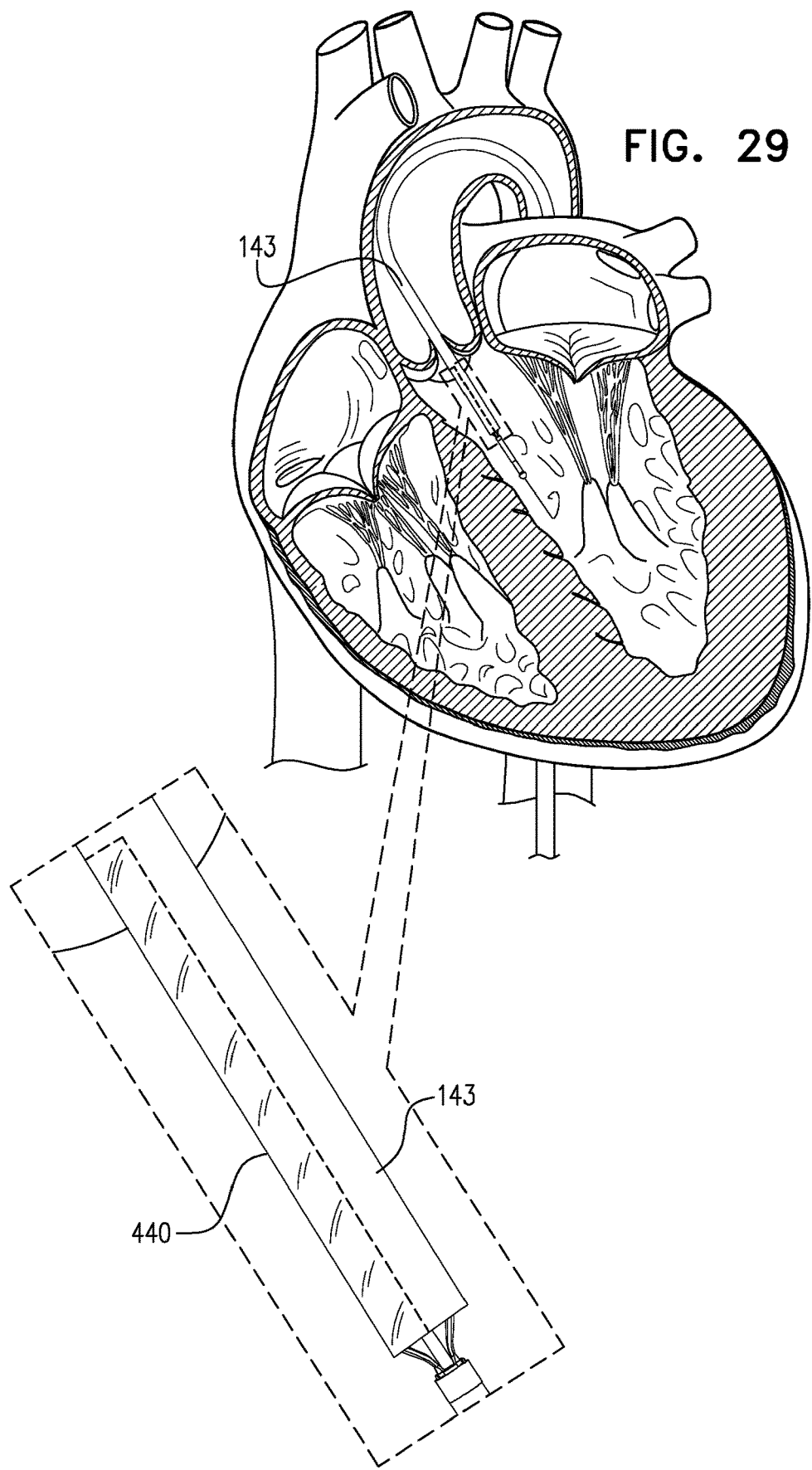
FIG. 29 is a schematic illustration of a delivery catheter that includes a sheath configured to facilitate reinsertion of a guidewire through a percutaneous puncture, in accordance with some applications of the present invention.

Reference is now made to FIG. 29, which is a schematic illustration of a delivery catheter that includes a sheath 440 configured to facilitate reinsertion of a guidewire through a percutaneous puncture, in accordance with some applications of the present invention. Typically the sheath comprises a covering (e.g., a polyurethane, polyester, silicone, polyethylene terephthalate (PET), and/or polyether block amide (PEBAX®) covering) that is disposed around at least a portion of the circumference of delivery catheter 143 along a distal section of the length of the delivery catheter (e.g., along a length of more than 10 mm, and/or less than 100 mm, e.g. 10-100 mm), as shown. As described with reference to FIGS. 28A-E, for some applications, when ventricular assist device is disposed inside the subject's body, it is desirable to insert another guidewire through the existing percutaneous puncture, rather than retracting ventricular assist device and then having to reinsert a guidewire through a percutaneous puncture. For some applications, ventricular assist device and the delivery catheter are retracted until the proximal end of sheath 440 has been retracted from the percutaneous puncture. Subsequently, a guidewire is inserted through the existing percutaneous puncture, by being advanced through the sheath 440 (i.e. between the covering and the outer surface of delivery catheter 143). The ventricular assist device and delivery catheter may then be removed from the percutaneous puncture, leaving the guidewire in place. For some applications, sheath 440 is disposed around a portion of outer tube 142 along a distal section of the length of the outer tube, the functionality of the sheath being generally as described above.

The scope of the present invention includes using sheath 440 on any type of percutaneous catheter, so as to facilitate reinsertion of a guidewire via an existing percutaneous puncture, and is not limited to being used with delivery catheter 143 of ventricular assist device 20.

Figure 30:
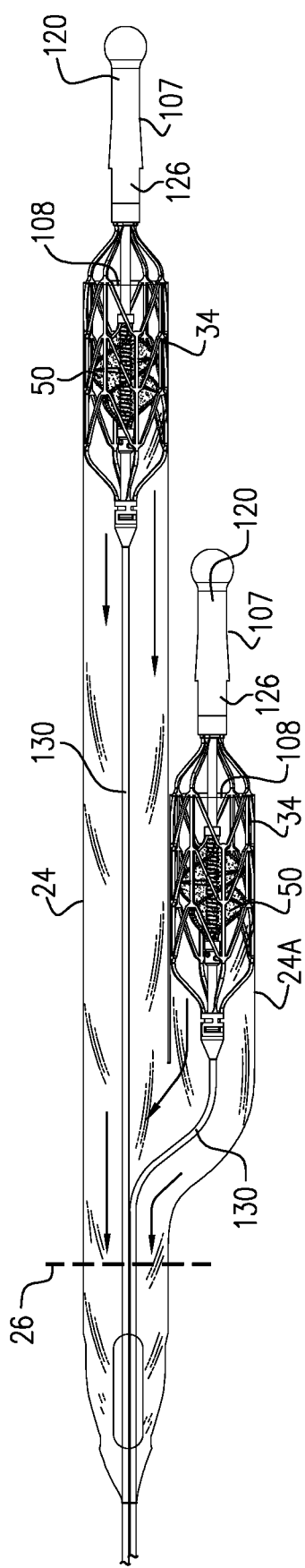
FIG. 30 is a schematic illustration of a ventricular assist device that includes two impellers, in accordance with some applications of the present invention.
Figure 31:
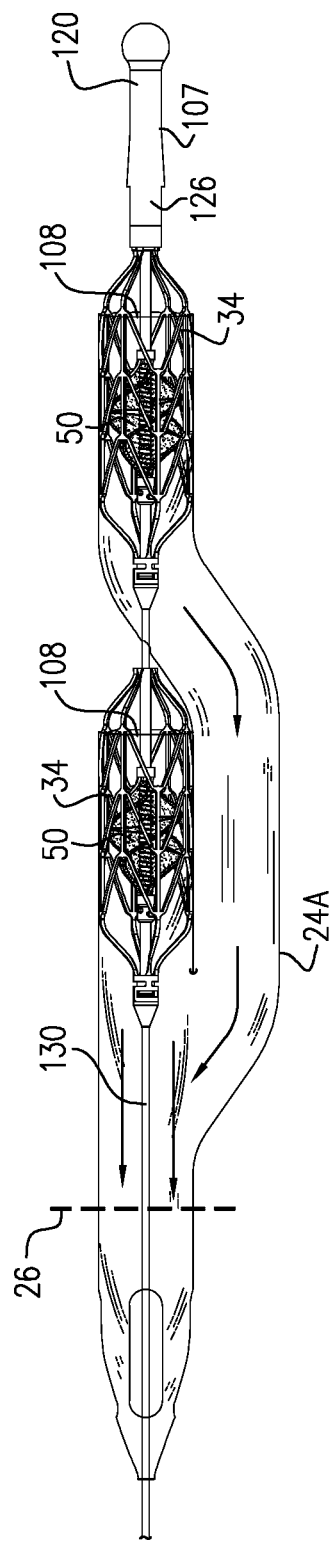
FIG. 31 is a schematic illustration of a ventricular assist device that includes two impellers, in accordance with some applications of the present invention.

Reference is now made to FIGS. 30 and 31, which are schematic illustrations of ventricular assist devices 20 that include two impellers 50, in accordance with some applications of the present invention. As shown in FIG. 30, for some applications, first and second impellers are disposed in parallel with each other, each of the impellers being driven by a respective drive cable 130. Typically, a first one of the impellers 50 and its corresponding frame 34 are disposed distally of a second impeller one of the impellers 50 and its corresponding frame 34, such that the impellers and frames are not in overlapping configurations with one another when they are disposed in radially constrained configurations within delivery catheter 143. For some applications, the proximal impeller pumps blood via a parallel tube 24A that runs parallel to tube 24, with fluid flow from parallel tube 24A flowing into tube 24 at a location that is configured to be downstream of the aortic valve 26 (the location of aortic valve 26 being illustrated schematically in FIG. 30). Thus, typically only tube 24 (without parallel tube 24A) passes through the aortic valve.

As shown in FIG. 31, for some applications, first and second impellers are disposed series with each other, each of the impellers being driven by a single drive cable 130. Typically, a first one of the impellers 50 and its corresponding frame 34 are disposed distally of a second impeller one of the impellers 50 and its corresponding frame 34, such that the impellers and frames are not in overlapping configurations with one another when they are disposed in radially constrained configurations within delivery catheter 143. Further typically, the impellers pump blood into respective blood inlet openings 108 and initially one of the impeller pumps blood through tube 24, while the second impeller pumps blood through parallel tube 24A of tube 24. Typically, fluid flow from parallel tube 24A flows into tube 24 at a location that is configured to be downstream of the aortic valve (the location of the aortic valve being illustrated schematically in FIG. 30). Thus, typically only tube 24 (without parallel tube 24A) passes through the aortic valve.

It is noted that, by having one of the impellers pump through parallel tube 24A while the second one of the impellers pumps blood via tube 24, it is not that case that the proximal impeller is pumping blood that has already been pumped by the distal impeller. It has been found by the inventors that, if a proximal impeller is used to pump blood that has already been pumped by a distal impeller, this can result in inefficient pumping of the blood by the proximal impeller. It is further noted that doubling the number of impellers will typically double the amount of hemolysis that is generated by ventricular assist device 20, ceteris paribus. By contrast, increasing the revolution rate of a single impeller and/or increasing the length of an impeller can result is a disproportionate increase in the amount of hemolysis that is generated by the impeller.

With regards to all aspects of ventricular assist device 20 described with reference to FIGS. 1A-31, it is noted that, although FIGS. 1A and 1B show ventricular assist device 20 in the subject's left ventricle, for some applications, device 20 is placed inside the subject's right ventricle, such that the device traverses the subject's pulmonary valve, and techniques described herein are applied, mutatis mutandis. For some applications, components of device 20 are applicable to different types of blood pumps. For example, aspects of the present invention may be applicable to a pump that is used to pump blood from the vena cava and/or the right atrium into the right ventricle, from the vena cava and/or the right atrium into the pulmonary artery, and/or from the renal veins into the vena cava. Such aspects may include features of tube 24 (e.g., the curvature of the tube), impeller 50, features of pump portion 27, drive cable 130, apparatus and methods for measuring blood pressure, etc. Alternatively or additionally, device 20 and/or a portion thereof (e.g., impeller 50, even in the absence of tube 24) is placed inside a different portion of the subject's body, in order to assist with the pumping of blood from that portion. For example, device 20 and/or a portion thereof (e.g., impeller 50, even in the absence of tube 24) may be placed in a blood vessel and may be used to pump blood through the blood vessel. For some applications, device 20 and/or a portion thereof (e.g., impeller 50, even in the absence of tube 24) is configured to be placed within the subclavian vein or jugular vein, at junctions of the vein with a lymph duct, and is used to increase flow of lymphatic fluid from the lymph duct into the vein, mutatis mutandis. Since the scope of the present invention includes using the apparatus and methods described herein in anatomical locations other than the left ventricle and the aorta, the ventricular assist device and/or portions thereof are sometimes referred to herein (in the specification and the claims) as a blood pump.

Some examples of devices that include components of ventricular assist device 20, but that are used at different anatomical locations are described hereinbelow with reference to FIGS. 32A-33.

Reference is now made to FIGS. 32A, 32B, 32C, 32D, and 32E, which are schematic illustration of a cardiac assist device 360 that is configured to assist the functioning of the right heart of a subject, in accordance with some applications of the present invention. For components of device 360 that are generally similar to components described hereinabove with reference to ventricular assist device 20, the same reference numerals are used as those used hereinabove. Typically, such components are generally as described hereinabove, except for the differences that are described below.

Figure 32A:
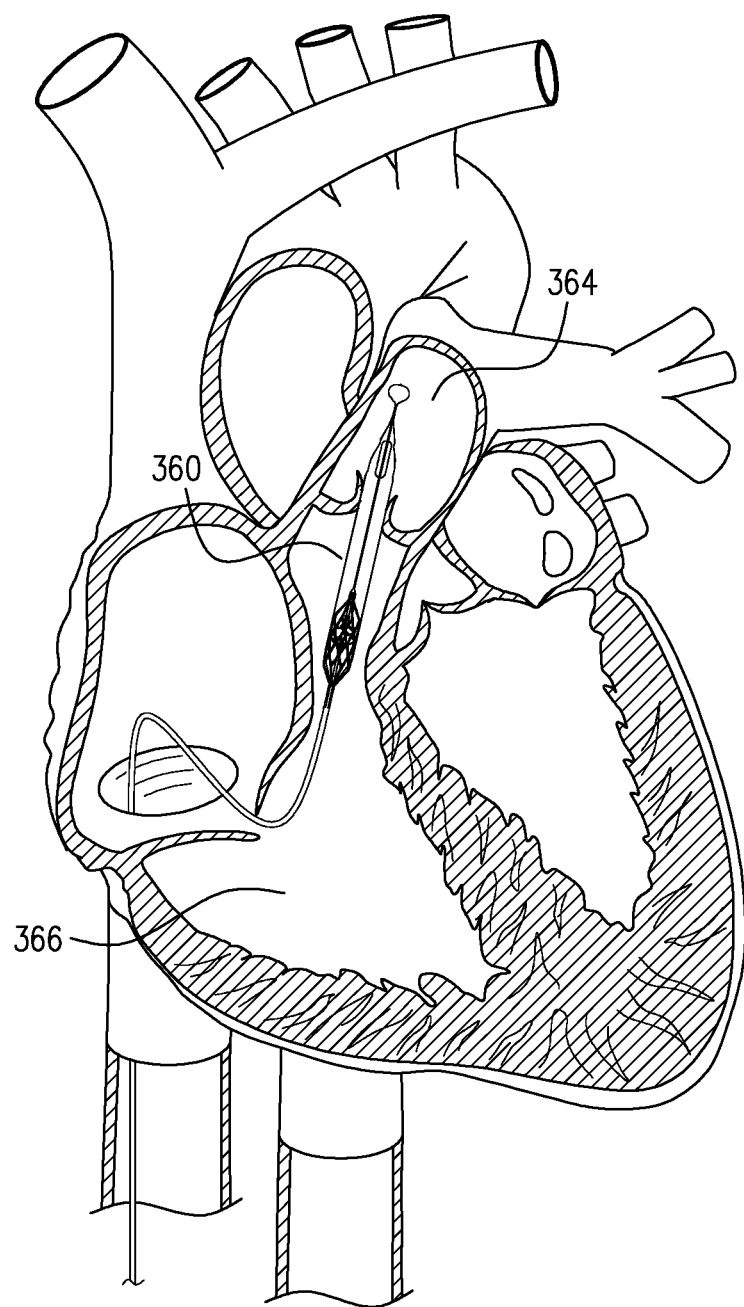
FIGS. 32A, 32B, 32C, 32D, and 32E are schematic illustration of a ventricular assist device that is configured to assist the functioning of the right heart of a subject, in accordance with some applications of the present invention.
Figure 32B:
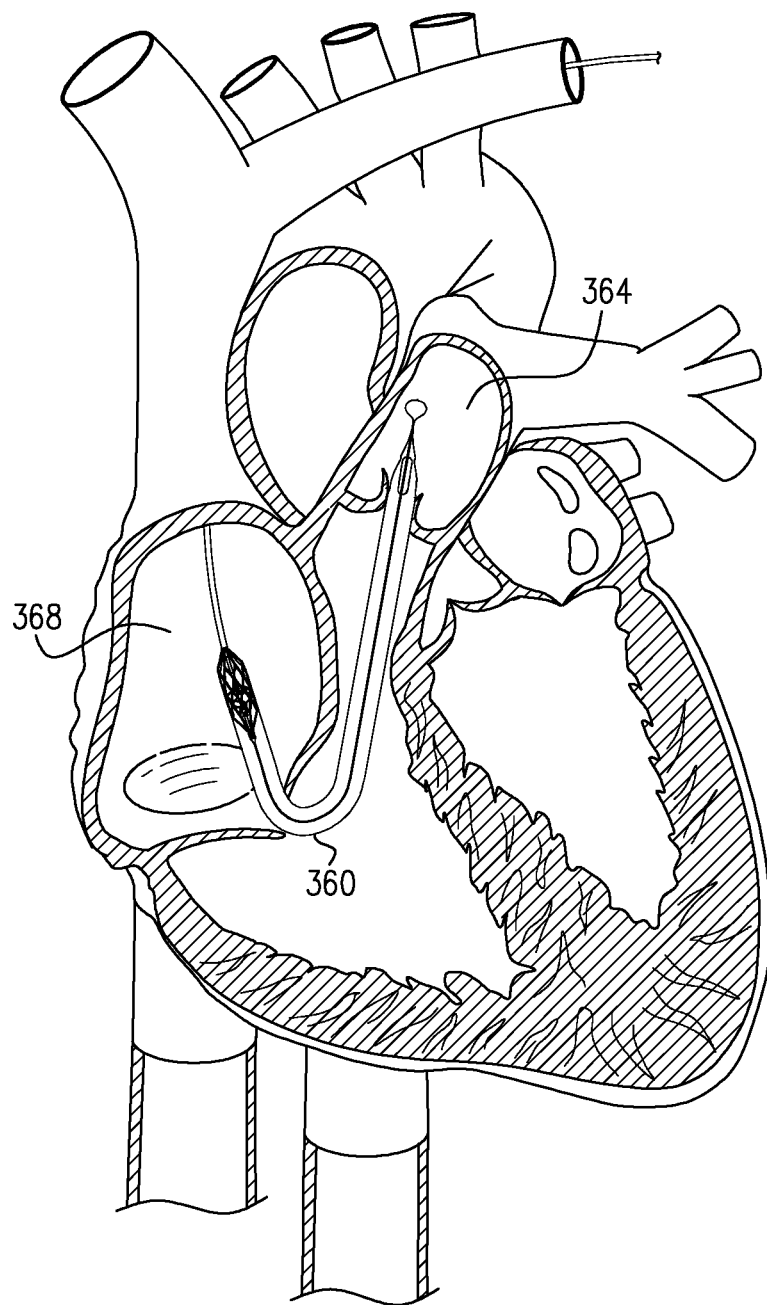
Figure 32C:
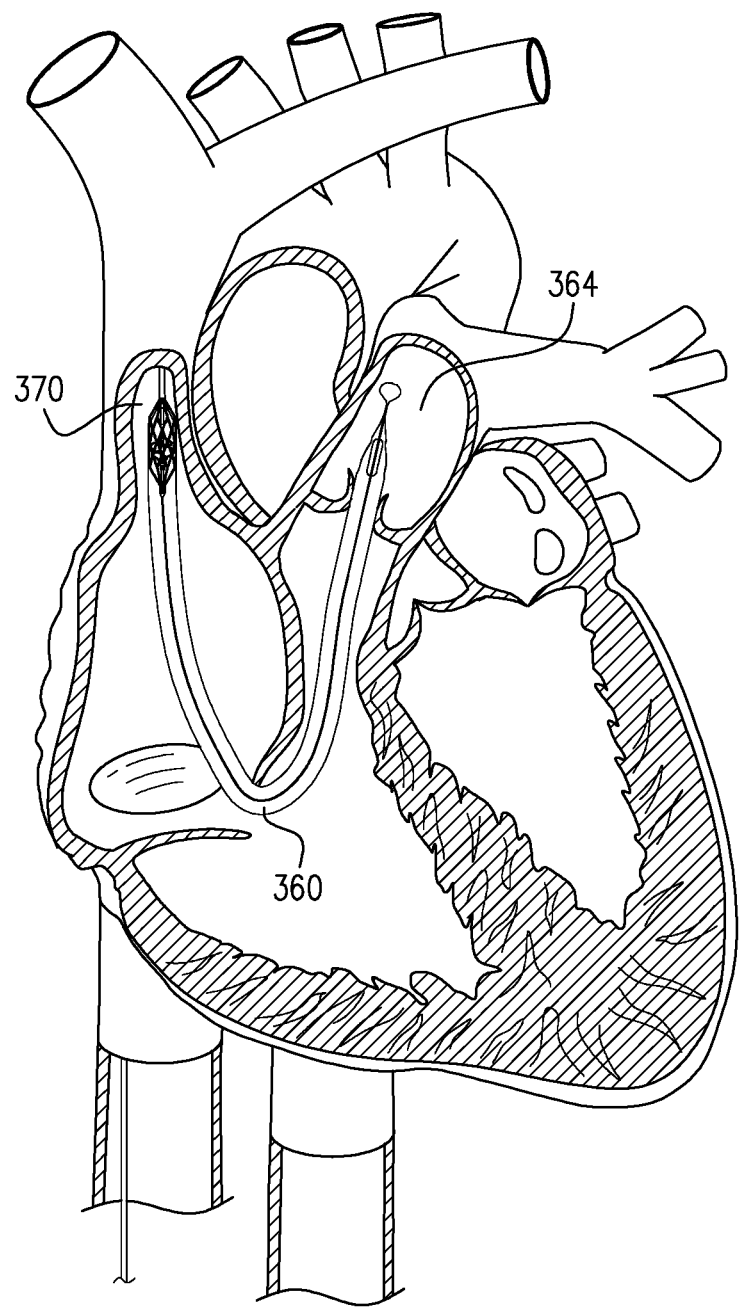
Figure 32D:
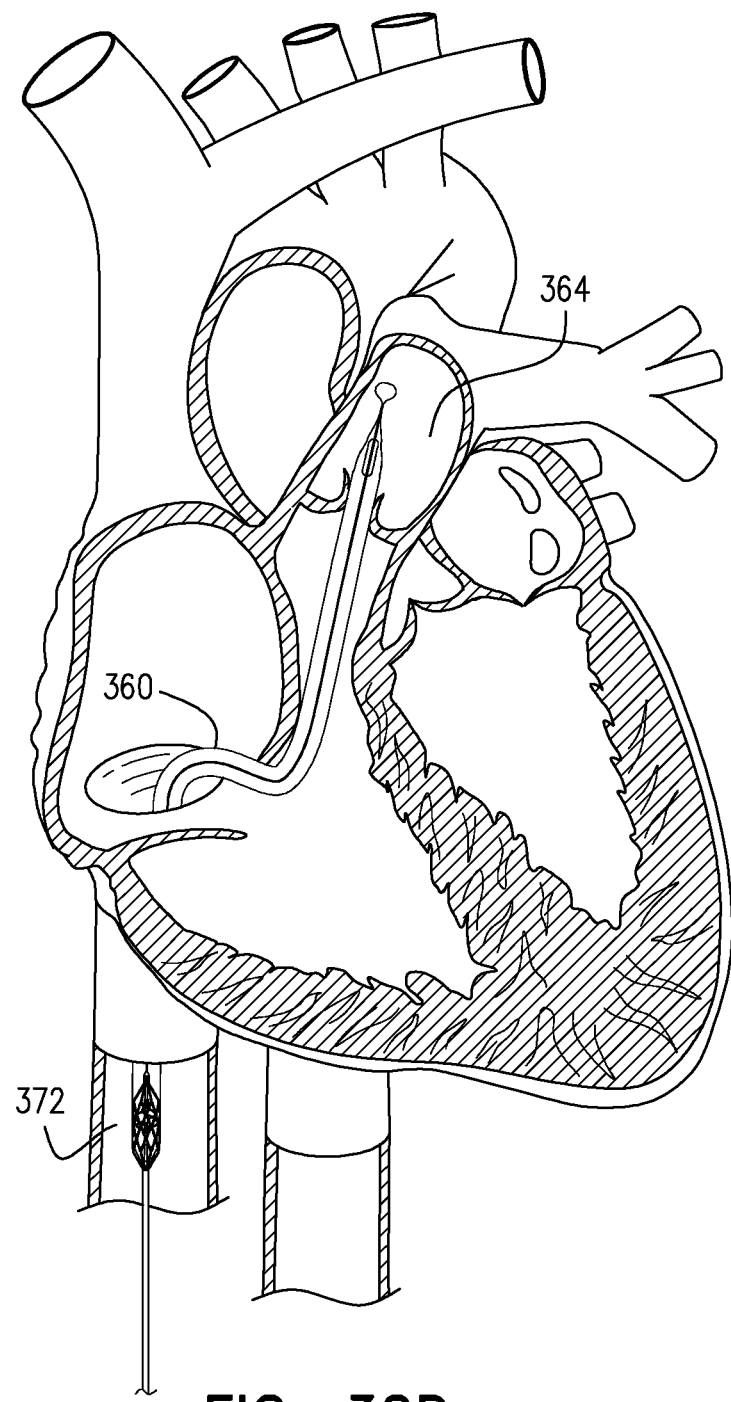
Figure 32E:
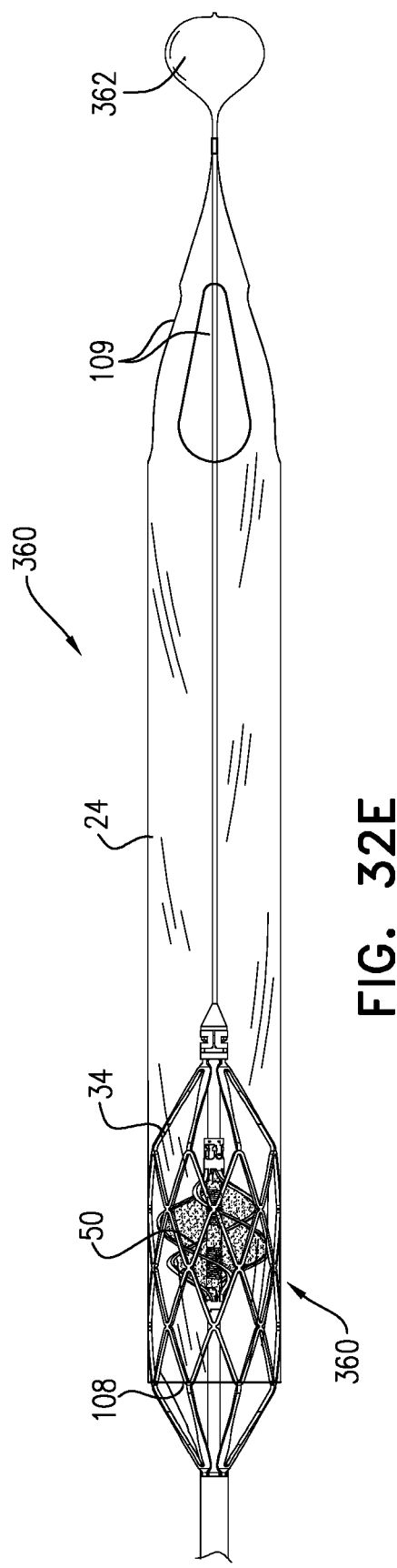

FIG. 32E shows device 360 in its non-radially-constrained configuration in the absence of the subject's anatomy. As shown, typically, to assist the functioning of the subject's right heart, impeller 50 and frame 34 are disposed at a proximal end of tube 24. Similarly, blood inlet opening(s) is disposed at the proximal end of the tube. The impeller is configured to pump blood through tube 24 in the distal direction, toward blood outlet openings 109 that are disposed at the distal end of tube 24. For some applications, a balloon 362 is disposed at the distal end of the device. Balloon 362 is configured to facilitate introduction of the distal end of the device into the pulmonary artery 364, by the balloon migrating to the pulmonary artery with the subject's blood flow. Typically, the blood outlet opening(s) is configured to be disposed within the pulmonary artery, such that the impeller pumps blood via tube 24, into the pulmonary artery.

As shown in FIG. 32A, for some applications, the blood inlet opening(s) 108 is disposed within the subject's right ventricle 366, such that the impeller pumps blood from the right ventricle, via tube 24, into pulmonary artery 364. Alternatively, the blood inlet opening(s) 108 is disposed within the subject's right atrium 368, such that the impeller pumps blood from the right atrium, via tube 24, into pulmonary artery 364, as shown in FIG. 32B. Further alternatively, the blood inlet opening(s) 108 is disposed within the subject's superior vena cava 370, such that the impeller pumps blood from the superior vena cava, via tube 24, into pulmonary artery 364, as shown in FIG. 32C. Further alternatively, the blood inlet opening(s) 108 is disposed within the subject's inferior vena cava 372, such that the impeller pumps blood from the inferior vena cava, via tube 24, into pulmonary artery 364, as shown in FIG. 32D.

It is noted that, in the configurations shown in FIGS. 32B-D, the cardiac assist device will lower preload on the right heart (by pumping blood from the right atrium or the vena cava), but will increase afterload (by pumping blood into the pulmonary artery). By contrast, in the configuration shown in FIG. 32A, the cardiac assist device effectively does not increase afterload, since the volume of blood that is pumped into the pulmonary artery by the impeller, is the same volume as is pumped out of the right ventricle.

Figure 33:
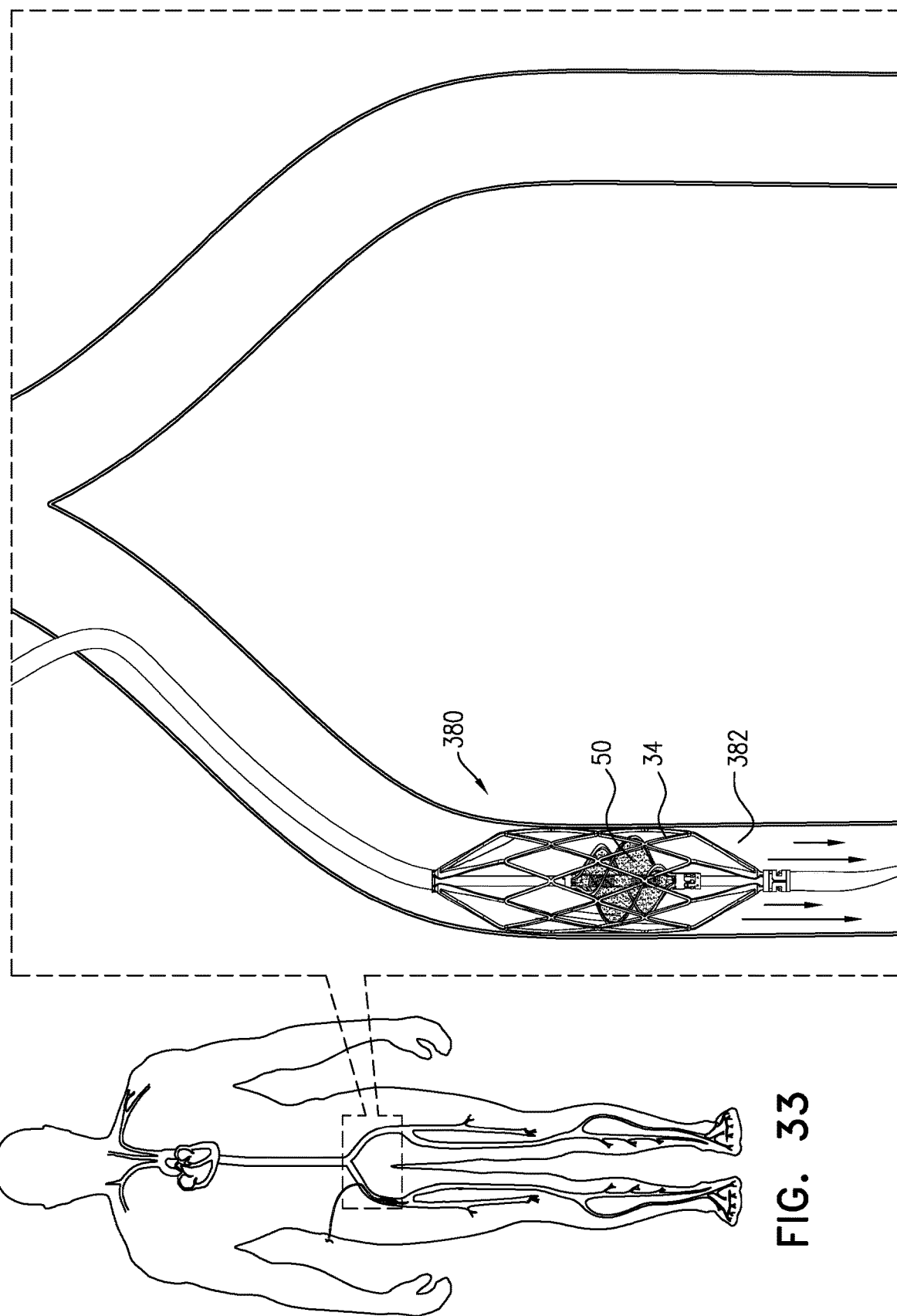
FIG. 33 is a schematic illustration of a venous assist device, in accordance with some applications of the present invention.

Reference is now made to FIG. 33, which is a schematic illustration of a venous assist device 380, in accordance with some applications of the present invention. For components of device 380 that are generally similar to components described hereinabove with reference to ventricular assist device 20, the same reference numerals are used as those used hereinabove. Typically, such components are generally as described hereinabove, except for the differences that are described below. For some applications, venous assist device 380 includes impeller 50 and frame 34, which are generally as described hereinabove. For some applications, the venous assist device does not include tube 24, for example, as shown in FIG. 33.

For some applications, venous assist device 380 is inserted into a vein of a subject in order to assist with the pumping of blood through the vein. For example, the venous assist device may be inserted into a vein 382 of a leg of a subject (such as the iliac vein or the femoral vein) suffering from an ischemic leg, and may be used to assist with the pumping of blood through the vein.

For some applications, the scope of the present application includes any one of the following apparatus and methods combined in combination with any of the other apparatus and methods described herein:

A method including:
coupling a rigid tube to a drive cable that includes a plurality of coiled wires, by:
placing ends of the drive cable and the rigid tube at a given location within a butt-welding overtube,
the ends of the drive cable and the rigid tube being visible when they are disposed at the given location within the butt-welding overtube via a window defined by the butt-welding overtube, and
the placement of the drive cable within the butt-welding overtube being such that a helical groove defined by a portion of the butt-welding overtube is disposed over the drive cable; and
forming welding rings around the butt-welding overtube.

For some applications, forming welding rings around the butt-welding overtube includes forming welding rings that are spaced from edges of the butt-welding overtube, such that the welding rings weld the butt-welding overtube to the rigid tube and the drive cable without the welding rings being welded directly onto outer surfaces of the rigid tube and the drive cable. For some applications, forming welding rings around the butt-welding overtube includes forming welding rings to a depth that is such that that the butt-welding overtube is welded to the rigid tube and the drive cable, without reducing a diameter of a lumen defined by the rigid tube and the drive cable. For some applications, forming welding rings around the butt-welding overtube includes forming at least one welding ring at the given location within the butt-welding overtube at which the ends of the drive cable and the rigid tube are placed. For some applications, coupling the drive cable to the rigid tube includes coupling the drive cable to an axial shaft that is configured to support an impeller. For some applications, coupling the drive cable to the rigid tube includes coupling the drive cable to a pin that is configured to be coupled to a magnet, the magnet being configured to be driven to rotate by a motor. Some examples of such applications are described hereinabove with reference to FIGS. 10D-E.

Apparatus including:
a drive cable including a plurality of coiled wires;
a rigid tube configured to be coupled to the drive cable; and
a butt-welding overtube, the butt-welding overtube configured to facilitate butt-welding of the drive cable to the rigid tube, the butt-welding overtube defining:
a window configured to facilitate placement of ends of the drive cable and the rigid tube at a given location within the butt-welding overtube, by providing visibility of the ends of the drive cable and the rigid tube when they are disposed at the given location within the butt-welding overtube; and
a helical groove within a portion of the butt-welding overtube that is configured to be disposed over the drive cable, and to provide flexibility to the portion of the butt-welding overtube that is configured to be disposed over drive cable.

For some applications, the apparatus includes an impeller, and the rigid tube includes an axial shaft that is configured to support the impeller. For some applications, the apparatus includes a motor and a magnet configured to be driven to rotate by the motor, and the rigid tube includes a pin that is configured to be coupled to the magnet. Some examples of such applications are described hereinabove with reference to FIGS. 10D-E.

A method including:
coupling to each other first and second portions of drive cable that includes a plurality of coiled wires, by:
placing ends of the first and second portions of the drive cable at a given location within a butt-welding overtube,
the ends of the first and second portions of the drive cable being visible when they are disposed at the given location within the butt-welding overtube via a window defined by the butt-welding overtube, and
the placement of at least one of the portions of the drive cable within the butt-welding overtube being such that a helical groove defined by a portion of the butt-welding overtube is disposed over the at least one of the portions of the drive cable; and
forming welding rings around the butt-welding overtube.

Some examples of such applications are described hereinabove with reference to FIGS. 10D-E.

A method including:
coupling a rigid tube to a drive cable that includes a plurality of coiled wires, by:
placing ends of the drive cable and the rigid tube at a given location within a butt-welding overtube,
the ends of the drive cable and the rigid tube being visible when they are disposed at the given location within the butt-welding overtube via a window defined by the butt-welding overtube; and
forming welding rings around the butt-welding overtube, the welding rings being spaced from edges of the butt-welding overtube, such that the welding rings weld the butt-welding overtube to the rigid tube and the drive cable without being welded directly onto outer surfaces of the rigid tube and the drive cable.

For some applications, forming welding rings around the butt-welding overtube includes forming welding rings to a depth that is such that that the butt-welding overtube is welded to the rigid tube and the drive cable, without reducing a diameter of a lumen defined by the rigid tube and the drive cable. For some applications, forming welding rings around the butt-welding overtube includes forming at least one welding ring at the given location within the butt-welding overtube at which the ends of the drive cable and the rigid tube are placed. For some applications, placing ends of the drive cable and the rigid tube at the given location within the butt-welding overtube includes placing the drive cable within the butt-welding overtube such that a helical groove defined by a portion of the butt-welding overtube is disposed over the drive cable. For some applications, coupling the drive cable to the rigid tube includes coupling the drive cable to an axial shaft that is configured to support an impeller. For some applications, coupling the drive cable to the rigid tube includes coupling the drive cable to a pin that is configured to be coupled to a magnet, the magnet being configured to be driven to rotate by a motor. Some examples of such applications are described hereinabove with reference to FIGS. 10D-E.

Apparatus including:
a blood pump configured to be placed inside a body of subject, the blood pump including:
an impeller;
a frame configured to be disposed around the impeller;
an axial shaft upon which the impeller is disposed;
proximal and distal radial bearings, configured to stabilize the axial shaft radially during rotation of the impeller;
an atraumatic distal-tip portion disposed distally with respect to the impeller, the atraumatic distal-tip portion including an inflatable portion; and
a purging fluid configured to be pumped toward the distal-tip portion, such as to (a) purge the distal bearing, and (b) inflate the inflatable portion of the distal-tip portion.

Some examples of such applications are described hereinabove with reference to FIG. 13D.

Apparatus including:
a blood pump configured to be placed inside a body of subject, the blood pump including:
a tube that defines at least one blood inlet opening and at least one blood outlet opening;
an impeller configured to pump blood of the subject into the blood inlet opening, through the tube, and out of the blood outlet opening;
a distal-tip portion disposed distally with respect to the blood inlet opening, the distal-tip portion defining a radially-converging shape, and being configured to be placed within a left ventricle of the subject while impeller pumps the subject's blood;
an inflatable portion disposed around the distal-tip portion, the inflatable portion being configured to define:
a) a deflated state, the distal-tip portion being configured to function as a dilator, during insertion of the blood pump via a puncture in skin of the subject, when the inflatable portion is in its deflated state,
b) a first inflation state in which the inflatable portion is configured to prevent the distal-tip portion from causing trauma to vasculature of the subject, during advancement of the distal-tip portion through the subject's vasculature, and
c) a second inflation state, in which the inflatable portion is more fully inflated than in the first inflation state, the inflatable portion when in its second inflation state being configured to separate the one or more blood inlet openings from inner structures of the subject's left ventricle in three dimensions, when the distal-tip portion is disposed within the subject's left ventricle.

Some examples of such applications are described hereinabove with reference to FIGS. 20A-C.

Apparatus including:
a left-ventricular assist device configured to assist left-ventricular functioning of a subject, the left-ventricular assist device including:
a tube configured such that a proximal portion of the tube traverses an aortic valve of the subject, and a distal portion of the tube is disposed within a left ventricle of the subject;
a frame disposed within the distal portion of the tube, the frame being configured to hold the distal portion of the tube in an open state,
the frame not being disposed within the proximal portion of the tube, and the proximal portion of the tube thereby being configured to collapse inwardly in response to pressure outside of the proximal portion of the tube exceeding pressure inside the proximal portion of the tube;
a pump disposed within the frame and configured to pump blood through the tube from the subject's left ventricle to the subject's aorta, such that during pumping of the blood through the tube:
the proximal portion of the tube is maintained in an open state, and
at least a portion of the tube becomes curved, such that the tube curves away from a posterior wall of the left ventricle.

For some applications, the pump is configured to pump blood through the tube from the subject's left ventricle to the subject's aorta, such that during pumping of the blood through the tube at least the portion of the tube becomes curved, such that the tube curves away from a septal wall of the left ventricle. Some examples of such applications are described hereinabove with reference to FIGS. 25A-F.

Apparatus including:
a left-ventricular assist device configured to assist left-ventricular functioning of a subject, the left-ventricular assist device including:
a tube configured such that a proximal portion of the tube traverse an aortic valve of the subject, and a distal portion of the tube is disposed within a left ventricle of the subject;

a frame disposed within the distal portion of the tube, the frame being configured to hold the distal portion of the tube in an open state, the frame not being disposed within the proximal portion of the tube, and the proximal portion of the tube thereby being configured to collapse inwardly in response to pressure outside of the proximal portion of the tube exceeding pressure inside the proximal portion of the tube;

a pump disposed within the frame and configured to pump blood through the tube from the subject's left ventricle to the subject's aorta, such that during pumping of the blood through the tube, the proximal portion of the tube is maintained in an open state; and a curved element disposed within the tube proximally with respect to the frame, the curved element being configured to cause at least a portion of the tube to become curved, such that the tube curves away from a posterior wall of the left ventricle.

For some applications, the curved element is configured to cause at least the portion of the tube to becomes curved, such that the tube curves away from a septal wall of the left ventricle. Some examples of such applications are described hereinabove with reference to FIGS. 25A-F.

Apparatus including:

a left-ventricular assist device configured to assist left-ventricular functioning of a subject, the left-ventricular assist device including:

a tube configured such that a proximal portion of the tube traverse an aortic valve of the subject, and a distal portion of the tube is disposed within a left ventricle of the subject;

a frame disposed within at least the distal portion of the tube;

a pump disposed within the frame and configured to pump blood through the tube from the subject's left ventricle to the subject's aorta, by pumping the blood into the tube via a set of one or more blood inlet openings that are defined by the tube and that are disposed within the subject's left ventricle, and by pumping blood out of the tube via a set of one or more blood outlet openings that are defined by the tube and that are disposed within the subject's aorta;

wherein at least one of the sets of openings in the tube is disposed in a non-axi-symmetric configuration with respect to the tube, such that the pumping of the blood through the at least one of the sets of openings causes at least a portion of the tube to become curved, such that the tube curves away from a posterior wall of the left ventricle.

For some applications, the at least one of the sets of openings in the tube is disposed in the non-axi-symmetric configuration with respect to the tube, such that the pumping of the blood through the at least one of the sets of openings causes at least the portion of the tube to become curved, such that the tube curves away from a septal wall of the left ventricle. Some examples of such applications are described hereinabove with reference to FIGS. 25A-F.

Apparatus including:

an impeller, including:

an impeller frame that includes proximal and distal end portions and at least one helical elongate element that winds from the proximal end portion to the distal end portion;

a material that is coupled to the at least one helical elongate element, such that the at least one helical elongate element with the material coupled thereto defines a blade of the impeller; and a coil coiled around the at least one helical elongate element, the coil being configured to facilitate coupling of the material to the at least one helical elongate element.

A method, including:

manufacturing an impeller by:

forming a structure having first and second end portions at proximal and distal ends of the structure, the end portions being connected to one another by at least one elongate element;

coiling a coil around the at least one elongate element;

causing the at least one elongate element to radially expand and form at least one helical elongate element, by axially compressing the structure; and coupling a material to the at least one helical elongate element, such that the at least one helical elongate element with the material coupled thereto defines a blade of the impeller, the coil being configured to facilitate coupling of the material to the helical elongate elements.

Some examples of such applications are described hereinabove with reference to FIGS. 3A-K.

Apparatus including:

an impeller, including:

an impeller frame that includes proximal and distal end portions and at least one helical elongate element that winds from the proximal end portion to the distal end portion;

a material that is coupled to the at least one helical elongate element, such that the at least one helical elongate element with the material coupled thereto defines a blade of the impeller; and a sleeve disposed around the at least one helical elongate element, the sleeve being configured to facilitate coupling of the material to the at least one helical elongate element.

A method, including:

manufacturing an impeller by:

forming a structure having first and second end portions at proximal and distal ends of the structure, the end portions being connected to one another by at least one elongate element;

placing a sleeve around the at least one elongate element;

causing the at least one elongate element to radially expand and form at least one helical elongate element, by axially compressing the structure; and coupling a material to the at least one helical elongate element, such that the at least one helical elongate element with the material coupled thereto defines a blade of the impeller, the sleeve being configured to facilitate coupling of the material to the helical elongate elements.

Some examples of such applications are described hereinabove with reference to FIGS. 3A-K.

Apparatus including:

an impeller, including:

an impeller frame that includes proximal and distal end portions and at least one helical elongate element that winds from the proximal end portion to the distal end portion, the helical elongate element having a rounded cross-section; and a material that is coupled to the at least one helical elongate element, such that the at least one helical elongate element with the material coupled thereto defines a blade of the impeller; and the roundness of the helical elongate element being configured to cause the material to form a layer having a substantially uniform thickness at an interface of the material with the helical elongate element.

A method, including:
manufacturing an impeller by:
forming a structure having first and second end portions at proximal and distal ends of the structure, the end portions being connected to one another by at least one elongate element, the elongate element having a rounded cross-section;
causing the at least one elongate element to radially expand and form at least one helical elongate element, by axially compressing the structure; and
coupling a material to the at least one helical elongate element, such that the at least one helical elongate element with the material coupled thereto defines a blade of the impeller,
the roundness of the helical elongate element being configured to cause the material to form a layer having a substantially uniform thickness at an interface between the material and the helical elongate element.

Some examples of such applications are described hereinabove with reference to FIGS. 3A-K.

A method, including:
manufacturing an impeller by:
forming a structure having first and second end portions at proximal and distal ends of the structure, the end portions being connected to one another by at least one elongate element;
causing the at least one elongate element to radially expand and form at least one helical elongate element, by axially compressing the structure;
looping a first end of a looped elongate element around the helical elongate element, the looped elongate element having a predefined length and being substantially non-stretchable;
inserting a spring along an axis defined by the first and second end portions, such that a second end of the looped elongate element is looped around the spring;
coupling a material to the at least one helical elongate element and the spring, such a film of material is supported between the helical elongate element and the spring, the film of material defining a blade of the impeller,
the looped elongate element being configured to maintain the helical elongate element within a given distance from the spring.

Some examples of such applications are described hereinabove with reference to FIGS. 3A-K.

Apparatus including:
a left ventricular blood pump including:
an impeller;
a motor configured to drive the impeller to pump blood from a left ventricle of a subject to an aorta of the subject by rotating the impeller; and
a computer processor configured to measure power consumption by the motor that is required to rotate the impeller at a given rotation rate, and to determine left ventricular blood pressure of the subject at least partially in response thereto.

Some examples of such applications are described hereinabove with reference to FIG. 9.

Apparatus including:
a left-ventricular assist device configured to assist left-ventricular functioning of a subject, the left-ventricular assist device including:

a blood-pump tube configured such that a proximal portion of the tube traverses an aortic valve of the subject, and a distal portion of the tube is disposed within a left ventricle of the subject, the tube defining at least one blood inlet opening that is configured to be disposed within the left ventricle and at least one blood outlet opening that is configured to be disposed within an aorta of the subject;
an impeller configured to pump blood through the tube from the subject's left ventricle to the subject's aorta, by pumping the blood into the tube via one or more blood inlet openings that are defined by the tube and that are disposed within the subject's left ventricle, and by pumping blood out of the tube via one or more blood outlet openings that are defined by the tube and that are disposed within the subject's aorta;
a drive cable configured to extend from the impeller to outside the subject's body;
one or more outer tubes within which the drive cable is configured to rotate;
a motor disposed outside the subject's body and configured to drive the impeller to rotate, via the drive cable; and
a stator configured to reduce rotational flow components from blood flow through the blood-pump tube, prior to the blood flowing from the at least one outlet opening, the stator including:
a frame that is coupled to the one or more outer tubes, within the blood-pump tube; and
a flexible material that is coupled to the frame, such that in a non-radially-constrained configuration of the stator, the stator defines a plurality of curved projections that extend radially from the one or more outer tubes.

For some applications, the frame is a self-expandable frame. Some examples of such applications are described hereinabove with reference to FIGS. 14A-C.

Apparatus including:
a left-ventricular assist device configured to assist left-ventricular functioning of a subject, the left-ventricular assist device including:
a blood-pump tube configured such that a proximal portion of the tube traverses an aortic valve of the subject, and a distal portion of the tube is disposed within a left ventricle of the subject, the tube defining at least one blood inlet opening that is configured to be disposed within the left ventricle and at least one blood outlet opening that is configured to be disposed within an aorta of the subject;
an impeller configured to pump blood through the tube from the subject's left ventricle to the subject's aorta, by pumping the blood into the tube via one or more blood inlet openings that are defined by the tube and that are disposed within the subject's left ventricle, and by pumping blood out of the tube via one or more blood outlet openings that are defined by the tube and that are disposed within the subject's aorta;
the blood-pump tube defining a stator that is configured to reduce rotational flow components from blood flow through the blood-pump tube, prior to the blood flowing from the at least one outlet opening.

For some applications, the stator includes one or more curved ribbons that curve within the blood-pump tube. For some applications, the stator includes a plurality of ribbons disposed within the blood-pump tube, such as to separate the blood-pump tube into a plurality of compartments. For some applications, the stator includes a portion of the blood-pump tube that includes a plurality of helical tubes. For some applications, the stator includes a portion of the blood-pump tube that is twisted, such that walls of the tube define folds that are such as to reduce rotational flow components from the blood flow through the blood-pump tube, prior to the blood flowing from the at least one outlet opening. Some examples of such applications are described hereinabove with reference to FIGS. 15A-E.

Apparatus including:
a blood pump configured to be placed inside a body of subject, the blood pump including:
  an impeller including proximal and distal bushings;
  a frame configured to be disposed around the impeller;
  proximal and distal radial bearings disposed, respectively, at proximal and distal ends of the frame;
  an axial shaft configured to pass through the proximal and distal radial bearings and the proximal and distal bushings of the impeller,
  the distal bushing of the impeller being coupled to the axial shaft, such that the proximal bushing is held in an axially-fixed position with respect to the axial shaft, and
  the proximal bushing of the impeller not being coupled to the axial shaft, such that the proximal bushing is not held in an axially-fixed position with respect to the axial shaft,
  the impeller being configured to pump blood in a proximal direction, and the impeller being configured to shorten axially by the proximal bushing sliding distally with respect to the axial shaft, in response to pressure exerted upon the impeller as a result of pumping of blood by the impeller.

Some examples of such applications are described hereinabove with reference to FIGS. 11A-C.

Apparatus including:
a left-ventricular assist device configured to assist left-ventricular functioning of a subject, the left-ventricular assist device including:
  a blood-pump tube configured such that a proximal portion of the tube traverses an aortic valve of the subject, and a distal portion of the tube is disposed within a left ventricle of the subject, the tube defining at least one blood inlet opening that is configured to be disposed within the left ventricle, at least one blood outlet opening that is configured to be disposed within an aorta of the subject, and a central cylindrical portion;
  an impeller configured to pump blood through the tube from the subject's left ventricle to the subject's aorta, by pumping the blood into the tube via one or more blood inlet openings that are defined by the tube and that are disposed within the subject's left ventricle, and by pumping blood out of the tube via one or more blood outlet openings that are defined by the tube and that are disposed within the subject's aorta;
  a pitot tube disposed within the blood-pump tube, the pitot tube being configured to facilitate measurement of blood flow through the blood-pump tube,
  the blood-pump tube being shaped to define a region within which the pitot tube is disposed, the region being disposed within the central, cylindrical portion of the blood-pump tube, and being narrowed with respect to the central, cylindrical portion of the blood-pump tube.

Some examples of such applications are described hereinabove with reference to FIGS. 17A-D.

Apparatus including:
a left-ventricular assist device configured to assist left-ventricular functioning of a subject, the left-ventricular assist device including:
  a distal impeller disposed within a first tube, the first tube defining at least one blood inlet opening, via which the distal impeller is configured to pump blood into the first tube;
  a proximal impeller disposed proximally with respect to the distal impeller, the proximal impeller being disposed within a second tube that is disposed in parallel with the first tube along at least a portion of the first and second tubes, and the second tube defining at least one blood inlet opening, via which the proximal impeller is configured to pump blood into the second tube;
  the first and second tubes combining into a single tube at a location proximal to the proximal impeller, the single tube being configured to pass through an aortic valve of the subject, when the distal and proximal impellers are disposed within a left ventricle of the subject, and the single tube defining at least one blood outlet opening, via which the distal and proximal impellers are configured to pump blood into an aorta of the subject.

Some examples of such applications are described hereinabove with reference to FIGS. 30-31.

Apparatus including:
a blood pump configured to be placed inside a body of subject, the blood pump including:
  an impeller including proximal and distal bushings;
  a frame configured to be disposed around the impeller;
  proximal and distal radial bearings disposed, respectively, at proximal and distal ends of the frame;
  an axial shaft configured to pass through the proximal and distal radial bearings and the proximal and distal bushings of the impeller,
  a first one of the bushings of the impeller being coupled to the axial shaft, such that the first bushing is held in an axially-fixed position with respect to the axial shaft, and
  a second one of the bushings of the impeller not being coupled to the axial shaft, such that the second bushing is configured to slide axially with respect to the axial shaft,
  the second bushing including a protrusion that protrudes from its inner surface, and the axial shaft defining a slot in its outer surface,
  the protrusion from the inner surface of the second bushing being configured to slide along the slot defined by the outer surface of the axial shaft, such as to prevent the second bushing from rotating with respect to the axial shaft as the second bushing slides axially with respect to the axial shaft.

For some applications, the slot defined by the outer surface of the axial shaft defines a stopper at its end, the stopper being configured to prevent the second bushing from sliding beyond the stopper, by preventing axial motion of the protrusion from the inner surface of the second bushing beyond the stopper. Some examples of such applications are described hereinabove with reference to FIGS. 6A-E.

The scope of the present invention includes combining any of the apparatus and methods described herein with any of the apparatus and methods described in one or more of the following applications, all of which are incorporated herein by reference:

US 2019/0209758 to Tuval, which is a continuation of International Application No. PCT/IB2019/050186 to Tuval (published as WO 19/138350), entitled "Ventricular assist device, filed Jan. 10, 2019, which claims priority from:

U.S. Provisional Patent Application 62/615,538 to Sohn, entitled "Ventricular assist device," filed Jan. 10, 2018;

U.S. Provisional Patent Application 62/665,718 to Sohn, entitled "Ventricular assist device," filed May 2, 2018;

U.S. Provisional Patent Application 62/681,868 to Tuval, entitled "Ventricular assist device," filed Jun. 7, 2018; and U.S. Provisional Patent Application 62/727,605 to Tuval, entitled "Ventricular assist device," filed Sep. 6, 2018;

US 2019/0269840 to Tuval, which is the US national phase of International Patent Application PCT/IL2017/051273 to Tuval (published as WO 18/096531), filed Nov. 21, 2017, entitled "Blood pumps," which claims priority from U.S. Provisional Patent Application 62/425,814 to Tuval, filed Nov. 23, 2016;

US 2019/0175806 to Tuval, which is a continuation of International Application No. PCT/IL2017/051158 to Tuval (published as WO 18/078615), entitled "Ventricular assist device," filed Oct. 23, 2017, which claims priority from U.S. 62/412,631 to Tuval filed Oct. 25, 2016, and U.S. 62/543,540 to Tuval, filed Aug. 10, 2017;

US 2019/0239998 to Tuval, which is the US national phase of International Patent Application PCT/IL2017/051092 to Tuval (published as WO 18/061002), filed Sep. 28, 2017, entitled "Blood vessel tube," which claims priority from U.S. Provisional Patent Application 62/401,403 to Tuval, filed Sep. 29, 2016;

US 2018/0169313 to Schwammenthal, which is the US national phase of International Patent Application PCT/IL2016/050525 to Schwammenthal (published as WO 16/185473), filed May 18, 2016, entitled "Blood pump," which claims priority from U.S. Provisional Patent Application 62/162,881 to Schwammenthal, filed May 18, 2015, entitled "Blood pump;"

US 2017/0100527 to Schwammenthal, which is the US national phase of International Patent Application PCT/IL2015/050532 to Schwammenthal (published as WO 15/177793), filed May 19, 2015, entitled "Blood pump," which claims priority from U.S. Provisional Patent Application 62/000,192 to Schwammenthal, filed May 19, 2014, entitled "Blood pump;"

U.S. Pat. No. 10,039,874 to Schwammenthal, which is the US national phase of International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. Pat. No. 9,764,113 to Tuval, issued Sep. 19, 2017, entitled "Curved catheter," which claims priority from U.S. Provisional Patent Application 61/914,470 to Tuval, filed Dec. 11, 2013, entitled "Curved catheter;" and U.S. Pat. No. 9,597,205 to Tuval, which is the US national phase of International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   a left-ventricular assist device configured to assist left-ventricular functioning of a subject, the left-ventricular assist device comprising:
   a tube configured such that a proximal portion of the tube traverses an aortic valve of the subject, and a distal portion of the tube is disposed within a left ventricle of the subject;
   a frame disposed within at least the distal portion of the tube;
   a pump disposed within the frame and configured to pump blood through the tube from the subject's left ventricle to the subject's aorta, by pumping the blood into the tube via at least one blood inlet opening that is defined by the tube and that is configured to be disposed within the subject's left ventricle, and by pumping blood out of the tube via at least one blood outlet opening that is defined by the tube and that is configured to be disposed within the subject's aorta; and
   a distal-tip element configured to define a straight proximal portion that defines a longitudinal axis, and a curved distal portion that is shaped such as to curve in a first direction with respect to the longitudinal axis of the straight proximal portion before passing through an inflection point and curving in a second direction with respect to the longitudinal axis of the straight proximal portion, such that the curved distal portion defines a bulge on one side of the longitudinal axis of the straight proximal portion.

2. The apparatus according to claim 1, wherein the distal-tip element is configured to separate the at least one blood inlet opening from a posterior wall of the subject's left ventricle when the distal-tip element is placed against an apex of the subject's left ventricle.

3. The apparatus according to claim 1, wherein the distal-tip element has a question-mark shape.

4. The apparatus according to claim 1, wherein the distal-tip element has a tennis-racket shape.

5. The apparatus according to claim 1, wherein the curved distal portion of the distal-tip element is shaped such that after passing through the inflection point the curved distal portion continues to curve such that the distal-tip portion crosses back over the longitudinal axis defined by the straight proximal portion.

6. The apparatus according to claim 1, wherein the curved distal portion of the distal-tip element is shaped such that after passing through the inflection point the curved distal portion does not cross back over the longitudinal axis defined by the straight proximal portion.

7. The apparatus according to claim 1, wherein the blood pump comprises an impeller disposed on an axial shaft, and wherein the distal-tip element comprises an axial-shaft receiving tube configured to receive the axial shaft of the blood pump, and a distal-tip portion configured to define the curved distal portion of the distal-tip element.

8. The apparatus according to claim 1, wherein the distal-tip element is configured to separate the at least one blood inlet opening from a septal wall of the subject's left ventricle as the distal-tip element contacts an apex of the subject's left ventricle.

9. The apparatus according to claim 8, wherein the distal-tip element is configured such that, when distal-tip element is inserted into the left ventricle such that the bulge bulges toward the septal wall, in response to the distal-tip element being pushed against the apex of the subject's left ventricle, the blood inlet opening gets pushed away from the septal wall and toward a free wall of the subject's left ventricle.

10. The apparatus according to claim 9, wherein the distal-tip element is configured such that, in response to the distal-tip element being pushed against the apex of the subject's left ventricle, the blood inlet opening gets pushed away from the septal wall and toward the free wall of the subject's left ventricle by the straight proximal portion of the distal-tip element pivoting about the curved distal portion of the distal-tip element.

11. The apparatus according to claim 1, wherein the distal-tip element is configured such that, upon being deployed within a descending aorta of the subject, the distal-tip element centers itself with respect to an aortic valve of the subject.

12. The apparatus according to claim 11, wherein the curved distal portion is shaped that after curving in the first direction the curved distal portion defines an elongated straight portion, before curving the in the second direction, such that the elongated straight portion protrudes at an angle with respect to the longitudinal axis of the proximal straight portion of the distal-tip element.

13. The apparatus according to claim 1, wherein a duckbill valve is disposed within a distal-most 10 mm of the distal-tip element.

14. The apparatus according to claim 13, wherein the duckbill valve defines a wide inlet and a narrow tip that defines a slit therethrough, the duckbill valve being proximally facing, such that the wide inlet faces a distal end of the distal-tip element and such that the narrow tip faces away from the distal end of the distal-tip element.

15. The apparatus according to claim 14, wherein:
the left-ventricular assist device is configured for use with a guidewire;
the distal-tip element defines a guidewire lumen; and
the left-ventricular assist device further comprises a guidewire guide disposed within the guidewire lumen at a location that is proximal to the duckbill valve, the guidewire guide shaped to define a hole therethrough, which narrows in diameter from a proximal end of the guidewire guide to a distal end of the guidewire guide, the shape of the guidewire guide being configured to guide a tip of the guidewire toward the slit at the narrow, proximal end of the duckbill valve, when the guidewire is inserted from a proximal end of the left-ventricular assist device.

16. The apparatus according to claim 15, wherein the duckbill valve is shaped to define a converging guide portion at its proximal end, the converging guide portion converging toward the slit, such that the guide portion is configured to further guide the tip of the guidewire toward the slit.

* * * * *